United States Patent
Raab et al.

(10) Patent No.: US 10,494,640 B2
(45) Date of Patent: Dec. 3, 2019

(54) TRANSGENIC PLANTS PRODUCING GLUCANASE

(71) Applicant: Agrivida, Inc., Woburn, MA (US)

(72) Inventors: R. Michael Raab, Arlington, MA (US); Oleg Bougri, Boise, ID (US); Xuemei Li, Belmont, MA (US)

(73) Assignee: AGRIVIDA, INC., Woburn, MA (US)

( * ) Notice: Subject to any disclaimer, the term of this patent is extended or adjusted under 35 U.S.C. 154(b) by 0 days.

(21) Appl. No.: 15/569,592

(22) PCT Filed: May 13, 2016

(86) PCT No.: PCT/US2016/032418
§ 371 (c)(1),
(2) Date: Oct. 26, 2017

(87) PCT Pub. No.: WO2016/183467
PCT Pub. Date: Nov. 17, 2016

(65) Prior Publication Data
US 2018/0295859 A1    Oct. 18, 2018

Related U.S. Application Data

(60) Provisional application No. 62/161,482, filed on May 14, 2015.

(51) Int. Cl.
| | | |
|---|---|---|
| *C12N 15/82* | (2006.01) | |
| *C12N 9/24* | (2006.01) | |
| *C12Q 1/6895* | (2018.01) | |
| *A23K 10/30* | (2016.01) | |

(52) U.S. Cl.
CPC .......... *C12N 15/8242* (2013.01); *A23K 10/30* (2016.05); *C12N 9/24* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | |
|---|---|---|
| 6,958,236 B2 | 10/2005 | Pascal |
| 2005/0246787 A1 | 11/2005 | Streatfield |
| 2008/0108072 A1 | 5/2008 | Chicoine |
| 2008/0289066 A1* | 11/2008 | Lanahan ............... C12N 9/2422 800/298 |
| 2013/0071884 A1 | 3/2013 | Raab |
| 2014/0295523 A1* | 10/2014 | Steer ....................... C09K 8/035 435/209 |

OTHER PUBLICATIONS

Noll et al. Endoglucanase [Thermotoga maritima MSB8]. (2013) GenBank Accession AHD18355; pp. 1-2 (Year: 2013).*
Biswas et al. Expression of biologically active Acidothermus cellulolyticus endoglucanase in transgenic maize plants. (2006) Plant Science; vol. 171; pp. 617-623 (Year: 2006).*
Zhang et al., 2013, Overexpression of an Acidic Endo-Beta-1,3-1,4-glucanase in Transgenic Maize Seed for Direct Utilization in Animal Feed, PLoS One 8(12): e81993, doi:10.1371/journal, pone, 0081992.
European Examination Report issued for European Patent Application No. 16793621.0 dated Aug. 28, 2018.
Andorf et al. (2015) MaizeGDB 2015: New tools, data, and interface for the maize model organism database. Nucleic Acids Research, 44: D1195-D1201.
Cozannet et al. (2010) Energy value of wheat distillers grains with solubles for growing pigs and adult sows. J. Anim, Sci., 88(7):2382-2392.
Hill and Anderson (1958) Comparison of metabolizable energy and productive energy determinations with growing chicks. J. Nutr. 64:587-603.
Lawrence et al. (2005) The Maize Genetics and Genomics Database. The community resource for access to diverse maize data. Plant Physiology 138:55-58.
Lawrence et al. (2004) MaizeGDB, the community database for maize genetics and genomics. Nucleic Acids Research 32:D393-D397.
Lee et al. (2003) Beta-Mannanase ameliorates viscosity-associated depression of growth in broiler chickens fed guar germ and hull fractions. Poult. Sci. 82:1925-1931.
Leeson and Caston (2000) Commercial enzyme and their influence on broilers fed wheat or barley. J. Appl. Poult. Res. 9:242-251.
Nutrient Requirements of Poultry, 1994, National Research Council, National Academy Press, Washington, D.C.
Sibbald (1976) A bioassay for true metabolizable energy in feedingstuffs. Poultry Science 55: 303-308.
Sievers et al. (2011) Fast, scalable generation of high-quality protein multiple sequence alignments using clustal Omega, Molecular Systems Biology 7: 539 doi: 10. 1038/ msb. 2011.75.
Smith TF, Waterman MS 1981 "Identification of Common Molecular Subsequences," Journal of Molecular Biology 147: 195-197.
Wicher et al. (2001) Deletion of a cytotoxic, N-terminal putative signal peptide results in a significant increase in production yields in *Escherichia coli* and improved specific activity of Cel12A from Rhodothermus marinus. Appl. Microbiol. Biotechnol. 55, p. 578.
T. Wu et al. (2011) Diverse substrate recognition mechanism revealed by Thermatoga maritima Cel5A structures in complex with cellotetraose, vellobiose and mannotriose. Biochim. Biophys. Acta 1814, 1832-1840.
Iji (1999) The impact of cereal non-starch polysaccharides on intestinal development and function in broiler chickens. Worlds Poult. Sci. J. 55:375-387.
Broiler Performance and Nutrition Supplement, Cobb-500™, L-2114-07EN, Jul. 2015.
Broiler Performance and Nutrition Supplement, Cobb-700™, L-21124-13EN, Dec. 21, 2012.

(Continued)

*Primary Examiner* — Cathy Kingdon Worley
(74) *Attorney, Agent, or Firm* — Volpe and Koenig, P.C.

(57) ABSTRACT

Methods and compositions are described for producing a glucanase in transgenic plants and then incorporating parts of the transgenic plants in animal feed. The feed glucanase enzyme displays activity across a broad pH range, and tolerance to temperatures that are often encountered during the process of preparing animal feeds. Producing the enzyme in the transgenic plant enhances the thermal stability of the enzyme.

29 Claims, 31 Drawing Sheets

Specification includes a Sequence Listing.

(56) References Cited

OTHER PUBLICATIONS

Broiler Performance and Nutrition Supplement, CobbAvian™, L-2144-04EN, Apr. 2012.
Broiler Performance and Nutrition Supplement, CobbSasso™, L-2154-01, May 7, 2008.
Ross 308 Broiler: Nutrition Specifications, 2014 Aviagen, 0814-AVNR-035.
Ross Nutrition Supplement 2009, Aviagen.
Ross 708 Broiler: Nutrition Specification, 2014 Aviagen, 0814-AVNR-036.
Ross PM3 Brioler Nutrition Specification, 2014 Aviagen, 0814-AVNR-03.
Arbor Acres Plus Broiler Nutrition Specifications, 2014 Aviagen, 1014-AVNAA-043.
Arbor Acres Broiler Nutrition Supplement, 2009 Aviagen.
"AC225983: *Zea mays* cultivar B73 chromosome 7 clone CH201-188F5," GenBank, May 19, 2008, pp. 1-38. Retrieved from the internet: <http://www.ncbi.nlm.nih.gov/nuccore/AC225983> on Aug. 24, 2016.

\* cited by examiner

SEQUENCE LISTING

```
<160> NUMBER OF SEQ ID NOS: 56

<210> SEQ ID NO 1
<211> LENGTH: 966
<212> TYPE: DNA
<213> ORGANISM: Artificial Sequence
<220> FEATURE:
<223> OTHER INFORMATION: Synthetic construct, AGR2314 coding sequence

<400> SEQUENCE: 1
ggcgtggacc cgttcgagag gaacaagatc ctgggcaggg gcatcaacat cggcaacgcc      60
ctggaggccc cgaacgaggg cgactggggc gtggtgatca aggacgagtt cttcgacatc     120
atcaaggagg ccggcttcag ccacgtgaga atcccgatca ggtggagcac ccacgcccag     180
gccttcccgc cgtacaagat cgagccgagc ttcttcaaga gggtggacga ggtgatcaac     240
ggcgccctga gagggggcct ggccgtggtg atcaacatcc accactacga ggagctgatg     300
aacgacccgg aggagcacaa ggagaggttc ctggccctgt ggaagcagat cgccgacagg     360
tacaaggact acccggagac cctgttcttc gagatcctga acgagccgca cggcaacctg     420
accccggaga agtggaacga gctgctggag gaggccctga aggtgatcag gagcatcgac     480
aagaagcaca ccgtgatcat cggcaccgcc gagtggggcg gcatcagcgc cctggagaag     540
ctgagggtgc cgaagtggga gaagaacgcc atcgtgacca tccactacta caacccgttc     600
gagttcaccc accagggcgc cgagtgggtg ccgggcagcg agaagtggct gggcaggaag     660
tggggcagcc cggacgacca gaagcacctg atcgaggagt tcaacttcat cgaggagtgg     720
agcaaggaga acaagaggcc gatctacatc ggcgagttcg gcgcctacag gaaggccgac     780
ctggagagca ggatcaagtg gaccagcttc gtggtgaggg aggccgagaa gaggggctgg     840
agctgggcct actgggagtt ctgcagcggc ttcggcgtgt acgacccgct gaggaagcag     900
tggaacaagg acctgctgga ggccctgatc ggcggcgaca gcatcgagag cgagaaggac     960
gagctg                                                                966
```

<210> SEQ ID NO 2
<211> LENGTH: 948
<212> TYPE: DNA
<213> ORGANISM: Artificial Sequence
<220> FEATURE:
<223> OTHER INFORMATION: Synthetic construct, AGR2414 coding sequence

<400> SEQUENCE: 2

```
ggcgtggacc cgttcgagag gaacaagatc ctgggcaggg gcatcaacat cggcaacgcc      60
ctggaggccc cgaacgaggg cgactggggc gtggtgatca aggacgagtt cttcgacatc     120
atcaaggagg ccggcttcag ccacgtgaga atcccgatca ggtggagcac ccacgcctac     180
gccttcccgc cgtacaagat catggacagg ttcttcaaga gggtggacga ggtgatcaac     240
ggcgccctga gaggggcct ggccgtggtg atcaacatcc accactacga ggagctgatg     300
aacgaccccgg aggagcacaa ggagaggttc ctggccctgt ggaagcagat cgccgacagg     360
tacaaggact acccggagac cctgttcttc gagatcctga cgagccgca cggcaacctg     420
accccggaga gtggaacga gctgctggag gaggccctga aggtgatcag gagcatcgac     480
aagaagcaca ccatcatcat cggcaccgcc gagtggggcg gcatcagcgc cctggagaag     540
ctgagcgtgc cgaagtggga agaaactcc atcgtgacca tccactacta caacccgttc     600
gagttcaccc caggggcgc cgagtgggtg gagggcagcg agaagtggct gggcaggaag     660
tggggcagcc cggacgacca gaagcacctg atcgaggagt tcaacttcat cgaggagtgg     720
agcaagaaga caagaggcc gatctacatc ggcgagttcg gcgcctacag gaaggccgac     780
ctggagagca ggatcaagtg gaccagcttc gtggtgaggg agatggagaa gaggcgctgg     840
agctgggcct actgggagtt ctgcagcggc ttcggcgtgt acgacaccct gaggaagacc     900
tggaacaagg acctgctgga ggccctgatc ggcggcgaca gcatcgag              948
```

<210> SEQ ID NO 3
<211> LENGTH: 951
<212> TYPE: DNA
<213> ORGANISM: Artificial Sequence
<220> FEATURE:
<223> OTHER INFORMATION: Synthetic construct, AGR2514 coding sequence

<400> SEQUENCE: 3

```
agcggcgtgg acccgttcga ggaacaag atcctgggca ggggcatcaa catcggcaac      60
gccctggagg cccgaacga gggcgactgg ggcgtggtga tcaaggacga gtacttcgac     120
atcatcaagg aggccggctt cagccacgtg agaatcccga tcaggtggag cacccacgcc     180
caggccttcc cgccgtacaa gatcgaggac aggttcttca gagggtgga cgaggtgatc     240
aacggcgccc tgaagagggg cctggccgtg tgatcaacc agcaccacta cgaggagctg     300
atgaacgacc cggaggagca aggagagg ttcctggccc tgtggaagca gatcgccgac     360
aggtacaagg actacccgga gaccctgttc ttcgagatcc tgaacgagcc gcacggcaac     420
ctgaccccgg agagtggaa cgagctgctg gaggaggccc tgaaggtgat caggagcatc     480
gacaagaagc acaccatcat catcggcacc gccgagtggg gcggcatcag cgccctggag     540
aagctgaggt gccgaagtg ggagaagaac gccatcgtga ccatccacta ctacaacccg     600
ttcgagttca cccaccaggg cgccgagtgg gtggagggca gcgagaagtg gctgggcagg     660
aagtggggca gcccggacga ccagaagcac ctgatcgagg agttcaactt catcgaggag     720
tggagcaaga agaacaagag gccgatctac atcggcgagt tcggcgccta caggaaggcc     780
gacctggaga gcaggatcaa gtggaccagc ttcgtggtga gggaggccga agaggaggag     840
```

```
tggagctggg cctactggga gttctgcagc ggcttcggcg tgtacgacac cctgaggaag      900
acctggaaca aggacctgct ggaggccctg atcggcggcg acagcatcga g               951
```

<210> SEQ ID NO 4
<211> LENGTH: 322
<212> TYPE: PRT
<213> ORGANISM: Artificial Sequence
<220> FEATURE:
<223> OTHER INFORMATION: Syntehtic construct, AGR2314 protein

<400> SEQUENCE: 4

```
Gly Val Asp Pro Phe Glu Arg Asn Lys Ile Leu Gly Arg Gly Ile Asn
1               5                   10                  15

Ile Gly Asn Ala Leu Glu Ala Pro Asn Glu Gly Asp Trp Gly Val Val
            20                  25                  30

Ile Lys Asp Glu Phe Phe Asp Ile Ile Lys Glu Ala Gly Phe Ser His
        35                  40                  45

Val Arg Ile Pro Ile Arg Trp Ser Thr His Ala Gln Ala Phe Pro Pro
    50                  55                  60

Tyr Lys Ile Glu Pro Ser Phe Phe Lys Arg Val Asp Glu Val Ile Asn
65                  70                  75                  80

Gly Ala Leu Lys Arg Gly Leu Ala Val Val Ile Asn Ile His His Tyr
                85                  90                  95

Glu Glu Leu Met Asn Asp Pro Glu Glu His Lys Glu Arg Phe Leu Ala
            100                 105                 110

Leu Trp Lys Gln Ile Ala Asp Arg Tyr Lys Asp Tyr Pro Glu Thr Leu
        115                 120                 125

Phe Phe Glu Ile Leu Asn Glu Pro His Gly Asn Leu Thr Pro Glu Lys
130                 135                 140

Trp Asn Glu Leu Leu Glu Glu Ala Leu Lys Val Ile Arg Ser Ile Asp
145                 150                 155                 160

Lys Lys His Thr Val Ile Ile Gly Thr Ala Glu Trp Gly Gly Ile Ser
                165                 170                 175

Ala Leu Glu Lys Leu Arg Val Pro Lys Trp Glu Lys Asn Ala Ile Val
            180                 185                 190

Thr Ile His Tyr Tyr Asn Pro Phe Glu Phe Thr His Gln Gly Ala Glu
        195                 200                 205

Trp Val Pro Gly Ser Glu Lys Trp Leu Gly Arg Lys Trp Gly Ser Pro
    210                 215                 220

Asp Asp Gln Lys His Leu Ile Glu Glu Phe Asn Phe Ile Glu Glu Trp
225                 230                 235                 240

Ser Lys Lys Asn Lys Arg Pro Ile Tyr Ile Gly Glu Phe Gly Ala Tyr
                245                 250                 255

Arg Lys Ala Asp Leu Glu Ser Arg Ile Lys Trp Thr Ser Phe Val Val
            260                 265                 270

Arg Glu Ala Glu Lys Arg Gly Trp Ser Trp Ala Tyr Trp Glu Phe Cys
        275                 280                 285

Ser Gly Phe Gly Val Tyr Asp Pro Leu Arg Lys Gln Trp Asn Lys Asp
    290                 295                 300

Leu Leu Glu Ala Leu Ile Gly Gly Asp Ser Ile Glu Ser Glu Lys Asp
305                 310                 315                 320

Glu Leu
```

<210> SEQ ID NO 5
<211> LENGTH: 316

```
<212> TYPE: PRT
<213> ORGANISM: Artificial Sequence
<220> FEATURE:
<223> OTHER INFORMATION: Synthetic construct, AGR2414 protein

<400> SEQUENCE: 5

Gly Val Asp Pro Phe Glu Arg Asn Lys Ile Leu Gly Arg Gly Ile Asn
1               5                   10                  15

Ile Gly Asn Ala Leu Glu Ala Pro Asn Glu Gly Asp Trp Gly Val Val
                20                  25                  30

Ile Lys Asp Glu Phe Phe Asp Ile Ile Lys Glu Ala Gly Phe Ser His
            35                  40                  45

Val Arg Ile Pro Ile Arg Trp Ser Thr His Ala Tyr Ala Phe Pro Pro
    50                  55                  60

Tyr Lys Ile Met Asp Arg Phe Phe Lys Arg Val Asp Glu Val Ile Asn
65                  70                  75                  80

Gly Ala Leu Lys Arg Gly Leu Ala Val Val Ile Asn Ile His Tyr
                85                  90                  95

Glu Glu Leu Met Asn Asp Pro Glu Glu His Lys Glu Arg Phe Leu Ala
                100                 105                 110

Leu Trp Lys Gln Ile Ala Asp Arg Tyr Lys Asp Tyr Pro Glu Thr Leu
            115                 120                 125

Phe Phe Glu Ile Leu Asn Glu Pro His Gly Asn Leu Thr Pro Glu Lys
    130                 135                 140

Trp Asn Glu Leu Leu Glu Glu Ala Leu Lys Val Ile Arg Ser Ile Asp
145                 150                 155                 160

Lys Lys His Thr Ile Ile Ile Gly Thr Ala Glu Trp Gly Gly Ile Ser
                165                 170                 175

Ala Leu Glu Lys Leu Ser Val Pro Lys Trp Glu Lys Asn Ser Ile Val
                180                 185                 190

Thr Ile His Tyr Tyr Asn Pro Phe Glu Phe Thr His Gln Gly Ala Glu
            195                 200                 205

Trp Val Glu Gly Ser Glu Lys Trp Leu Gly Arg Lys Trp Gly Ser Pro
    210                 215                 220

Asp Asp Gln Lys His Leu Ile Glu Glu Phe Asn Phe Ile Glu Glu Trp
225                 230                 235                 240

Ser Lys Lys Asn Lys Arg Pro Ile Tyr Ile Gly Glu Phe Gly Ala Tyr
                245                 250                 255

Arg Lys Ala Asp Leu Glu Ser Arg Ile Lys Trp Thr Ser Phe Val Val
                260                 265                 270

Arg Glu Met Glu Lys Arg Arg Trp Ser Trp Ala Tyr Trp Glu Phe Cys
            275                 280                 285

Ser Gly Phe Gly Val Tyr Asp Thr Leu Arg Lys Thr Trp Asn Lys Asp
    290                 295                 300

Leu Leu Glu Ala Leu Ile Gly Gly Asp Ser Ile Glu
305                 310                 315

<210> SEQ ID NO 6
<211> LENGTH: 317
<212> TYPE: PRT
<213> ORGANISM: Artificial Sequence
<220> FEATURE:
<223> OTHER INFORMATION: Synthetic construct, AGR2514 protein

<400> SEQUENCE: 6

Ser Gly Val Asp Pro Phe Glu Arg Asn Lys Ile Leu Gly Arg Gly Ile
1               5                   10                  15
```

Asn Ile Gly Asn Ala Leu Glu Ala Pro Asn Glu Gly Asp Trp Gly Val
            20                  25                  30

Val Ile Lys Asp Glu Tyr Phe Asp Ile Ile Lys Glu Ala Gly Phe Ser
        35                  40                  45

His Val Arg Ile Pro Ile Arg Trp Ser Thr His Ala Gln Ala Phe Pro
    50                  55                  60

Pro Tyr Lys Ile Glu Asp Arg Phe Phe Lys Arg Val Asp Glu Val Ile
65                  70                  75                  80

Asn Gly Ala Leu Lys Arg Gly Leu Ala Val Val Ile Asn Gln His His
                85                  90                  95

Tyr Glu Glu Leu Met Asn Asp Pro Glu Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Ile Gly Thr Ala Glu Trp Gly Gly Ile
                165                 170                 175

Ser Ala Leu Glu Lys Leu Arg Val Pro Lys Trp Glu Lys Asn Ala Ile
            180                 185                 190

Val Thr Ile His Tyr Tyr Asn Pro Phe Glu Phe Thr His Gln Gly Ala
        195                 200                 205

Glu Trp Val Glu Gly Ser Lys Trp Leu Gly Arg Lys Trp Gly Ser
        210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Ala Glu Lys Arg Arg Trp Ser Trp Ala Tyr Trp Glu Phe
        275                 280                 285

Cys Ser Gly Phe Gly Val Tyr Asp Thr Leu Arg Lys Thr Trp Asn Lys
    290                 295                 300

Asp Leu Leu Glu Ala Leu Ile Gly Gly Asp Ser Ile Glu
305                 310                 315

<210> SEQ ID NO 7
<211> LENGTH: 3004
<212> TYPE: DNA
<213> ORGANISM: Artificial Sequence
<220> FEATURE:
<223> OTHER INFORMATION: Syntehtic construct, pAG4258

<400> SEQUENCE: 7
cggtatgaat ttggaaacaa attcagtact tttaaaaaaa tttgttgtag ggagcaaata     60
atacataaaa taatttatgc attatttat tttttatttg taataatatg cttgaaacga    120
taattcagta tgcatgttgt gccagtgtac tacacgggcg gggggagggg attgagtggg    180
ccagcgcggt gcgtagggta gatgggctga aattgataac tcaagtccga ctaggttctc    240
ttttattttc ccttccttt ctattttcct ttcttttaat tttcatgctt tcaaactaaa    300
ttcaaattcg agttttgaat ttcagcttct aaattgtaca ctaaaattat atgataaggt    360

```
aaccccctact attactttta attttttttat tctaccccat attgtttact taggggagaa    420
taattgactt aatcacattc ttccttaggt ttcaattctc aatctttcaa atccacattt    480
ttagatttct attttgaatt taaataccag tttggattta gagttcaatt tcaaaataca    540
caaccaaaat accagcatga atgcaaatat attttatgtt tatgtattta cttttctttt    600
atactttgct caaaatagtt attttcatgt atgaaactca ataagcaagg aactcacgtt    660
attatataac ctaataggaa taatttaggt aacataattt atcatcctct tgatttaaaa    720
gagatatgcc tccagaataa gacacatact aaaaataact ctaatattga ataactaaag    780
tcgtacaaat ctctactatt attcctataa aataataaag aactagctac aacttcttta    840
aggcattatt cagggtttac agcttgagag gcatgaaccc atcctgtata ctcctggact    900
tggaagacaa aatgtcaacc aaagtgaaag gttttcttat ggttgctgct aagagataga    960
ttgaacacta gatctctcct aagacgtcag ggcatgcgtt tagactccta cacatgcgaa   1020
aactgcatct tacagttgga agaaactata tctcaccact tcctgcggtg taactttgcc   1080
caaagatgtt ggctcactgt tggaatcact ccgccccgaa ctttggatct aacgcttgca   1140
gtgctacata ttagagcaag actaacaatg ccgtggagaa tggaaggtat tataaccatg   1200
tcatggtgca tatggaaatg tcgaaataac tggatattcg aaaacatacc gccaacggtg   1260
gcggcctgca aggaaatgtt caagactgaa atgaactaca tctgctacca agttaagctc   1320
gagacaggag ctaaaagtag aaactggata caacactttg taacatagtg acactcccct   1380
tttcctttct tttaccttag aactatacat acaatccaca ttcaataaaa atttgtaggt   1440
acgccataca cactaccgga atccggctct ttgccgagtg tgaggcgctt tgtcgagtgc   1500
ttttgtccaa gcactcggca aaaaagtctt tgccatgtgc cgcactcggc aaagtcctgc   1560
tctcggtaac gaccgcgttt accgagagca ggactctcga cacagaaata cactcgacaa   1620
agaaatcttt gccgagagcc aaacactcgg cgaacggcag cgctcggcaa agggtcgtca   1680
gccgccgtct aaagctgacg gtcgttatct ttgtcgagtg cccccctcgtc cgacactcag   1740
tagagcaagc ttgccgagtg ccatccttgg acactcgata agtatattt tattttttt   1800
tattttgcca accaaacttt ttgtggtatg ttcctacact atgtagatct acatgtacca   1860
ttttggcaca attacaaaaa tgttttctat aactattaga tttagttcgt ttatttgaat   1920
ttcttcggaa aattcacata tgaactgcaa gtcactcgaa acatgaaaaa ccgtgcatgc   1980
aaaataaatg atatgcatgt tatctagcac aagttacgac cgaattcaga agcagaccag   2040
aatcttcaag caccatgctc actaaacatg accgtgaact tgttatccag ttgtttaaaa   2100
attgtataaa acacaaataa agtcagaaat taatgaaact tgtccacatg tcatgatatc   2160
atatatagag gttgtgataa aaatttgata atgtttcggt aaagtgtgaa cgtactatgt   2220
gtagaaacct aagtgaccta cacataaaat catagagttt caatgtagtt cactcgacaa   2280
agactttgtc aagtgtccga taaaagtat tcagcaaaga agccgttgtc gatttactgt   2340
tcgtcgagat ctctttgccg agtgtcacac taggcaaagt ctttacggag tgttttcag    2400
gctttgacac tcggcaaagc gctcgattcc agtagtgaca gtaatttgca tcaaaaatag   2460
ccgagagatt taaaatgagt caactaatag accaactaat tattagctat tagtcgttag   2520
cttctttaat ctaagctaaa accaactaat agcttatttg ttgaattaca attagctcaa   2580
cggaattctc tgtttttct ataaaaaaaa gggaaactgc ccctcattta cagcaaactg   2640
tccgctgcct gtcgtccaga tacaatgaac gtacctagta ggaactcttt tacacgctcg   2700
```

```
gtcgctcgcc gcggatcgga gtcccaggaa cacgacacca ctgtggaaca cgacaaagtc    2760
tgctcagagg cggccacacc ctggcgtgca ccgagccgga gcccggataa gcacggtaag    2820
gagagtacgg cgggacgtgg cgacccgtgt gtctgctgcc acgcagcctt cctccacgta    2880
gccgcgcggc cgcgccacgt accagggccc ggcgctggta taaatgcgcg ccacctccgc    2940
tttagttctg catacagcca acccaacaca cacccgagca tatcacagtg acagacacta    3000
cacg                                                                3004

<210> SEQ ID NO 8
<211> LENGTH: 3292
<212> TYPE: DNA
<213> ORGANISM: Artificial Sequence
<220> FEATURE:
<223> OTHER INFORMATION: Synthetic construct, pAG4588

<400> SEQUENCE: 8
tccatgctgt cctactactt gcttcatccc cttctacatt ttgttctggt ttttggcctg      60
catttcggat catgatgtat gtgatttcca atctgctgca atatgaatgg agactctgtg     120
ctaaccatca acaacatgaa atgcttatga ggcctttgct gagcagccaa tcttgcctgt     180
gtttatgtct tcacaggccg aattcctctg ttttgttttt caccctcaat atttggaaac     240
atttatctag ttgtttgtg tccaggccta taaatcatac atgatgttgt cgtattggat      300
gtgaatgtgg tggcgtgttc agtgccttgg atttgagttt gatgagagtt gcttctgggt     360
caccactcac cattatcgat gctcctcttc agcataaggt aaaagtcttc cctgtttacg     420
ttattttacc cactatggtt gcttgggttg gttttttcct gattgcttat gccatggaaa     480
gtcatttgat atgttgaact tgaattaact gtagaattgt atacatgttc catttgtgtt     540
gtacttcctt cttttctatt agtagcctca gatgagtgtg aaaaaaacag attatataac     600
ttgccctata aatcatttga aaaaatatt gtacagtgag aaattgatat atagtgaatt      660
tttaagagca tgttttccta aagaagtata tattttctat gtacaaaggc cattgaagta     720
attgtagata caggataatg tagacttttt ggacttacac tgctaccttt aagtaacaat     780
catgagcaat agtgttgcaa tgatatttag gctgcattcg tttactctct tgatttccat     840
gagcacgctt cccaaactgt taaactctgt gttttttgcc aaaaaaaaat gcataggaaa     900 gttgcttta aaaatcata tcaatccatt ttttaagtta tagctaatac ttaattaatc       960
atgcgctaat aagtcactct gttttcgta ctagagagat tgttttgaac cagcactcaa     1020
gaacacagcc ttaacccagc caaataatgc tacaacctac cagtccacac ctcttgtaaa    1080
gcatttgttg catggaaaag ctaagatgac agcaacctgt tcaggaaaac aactgacaag    1140
gtcataggga gagggagctt ttggaaaggt gccgtgcagt tcaaacaatt agttagcagt    1200
agggtgttgg ttttgctca cagcaataag aagttaatca tggtgtaggc aacccaaata    1260
aaacaccaaa atatgcacaa ggcagttttgt tgtattctgt agtacagaca aaactaaaag    1320
taatgaaaga agatgtggtg ttagaaaagg aaacaatatc atgagtaatg tgtgggcatt    1380
atgggaccac gaaataaaaa gaacattttg atgagtcgtg tatcctcgat gagcctcaaa    1440
agttctctca ccccggataa gaaacccctta agcaatgtgc aaagtttgca ttctccactg    1500
acataatgca aaataagata tcatcgatga catagcaact catgcatcat atcatgcctc    1560
tctcaaccta ttcattccta ctcatctaca taagtatctt cagctaaatg ttagaacata    1620
aacccataag tcacgtttga tgagtattag gcgtgacaca tgacaaatca cagactcaag    1680
caagataaag caaaatgatg tgtacataaa actccagagc tatatgtcat attgcaaaaa    1740
```

```
gaggagagct tataagacaa ggcatgactc acaaaaattc atttgccttt cgtgtcaaaa      1800
agaggagggc tttacattat ccatgtcata ttgcaaaaga aagagagaaa gaacaacaca      1860
atgctgcgtc aattatacat atctgtatgt ccatcattat tcatccacct ttcgtgtacc      1920
acacttcata tatcatgagt cacttcatgt ctggacatta acaaactcta tcttaacatt      1980
tagatgcaag agcctttatc tcactataaa tgcacgatga tttctcattg tttctcacaa      2040
aaagcattca gttcattagt cctacaacaa cggatccacc atgagggtgt tgctcgttgc      2100
cctcgctctc ctggctctcg ctgcgagcgc caccagcggc gtggacccgt tcgagaggaa      2160
caagatcctg gcaggggca tcaacatcgg caacgccctg gaggccccga acgagggcga      2220
ctggggcgtg gtgatcaagg acgagttctt cgacatcatc aaggaggccg gcttcagcca      2280
cgtgagaatc ccgatcaggt ggagcaccca cgcccaggcc ttcccgccgt acaagatcga      2340
gccgagcttc ttcaagaggg tggacgaggt gatcaacggc gccctgaaga ggggcctggc      2400
cgtggtgatc aacatccacc actacgagga gctgatgaac gacccggagg agcacaagga      2460
gaggttcctg gccctgtgga agcagatcgc cgacaggtac aaggactacc cggagaccct      2520
gttcttcgag atcctgaacg agccgcacgg caacctgacc ccggagaagt ggaacgagct      2580
gctggaggag gccctgaagg tgatcaggag catcgacaag aagcacaccg tgatcatcgg      2640
caccgccgag tggggcggca tcagcgcct ggagaagctg agggtgccga agtgggagaa      2700
gaacgccatc gtgaccatcc actactacaa cccgttcgag ttcacccacc agggcgccga      2760
gtgggtgccg ggcagcgaga gtggctggg caggaagtgg ggcagcccgg acgaccagaa      2820
gcacctgatc gaggagttca acttcatcga ggagtggagc aagaagaaca agaggccgat      2880
ctacatcggc gagttcggcg cctacaggaa ggccgacctg gagagcagga tcaagtggac      2940
cagcttcgtg gtgagggagg ccgagaagag gggctggagc tgggcctact gggagttctg      3000
cagcggcttc ggcgtgtacg acccgctgag gaagcagtgg aacaaggacc tgctggaggc      3060
cctgatcggc ggcgacagca tcgagagcga gaaggacgag ctgtgaccta ggctgcacaa      3120
agtggagtag tcagtcatcg atcaggaacc agacaccaga cttttattca tacagtgaag      3180
tgaagtgaag tgcagtgcag tgagttgctg gtttttgtac aacttagtat gtatttgtat      3240
ttgtaaaata cttctatcaa taaaatttct aattcctaaa accaaaatcc ag            3292
```

<210> SEQ ID NO 9
<211> LENGTH: 2584
<212> TYPE: DNA
<213> ORGANISM: Artificial Sequence
<220> FEATURE:
<223> OTHER INFORMATION: Synthetic construct, pAG4597

<400> SEQUENCE: 9

```
aaagtaatca tattatttta tgtgtgaatc ttctttactt tttcatttga ttatgattat       60
gaaggtatga ccttcataac cttcgtccga aatccattat atccaaagga aaataatgct      120
tcgaaggacg aaggattttg atatttaaca ttttatgttg ccttgttctt aattcatagc      180
atttgagaac aagtcccaa caccaatctt tatctttact atattaaagc accagttcaa      240
cgatcgtctc gtgtcaatat tattaaaaaa ctcctacatt tctttataat caacccgcac      300
tcttataatc tcttctctta ctactataat aagagagttt atgtacaaaa taaggtgaaa      360
ttatgtataa gtgttctgga ccttggttgt tggctcatat tcacacaacc taatcaatag      420
aaaacatatg tttatttaaa acaaaattta tcatatatat atatatatat atatatatat      480
```

```
atatatatat atataatata aaccgtagca atgcacaggc atatgactag tggcaactta    540
ataccatgtg tgtattaaga tgaataagag gtatccaaat aaataacttg ttcgcttacg    600
tctggatcga aaggggttgg aaacgattaa atctcttcct agtcaaaatt aaatagaagg    660
agatttaatc gatttctccc aatccccttc gatccaggtg caaccgaata agtccttaaa    720
tgttgaggaa cacgaaacaa ccatgcattg gcatgtaaag ctccaagaat tcgttgtatc    780
cttaacaact cacagaacat caaccaaaat tgcacgtcaa gggtattggg taagaaacaa    840
tcaaacaaat cctctctgtg tgcaaagaaa cacggtgagt catgccgaga tcatactcat    900
ctgatataca tgcttacagc tcacaagaca ttacaaacaa ctcatattgc attacaaaga    960
tcgtttcatg aaaaataaaa taggccggaa caggacaaaa atccttgacg tgtaaagtaa   1020
atttacaaca aaaaaaaagc catatgtcaa gctaaatcta attcgtttta cgtagatcaa   1080
caacctgtag aaggcaacaa aactgagcca cgcagaagta cagaatgatt ccagatgaac   1140
catcgacgtg ctacgtaaag agagtgacga gtcatataca tttggcaaga aaccatgaag   1200
ctgcctacag ccgtctcggt ggcataagaa cacaagaaat tgtgttaatt aatcaaagct   1260
ataaataacg ctcgcatgcc tgtgcacttc tccatcacca ccactgggtc ttcagaccat   1320
tagctttatc tactccagag cgcagaagaa cccgatcgac accggatcca ccatgagggt   1380
gttgctcgtt gccctcgctc tcctggctct cgctgcgagc gccaccagcg gcgtggaccc   1440
gttcgagagg aacaagatcc tgggcagggg catcaacatc ggcaacgccc tggaggcccc   1500
gaacgagggc gactggggcg tggtgatcaa ggacgagttc ttcgacatca tcaaggaggc   1560
cggcttcagc cacgtgagaa tcccgatcag gtggagcacc cacgcccagg ccttcccgcc   1620
gtacaagatc gagccgagct tcttcaagag ggtggacgag gtgatcaacg gcgccctgaa   1680
gaggggcctg gccgtggtga tcaacatcca ccactacgag gagctgatga acgacccgga   1740
ggagcacaag gagaggttcc tggccctgtg gaagcagatc gccgacaggt acaaggacta   1800
cccggagacc ctgttcttcg agatcctgaa cgagccgcac ggcaacctga ccccggagaa   1860
gtggaacgag ctgctggagg aggccctgaa ggtgatcagg agcatcgaca agaagcacac   1920
cgtgatcatc ggcaccgccg agtggggcgg catcagcgcc ctggagaagc tgaggtgcc   1980 gaagtgggag aagaacgcca tcgtgaccat ccactactac aacccgttcg agttcacccca   2040 ccagggcgcc gagtgggtgc cgggcagcga gaagtggctg ggcaggaagt ggggcagccc   2100
ggacgaccag aagcacctga tcgaggagtt caacttcatc gaggagtgga gcaagaagaa   2160
caagaggccg atctacatcg gcgagttcgg cgcctacagg aaggccgacc tggagagcag   2220
gatcaagtgg accagcttcg tggtgaggga ggccgagaag aggggctgga gctgggccta   2280
ctgggagttc tgcagcggct tcggcgtgta cgacccgctg aggaagcagt ggaacaagga   2340
cctgctggag gccctgatcg gcggcgacag catcgagagc gagaaggacg agctgtgacc   2400
taggctgcac aaagtggagt agtcagtcat cgatcaggaa ccagacacca gactttatt    2460 catacagtga agtgaagtga agtgcagtgc agtgagttgc tggttttgt acaacttagt    2520 atgtatttgt atttgtaaaa tacttctatc aataaaattt ctaattccta aaaccaaaat   2580
ccag                                                                 2584
```

<210> SEQ ID NO 10
<211> LENGTH: 3317
<212> TYPE: DNA
<213> ORGANISM: Artificial Sequence
<220> FEATURE:
<223> OTHER INFORMATION: Synthetic construct, pAG4708

<400> SEQUENCE: 10

```
ataaaatttt agtgaagcta aagcggtgaa agattataga atttgatgtg ccagattaat      60
aaatcgatta actcctaaag ttcaagccga gactacagac acatgagcta cataaatgag     120
ccaaggactc gagcaaagac aaatcgacac agacattata attcaagtca ttctagaaga     180
ttcatgagaa gagtatcatt tatttaaatc aatgacttga tcaaataaga cctaggagct     240
actattgata atatatatca tgggtatcta gatcaagcat tatgaagaag agcctaagta     300
gaaggcccca tgggctcgac cacaaaccca aggactcgac aataaagtct aggagggatc     360
ccatagctaa aaggactcta gaagtgtatg tatggtaaag attttatcga dacaagaaat     420
acgataaaga tcttaacaga atcggagtca tacttgtaaa aatagagttg gactcgtgta     480
caacttggtc ttcgacttag ttcggtcatg aattcagtaa ccgactagat atgtaccatg     540
gaaccctag ggcatgaggc tatgagccat aggatcatca gatccaaaca tacaccaaca     600
aatccatcac acaccgaaga tccatattaa caagggatta gctactttac aatttcagag     660
taacaaatag agccaaactc atagcacagg ggaacttcat atcacaaatg gaggcattga     720
attgatataa aaagctaaag ttctaaaaag tttgaagtgc tgaaacttca aagccgctaa     780
ctagtgaagc accgaagcct tccggggaga gaagacatac acgacacgtt agggacgtaa     840
aatgacgaaa ttatacaact acctctatat gtaacactta tgtaatagaa aagacagaat     900
ccatatgaag atgtataatg gatcaaccat ataaatagat aaacaatata tctgctatgg     960
ggattggcat tcttgtatcc ctacgcctgt atatcccctg tttagagaac ctccgaaggt    1020
atatgatgct gaagattatt gttgtcttgt cttt catcat atatcgagtc tttccctagg    1080
atattattat tcgcaatgtg cattacatgg ttaatcgatt gagagaacat gcatctcacc    1140
tttagctgat aaacgataat ccatgtttta cacttcgtag ctactcatga gtttcgatat    1200
acaaatttgt tttctggact acgtaccatt ccatcctctt aggagaggag aggaagtgtc    1260
ctcgatttaa ttatgttgtc attttgtagt tcttcacaaa atctcaacag gtaccaaaca    1320
cattgtttcc acaagacata ttttagtcac aacaaatcta tattattatt aatcactaaa    1380
actatactga ggctcagatg cttttactag ctcttgctag tatgtgatgt aggtctcttt    1440
cgacatcatt ccatcaaaat catatgatta gcccatacca acatttcta taccattcag     1500
agaccagaat agtcttttct aatagaaaaa aggaaaatag agtgggccga cgacgacaca    1560
aattactgcg tggaccagaa aatagtgaga cacggaagac aaaagaagta aaagaggcaa    1620
ggactacggc ccacatgaga ttcggccccg ccacctccgg caaccagcgg ccgatccaac    1680
ggcagtgcat cctcaacggc gcgcgcgcgc gcgcgcgcgc acaacctcgt atatatcgcc    1740
gcgcggaagc ggcgcgaccg aggaagcctt gtcctcgaca cccctacac aggtgtcgcg     1800
ctgcccccga cacgagtccc gcatgcgtcc cacgcggccg cgccagatcc cgcctccgcg    1860
cgttgccacg ccctctataa acacccagct ctctccctcg ccctcatcta tcgcactcgt    1920
agtcgtagct caagcatcag cggcaggagc tctgggcagc gtgcgcacgt ggggtaccta    1980
gctcgctctg ctagcctacc ggatccacca tgagggtgtt gctcgttgcc ctcgctctcc    2040
tggctctcgc tgcgagcgcc accagcggcg tggacccgtt cgagaggaac aagatcctgg    2100
gcagggggcat caacatcggc aacgccctgg aggccccgaa cgagggcgac tggggcgtgg    2160
tgatcaagga cgagttcttc gacatcatca aggaggccgg cttcagccac gtgagaatcc    2220
cgatcaggtg gagcacccac gcccaggcct tcccgccgta caagatcgag ccgagcttct    2280
```

| | |
|---|---|
| tcaagagggt ggacgaggtg atcaacggcg ccctgaagag gggcctggcc gtggtgatca | 2340 |
| acatccacca ctacgaggag ctgatgaacg acccggagga gcacaaggag aggttcctgg | 2400 |
| ccctgtggaa gcagatcgcc gacaggtaca aggactaccc ggagaccctg ttcttcgaga | 2460 |
| tcctgaacga gccgcacggc aacctgaccc cggagaagtg gaacgagctg ctggaggagg | 2520 |
| ccctgaaggt gatcaggagc atcgacaaga agcacaccgt gatcatcggc accgccgagt | 2580 |
| ggggcggcat cagcgccctg gagaagctga gggtgccgaa gtgggagaag aacgccatcg | 2640 |
| tgaccatcca ctactacaac ccgttcgagt cacccacca gggcgccgag tgggtgccgg | 2700 |
| gcagcgagaa gtggctgggc aggaagtggg gcagcccgga cgaccagaag cacctgatcg | 2760 |
| aggagttcaa cttcatcgag gagtggagca agaagaacaa gaggccgatc tacatcggcg | 2820 |
| agttcggcgc ctacaggaag gccgacctgg agagcaggat caagtggacc agcttcgtgg | 2880 |
| tgagggaggc cgagaagagg ggctggagct gggcctactg ggagttctgc agcggcttcg | 2940 |
| gcgtgtacga cccgctgagg aagcagtgga caaggacct gctggaggcc ctgatcggcg | 3000 |
| gcgacagcat cgagagcgag aaggacgagc tgtgacctag gtccccgaat tccccgatc | 3060 |
| gttcaaacat ttggcaataa agtttcttaa gattgaatcc tgttgccggt cttgcgatga | 3120 |
| ttatcatata atttctgttg aattacgtta agcatgtaat aattaacatg taatgcatga | 3180 |
| cgttatttat gagatgggtt tttatgatta gagtcccgca attatacatt taatacgcga | 3240 |
| tagaaaacaa aatatagcgc gcaaactagg ataaattatc gcgcgcggtg tcatctatgt | 3300 |
| tactagatcg ggaattg | 3317 |

<210> SEQ ID NO 11
<211> LENGTH: 3388
<212> TYPE: DNA
<213> ORGANISM: Artificial Sequence
<220> FEATURE:
<223> OTHER INFORMATION: Synthetic construct, pAG4766

<400> SEQUENCE: 11

| | |
|---|---|
| tccatgctgt cctactactt gcttcatccc cttctacatt ttgttctggt ttttggcctg | 60 |
| catttcggat catgatgtat gtgatttcca atctgctgca atatgaatgg agactctgtg | 120 |
| ctaaccatca acaacatgaa atgcttatga ggcctttgct gagcagccaa tcttgcctgt | 180 |
| gtttatgtct tcacaggccg aattcctctg ttttgttttt caccctcaat atttggaaac | 240 |
| atttatctag gttgtttgtg tccaggccta taaatcatac atgatgttgt cgtattggat | 300 |
| gtgaatgtgg tggcgtgttc agtgccttgg atttgagttt gatgagagtt gcttctgggt | 360 |
| caccactcac cattatcgat gctcctcttc agcataaggt aaaagtcttc cctgtttacg | 420 |
| ttatttttacc cactatggtt gcttgggttg gttttttcct gattgcttat gccatggaaa | 480 |
| gtcatttgat atgttgaact tgaattaact gtagaattgt atacatgttc catttgtgtt | 540 |
| gtacttcctt cttttctatt agtagcctca gatgagtgtg aaaaaaacag attatataac | 600 |
| ttgccctata aatcatttga aaaaatatt gtacagtgag aaattgatat atagtgaatt | 660 |
| tttaagagca tgttttccta agaagtata tattttctat gtacaaaggc cattgaagta | 720 |
| attgtagata caggataatg tagacttttt ggacttacac tgctaccttt aagtaacaat | 780 |
| catgagcaat agtgttgcaa tgatatttag gctgcattcg tttactctct tgatttccat | 840 |
| gagcacgctt cccaaactgt taaactctgt gttttttgcc aaaaaaaaat gcataggaaa | 900 |
| gttgctttta aaaatcata tcaatccatt ttttaagtta tagctaatac ttaattaatc | 960 |
| atgcgctaat aagtcactct gttttttcgta ctagagagat tgttttgaac cagcactcaa | 1020 |

```
gaacacagcc ttaacccagc caaataatgc tacaacctac cagtccacac ctcttgtaaa    1080
gcatttgttg catggaaaag ctaagatgac agcaacctgt tcaggaaaac aactgacaag    1140
gtcataggga gagggagctt ttggaaaggt gccgtgcagt tcaaacaatt agttagcagt    1200
agggtgttgg tttttgctca cagcaataag aagttaatca tggtgtaggc aacccaaata    1260
aaacaccaaa atatgcacaa ggcagtttgt tgtattctgt agtacagaca aaactaaaag    1320
taatgaaaga agatgtggtg ttagaaaagg aaacaatatc atgagtaatg tgtgggcatt    1380
atgggaccac gaaataaaaa gaacattttg atgagtcgtg tatcctcgat gagcctcaaa    1440
agttctctca ccccggataa gaaacccttta agcaatgtgc aaagtttgca ttctccactg    1500
acataatgca aaataagata tcatcgatga catagcaact catgcatcat atcatgcctc    1560
tctcaaccta ttcattccta ctcatctaca taagtatctt cagctaaatg ttagaacata    1620
aacccataag tcacgtttga tgagtattag gcgtgacaca tgacaaatca cagactcaag    1680
caagataaag caaatgatg tgtacataaa actccagagc tatatgtcat attgcaaaaa    1740
gaggagagct tataagacaa ggcatgactc acaaaaattc atttgccttt cgtgtcaaaa    1800
agaggagggc tttacattat ccatgtcata ttgcaaaaga aagagagaaa gaacaacaca    1860
atgctgcgtc aattatacat atctgtatgt ccatcattat tcatccacct ttcgtgtacc    1920
acacttcata tatcatgagt cacttcatgt ctggacatta acaaactcta tcttaacatt    1980
tagatgcaag agcctttatc tcactataaa tgcacgatga tttctcattg tttctcacaa    2040
aaagcattca gttcattagt cctacaacaa cggatccacc atgagggtgt tgctcgttgc    2100
cctcgctctc ctggctctcg ctgcgagcgc caccagcggc gtggacccgt tcgagaggaa    2160
caagatcctg gcaggggca tcaacatcgg caacgccctg gaggcccga acgagggcga    2220 ctggggcgtg gtgatcaagg acgagttctt cgacatcatc aaggaggccg gcttcagcca    2280
cgtgagaatc ccgatcaggt ggagcaccca cgcccaggcc ttcccgccgt acaagatcga    2340
gccgagcttc ttcaagaggg tggacgaggt gatcaacggc gccctgaaga ggggcctggc    2400
cgtggtgatc aacatccacc actacgagga gctgatgaac gacccggagg agcacaagga    2460
gaggttcctg gccctgtgga gcagatcgc cgacaggtac aaggactacc ggagaccct    2520 gttcttcgag atcctgaacg agccgcacgg caacctgacc ccggagaagt ggaacgagct    2580
gctggaggag gccctgaagg tgatcaggag catcgacaag aagcacaccg tgatcatcgg    2640
caccgccgag tggggcggca tcagcgccct ggagaagctg agggtgccga agtgggagaa    2700
gaacgccatc gtgaccatcc actactacaa cccgttcgag ttcacccacc agggcgccga    2760
gtgggtgccg ggcagcgaga agtggctggg caggaagtgg ggcagcccgg acgaccagaa    2820
gcacctgatc gaggagttca acttcatcga ggagtggagc aagaagaaca gaggccgat    2880 ctacatcggc gagttcggcg cctacaggaa ggccgacctg gagagcagga tcaagtggac    2940
cagcttcgtg gtgagggagg ccgagaagag gggctggagc tgggcctact gggagttctg    3000
cagcggcttc ggcgtgtacg acccgctgag gaagcagtgg aacaaggacc tgctggaggc    3060
cctgatcggc ggcgacagca tcgagagcga aaggacgag ctgtgaccta ggtccccgaa    3120
tttccccgat cgttcaaaca tttggcaata agtttctta agattgaatc ctgttgccgg    3180
tcttgcgatg attatcatat aatttctgtt gaattacgtt aagcatgtaa taattaacat    3240
gtaatgcatg acgttatttta tgagatgggt ttttatgatt agagtcccgc aattatacat    3300
ttaatacgcg atagaaaaca aaatatagcg cgcaaactag gataaattat cgcgcgcggt    3360
```

```
gtcatctatg ttactagatc gggaattg                                    3388
```

<210> SEQ ID NO 12
<211> LENGTH: 4321
<212> TYPE: DNA
<213> ORGANISM: Artificial Sequence
<220> FEATURE:
<223> OTHER INFORMATION: Synthetic construct, pAG4767

<400> SEQUENCE: 12

```
cggtatgaat ttggaaacaa attcagtact tttaaaaaaa tttgttgtag ggagcaaata    60
atacataaaa taatttatgc attattttat tttttatttg taataatatg cttgaaacga   120
taattcagta tgcatgttgt gccagtgtac tacacgggcg gggggagggg attgagtggg   180
ccagcgcggt gcgtagggta gatgggctga aattgataac tcaagtccga ctaggttctc   240
tttttatttc ccttcctttt ctattttcct ttcttttaat tttcatgctt tcaaactaaa   300
ttcaaattcg agttttgaat ttcagcttct aaattgtaca ctaaaattat atgataaggt   360
aaccccctact attacttttta atttttttat tctaccccat attgtttact taggggagaa   420
taattgactt aatcacattc ttccttaggt ttcaattctc aatctttcaa atccacattt   480
ttagatttct attttgaatt taaataccag tttggattta gagttcaatt tcaaaataca   540
caaccaaaat accagcatga atgcaaatat attttatgtt tatgtattta cttttctttt   600
atactttgct caaatagtt attttcatgt atgaaactca ataagcaagg aactcacgtt   660
attatataac ctaataggaa taatttaggt aacataattt atcatcctct tgatttaaaa   720
gagatatgcc tccagaataa gacacatact aaaaataact ctaatattga ataactaaag   780
tcgtacaaat ctctactatt attcctataa aataataaag aactagctac aacttcttta   840
aggcattatt cagggtttac agcttgagag gcatgaaccc atcctgtata ctcctggact   900
tggaagacaa aatgtcaacc aaagtgaaag gttttcttat ggttgctgct aagagataga   960
ttgaacacta gatctctcct aagacgtcag ggcatgcgtt tagactccta cacatgcgaa  1020
aactgcatct tacagttgga agaaactata tctcaccact tcctgcggtg taactttgcc  1080
caaagatgtt ggctcactgt tggaatcact ccgccccgaa ctttggatct aacgcttgca  1140
gtgctacata ttagagcaag actaacaatg ccgtggagaa tggaaggtat tataaccatg  1200
tcatggtgca tatggaaatg tcgaaataac tggatattcg aaaacatacc gccaacggtg  1260
gcggcctgca aggaaatgtt caagactgaa atgaactaca tctgctacca agttaagctc  1320
gagacaggag ctaaaagtag aaactggata caacactttg taacatagtg acactcccct  1380
tttccttttct tttaccttag aactatacat acaatccaca ttcaataaaa atttgtaggt  1440
acgccataca cactaccgga atccggctct tgccgagtg tgaggcgctt tgtcgagtgc  1500
tttttgtcca gcactcggca aaaaagtctt tgccatgtgc cgcactcggc aaagtcctgc  1560
tctcggtaac gaccgcgttt accgagagca ggactctcga cacagaaata cactcgacaa  1620
agaaatcttt gccgagagcc aaacactcgg cgaacggcag cgctcggcaa agggtcgtca  1680
gccgccgtct aaagctgacg gtcgttatct ttgtcgagtg cccccctcgtc cgacactcag  1740
tagagcaagc ttgccgagtg ccatccttgg cactcgata agtatatttt tattttttt   1800
tattttgcca accaaacttt tgtggtatg ttcctacact atgtagatct acatgtacca  1860
ttttggcaca attacaaaaa tgttttctat aactattaga tttagttcgt ttatttgaat  1920
ttcttcggaa aattcacata tgaactgcaa gtcactcgaa acatgaaaaa ccgtgcatgc  1980
aaaataaatg atatgcatgt tatctagcac aagttacgac cgaattcaga agcagaccag  2040
```

```
aatcttcaag caccatgctc actaaacatg accgtgaact tgttatccag ttgtttaaaa    2100
attgtataaa acacaaataa agtcagaaat taatgaaact tgtccacatg tcatgatatc    2160
atatatagag gttgtgataa aaatttgata atgtttcggt aaagttgtga cgtactatgt    2220
gtagaaacct aagtgaccta cacataaaat catagagttt caatgtagtt cactcgacaa    2280
agactttgtc aagtgtccga taaaaagtat tcagcaaaga agccgttgtc gatttactgt    2340
tcgtcgagat ctctttgccg agtgtcacac taggcaaagt cttacggag tgttttcag     2400
gctttgacac tcggcaaagc gctcgattcc agtagtgaca gtaatttgca tcaaaaatag    2460
ccgagagatt taaaatgagt caactaatag accaactaat tattagctat tagtcgttag    2520
cttctttaat ctaagctaaa accaactaat agcttatttg ttgaattaca attagctcaa    2580
cggaattctc tgttttttct ataaaaaaaa gggaaactgc ccctcattta cagcaaactg    2640
tccgctgcct gtcgtccaga tacaatgaac gtacctagta ggaactcttt tacacgctcg    2700
gtcgctcgcc gcggatcgga gtcccaggaa cacgacacca ctgtggaaca cgacaaagtc    2760
tgctcagagg cggccacacc ctggcgtgca ccgagccgga gcccggataa gcacggtaag    2820
gagagtacgg cgggacgtgg cgacccgtgt gtctgctgcc acgcagcctt cctccacgta    2880
gccgcgcggc cgcgccacgt accagggccc ggcgctggta taaatgcgcg ccacctccgc    2940
tttagttctg catacagcca acccaacaca caccgagca tatcacagtg acagacacta     3000
cacgggatcc accatgaggg tgttgctcgt tgccctcgct ctcctggctc tcgctgcgag    3060
cgccaccagc ggcgtggacc cgttcgagag gaacaagatc ctgggcaggg gcatcaacat    3120
cggcaacgcc ctggaggccc cgaacgaggg cgactggggc gtggtgatca aggacgagtt    3180
cttcgacatc atcaaggagg ccggcttcag ccacgtgaga atcccgatca ggtggagcac    3240
ccacgcccag gccttcccgc cgtacaagat cgagccgagc ttcttcaaga gggtggacga    3300
ggtgatcaac ggcgccctga gaggggcct ggccgtggtg atcaacatcc accactacga    3360
ggagctgatg aacgacccgg aggagcacaa ggagaggttc ctggccctgt ggaagcagat    3420
cgccgacagg tacaaggact acccggagac cctgttcttc gagatcctga cgagccgca    3480
cggcaacctg accccggaga gtggaacga gctgctggag gaggccctga aggtgatcag    3540
gagcatcgac aagaagcaca ccgtgatcat cggcaccgcc gagtggggcg gcatcagcgc    3600
cctggagaag ctgagggtgc cgaagtggga aagaacgcc atcgtgacca tccactacta    3660
caacccgttc gagttcaccc accagggcgc cgagtgggtg ccgggcagcg agaagtggct    3720
gggcaggaag tggggcagcc cggacgacca gaagcacctg atcgaggagt tcaacttcat    3780
cgaggagtgg agcaagaaga acaagaggcc gatctacatc ggcgagttcg cgcctacag    3840
gaaggccgac ctggagagca ggatcaagtg gaccagcttc gtggtgaggg aggccgagaa    3900
gaggggctgg agctgggcct actgggagtt ctgcagcggc ttcggcgtgt acgacccgct    3960
gaggaagcag tggaacaagg acctgctgga ggccctgatc ggcggcgaca gcatcgagag    4020
cgagaaggac gagctgtgac ctaggtcccc gaatttcccc gatcgttcaa acatttggca    4080
ataaagtttc ttaagattga atcctgttgc cggtcttgcg atgattatca tataatttct    4140
gttgaattac gttaagcatg taataattaa catgtaatgc atgacgttat ttatgagatg    4200
ggttttatg attagagtcc cgcaattata catttaatac gcgatagaaa acaaaatata    4260
gcgcgcaaac taggataaat tatcgcgcgc ggtgtcatct atgttactag atcgggaatt    4320
g                                                                    4321
```

<210> SEQ ID NO 13
<211> LENGTH: 10425
<212> TYPE: DNA
<213> ORGANISM: Artificial Sequence
<220> FEATURE:
<223> OTHER INFORMATION: Synthetic construct, pAG4770

<400> SEQUENCE: 13

```
aaagtaatca tattatttta tgtgtgaatc ttctttactt tttcatttga ttatgattat    60
gaaggtatga ccttcataac cttcgtccga aatccattat atccaaagga aaataatgct   120
tcgaaggacg aaggattttg atatttaaca ttttatgttg ccttgttctt aattcatagc   180
atttgagaac aagtccccaa caccaatctt tatctttact atattaaagc accagttcaa   240
cgatcgtctc gtgtcaatat tattaaaaaa ctcctacatt tctttataat caacccgcac   300
tcttataatc tcttctctta ctactataat aagagagttt atgtacaaaa taaggtgaaa   360
ttatgtataa gtgttctgga ccttggttgt tggctcatat tcacacaacc taatcaatag   420
aaaacatatg ttttattaaa acaaaattta tcatatatat atatatatat atatatatat   480
atatatatat ataaatata  aaccgtagca atgcacaggc atatgactag tggcaactta   540
ataccatgtg tgtattaaga tgaataagag gtatccaaat aaataacttg ttcgcttacg   600
tctggatcga aggggttgg  aaacgattaa atctcttcct agtcaaaatt aaatagaagg   660
agatttaatc gatttctccc aatcccttc  gatccaggtg caaccgaata agtccttaaa   720
tgttgaggaa cacgaaacaa ccatgcattg gcatgtaaag ctccaagaat cgttgtatc    780
cttaacaact cacagaacat caaccaaaat tgcacgtcaa gggtattggg taagaaacaa   840
tcaaacaaat cctctctgtg tgcaaagaaa cacggtgagt catgccgaga tcatactcat   900
ctgatataca tgcttacagc tcacaagaca ttacaaacaa ctcatattgc attacaaaga   960
tcgtttcatg aaaaataaaa taggccggaa caggacaaaa atccttgacg tgtaaagtaa  1020
atttacaaca aaaaaaaagc catatgtcaa gctaaatcta attcgtttta cgtagatcaa  1080
caacctgtag aaggcaacaa aactgagcca cgcagaagta cagaatgatt ccagatgaac  1140
catcgacgtg ctacgtaaag agagtgacga gtcatatca  tttggcaaga aaccatgaag  1200
ctgcctacag ccgtctcggt ggcataagaa cacaagaaat tgtgttaatt aatcaaagct  1260
ataaataacg ctcgcatgcc tgtgcacttc tccatcacca ccactgggtc ttcagaccat  1320
tagctttatc tactccagag cgcagaagaa cccgatcgac accggatcca ccatgagggt  1380
gttgctcgtt gccctcgctc tcctggctct cgctgcgagc gccaccagcg cgtggaccc   1440
gttcgagagg aacaagatcc tgggcagggg catcaacatc ggcaacgccc tggaggcccc  1500
gaacgagggc gactgggcg  tggtgatcaa ggacgagttc ttcgacatca tcaaggaggc  1560
cggcttcagc cacgtgagaa tcccgatcag gtggagcacc cacgcccagg ccttcccgcc  1620
gtacaagatc gagccgagct tcttcaagag ggtggacgag gtgatcaacg cgccctgaa   1680
gaggggcctg gccgtggtga tcaacatcca ccactacgag gagctgatga acgacccgga  1740
ggagcacaag gagaggttcc tggccctgtg gaagcagatc gccgacaggt acaaggacta  1800
cccggagacc ctgttcttcg agatcctgaa cgagccgcac ggcaacctga ccccggagaa  1860
gtggaacgag ctgctggagg aggccctgaa ggtgatcagg agcatcgaca agaagcacac  1920
cgtgatcatc ggcaccgccg agtgggcg  catcagcgcc ctggagaagc tgagggtgcc  1980
gaagtgggag aagaacgcca tcgtgacca  ccactactac aacccgttcg agttcaccca  2040
ccagggcgcc gagtgggtgc cgggcagcga gaagtggctg ggcaggaagt ggggcagccc  2100
```

```
ggacgaccag aagcacctga tcgaggagtt caacttcatc gaggagtgga gcaagaagaa    2160
caagaggccg atctacatcg gcgagttcgg cgcctacagg aaggccgacc tggagagcag    2220
gatcaagtgg accagcttcg tggtgaggga ggccgagaag aggggctgga gctgggccta    2280
ctgggagttc tgcagcggct tcggcgtgta cgacccgctg aggaagcagt ggaacaagga    2340
cctgctggag gccctgatcg gcggcgacag catcgagagc gagaaggacg agctgtgacc    2400
taggtccccg aatttccccg atcgttcaaa catttggcaa taaagtttct taagattgaa    2460
tcctgttgcc ggtcttgcga tgattatcat ataatttctg ttgaattacg ttaagcatgt    2520
aataattaac atgtaatgca tgacgttatt tatgagatgg ttttttatga ttagagtccc    2580
gcaattatac atttaatacg cgatagaaaa caaaatatag cgcgcaaact aggataaatt    2640
atcgcgcgcg gtgtcatcta tgttactaga tcgggaattg tacgtaccaa atccatggaa    2700
tcaaggtacc tccatgctgt cctactactt gcttcatccc cttctacatt ttgttctggt    2760
ttttggcctg catttcggat catgatgtat gtgatttcca atctgctgca atatgaatgg    2820
agactctgtg ctaaccatca acaacatgaa atgcttatga ggcctttgct gagcagccaa    2880
tcttgcctgt gtttatgtct tcacaggccg aattcctctg ttttgttttt caccctcaat    2940
atttggaaac atttatctag gttgtttgtg tccaggccta taaatcatac atgatgttgt    3000
cgtattggat gtgaatgtgg tggcgtgttc agtgccttgg atttgagttt gatgagagtt    3060
gcttctgggt caccactcac cattatcgat gctcctcttc agcataaggt aaaagtcttc    3120
cctgtttacg ttatttttacc cactatggtt gcttgggttg ttttttttcct gattgcttat   3180 gccatggaaa gtcatttgat atgttgaact tgaattaact gtagaattgt atacatgttc    3240
catttgtgtt gtacttcctt cttttctatt agtagcctca gatgagtgtg aaaaaaacag    3300
attatataac ttgccctata aatcatttga aaaaaatatt gtacagtgag aaattgatat    3360
atagtgaatt tttaagagca tgttttccta aagaagtata tattttctat gtacaaaggc    3420
cattgaagta attgtagata caggataatg tagactttt ggacttacac tgctaccttt      3480
aagtaacaat catgagcaat agtgttgcaa tgatatttag gctgcattcg tttactctct    3540
tgatttccat gagcacgctt cccaaactgt taaactctgt gtttttgcc aaaaaaaaat      3600 gcataggaaa gttgctttta aaaaatcata tcaatccatt ttttaagtta tagctaatac    3660
ttaattaatc atgcgctaat aagtcactct gtttttcgta ctagagagat tgttttgaac    3720
cagcactcaa gaacacagcc ttaacccagc caaataatgc tacaacctac cagtccacac    3780
ctcttgtaaa gcatttgttg catggaaaag ctaagatgac agcaacctgt tcaggaaaac    3840
aactgacaag gtcataggga gagggagctt ttggaaaggt gccgtgcagt tcaaacaatt    3900
agttagcagt agggtgttgg ttttttgctca cagcaataag aagttaatca tggtgtaggc    3960
aacccaaata aaacaccaaa atatgcacaa ggcagtttgt tgtattctgt agtacagaca    4020
aaactaaaag taatgaaaga agatgtggtg ttagaaaagg aaacaatatc atgagtaatg    4080
tgtgggcatt atgggaccac gaaataaaaa gaacattttg atgagtcgtg tatcctcgat    4140
gagcctcaaa agttctctca ccccggataa gaaaccctta agcaatgtgc aaagtttgca    4200
ttctccactg acataatgca aaataagata tcatcgatga catagcaact catgcatcat    4260
atcatgcctc tctcaaccta ttcattccta ctcatctaca taagtatctt cagctaaatg    4320
ttagaacata aacccataag tcacgtttga tgagtattag gcgtgacaca tgacaaatca    4380
cagactcaag caagataaag caaaatgatg tgtacataaa actccagagc tatatgtcat    4440
```

```
attgcaaaaa gaggagagct tataagacaa ggcatgactc acaaaaattc atttgccttt    4500
cgtgtcaaaa agaggagggc tttacattat ccatgtcata ttgcaaaaga aagagagaaa    4560
gaacaacaca atgctgcgtc aattatacat atctgtatgt ccatcattat tcatccacct    4620
ttcgtgtacc acacttcata tatcatgagt cacttcatgt ctggacatta acaaactcta    4680
tcttaacatt tagatgcaag agcctttatc tcactataaa tgcacgatga tttctcattg    4740
tttctcacaa aaagcattca gttcattagt cctacaacaa cggatccacc atgagggtgt    4800
tgctcgttgc cctcgctctc ctggctctcg ctgcgagcgc caccagcggc gtggacccgt    4860
tcgagaggaa caagatcctg ggcaggggca tcaacatcgg caacgccctg gaggccccga    4920
acgagggcga ctgggcgtg gtgatcaagg acgagttctt cgacatcatc aaggaggccg    4980
gcttcagcca cgtgagaatc ccgatcaggt ggagcaccca cgcccaggcc ttcccgccgt    5040
acaagatcga gccgagcttc ttcaagaggg tggacgaggt gatcaacggc gccctgaaga    5100
ggggcctggc cgtggtgatc aacatccacc actacgagga gctgatgaac gacccggagg    5160
agcacaagga gaggttcctg gccctgtgga agcagatcgc cgacaggtac aaggactacc    5220
cggagaccct gttcttcgag atcctgaacg agccgcacgg caacctgacc ccggagaagt    5280
ggaacgagct gctggaggag gccctgaagg tgatcaggag catcgacaag aagcacaccg    5340
tgatcatcgg caccgccgag tggggcggca tcagcgccct ggagaagctg agggtgccga    5400
agtgggagaa gaacgccatc gtgaccatcc actactacaa cccgttcgag ttcacccacc    5460
agggcgccga gtgggtgccg ggcagcgaga gtggctggg caggaagtgg ggcagcccgg    5520
acgaccagaa gcacctgatc gaggagttca acttcatcga ggagtggagc aagaagaaca    5580
agaggccgat ctacatcggc gagttcggcg cctacaggaa ggccgacctg gagagcagga    5640
tcaagtggac cagcttcgtg gtgagggagg ccgagaagag gggctggagc tgggcctact    5700
gggagttctg cagcggcttc ggcgtgtacg acccgctgag gaagcagtgg aacaaggacc    5760
tgctggaggc cctgatcggc ggcgacagca tcgagagcga aaggacgag ctgtgaccta    5820 ggtccccgaa tttccccgat cgttcaaaca tttggcaata aagtttctta agattgaatc    5880
ctgttgccgg tcttgcgatg attatcatat aatttctgtt gaattacgtt aagcatgtaa    5940
taattaacat gtaatgcatg acgttattta tgagatgggt ttttatgatt agagtcccgc    6000
aattatacat ttaatacgcg atagaaaaca aaatatagcg cgcaaactag gataaattat    6060
cgcgcgcggt gtcatctatg ttactagatc gggaattggg tacccggtat gaatttggaa    6120
acaaattcag tacttttaaa aaatttgtt gtagggagca ataatacat aaaataattt     6180 atgcattatt ttattttta tttgtaataa tatgcttgaa acgataattc agtatgcatg    6240
ttgtgccagt gtactacacg ggcggggga ggggattgag tgggccagcg cggtgcgtag     6300
ggtagatggg ctgaaattga taactcaagt ccgactaggt tctcttttta tttcccttcc    6360
ttttctattt tccttctctt taattttcat gctttcaaac taaattcaaa ttcgagtttt    6420
gaatttcagc ttctaaattg tacactaaaa ttatatgata aggtaacccc tactattact    6480
tttaattttt ttattctacc ccatattgtt tacttagggg agaataattg acttaatcac    6540
attcttcctt aggtttcaat tctcaatctt tcaaatccac atttttagat ttctattttg    6600
aatttaaata ccagtttgga tttagagttc aatttcaaaa tacacaacca aaataccagc    6660
atgaatgcaa atatatttta tgtttatgta tttacttttc ttttatactt tgctcaaaat    6720
agttattttc atgtatgaaa ctcaataagc aaggaactca cgttattata taacctaata    6780
ggaataattt aggtaacata atttatcatc ctcttgattt aaaagagata tgcctccaga    6840
```

```
ataagacaca tactaaaaat aactctaata ttgaataact aaagtcgtac aaatctctac    6900
tattattcct ataaaataat aaagaactag ctacaacttc tttaaggcat tattcagggt    6960
ttacagcttg agaggcatga acccatcctg tatactcctg gacttggaag acaaaatgtc    7020
aaccaaagtg aaaggttttc ttatggttgc tgctaagaga tagattgaac actagatctc    7080
tcctaagacg tcagggcatg cgtttagact cctacacatg cgaaaactgc atcttacagt    7140
tggaagaaac tatatctcac cacttcctgc ggtgtaactt tgcccaaaga tgttggctca    7200
ctgttggaat cactccgccc cgaactttgg atctaacgct tgcagtgcta catattagag    7260
caagactaac aatgccgtgg agaatggaag gtattataac catgtcatgg tgcatatgga    7320
aatgtcgaaa taactggata ttcgaaaaca taccgccaac ggtggcggcc tgcaaggaaa    7380
tgttcaagac tgaaatgaac tacatctgct accaagttaa gctcgagaca ggagctaaaa    7440
gtagaaactg gatacaacac tttgtaacat agtgacactc cccttttcct ttcttttacc    7500
ttagaactat acatacaatc cacattcaat aaaaatttgt aggtacgcca tacacactac    7560
cggaatccgg ctctttgccg agtgtgaggc gctttgtcga gtgctttttg tccagcactc    7620
ggcaaaaaag tctttgccat gtgccgcact cggcaaagtc ctgctctcgg taacgaccgc    7680
gtttaccgag agcaggactc tcgacacaga aatacactcg acaagaaat ctttgccgag    7740 agccaaacac tcggcgaacg gcagcgctcg gcaaagggtc gtcagccgcc gtctaaagct    7800
gacggtcgtt atctttgtcg agtgcccccct cgtccgacac tcagtagagc aagcttgccg    7860
agtgccatcc ttggacactc gataaagtat atttttatttt tttttatttt gccaaccaaa    7920 cttttttgtgg tatgttccta cactatgtag atctacatgt accattttgg cacaattaca    7980
aaaatgtttt ctataactat tagatttagt tcgtttattt gaatttcttc ggaaaattca    8040
catatgaact gcaagtcact cgaaacatga aaaccgtgc atgcaaaata aatgatatgc    8100
atgttatcta gcacaagtta cgaccgaatt cagaagcaga ccagaatctt caagcaccat    8160
gctcactaaa catgaccgtg aacttgttat ccagttgttt aaaaattgta taaaacacaa    8220
ataaagtcag aaattaatga aacttgtcca catgtcatga tatcatatat agaggttgtg    8280
ataaaatttt gataatgttt cggtaaagtt gtgacgtact atgtgtagaa acctaagtga    8340
cctacacata aaatcataga gttttcaatgt agttcactcg acaaagactt tgtcaagtgt    8400
ccgataaaaa gtattcagca aagaagccgt tgtcgattta ctgttcgtcg agatctcttt    8460
gccgagtgtc acactaggca aagtctttac ggagtgtttt tcaggctttg cactcggca    8520 aagcgctcga ttccagtagt gacagtaatt tgcatcaaaa atagccgaga gatttaaaat    8580
gagtcaacta atagaccaac taattattag ctattagtcg ttagcttctt taatctaagc    8640
taaaaccaac taatagctta tttgttgaat tacaattagc tcaacggaat tctctgtttt    8700
ttctataaaa aaagggaaa ctgcccctca tttacagcaa actgtccgct gcctgtcgtc    8760
cagatacaat gaacgtacct agtaggaact cttttacacg ctcggtcgct cgccgcggat    8820
cggagtccca ggaacacgac accactgtgg aacacgacaa agtctgctca gaggcggcca    8880
caccctggcg tgcaccgagc cggagcccgg ataagcacgg taaggagagt acggcgggac    8940
gtggcgaccc gtgtgtctgc tgccacgcag ccttcctcca cgtagccgcg cggccgcgcc    9000
acgtaccagg gcccggcgct ggtataaatg cgcgccacct ccgctttagt tctgcataca    9060 gccaaccccaa cacacacccg agcatatcac agtgacagac actacacggg atccaccatg    9120
agggtgttgc tcgttgccct cgctctcctg gctctcgctg cgagcgccac cagcggcgtg    9180
```

```
gacccgttcg agaggaacaa gatcctgggc aggggcatca acatcggcaa cgccctggag    9240
gccccgaacg agggcgactg gggcgtggtg atcaaggacg agttcttcga catcatcaag    9300
gaggccggct tcagccacgt gagaatcccg atcaggtgga gcacccacgc ccaggccttc    9360
ccgccgtaca agatcgagcc gagcttcttc aagagggtgg acgaggtgat caacggcgcc    9420
ctgaagaggg gcctggccgt ggtgatcaac atccaccact acgaggagct gatgaacgac    9480
ccggaggagc acaaggagag gttcctggcc ctgtggaagc agatcgccga caggtacaag    9540
gactacccgg agaccctgtt cttcgagatc ctgaacgagc cgcacggcaa cctgaccccg    9600
gagaagtgga acgagctgct ggaggaggcc ctgaaggtga tcaggagcat cgacaagaag    9660
cacaccgtga tcatcggcac cgccgagtgg ggcggcatca gcgccctgga agctgagg     9720
gtgccgaagt gggagaagaa cgccatcgtg accatccact actacaaccc gttcgagttc    9780
acccaccagg gcgccgagtg ggtgccgggc agcgagaagt ggctgggcag gaagtggggc    9840
agcccgacg accagaagca cctgatcgag gagttcaact tcatcgagga gtggagcaag    9900
aagaacaaga ggccgatcta catcggcgag ttcggcgcct acaggaaggc cgacctggag    9960
agcaggatca agtggaccag cttcgtggtg agggaggccg agaagagggg ctggagctgg   10020
gcctactggg agttctgcag cggcttcggc gtgtacgacc cgctgaggaa gcagtggaac   10080
aaggacctgc tggaggccct gatcggcggc gacagcatcg agagcgagaa ggacgagctg   10140
tgacctaggt ccccgaattt ccccgatcgt tcaaacattt ggcaataaag tttcttaaga   10200
ttgaatcctg ttgccggtct tgcgatgatt atcatataat ttctgttgaa ttacgttaag   10260
catgtaataa ttaacatgta atgcatgacg ttatttatga gatgggtttt tatgattaga   10320
gtcccgcaat tatacattta atacgcgata gaaaacaaaa tatagcgcgc aaactaggat   10380
aaattatcgc gcgcggtgtc atctatgtta ctagatcggg aattg                   10425
```

<210> SEQ ID NO 14
<211> LENGTH: 10413
<212> TYPE: DNA
<213> ORGANISM: Artificial Sequence
<220> FEATURE:
<223> OTHER INFORMATION: Synthetic construct, pAG4771

<400> SEQUENCE: 14

```
tccatgctgt cctactactt gcttcatccc cttctacatt ttgttctggt ttttggcctg      60
catttcggat catgatgtat gtgatttcca atctgctgca atatgaatgg agactctgtg     120
ctaaccatca acaacatgaa atgcttatga ggcctttgct gagcagccaa tcttgcctgt     180
gtttatgtct tcacaggccg aattcctctg ttttgttttt caccctcaat atttggaaac     240
atttatctag gttgtttgtg tccaggccta taaatcatac atgatgttgt cgtattggat     300
gtgaatgtgg tggcgtgttc agtgccttgg atttgagttt gatgagagtt gcttctgggt     360
caccactcac cattatcgat gctcctcttc agcataaggt aaaagtcttc cctgtttacg     420
ttattttacc cactatggtt gcttgggttg gttttttcct gattgcttat gccatggaaa     480
gtcatttgat atgttgaact tgaattaact gtagaattgt atacatgttc catttgtgtt     540
gtacttcctt cttttctatt agtagcctca gatgagtgtg aaaaaaacag attatataac     600
ttgccctata aatcatttga aaaaatatt gtacagtgag aaattgatat atagtgaatt      660
tttaagagca tgttttccta agaagtata tattttctat gtacaaggc cattgaagta      720
attgtagata caggataatg tagactttt ggacttacac tgctaccttt aagtaacaat     780
catgagcaat agtgttgcaa tgatatttag gctgcattcg tttactctct tgatttccat     840
```

```
gagcacgctt cccaaactgt taaactctgt gttttttgcc aaaaaaaaat gcataggaaa      900
gttgctttta aaaaatcata tcaatccatt ttttaagtta tagctaatac ttaattaatc      960
atgcgctaat aagtcactct gttttcgta ctagagagat tgttttgaac cagcactcaa     1020
gaacacagcc ttaacccagc caaataatgc tacaacctac cagtccacac ctcttgtaaa     1080
gcatttgttg catggaaaag ctaagatgac agcaacctgt tcaggaaaac aactgacaag     1140
gtcataggga gagggagctt ttggaaaggt gccgtgcagt tcaaacaatt agttagcagt     1200
agggtgttgg tttttgctca cagcaataag aagttaatca tggtgtaggc aacccaaata     1260
aaacaccaaa atatgcacaa ggcagtttgt tgtattctgt agtacagaca aaactaaaag     1320
taatgaaaga agatgtggtg ttagaaaagg aaacaatatc atgagtaatg tgtgggcatt     1380
atgggaccac gaaataaaaa gaacattttg atgagtcgtg tatcctcgat gagcctcaaa     1440
agttctctca ccccggataa gaaaccctta agcaatgtgc aaagtttgca ttctccactg     1500
acataatgca aaataagata tcatcgatga catagcaact catgcatcat atcatgcctc     1560
tctcaaccta ttcattccta ctcatctaca taagtatctt cagctaaatg ttagaacata     1620
aacccataag tcacgtttga tgagtattag gcgtgacaca tgacaaatca cagactcaag     1680
caagataaag caaaatgatg tgtacataaa actccagagc tatatgtcat attgcaaaaa     1740
gaggagagct tataagacaa ggcatgactc acaaaaattc atttgccttt cgtgtcaaaa     1800
agaggagggc tttacattat ccatgtcata ttgcaaaaga aagagagaaa gaacaacaca     1860
atgctgcgtc aattatacat atctgtatgt ccatcattat tcatccacct ttcgtgtacc     1920
acacttcata tatcatgagt cacttcatgt ctggacatta acaaactcta tcttaacatt     1980
tagatgcaag agcctttatc tcactataaa tgcacgatga tttctcattg tttctcacaa     2040
aaagcattca gttcattagt cctacaacaa cggatccacc atgagggtgt tgctcgttgc     2100
cctcgctctc ctggctctcg ctgcgagcgc caccagcggc gtggaccgt tcgagaggaa     2160
caagatcctg ggcagggggca tcaacatcgg caacgccctg gaggccccga cgagggcga     2220
ctggggcgtg gtgatcaagg acgagttctt cgacatcatc aaggaggccg gcttcagcca     2280
cgtgagaatc ccgatcaggt ggagcaccca cgcccaggcc ttcccgccgt acaagatcga     2340
gccgagcttc ttcaagaggg tggacgaggt gatcaacggc gccctgaaga ggggcctggc     2400
cgtggtgatc aacatccacc actacgagga gctgatgaac gacccggagg agcacaagga     2460
gaggttcctg gccctgtgga agcagatcgc cgacaggtac aaggactacc cggagaccct     2520
gttcttcgag atcctgaacg agccgcacgg caacctgacc ccggagaagt ggaacgagct     2580
gctggaggag gccctgaagg tgatcaggag catcgacaag aagcacaccg tgatcatcgg     2640
caccgccgag tggggcggca tcagcgccct ggagaagctg agggtgccga agtgggagaa     2700
gaacgccatc gtgaccatcc actactacaa cccgttcgag ttcacccacc agggcgccga     2760
gtgggtgccg gcagcgaga agtggctggg caggaagtgg ggcagcccgg acgaccagaa     2820
gcacctgatc gaggagttca acttcatcga ggagtggagc aagaagaaca agaggccgat     2880
ctacatcggc gagttcggcg cctacaggaa ggccgacctg gagagcagga tcaagtggac     2940
cagcttcgtg gtgagggagg ccgagaagag gggctggagc tgggcctact gggagttctg     3000
cagcggcttc ggcgtgtacg acccgctgag gaagcagtgg aacaaggacc tgctggaggc     3060
cctgatcggc ggcgacagca tcgagagcga aaggacgag ctgtgaccta ggtcccgaa     3120
tttccccgat cgttcaaaca tttggcaata aagtttctta agattgaatc ctgttgccgg     3180
```

-continued

```
tcttgcgatg attatcatat aatttctgtt gaattacgtt aagcatgtaa taattaacat    3240
gtaatgcatg acgttattta tgagatgggt ttttatgatt agagtcccgc aattatacat    3300
ttaatacgcg atagaaaaca aaatatagcg cgcaaactag gataaattat cgcgcgcggt    3360
gtcatctatg ttactagatc gggaattgcc atggaatcaa ggtaccaaag taatcatatt    3420
attttatgtg tgaatcttct ttacttttc atttgattat gattatgaag gtatgacctt    3480
cataaccttc gtccgaaatc cattatatcc aaaggaaaat aatgcttcga aggacgaagg    3540
attttgatat ttaacatttt atgttgcctt gttcttaatt catagcattt gagaacaagt    3600
ccccaacacc aatctttatc tttactatat taaagcacca gttcaacgat cgtctcgtgt    3660
caatattatt aaaaaactcc tacatttctt tataatcaac ccgcactctt ataatctctt    3720
ctcttactac tataataaga gagtttatgt acaaaataag gtgaaattat gtataagtgt    3780
tctggacctt ggttgttggc tcatattcac acaacctaat caatagaaaa catatgtttt    3840
attaaaacaa aatttatcat atatatatat atatatatat atatatatat atatatatat    3900
aatataaacc gtagcaatgc acaggcatat gactagtggc aacttaatac catgtgtgta    3960
ttaagatgaa taagaggtat ccaaataaat aacttgttcg cttacgtctg gatcgaaagg    4020
ggttggaaac gattaaatct cttcctagtc aaaattaaat agaaggagat ttaatcgatt    4080
tctcccaatc cccttcgatc caggtgcaac cgaataagtc cttaaatgtt gaggaacacg    4140
aaacaaccat gcattggcat gtaaagctcc aagaattcgt tgtatcctta acaactcaca    4200
gaacatcaac caaaattgca cgtcaagggt attgggtaag aaacaatcaa acaaatcctc    4260
tctgtgtgca aagaaacacg gtgagtcatg ccgagatcat actcatctga tatacatgct    4320
tacagctcac aagacattac aaacaactca tattgcatta caaagatcgt ttcatgaaaa    4380
ataaaatagg ccggaacagg acaaaaatcc ttgacgtgta aagtaaattt acaacaaaaa    4440
aaaagccata tgtcaagcta aatctaattc gttttacgta gatcaacaac ctgtagaagg    4500
caacaaaact gagccacgca gaagtacaga atgattccag atgaaccatc gacgtgctac    4560
gtaaagagag tgacgagtca tatacatttg gcaagaaacc atgaagctgc ctacagccgt    4620
ctcggtggca taagaacaca agaaattgtg ttaattaatc aaagctataa ataacgctcg    4680
catgcctgtg cacttctcca tcaccaccac tgggtcttca gaccattagc tttatctact    4740
ccagagcgca gaagaacccg atcgacaccg atccaccat gagggtgttg ctcgttgccc    4800
tcgctctcct ggctctcgct gcgagcgcca ccagcggcgt ggacccgttc gagaggaaca    4860
agatcctggg caggggcatc aacatcggca acgccctgga ggccccgaac gagggcgact    4920
ggggcgtggt gatcaaggac gagttcttcg acatcatcaa ggaggccggc ttcagccacg    4980
tgagaatccc gatcaggtgg agcacccacg cccaggcctt cccgccgtac aagatcgagc    5040
cgagcttctt caagagggtg gacgaggtga tcaacggcgc cctgaagagg ggcctggccg    5100
tggtgatcaa catccaccac tacgaggagc tgatgaacga cccggaggag cacaaggaga    5160
ggttcctggc cctgtggaag cagatcgccg acaggtacaa ggactacccg agaccctgt    5220
tcttcgagat cctgaacgag ccgcacggca acctgacccc ggagaagtgg aacgagctgc    5280
tggaggaggc cctgaaggtg atcaggagca tcgacaagaa gcacaccgtg atcatcggca    5340
ccgccgagtg gggcggcatc agcgccctgg agaagctgag ggtgccgaag tgggagaaga    5400
acgccatcgt gaccatccac tactacaacc cgttcgagtt cacccaccag ggcgccgagt    5460
gggtgccggg cagcgagaag tggctgggca ggaagtgggg cagcccggac gaccagagct    5520
acctgatcga ggagttcaac ttcatcgagg agtggagcaa gaagaacaag aggccgatct    5580
```

```
acatcggcga gttcggcgcc tacaggaagg ccgacctgga gagcaggatc aagtggacca    5640
gcttcgtggt gagggaggcc gagaagaggg gctggagctg gcctactgg gagttctgca    5700 gcggcttcgg cgtgtacgac ccgctgagga agcagtggaa caaggacctg ctggaggccc    5760
tgatcggcgg cgacagcatc gagagcgaga aggacgagct gtgacctagg tccccgaatt    5820
tccccgatcg ttcaaacatt tggcaataaa gtttcttaag attgaatcct gttgccggtc    5880
ttgcgatgat tatcatataa tttctgttga attacgttaa gcatgtaata attaacatgt    5940
aatgcatgac gttatttatg agatgggttt ttatgattag agtcccgcaa ttatacattt    6000
aatacgcgat agaaaacaaa atatagcgcg caaactagga taaattatcg cgcgcggtgt    6060
catctatgtt actagatcgg gaattgggta cccggtatga atttggaaac aaattcagta    6120
cttttaaaaa aatttgttgt agggagcaaa taatacataa aataatttat gcattatttt    6180 atttttttatt tgtaataata tgcttgaaac gataattcag tatgcatgtt gtgccagtgt    6240
actacacggg cgggggagg ggattgagtg ggccagcgcg gtgcgtaggg tagatgggct    6300
gaaattgata actcaagtcc gactaggttc tcttttatt tcccttcctt ttctattttc    6360 cttctttta attttcatgc tttcaaacta aattcaaatt cgagttttga atttcagctt    6420
ctaaattgta cactaaaatt atatgataag gtaaccccta ctattacttt taatttttt     6480 attctacccc atattgttta cttaggggag aataattgac ttaatcacat tcttccttag    6540
gtttcaattc tcaatctttc aaatccacat ttttagattt ctattttgaa tttaaatacc    6600
agtttggatt tagagttcaa tttcaaaata cacaaccaaa ataccagcat gaatgcaaat    6660
atattttatg tttatgtatt tacttttctt ttatactttg ctcaaaatag ttattttcat    6720
gtatgaaact caataagcaa ggaactcacg ttattatata acctaatagg aataatttag    6780
gtaacataat ttatcatcct cttgatttaa aagagatatg cctccagaat aagacacata    6840
ctaaaaataa ctctaatatt gaataactaa agtcgtacaa atctctacta ttattcctat    6900
aaaataataa agaactagct acaacttctt taaggcatta ttcagggttt acagcttgag    6960
aggcatgaac ccatcctgta tactcctgga cttggaagac aaaatgtcaa ccaaagtgaa    7020
aggttttctt atggttgctg ctaagagata gattgaacac tagatctctc ctaagacgtc    7080
agggcatgcg tttagactcc tacacatgcg aaaactgcat cttacagttg gaagaaacta    7140
tatctcacca cttcctgcgg tgtaactttg cccaaagatg ttggctcact gttgaaatca    7200
ctccgccccg aactttggat ctaacgcttg cagtgctaca tattagagca agactaacaa    7260
tgccgtggag aatggaaggt attataacca tgtcatggtg catatggaaa tgtcgaaata    7320
actggatatt cgaaaacata ccgccaacgg tggcggcctg caaggaaatg ttcaagactg    7380 aaaatgaacta catctgctac caagttaagc tcgagacagg agctaaaagt agaaactgga    7440
tacaacactt tgtaacatag tgacactccc cttttccttt cttttacctt agaactatac    7500
atacaatcca cattcaataa aaatttgtag gtacgccata cacactaccg gaatccggct    7560
ctttgccgag tgtgaggcgc tttgtcgagt gcttttgtc cagcactcgg caaaaaagtc    7620
tttgccatgt gccgcactcg gcaaagtcct gctctcggta acgaccgcgt ttaccgagag    7680
caggactctc gacacagaaa tacactcgac aaagaaatct ttgccgagag ccaaacactc    7740
ggcgaacggc agcgctcggc aaagggtcgt cagccgccgt ctaaagctga cggtcgttat    7800
ctttgtcgag tgccccctcg tccgacactc agtagagcaa gcttgccgag tgccatcctt    7860
ggacactcga taaagtatat tttatttttt tttatttgc caaccaaact ttttgtggta    7920
```

```
tgttcctaca ctatgtagat ctacatgtac cattttggca caattacaaa aatgttttct    7980
ataactatta gatttagttc gtttatttga atttcttcgg aaaattcaca tatgaactgc    8040
aagtcactcg aaacatgaaa aaccgtgcat gcaaaataaa tgatatgcat gttatctagc    8100
acaagttacg accgaattca gaagcagacc agaatcttca agcaccatgc tcactaaaca    8160
tgaccgtgaa cttgttatcc agttgtttaa aaattgtata aaacacaaat aaagtcagaa    8220
attaatgaaa cttgtccaca tgtcatgata tcatatatag aggttgtgat aaaaatttga    8280
taatgtttcg gtaaagttgt gacgtactat gtgtagaaac ctaagtgacc tacacataaa    8340
atcatagagt ttcaatgtag ttcactcgac aaagactttg tcaagtgtcc gataaaaagt    8400
attcagcaaa gaagccgttg tcgatttact gttcgtcgag atctctttgc cgagtgtcac    8460
actaggcaaa gtctttacgg agtgttttc aggctttgac actcggcaaa gcgctcgatt    8520
ccagtagtga cagtaatttg catcaaaaat agccgagaga tttaaaatga gtcaactaat    8580
agaccaacta attattagct attagtcgtt agcttcttta atctaagcta aaaccaacta    8640
atagcttatt tgttgaatta caattagctc aacggaattc tctgtttttt ctataaaaaa    8700
aagggaaact gccctcatt tacagcaaac tgtccgctgc ctgtcgtcca gatacaatga    8760
acgtacctag taggaactct tttacacgct cggtcgctcg ccgcggatcg gagtcccagg    8820
aacacgacac cactgtggaa cacgacaaag tctgctcaga ggcggccaca ccctggcgtg    8880
caccgagccg gagcccggat aagcacggta aggagagtac ggcgggacgt ggcgacccgt    8940
gtgtctgctg ccacgcagcc ttcctccacg tagccgcgcg gccgcgccac gtaccagggc    9000
ccggcgctgg tataaatgcg cgccacctcc gctttagttc tgcatacagc caacccaaca    9060
cacaccgag catatcacag tgacagacac tacacgggat ccaccatgag ggtgttgctc    9120
gttgccctcg ctctcctggc tctcgctgcg agcgccacca gcggcgtgga cccgttcgag    9180
aggaacaaga tcctgggcag gggcatcaac atcggcaacg ccctggaggc cccgaacgag    9240
ggcgactggg gcgtggtgat caaggacgag ttcttcgaca tcatcaagga ggccggcttc    9300
agccacgtga gaatcccgat caggtggagc acccacgccc aggccttccc gccgtacaag    9360
atcgagccga gcttcttcaa gagggtggac gaggtgatca acggcgccct gaagaggggc    9420
ctggccgtgg tgatcaacat ccaccactac gaggagctga tgaacgaccc ggaggagcac    9480
aaggagaggt tcctggccct gtggaagcag atcgccgaca ggtacaagga ctacccggag    9540
accctgttct tcgagatcct gaacgagccg cacggcaacc tgaccccgga agtggaaac    9600
gagctgctgg aggaggccct gaaggtgatc aggagcatcg acaagaagca caccgtgatc    9660
atcggcaccg ccgagtgggg cggcatcagc gccctggaga agctgagggt gccgaagtgg    9720
gagaagaacg ccatcgtgac catccactac tacaacccgt cgagttcac ccaccagggc    9780
gccgagtggg tgccgggcag cgagaagtgg ctgggcagga gtggggcag cccggacgac    9840
cagaagcacc tgatcgagga gttcaacttc atcgaggagt ggagcaagaa gaacaagagg    9900
ccgatctaca tcggcgagtt cggcgcctac aggaaggccg acctggagag caggatcaag    9960
tggaccagct tcgtggtgag ggaggccgag aagaggggct ggagctgggc ctactgggag   10020
ttctgcagcg gcttcggcgt gtacgacccg ctgaggaagc agtggaacaa ggacctgctg   10080
gaggccctga tcggcggcga cagcatcgag agcgagaagg acgagctgtg acctaggtcc   10140
ccgaatttcc ccgatcgttc aaacatttgg caataaagtt tcttaagatt gaatcctgtt   10200
gccggtcttg cgatgattat catataattt ctgttgaatt acgttaagca tgtaataatt   10260
aacatgtaat gcatgacgtt atttatgaga tgggttttta tgattagagt cccgcaatta   10320
```

```
tacatttaat acgcgataga aaacaaaata tagcgcgcaa actaggataa attatcgcgc    10380
gcggtgtcat ctatgttact agatcgggaa ttg                                10413

<210> SEQ ID NO 15
<211> LENGTH: 2680
<212> TYPE: DNA
<213> ORGANISM: Artificial Sequence
<220> FEATURE:
<223> OTHER INFORMATION: Synthetic construct, expression cassette from
      pAG4257

<400> SEQUENCE: 15
aaagtaatca tattatttta tgtgtgaatc ttctttactt tttcatttga ttatgattat      60
gaaggtatga ccttcataac cttcgtccga aatccattat atccaaagga aaataatgct     120
tcgaaggacg aaggattttg atatttaaca ttttatgttg ccttgttctt aattcatagc     180
atttgagaac aagtcccaa caccaatctt tatctttact atattaaagc accagttcaa      240
cgatcgtctc gtgtcaatat tattaaaaaa ctcctacatt tctttataat caacccgcac     300
tcttataatc tcttctctta ctactataat aagagagttt atgtacaaaa taaggtgaaa     360
ttatgtataa gtgttctgga ccttggttgt tggctcatat tcacacaacc taatcaatag     420
aaaacatatg ttttattaaa acaaaattta tcatatatat atatatatat atatatatat     480
atatatatat ataataata accgtagca atgcacaggc atatgactag tggcaactta      540
ataccatgtg tgtattaaga tgaataagag gtatccaaat aaataacttg ttcgcttacg     600
tctggatcga aaggggttgg aaacgattaa atctcttcct agtcaaaatt aaatagaagg     660
agatttaatc gatttctccc aatccccttc gatccaggtg caaccgaata agtccttaaa     720
tgttgaggaa cacgaaacaa ccatgcattg gcatgtaaag ctccaagaat tcgttgtatc     780
cttaacaact cacagaacat caaccaaaat tgcacgtcaa gggtattggg taagaaacaa     840
tcaaacaaat cctctctgtg tgcaaagaaa acggtgagt catgccgaga tcatactcat      900
ctgatataca tgcttacagc tcacaagaca ttacaaacaa ctcatattgc attacaaaga     960
tcgtttcatg aaaaataaaa taggccggaa caggacaaaa atccttgacg tgtaaagtaa    1020
atttacaaca aaaaaaagc catatgtcaa gctaaatcta attcgtttta cgtagatcaa     1080
caacctgtag aaggcaacaa aactgagcca cgcagaagta cagaatgatt ccagatgaac    1140
catcgacgtg ctacgtaaag agagtgacga gtcatataca tttggcaaga aaccatgaag    1200
ctgcctacag ccgtctcggt ggcataagaa cacaagaaat tgtgttaatt aatcaaagct    1260
ataaataacg ctcgcatgcc tgtgcacttc tccatcacca ccactgggtc ttcagaccat    1320
tagctttatc tactccagag cgcagaagaa cccgatcgac accggatcca ccatgagggt    1380
gttgctcgtt gccctcgctc tcctggctct cgctgcgagc gccaccagcg gcgtggaccc    1440
gttcgagagg aacaagatcc tgggcagggg catcaacatc ggcaacgccc tggaggcccc    1500
gaacgagggc gactggggcg tggtgatcaa ggacgagtac ttcgacatca tcaaggaggc    1560
cggcttcagc cacgtgagaa tcccgatcag gtggagcacc cacgcccagg ccttcccgcc    1620
gtacaagatc gaggacaggt tcttcaagag ggtggacgag gtgatcaacg cgcccctgaa    1680
gaggggcctg gccgtggtga tcaaccagca ccactacgag gagctgatga acgacccgga    1740
ggagcacaag gagaggttcc tggccctgtg gaagcagatc ccgacaggt acaaggacta     1800 cccggagacc ctgttcttcg agatcctgaa cgagccgcac ggcaacctga ccccggaaa     1860 gtggaacgag ctgctggagg aggccctgaa ggtgatcagg agcatcgaca agaagcacac    1920
```

```
catcatcatc ggcaccgccg agtggggcgg catcagcgcc ctggagaagc tgagggtgcc    1980
gaagtgggag aagaacgcca tcgtgaccat ccactactac aacccgttcg agttcaccca    2040
ccagggcgcc gagtgggtgg agggcagcga gaagtggctg ggcaggaagt ggggcagccc    2100
ggacgaccag aagcacctga tcgaggagtt caacttcatc gaggagtgga gcaagaagaa    2160
caagaggccg atctacatcg gcgagttcgg cgcctacagg aaggccgacc tggagagcag    2220
gatcaagtgg accagcttcg tggtgaggga ggccgagaag aggaggtgga gctgggccta    2280
ctgggagttc tgcagcggct cggcgtgta cgacaccctg aggaagacct ggaacaagga    2340
cctgctggag gccctgatcg gcggcgacag catcgagagc gagaaggacg agctgtgacc    2400
taggtccccg aatttccccg atcgttcaaa catttggcaa taaagtttct taagattgaa    2460
tcctgttgcc ggtcttgcga tgattatcat ataatttctg ttgaattacg ttaagcatgt    2520
aataattaac atgtaatgca tgacgttatt tatgagatgg gttttatga ttagagtccc    2580 gcaattatac atttaatacg cgatagaaaa caaaatatag cgcgcaaact aggataaatt    2640
atcgcgcgcg gtgtcatcta tgttactaga tcgggaattg                         2680
```

<210> SEQ ID NO 16
<211> LENGTH: 3292
<212> TYPE: DNA
<213> ORGANISM: Artificial Sequence
<220> FEATURE:
<223> OTHER INFORMATION: Synthetic construct, expression cassetter from
      pAG4692

<400> SEQUENCE: 16

```
tccatgctgt cctactactt gcttcatccc cttctacatt tgttctggt ttttggcctg      60 catttcggat catgatgtat gtgatttcca atctgctgca atatgaatgg agactctgtg    120
ctaaccatca acaacatgaa atgcttatga ggcctttgct gagcagccaa tcttgcctgt    180
gtttatgtct tcacaggccg aattcctctg ttttgttttt caccctcaat atttggaaac    240
atttatctag gttgtttgtg tccaggccta taaatcatac atgatgttgt cgtattggat    300
gtgaatgtgg tggcgtgttc agtgccttgg atttgagttt gatgagagtt gcttctgggt    360
caccactcac cattatcgat gctcctcttc agcataaggt aaaagtcttc cctgtttacg    420
ttattttacc cactatggtt gcttgggttg gtttttcct gattgcttat gccatggaaa    480
gtcatttgat atgttgaact tgaattaact gtagaattgt atacatgttc catttgtgtt    540
gtacttcctt cttttctatt agtagcctca gatgagtgtg aaaaaaacag attatataac    600
ttgccctata aatcatttga aaaaatatt gtacagtgag aaattgatat atagtgaatt    660
tttaagagca tgttttccta agaagtata tattttctat gtacaaaggc cattgaagta    720
attgtagata caggataatg tagactttt ggacttacac tgctacctt aagtaacaat    780 catgagcaat agtgttgcaa tgatatttag gctgcattcg tttactctct tgatttccat    840
gagcacgctt cccaaactgt taaactctgt gttttttgcc aaaaaaaat gcataggaaa    900 gttgcttta aaaatcata tcaatccatt ttttaagtta tagctaatac ttaattaatc    960
atgcgctaat aagtcactct gttttcgta ctagagagat tgttttgaac cagcactcaa   1020
gaacacagcc ttaacccagc caaataatgc tacaacctac cagtccacac ctcttgtaaa   1080
gcatttgttg catggaaaag ctaagatgac agcaacctgt tcaggaaaac aactgacaag   1140 gtcatagga gagggagctt ttggaaaggt gccgtgcagt tcaaacaatt agttagcagt   1200
agggtgttgg ttttttgctca cagcaataag aagttaatca tggtgtaggc aacccaaata   1260
```

-continued

```
aaacaccaaa atatgcacaa ggcagtttgt tgtattctgt agtacagaca aaactaaaag    1320
taatgaaaga agatgtggtg ttagaaaagg aaacaatatc atgagtaatg tgtgggcatt    1380
atgggaccac gaaataaaaa gaacattttg atgagtcgtg tatcctcgat gagcctcaaa    1440
agttctctca ccccggataa gaaacccttta agcaatgtgc aaagtttgca ttctccactg    1500
acataatgca aaataagata tcatcgatga catagcaact catgcatcat atcatgcctc    1560
tctcaaccta ttcattccta ctcatctaca taagtatctt cagctaaatg ttagaacata    1620
aacccataag tcacgtttga tgagtattag gcgtgacaca tgacaaatca cagactcaag    1680
caagataaag caaatgatg tgtacataaa actccagagc tatatgtcat attgcaaaaa    1740
gaggagagct tataagacaa ggcatgactc acaaaaattc atttgccttt cgtgtcaaaa    1800
agaggagggc tttacattat ccatgtcata ttgcaaaaga aagagagaaa gaacaacaca    1860
atgctgcgtc aattatacat atctgtatgt ccatcattat tcatccacct ttcgtgtacc    1920
acacttcata tatcatgagt cacttcatgt ctggacatta acaaactcta tcttaacatt    1980
tagatgcaag agcctttatc tcactataaa tgcacgatga tttctcattg tttctcacaa    2040
aaagcattca gttcattagt cctacaacaa cggatccacc atgagggtgt tgctcgttgc    2100
cctcgctctc ctggctctcg ctgcgagcgc caccagcggc gtggaccgt tcgagaggaa    2160 caagatcctg ggcaggggca tcaacatcgg caacgccctg gaggcccga acgagggcga    2220 ctggggcgtg gtgatcaagg acgagttctt cgacatcatc aaggaggccg gcttcagcca    2280
cgtgagaatc ccgatcaggt ggagcaccca cgcctacgcc ttcccgccgt acaagatcat    2340
ggacaggttc ttcaagaggg tggacgaggt gatcaacggc gccctgaaga ggggcctggc    2400
cgtggtgatc aacatccacc actacgagga gctgatgaac gacccggagg agcacaagga    2460
gaggttcctg gccctgtgga agcagatcgc cgacaggtac aaggactacc cggagaccct    2520
gttcttcgag atcctgaacg agccgcacgg caacctgacc ccggagaagt ggaacgagct    2580
gctggaggag gccctgaagg tgatcaggag catcgacaag aagcacacca tcatcatcgg    2640
caccgccgag tggggcggca tcagcgccct ggagaagctg agcgtgccga agtgggagaa    2700
gaactccatc gtgaccatcc actactacaa cccgttcgag ttcacccacc agggcgccga    2760
gtgggtggag ggcagcgaga agtggctggg caggaagtgg ggcagcccgg acgaccagaa    2820
gcacctgatc gaggagttca acttcatcga ggagtggagc aagaagaaca agaggccgat    2880
ctacatcggc gagttcggcg cctacaggaa ggccgacctg agagcaggaa tcaagtggac    2940
cagcttcgtg gtgagggaga tggagaagag gcgctggagc tgggcctact gggagttctg    3000
cagcggcttc ggcgtgtacg acaccctgag gaagacctgg aacaaggacc tgctggaggc    3060
cctgatcggc ggcgacagca tcgagagcga gaaggacagg ctgtgaccta ggctgcacaa    3120
agtggagtag tcagtcatcg atcaggaacc agacaccaga cttttattca tacagtgaag    3180
tgaagtgaag tgcagtgcag tgagttgctg gtttttgtac aacttagtat gtatttgtat    3240
ttgtaaaata cttctatcaa taaatttct aattcctaaa accaaaatcc ag             3292
```

<210> SEQ ID NO 17
<211> LENGTH: 2584
<212> TYPE: DNA
<213> ORGANISM: Artificial Sequence
<220> FEATURE:
<223> OTHER INFORMATION: Synthetic construct, expression cassette from
      pAG 4693

<400> SEQUENCE: 17

-continued

```
aaagtaatca tattatttta tgtgtgaatc ttctttactt tttcatttga ttatgattat      60
gaaggtatga ccttcataac cttcgtccga aatccattat atccaaagga aaataatgct     120
tcgaaggacg aaggattttg atatttaaca tttatgttg ccttgttctt aattcatagc      180
atttgagaac aagtccccaa caccaatctt tatctttact atattaaagc accagttcaa     240
cgatcgtctc gtgtcaatat tattaaaaaa ctcctacatt tctttataat caacccgcac     300
tcttataatc tcttctctta ctactataat aagagagttt atgtacaaaa taaggtgaaa     360
ttatgtataa gtgttctgga ccttggttgt tggctcatat tcacacaacc taatcaatag     420
aaaacatatg ttttattaaa acaaaattta tcatatatat atatatatat atatatatat     480
atatatatat atataatata aaccgtagca atgcacaggc atatgactag tggcaactta     540
ataccatgtg tgtattaaga tgaataagag gtatccaaat aaataacttg ttcgcttacg     600
tctggatcga aaggggttgg aaacgattaa atctcttcct agtcaaaatt aaatagaagg     660
agatttaatc gatttctccc aatcccctcc gatccaggtg caaccgaata agtccttaaa     720
tgttgaggaa cacgaaacaa ccatgcattg gcatgtaaag ctccaagaat tcgttgtatc     780
cttaacaact cacagaacat caaccaaaat tgcacgtcaa gggtattggg taagaaacaa     840
tcaaacaaat cctctctgtg tgcaaagaaa cacggtgagt catgccgaga tcatactcat     900
ctgatataca tgcttacagc tcacaagaca ttacaaacaa ctcatattgc attacaaaga     960
tcgtttcatg aaaaataaaa taggccggaa caggacaaaa atccttgacg tgtaaagtaa    1020
atttacaaca aaaaaaaagc catatgtcaa gctaaatcta attcgtttta cgtagatcaa    1080
caacctgtag aaggcaacaa aactgagcca cgcagaagta cagaatgatt ccagatgaac    1140
catcgacgtg ctacgtaaag agagtgacga gtcatataca tttggcaaga aaccatgaag    1200
ctgcctacag ccgtctcggt ggcataagaa cacaagaaat tgtgttaatt aatcaaagct    1260
ataaataacg ctcgcatgcc tgtgcacttc tccatcacca ccactgggtc ttcagaccat    1320
tagctttatc tactccagag cgcagaagaa cccgatcgac accggatcca ccatgagggt    1380
gttgctcgtt gccctcgctc tcctggctct cgctgcgagc gccaccagcg gcgtggaccc    1440
gttcgagagg aacaagatcc tgggcagggg catcaacatc ggcaacgccc tggaggcccc    1500
gaacgagggc gactggggcg tggtgatcaa ggacgagttc ttcgacatca tcaaggaggc    1560
cggcttcagc cacgtgagaa tcccgatcag gtggagcacc cacgcctacg ccttcccgcc    1620
gtacaagatc atggacaggt tcttcaagag ggtggacgag gtgatcaacg gcgccctgaa    1680
gaggggcctg gccgtggtga tcaacatcca ccactacgag gagctgatga acgacccgga    1740
ggagcacaag gagaggttcc tggccctgtg gaagcagatc gccgacaggt acaaggacta    1800
cccggagacc ctgttcttcg agatcctgaa cgagccgcac ggcaacctga ccccggagaa    1860
gtggaacgag ctgctggagg aggccctgaa ggtgatcagg agcatcgaca agaagcacac    1920
catcatcatc ggcaccgccg agtggggcgg catcagcgcc ctggagaagc tgagcgtgcc    1980
gaagtgggag aagaactcca tcgtgaccat ccactactac aacccgttcg agttcaccca    2040
ccagggcgcc gagtggggtgg agggcagcga aagtggctg gcaggaagt ggggcagccc    2100 ggacgaccag aagcacctga tcgaggagtt caacttcatc gaggagtgga gcaagaagaa    2160
caagaggccg atctacatcg gcgagttcgg cgcctacagg aaggccgacc tggagagcag    2220
gatcaagtgg accagcttcg tggtgaggga atggagaag aggcgctgga gctgggccta    2280
ctgggagttc tgcagcggct tcggcgtgta cgacaccctg aggaagacct ggaacaagga    2340
```

```
cctgctggag gccctgatcg gcggcgacag catcgagagc gagaaggacg agctgtgacc      2400
taggctgcac aaagtggagt agtcagtcat cgatcaggaa ccagacacca gactttatt      2460 catacagtga agtgaagtga agtgcagtgc agtgagttgc tggttttgt acaacttagt      2520 atgtatttgt atttgtaaaa tacttctatc aataaaattt ctaattccta aaaccaaaat     2580
ccag                                                                   2584
```

<210> SEQ ID NO 18
<211> LENGTH: 3292
<212> TYPE: DNA
<213> ORGANISM: Artificial Sequence
<220> FEATURE:
<223> OTHER INFORMATION: Synthetic construct, expression cassetter from
      pAG4705

<400> SEQUENCE: 18

```
tccatgctgt cctactactt gcttcatccc cttctacatt ttgttctggt ttttggcctg      60
catttcggat catgatgtat gtgatttcca atctgctgca atatgaatgg agactctgtg     120
ctaaccatca acaacatgaa atgcttatga ggcctttgct gagcagccaa tcttgcctgt     180
gtttatgtct tcacaggccg aattcctctg ttttgttttt caccctcaat atttggaaac     240
atttatctag gttgtttgtg tccaggccta taaatcatac atgatgttgt cgtattggat     300
gtgaatgtgg tggcgtgttc agtgccttgg atttgagttt gatgagagtt gcttctgggt     360
caccactcac cattatcgat gctcctcttc agcataaggt aaaagtcttc cctgtttacg     420 ttatttacc cactatggtt gcttgggttg gttttttcct gattgcttat gccatggaaa     480
gtcatttgat atgttgaact tgaattaact gtagaattgt atacatgttc catttgtgtt     540
gtacttcctt cttttctatt agtagcctca gatgagtgtg aaaaaaacag attatataac     600
ttgccctata aatcatttga aaaaaatatt gtacagtgag aaattgatat atagtgaatt     660
tttaagagca tgtttttccta agaagtata tattttctat gtacaaaggc cattgaagta     720
attgtagata caggataatg tagactttt ggacttacac tgctaccttt aagtaacaat     780
catgagcaat agtgttgcaa tgatatttag gctgcattcg tttactctct tgatttccat     840
gagcacgctt cccaaactgt taaactctgt gttttttgcc aaaaaaaaat gcataggaaa     900
gttgctttta aaaatcata tcaatccatt ttttaagtta tagctaatac ttaattaatc      960
atgcgctaat aagtcactct gttttcgta ctagagagat tgttttgaac cagcactcaa     1020
gaacacagcc ttaacccagc caaataatgc tacaacctac cagtccacac ctcttgtaaa     1080
gcatttgttg catggaaaag ctaagatgac agcaacctgt tcaggaaaac aactgacaag     1140
gtcataggga gagggagctt ttggaaaggt gccgtgcagt tcaaacaatt agttagcagt     1200
agggtgttgg ttttgctca cagcaataag aagttaatca tggtgtaggc aacccaaata     1260
aaacaccaaa atatgcacaa ggcagtttgt tgtattctgt agtacagaca aaactaaaag     1320
taatgaaaga agatgtggtg ttagaaaagg aaacaatatc atgagtaatg tgtgggcatt     1380
atgggaccac gaaataaaaa gaacattttg atgagtcgtg tatcctcgat gagcctcaaa     1440
agttctctca ccccggataa gaaaccctta agcaatgtgc aaagtttgca ttctccactg     1500
acataatgca aaataagata tcatcgatga catagcaact catgcatcat atcatgcctc     1560
tctcaaccta ttcattccta ctcatctaca taagtatctt cagctaaatg ttagaacata     1620
aacccataag tcacgtttga tgagtattag gcgtgacaca tgacaaatca cagactcaag     1680
caagataaag caaaatgatg tgtacataaa actccagagc tatatgtcat attgcaaaaa     1740
```

| | |
|---|---|
| gaggagagct tataagacaa ggcatgactc acaaaaattc atttgccttt cgtgtcaaaa | 1800 |
| agaggagggc tttacattat ccatgtcata ttgcaaaaga aagagagaaa gaacaacaca | 1860 |
| atgctgcgtc aattatacat atctgtatgt ccatcattat tcatccacct ttcgtgtacc | 1920 |
| acacttcata tatcatgagt cacttcatgt ctggacatta acaaactcta tcttaacatt | 1980 |
| tagatgcaag agcctttatc tcactataaa tgcacgatga tttctcattg tttctcacaa | 2040 |
| aaagcattca gttcattagt cctacaacaa cggatccacc atgagggtgt tgctcgttgc | 2100 |
| cctcgctctc ctggctctcg ctgcgagcgc caccagcggc gtggacccgt tcgagaggaa | 2160 |
| caagatcctg gcaggggca tcaacatcgg caacgccctg gaggcccga acgagggcga | 2220 |
| ctggggcgtg gtgatcaagg acgagtactt cgacatcatc aaggaggccg gcttcagcca | 2280 |
| cgtgagaatc ccgatcaggt ggagcaccca cgcccaggcc ttcccgccgt acaagatcga | 2340 |
| ggacaggttc ttcaagaggg tggacgaggt gatcaacggc gccctgaaga ggggcctggc | 2400 |
| cgtggtgatc aaccagcacc actacgagga gctgatgaac gacccggagg agcacaagga | 2460 |
| gaggttcctg gccctgtgga gcagatcgc cgacaggtac aaggactacc cggagaccct | 2520 |
| gttcttcgag atcctgaacg agccgcacgg caacctgacc ccggagaagt ggaacgagct | 2580 |
| gctggaggag gccctgaagg tgatcaggag catcgacaag aagcacacca tcatcatcgg | 2640 |
| caccgccgag tggggcggca tcagcgccct ggagaagctg agggtgccga agtgggagaa | 2700 |
| gaacgccatc gtgaccatcc actactacaa cccgttcgag ttcacccacc agggcgccga | 2760 |
| gtgggtggag ggcagcgaga agtggctggg caggaagtgg ggcagcccgg acgaccagaa | 2820 |
| gcacctgatc gaggagttca acttcatcga ggagtggagc aagaagaaca agaggccgat | 2880 |
| ctacatcggc gagttcggcg cctacaggaa ggccgacctg gagagcagga tcaagtggac | 2940 |
| cagcttcgtg gtgagggagg ccgagaagag gaggtggagc tgggcctact gggagttctg | 3000 |
| cagcggcttc ggcgtgtacg acaccctgag gaagacctgg aacaaggacc tgctggaggc | 3060 |
| cctgatcggc ggcgacagca tcgagagcga aaggacgag ctgtgaccta ggctgcacaa | 3120 |
| agtggagtag tcagtcatcg atcaggaacc agacaccaga ctttattca tacagtgaag | 3180 |
| tgaagtgaag tgcagtgcag tgagttgctg gttttttgtac aacttagtat gtatttgtat | 3240 |
| ttgtaaaata cttctatcaa taaaatttct aattcctaaa accaaaatcc ag | 3292 |

<210> SEQ ID NO 19
<211> LENGTH: 3317
<212> TYPE: DNA
<213> ORGANISM: Artificial Sequence
<220> FEATURE:
<223> OTHER INFORMATION: Synthetic construct, expression cassette from pAG4706

<400> SEQUENCE: 19

| | |
|---|---|
| ataaaatttt agtgaagcta aagcggtgaa agattataga atttgatgtg ccagattaat | 60 |
| aaatcgatta actcctaaag ttcaagccga gactacagac acatgagcta cataaatgag | 120 |
| ccaaggactc gagcaaagac aaatcgacac agacattata attcaagtca ttctagaaga | 180 |
| ttcatgagaa gagtatcatt tatttaaatc aatgacttga tcaaataaga cctaggagct | 240 |
| actattgata atatatatca tgggtatcta gatcaagcat tatgaagaag agcctaagta | 300 |
| gaaggcccca tgggctcgac cacaaaccca aggactcgac aataaagtct aggagggatc | 360 |
| ccatagctaa aaggactcta gaagtgtatg tatggtaaag attttatcga dacaagaaat | 420 |
| acgataaaga tcttaacaga atcggagtca tacttgtaaa aatagagttg gactcgtgta | 480 |

```
caacttggtc ttcgacttag ttcggtcatg aattcagtaa ccgactagat atgtaccatg      540 gaaccccctag ggcatgaggc tatgagccat aggatcatca gatccaaaca tacaccaaca     600
aatccatcac acaccgaaga tccatattaa caagggatta gctactttac aatttcagag     660
taacaaatag agccaaactc atagcacagg ggaacttcat atcacaaatg gaggcattga     720
attgatataa aaagctaaag ttctaaaaag tttgaagtgc tgaaacttca agccgctaa      780 ctagtgaagc accgaagcct tccggggaga aagacatac acgacacgtt agggacgtaa      840
aatgacgaaa ttatacaact acctctatat gtaacactta tgtaatagaa aagacagaat     900
ccatatgaag atgtataatg gatcaaccat ataaatagat aaacaatata tctgctatgg     960
ggattggcat tcttgtatcc ctacgcctgt atatccctg tttagagaac ctccgaaggt     1020
atatgatgct gaagattatt gttgtcttgt ctttcatcat atatcgagtc tttccctagg    1080
atattattat tcgcaatgtg cattacatgg ttaatcgatt gagagaacat gcatctcacc    1140
tttagctgat aaacgataat ccatgtttta cacttcgtag ctactcatga gtttcgatat    1200
acaaatttgt tttctggact acgtaccatt ccatcctctt aggagaggag aggaagtgtc    1260
ctcgatttaa ttatgttgtc attttgtagt tcttcacaaa atctcaacag gtaccaaaca    1320
cattgtttcc acaagacata ttttagtcac aacaaatcta tattattatt aatcactaaa    1380
actatactga ggctcagatg cttttactag ctcttgctag tatgtgatgt aggtctcttt    1440
cgacatcatt ccatcaaaat catatgatta gcccatacca aacatttcta taccattcag    1500
agaccagaat agtcttttct aatagaaaaa aggaaaatag agtgggccga cgacgacaca    1560
aattactgcg tggaccagaa aatagtgaga cacggaagac aaaagaagta aaagaggcaa    1620
ggactacggc ccacatgaga ttcggccccg ccacctccgg caaccagcgg ccgatccaac    1680
ggcagtgcat cctcaacggc gcgcgcgcgc gcgcgcgcgc acaacctcgt atatatcgcc    1740
gcgcggaagc ggcgcgaccg aggaagcctt gtcctcgaca ccccctacac aggtgtcgcg    1800
ctgcccccga cacgagtccc gcatgcgtcc cacgcggccg cgccagatcc cgcctccgcg    1860
cgttgccacg ccctctataa acacccagct ctctccctcg ccctcatcta tcgcactcgt    1920
agtcgtagct caagcatcag cggcaggagc tctgggcagc gtgcgcacgt ggggtaccta    1980
gctcgctctg ctagcctacc ggatccacca tgagggtgtt gctcgttgcc ctcgctctcc    2040
tggctctcgc tgcgagcgcc accagcgcg tggacccgtt cgagaggaac aagatcctgg    2100 gcagggcat caacatcggc aacgccctgg aggccccgaa cgagggcgac tggggcgtgg    2160
tgatcaagga cgagtacttc gacatcatca aggaggccgg cttcagccac gtgagaatcc    2220
cgatcaggtg gagcacccac gcccaggcct tcccgccgta caagatcgag gacaggttct    2280
tcaagagggt ggacgaggtg atcaacggcg ccctgaagag gggcctggcc gtggtgatca    2340
accagcacca ctacgaggag ctgatgaacg acccggagga gcacaaggag aggttcctgg    2400
ccctgtggaa gcagatcgcc gacaggtaca aggactaccc ggagaccctg ttcttcgaga    2460
tcctgaacga gccgcacggc aacctgaccc cggagaagtg gaacgagctg ctggaggagg    2520
ccctgaaggt gatcaggagc atcgacaaga agcacaccat catcatcggc accgccgagt    2580
ggggcggcat cagcgccctg gagaagctga gggtgccgaa gtgggagaag aacgccatcg    2640
tgaccatcca ctactacaac ccgttcgagt tcacccacca gggcgccgag tgggtggagg    2700
gcagcgagaa gtggctgggc aggaagtggg gcagcccgga cgaccagaag cacctgatcg    2760
aggagttcaa cttcatcgag gagtggagca agaagaacaa gaggccgatc tacatcggcg    2820
agttcggcgc ctacaggaag gccgacctgg agagcaggat caagtggacc agcttcgtgg    2880
```

```
tgagggaggc cgagaagagg aggtggagct gggcctactg ggagttctgc agcggcttcg    2940
gcgtgtacga caccctgagg aagacctgga acaaggacct gctggaggcc ctgatcggcg    3000
gcgacagcat cgagagcgag aaggacgagc tgtgacctag gtccccgaat tccccgatc    3060 gttcaaacat ttggcaataa agtttcttaa gattgaatcc tgttgccggt cttgcgatga    3120
ttatcatata atttctgttg aattacgtta agcatgtaat aattaacatg taatgcatga    3180
cgttatttat gagatgggtt tttatgatta gagtcccgca attatacatt taatacgcga    3240
tagaaaacaa aatatagcgc gcaaactagg ataaattatc gcgcgcggtg tcatctatgt    3300
tactagatcg ggaattg                                                   3317

<210> SEQ ID NO 20
<211> LENGTH: 285
<212> TYPE: DNA
<213> ORGANISM: Artificial Sequence
<220> FEATURE:
<223> OTHER INFORMATION: Synthetic construct, pAG4500_multiple cloning
      site

<400> SEQUENCE: 20
gtttaaactg aaggcgggaa acgacaacct gatcatgagc ggagaattaa gggagtcacg      60
ttatgacccc cgccgatgac gcgggacaag ccgttttacg tttggaactg acagaaccgc     120
aacgttgaag gagccactca gcctaagcgg ccgcattgga cttaattaag tgaggccggc     180
caagcgtcga tttaaatgta ccacatggcg cgccaactat catgcgatcg cttcatgtct     240
aactcgagtt actggtacgt accaaatcca tggaatcaag gtacc                    285

<210> SEQ ID NO 21
<211> LENGTH: 315
<212> TYPE: PRT
<213> ORGANISM: Artificial Sequence
<220> FEATURE:
<223> OTHER INFORMATION: Synthetic construct, catalytic domain of
      AGR2314

<400> SEQUENCE: 21

Gly Val Asp Pro Phe Glu Arg Asn Lys Ile Leu Gly Arg Gly Ile Asn
1               5                   10                  15

Ile Gly Asn Ala Leu Glu Ala Pro Asn Glu Gly Asp Trp Val Val
            20                  25                  30

Ile Lys Asp Glu Phe Phe Asp Ile Ile Lys Glu Ala Gly Phe Ser His
        35                  40                  45

Val Arg Ile Pro Ile Arg Trp Ser Thr His Ala Ala Phe Pro Pro Tyr
    50                  55                  60

Lys Ile Glu Pro Ser Phe Phe Lys Arg Val Asp Glu Val Ile Asn Gly
65                  70                  75                  80

Ala Leu Lys Arg Gly Leu Ala Val Val Ile Asn Ile His His Tyr Glu
                85                  90                  95

Glu Leu Met Asn Asp Pro Glu Glu His Lys Glu Arg Phe Leu Ala Leu
            100                 105                 110

Trp Lys Gln Ile Ala Asp Arg Tyr Lys Asp Tyr Pro Glu Thr Leu Phe
        115                 120                 125

Phe Glu Ile Leu Asn Glu Pro His Gly Asn Leu Thr Pro Glu Lys Trp
    130                 135                 140

Asn Glu Leu Leu Glu Glu Ala Leu Lys Val Ile Arg Ser Ile Asp Lys
145                 150                 155                 160
```

Lys His Thr Val Ile Ile Gly Thr Ala Glu Trp Gly Gly Ile Ser Ala
            165                 170                 175

Leu Glu Lys Leu Arg Val Pro Lys Trp Glu Lys Asn Ala Ile Val Thr
        180                 185                 190

Ile His Tyr Tyr Asn Pro Phe Glu Phe Thr His Gln Gly Ala Glu Trp
            195                 200                 205

Val Pro Gly Ser Glu Lys Trp Leu Gly Arg Lys Trp Gly Ser Pro Asp
    210                 215                 220

Asp Gln Lys His Leu Ile Glu Glu Phe Asn Phe Ile Glu Glu Trp Ser
225                 230                 235                 240

Lys Lys Asn Lys Arg Pro Ile Tyr Ile Gly Glu Phe Gly Ala Tyr Arg
                245                 250                 255

Lys Ala Asp Leu Glu Ser Arg Ile Lys Trp Thr Ser Phe Val Val Arg
                260                 265                 270

Glu Ala Glu Lys Arg Gly Trp Ser Trp Ala Tyr Trp Glu Phe Cys Ser
            275                 280                 285

Gly Phe Gly Val Tyr Asp Pro Leu Arg Lys Gln Trp Asn Lys Asp Leu
    290                 295                 300

Leu Glu Ala Leu Ile Gly Gly Asp Ser Ile Glu
305                 310                 315

<210> SEQ ID NO 22
<211> LENGTH: 795
<212> TYPE: DNA
<213> ORGANISM: Artificial Sequence
<220> FEATURE:
<223> OTHER INFORMATION: Synthetic construct, OB-2880

<400> SEQUENCE: 22
cttagattag agaatgaaaa tttgattgct aaggcccaag attttgatgt ttgcaaagat    60
acaattaccg atcttagaga taagaatgat atacttcgtg ctaagattgt tgaacttaca   120
ccacaacctt ctatgccttc tgtgacatta acattacgtc acaaacaata gtatttttgt   180
cataccttac atgttggtga cgtgattgtg acgaaaatca catcgtcaca gaaggtgcgt   240
gttaaatggt gtactatgac gaataacaaa aaaacgtcat aatagtttat gacgcaaact   300
acaaacgtca ctaatctatg acactcgaat tcgtcactaa ttatgtctaa atacgtcaca   360
attcatgtag tcgtgccttg ccacgtggct gattacgtgg cgagatgaca tggcagttga   420
cgtggcaggt gatgtggcga aatgttgtg acgagttcat tcgtcacaga tgttatgacg   480
tggcatgcca catggcagat gatgtggcaa aattatgtga caaaatatt tgtcataaat   540 atcaatgagg tggcaatata tgtgtgacga aatttttcat cacaaagtac gatgacgttg   600
caatatattt atgacgaatt gttcatcata aggcgtgatg aattcatagc gtcatggaat   660
attatgaaat cacatgctca aacactgata gtttaaactg aaggcgggaa acgacaacct   720
gatcatgagc ggagaattaa gggagtcacg ttatgacccc cgccgatgac gcgggacaag   780
ccgttttacg tttgg                                                    795

<210> SEQ ID NO 23
<211> LENGTH: 1211
<212> TYPE: DNA
<213> ORGANISM: Artificial Sequence
<220> FEATURE:
<223> OTHER INFORMATION: Synthetic construct, OB-2832

<400> SEQUENCE: 23
tcgttcaaac atttggcaat aaagtttctt aagattgaat cctgttgccg gtcttgcgat    60

-continued

```
gattatcata taatttctgt tgaattacgt taagcatgta ataattaaca tgtaatgcat      120
gacgttattt atgagatggg tttttatgat tagagtcccg caattataca tttaatacgc      180
gatagaaaac aaaatatagc gcgcaaacta ggataaatta tcgcgcgcgg tgtcatctat      240
gttactagat cgggaattgg cgagctcgaa ttaattcagt acattaaaaa cgtccgcaat      300
gtgttattaa gttgtctaag cgtcaatttg tttacaccac aatatatact aaaaaaactc      360
aaggatctgt ctccagaaag gccttgcagg gtttggccac gcccacggac attccatctc      420
agagccatga ttagaacgaa aaacacatga gagccgtcgt tgctaggagt cggtttcata      480
tgttcgctaa acaagagat ttgttttttt tctctctcgt acatacacga gtcagcccct      540
ttaatctcag gttgacgtgc aatgtcgctc gtctaagcag aacattttga gaacaaatgt      600
gttgtacatg agagttttgt gtacatggta cgtacattaa aacatcatca tttatcttag      660
atctaacatc tctacttgct tgttatatat ttttttgta aaataacatc tttcaccact      720
ttatatggtg ttgtttgcaa aatatacaga gcaattagag acgttagatt tgagatggac      780
ggtgataatt taatacatgc ataatgtaca agaaaatcct aactgcacta gatatgttgt      840
caaacatttt accttgtta caaaagaaa tgaatagatg ttgaacggtt gtctttcaag      900
cctgttcgct gcggctttaa ttcaccaact gcaatgaaca acctgaaagg tgatcgttgc      960
cgaacacatg ctgtttggca aagctagtag tacctttttt gtctgtcacc tggaatgatg     1020
agaaaggaga caagaggaga gggctggcca ttgtttatat atatacgtat ttccattgct     1080
ttgtggcatg caacagttca agggtccaaa ctggcaggtt ttcagccccg acaaatataa     1140
taaaaaaact acaaaaaaaa aaggtccgtt tacattcctt ttttgacaac gctagtccgt     1200
gcggagcgag c                                                          1211
```

<210> SEQ ID NO 24
<211> LENGTH: 696
<212> TYPE: DNA
<213> ORGANISM: Artificial Sequence
<220> FEATURE:
<223> OTHER INFORMATION: Synthetic construct, OB-3252

<400> SEQUENCE: 24

```
ggtgaaacaa ggtgcagaac tggacttccc gattccagtg gatgattttg ccttctcgct       60
gcatgacctt agtgataaag aaaccaccat tagccagcca agtgccgcca ttttgttctg      120
cgtcgaaggc gatgcaacgt tgtggaaagg ttctcagcag ttacagctta aaccgggtga      180
atcagcgttt attgccgcca acgaatcacc ggtgactgtc aaaggccacg ccgtttagc       240
gcgtgtttac aacaagctgt aagagcttac tgaaaaaatt aacatctctt gctaagctgg      300
gagctctaga tccccgaatt tccccgatcg ttcaaacatt tggcaataaa gtttcttaag      360
attgaatcct gttgccggtc ttgcgatgat tatcatataa tttctgttga attacgttaa      420
gcatgtaata attaacatgt aatgcatgac gttatttatg agatgggttt ttatgattag      480
agtcccgcaa ttatacattt aatacgcgat agaaaacaaa atatagcgcg caaactagga      540
taaattatcg cgcgcggtgt catctatgtt actagatcgg gaattggcga gctcgaatta      600
attcaagtgt cttcgtacaa actggggat ggggcagacc gccaggttca aaccgtttga      660
ctagatgcgg ctggcaggct actttgcagt gcatgc                                696
```

<210> SEQ ID NO 25
<211> LENGTH: 970
<212> TYPE: DNA

<213> ORGANISM: Artificial Sequence
<220> FEATURE:
<223> OTHER INFORMATION: Synthetic construct, OB-2861

<400> SEQUENCE: 25

```
gaatcctgtt gccggtcttg cgatgattat catataattt ctgttgaatt acgttaagca      60
tgtaataatt aacatgtaat gcatgacgtt atttatgaga tgggttttta tgattagagt     120
cccgcaatta tacatttaat acgcgataga aaacaaaata tagcgcgcaa actaggataa     180
attatcgcgc gcggtgtcat ctatgttact agatcgggaa ttggcgagct cgaattaatt     240
cagtacatta aaaacgtccg caatgtgtta ttaagttgtc taagcgtcaa tttgttatca     300
agttgtctaa gcgtcaaaca ctgatagttt aaactgaagg cgggaaacga caacctgatc     360
atgagcggag aattaaggga gtcacgttat gaccccgcc gatgacgcgg gacaagccgt      420
tttacgtttg gaactgacag aaccgcaacg ttgaaggagc cactcagcct aagcggccgc     480
attggactta attaagtgag gccggccaag cgtcgattta atgtaccac atggcgcgcc      540
aactatcatg cgatcgcttc atgtctaact cgagttactg gtacgtacca aatccatgga     600
atcaaggtac ctccatgctg tcctactact tgcttcatcc ccttctacat tttgttctgg     660
tttttggcct gcatttcgga tcatgatgta tgtgatttcc aatctgctgc aatataaatg     720
gagactctgt gctaaccatc aacaacatga aatgcttatg aggcctttgc tgagcagcca     780
atcttgcctg tgtttatgtc ttcacaggcc gaattcctct gttttgtttt tcaccctcaa     840
tatttggaaa catttatcta ggttgtttgt gtccaggcct ataaatcata catgatgttg     900
tcgtattgga tgtgaatgtg gtggcgtgtt cagtgccttg gatttgagtt tgatgagagt     960
tgcttctggg                                                            970
```

<210> SEQ ID NO 26
<211> LENGTH: 1127
<212> TYPE: DNA
<213> ORGANISM: Artificial Sequence
<220> FEATURE:
<223> OTHER INFORMATION: Synthetic construct, OB-2868

<400> SEQUENCE: 26

```
aaaatcccgc gcgctggcga ttttaaaatc ggccctcgat agccagcagg gtgaaccgtg      60
gcaaacgatt cgtttaattt ctgaatttta cccggaagac agcggtctgt tctcccccgct    120
attgctgaat gtggtgaaat tgaaccctgg cgaagcgatg ttcctgttcg ctgaaacacc     180
gcacgcttac ctgcaaggcg tggcgctgga agtgatggca aactccgata acgtgctgcg     240
tgcgggtctg acgcctaaat acattgatat tccggaactg gttgccaatg tgaaattcga     300
agccaaaccg gctaaccagt tgttgaccca gccggtgaaa caaggtgcag aactggactt     360
cccgattcca gtggatgatt ttgccttctc gctgcatgac cttagtgata agaaaccac      420
cattagccag cagagtgccg ccattttgtt ctgcgtcgaa ggcgatgcaa cgttgtggaa     480
aggttctcag cagttacagc tcaaaccggg tgaatcagcg tttattgccg ccaacgaatc     540
accggtgact gtcaaaggcc acggccgttt agcgcgtgtt tacaacaagc tgtaagagct     600
tactgaaaaa attaacatct cttgctaagc tgggagctct agatcccga atttccccga     660
tcgttcaaac atttggcaat aaagtttctt aagattgaat cctgttgccg gtcttgcgat     720
gattatcata taatttctgt tgaattacgt taagcatgta ataattaaca tgtaatgcat     780
gacgttattt atgagatggg ttttatgat tagagtcccg caattataca tttaatacgc      840
gatagaaaac aaaatatagc gcgcaaacta ggataaatta tcgcgcgcgg tgtcatctat     900
```

```
gttactagat cgggaattgg cgagctcgaa ttaattcagt acattaaaaa cgtccgcaat    960
gtgttattaa gttgtctaag cgtcaatttg ttatcaagtt gtctaagcgt caaacactga   1020
tagtttaaac tgaaggcggg aaacgacaac ctgatcatga gcggagaatt aagggagtca   1080
cgttatgacc cccgccgatg acgcgggaca agccgtttta cgtttgg               1127
```

<210> SEQ ID NO 27
<211> LENGTH: 1303
<212> TYPE: DNA
<213> ORGANISM: Artificial Sequence
<220> FEATURE:
<223> OTHER INFORMATION: Synthetic construct, OB-3170

<400> SEQUENCE: 27

```
ttggggttcc ttatcctgtt gtcggagttg tgccattatc ctttccatgg ttgacctgag     60
ctttagcctg tacactgtag actctactag aggtttacct gaggctgaat tcccgctgct    120
aagatgtgat gttcccggcc ataagcaaag atgcaggttg tctttgcttt gtaaagatga    180
aggttgtctt tgttttgtaa tcgaaaaaaa aaccctccga cttcgatagc aatccatttc    240
ttgaaacgat atagctataa gctgcagcca caccttgcgt tgatgatgcc aaagcttttct   300 ttcgagtgcg atgcatgcac tggcctgttg agatcttatc aatatggcaa acagtaacct    360
aacgtatatg actacatggt cttcatgctt ttgagaggtg cctcatagga aacagtcagg    420
ccaatgattt tagggaatac aatatatttt tgctgttttt tttttgcaaa ttgtccatat    480
tattacaaaa aaaactaaac atgcccaaag gcaatagctt tctaaataaa atgaataac     540 ggtccactta tatatgttgg ccagtaatca attctgaggc ctgacaaacc atgcatatat    600
taacagtagg ttaatggccg tgcgtgaaaa aatttcaata caacaagaga ttgaaaaaaa    660
agagtgtctt accaatatgt tatttttataa gtaccaaatg tgtaggaaac ttgcattcat   720
tttttccctg agaatggaaa aaaacaagac atactcattt tcaagttgaa ttgtcatagc    780
aacacacatg ttgtatctgc cggttcatgc aattgtgcca accaaaatat ctaaatgaga    840
tattcaagac tcaacagaat taaagtatgg aatagggtgt atatacactc aaccattatt    900
aaatggtata atcatctatc tatatcacta taaaatctac cagtttaaac ttcacaaaac    960
tcatctagct aatggaggcg ggaaacgaca acctgatcat gagcggagaa ttaagggagt   1020
cacgttatga cccccgccga tgacgcggga caagccgttt tacgtttgga actgacagaa   1080
ccgcaacgtt gaaggagcca ctcagcctaa gcggccgcat tggacttaat taagtgaggc   1140
cggccaagcg tcgatttaaa tgtaccacat ggcgcgccaa ctatcatgcg atcgcttcat   1200
gtctaactcg agttactggt acgtaccaaa tccatggaat caaggtacct ccatgctgtc   1260
ctactacttg cttcatcccc ttctacattt tgttctggtt ttg                    1303
```

<210> SEQ ID NO 28
<211> LENGTH: 960
<212> TYPE: DNA
<213> ORGANISM: Artificial Sequence
<220> FEATURE:
<223> OTHER INFORMATION: Synthetic construct, OB-3237

<400> SEQUENCE: 28

```
aaacatttgg caataaagtt tcttaagatt gaatcctgtt gccggtcttg cgatgattat     60
catataattt ctgttgaatt acgttaagca tgtaataatt aacatgtaat gcatgacgtt    120
atttatgaga tgggttttta tgattagagt cccgcaatta tacatttaat acgcgataga    180
```

| | |
|---|---|
| aaacaaaata tagcgcgcaa actaggataa attatcgcgc gcggtgtcat ctatgttact | 240 |
| agatcgggaa ttggcgagct cgaattaatt cagtacatta aaaacgtccg caatgtgtta | 300 |
| ttaagttgtc taagcgtcaa tttgtttaca ccacaatata aaatctacct gttcgctgat | 360 |
| aagccgttag gttgactatg tgactgttgg gcggcaaaat gaccacgcgg acggtctagc | 420 |
| cccaaagccg gacggtccgc ggtccagaca gtctgcactg gtggtgtcgg cgtttcgacc | 480 |
| ccggggggtc cctggaccga cgagtaaatt gtcgctgcgt gtcccagccc agatgggtcc | 540 |
| gcgcgagacg gaacgcgaag atgggaaaac agcaaggggg aacccgcggc cttcgtgttg | 600 |
| tcctgcgccc aggtcgggtg cgcttgcagt aggggggttac aaccgttcgc gtgggagaga | 660 |
| cagagagaga gcgagagcct tatgcgtcgg cccgttctcc cgcgcggcca accctctcgt | 720 |
| acgagagccc tggaccttcc ttttatagac gtaaggagag ggcccaggtg tacaatgggg | 780 |
| ggtgtagcag agtgctaacg tgtctagcag agaggagccg gagccctaag tacatgtcgt | 840 |
| cgtggctgtc ggagaggttt tggcgccctg ttcatgtgat gtcgtggccg tcggaggagc | 900 |
| gcttgagccc cgtggaagta cagctgtcgg ggctgtcgga tccttgctga cgtctccttg | 960 |

<210> SEQ ID NO 29
<211> LENGTH: 2855
<212> TYPE: DNA
<213> ORGANISM: Artificial Sequence
<220> FEATURE:
<223> OTHER INFORMATION: Synthetic construct, OB-4448

<400> SEQUENCE: 29

| | |
|---|---|
| caccctcgct gttggtaaac gtgcgccttg ggtatgtcct cacctgcatg atacgacatg | 60 |
| ttgaaaaagg tacatggctg gcggattta aacagtagaa tgaaaaggtg ccacaagaaa | 120 |
| actcgtcaaa gaattgacta cgcgtcaatg ttccatagtt aaaaagactt gaactctgga | 180 |
| tcagggactt tcaaacaagg atagctgcct ggtcaccagt cattaactgt aatgtaatgg | 240 |
| ccatagatga tgcatgagta caataataaa aaaacaccat ccagccaaat atatactccc | 300 |
| tgtcacaaat gaaaattcgt tttagataat tagtggattc atacaatatt tgttgtatgt | 360 |
| gttttatgtg tctagattca tcatcctcta tttgaatata gacagaaaaa tcataactaa | 420 |
| aacgaatact atttgggaac ggagggagta ctactttggc agaatgcccc caggaaagta | 480 |
| ccagtttcag gggtagtttg gaaggctaaa cctagggagg gaaaacccccc cacatgtaac | 540 |
| taaatatctt attcaaatgt taccccctagg gattactcac cctgggaaat gagaagggtc | 600 |
| ccaagggggat ttcggtttct attatttttt ctgcaaacca tttcagagca atgatatgaa | 660 |
| accaagctaa ctacttataa catttcttaa gaatatcaga cataggaaag tgatggcctg | 720 |
| gaaccaaagt aagactggta gataaataga tcactgagaat aaaccctgac agttcatagc | 780 |
| cttcatagaa gcaaaaggaa acactacggg agcaattggt tgcttgcact agcaattcac | 840 |
| tgcattgggt ctaatgcagg atagactaag ccagcataag tgtgcgcaat gtgtttgtgt | 900 |
| ttggttgcca tgttataagt aagttgcatt tgctaatatc tttctcctga ctctaatgag | 960 |
| tccacttttg ctgactggtg ggcgaaagta agtaagcaag tgcacaaatc caaagaagaa | 1020 |
| ggctttaaca gtatcatcat cttggggggct tggtgtttat ggcttcatcg taataaggtg | 1080 |
| gttttttgatg gtgtcagtcc ttcaattatt ggcataaagg caattttttt ggatgaagtt | 1140 |
| gaattctgga ggcttgccgg tgctaggcat cttgaggctt tggttcctgg tgctggaatt | 1200 |
| tttaggtcaa gggttctttt gggtgattag tgaagagcag gtgtgtgtgg tctgctcgca | 1260 |
| cttttttgttg ttcgttctcc tattgcgtgc tgttgtttcc aggcgcattt atggaggctg | 1320 |

```
cagttttgtg cgcagcagaa gttggtggtt ttgtgttttg tgttttgcct attttggcat    1380
tgtactttgg tccattttgg actgttttct tctcttaatt taatgatgtg cagctctcct    1440
gcgcgtttaa gaaaaaaaaa agttggctgt tttgtatttc ttgtgatcac ccatgcttgt    1500
tgtggtcaga ttaaactctc acgtttaatg ctacagaagc atccatgaga caatgaaaca    1560
ccgctcaaaa gccacgtagt agcatacccct gacttatgaa taaagcaact cgatctgatt    1620
```
```
tatttgagaa aacaggaaac tgacaagtta ttttttaacac aaaatttcat taaaaacgaa    1680
tggtagacaa ttaccaatct gtaggtccct ggcttgcaag tcctcccaat gtctaagaaa    1740
tcaaatagga actgcaggca agccagcaag aaagtattaa tcactggata taaaatataa    1800
agaaaaaaga aggaaagacg gctactcggc tagcatatgt ttttgttagg ggtgaaaatg    1860
gatacttatt cagaaatcat ttttgatctt ttttctttaa ttaggaataa ataggatata    1920
gaatatgcta agcaaattca tattcttgtt cttagcattg ggcttgtaaa gattcataaa    1980
aggtaaatct caaatttatc atatatctta aatggtagat ataaaattca gatacaaata    2040
tttttcaact tttttgttgt agggaacaaa ttatattaaa aaaaattatg cacaattcta    2100
ttcttatttg taataatgtg cttgataaca taataaaaga ttaccatcaa atttcacaca    2160
cacccaccca cccacccacc cctgcacgca cgcgcgcgca cacacactat atgtgtgttc    2220
aaacactgat agtttaaact gaaggcggga acgacaacc tgatcatgag cggagaatta    2280
agggagtcac gttatgaccc ccgccgatga cgcgggacaa gccgttttac gtttggaact    2340
gacagaaccg caacgttgaa ggagccactc agcctaagcg gccgcattgg acttaattaa    2400
gtgaggccgg ccaagcgtcg atttaaatgt accacatggc gcgccaacta tcatgcgatc    2460
gcttcatgtc taactcgagt tactggtacg taccaaatcc atggaatcaa ggtacctcca    2520
tgctgtccta ctacttgctt catcccccttc tacattttgt tctggttttt ggcctgcatt    2580
tcggatcatg atgtatgtga tttccaatct gctgcaatat gaatggagac tctgtgctaa    2640
ccatcaacaa catgaaatgc ttatgaggcc tttgctgagc agccaatctt gcctgtgttt    2700
atgtcttcac aggccgaatt cctctgtttt gttttttcacc ctcaatattt ggaaacattt    2760
atctaggttg ttttgtgtcc aggcctataa atcataaatg atgttgtcgt attggatgtg    2820
aatgtggtgg cgtgttcagt gccttggatt tgagt                                2855

<210> SEQ ID NO 30
<211> LENGTH: 2336
<212> TYPE: DNA
<213> ORGANISM: Artificial Sequence
<220> FEATURE:
<223> OTHER INFORMATION: Synthetic construct, RB_BC2ES2_472x

<400> SEQUENCE: 30
caccctcgct gttggtaaac gtgcgccttg ggtatgtcct cacctgcatg atacgacatg      60
ttgaaaaagg tacaaggctg gcggattta aacagtagaa tgaaaaggtg ccacaagaaa     120
actcgtcaaa gaattgacta cgcgtcaatg ttccatagtt aaaaagactt gaactctgga     180
tcagggactt tcaaacaagg atagctgcct ggtcaccagt cattaactgt aatgtaatgg     240
ccatagatga tgcatgagta caataataaa aaaacaccat ccagccaaat atatactccc     300
tgtcacaaat gaaaattcgt tttagataat tagtggattc atacaatatt tgttgtatgt     360
gttttatgtg tctagattca tcatcctcta tttgaatata gacagaaaaa tcataactaa     420
aacgaatact atttgggaac ggagggagta ctactttggc agaatgcccc caggaaagta     480
```

```
ccagtttcag gggtagtttg gaaggctaaa cctagggagg gaaaaccccc cacatgtaac      540
taaatatctt attcaaatgt taccoctagg gattactcac cctgggaaat gagaagggtc      600
ccaaggggat ttcggtttct attattttt  ctgcaaacca tttcagagca atgatatgaa      660
accaagctaa ctacttataa catttcttaa gaatatcaga cataggaaag tgatggcctg      720
gaaccaaagt aagactggta gataaataga tcactagaat aaaccctgac agttcatagc      780
cttcatagaa gcaaaaggaa acactacggg agcaattggt tgcttgcact agcaattcac      840
tgcattgggt ctaatgcagg atagactaag ccagcataag tgtgcgcaat gtgtttgtgt      900
ttggttgcca tgttataagt aagttgcatt tgctaatatc tttctcctga ctctaatgag      960 tccactttg  ctgactggtg ggcgaaagta agtaagcaag tgcacaaatc caaagaaga     1020 ggctttaaca gtatcatcat cttgggggct tggtgtttat ggcttcatcg taataaggtg     1080 gttttttgatg gtgtcagtcc ttcaattatt ggcataaagg caattttttt ggatgaagtt     1140
gaattctgga ggcttgccgg tgctaggcat cttgaggctt tggttcctgg tgctggaatt     1200
tttaggtcaa gggttctttt gggtgattag tgaagagcag gtgtgtgtgg tctgctcgca     1260 cttttttgttg ttcgttctcc tattgcgtgc tgttgtttcc aggcgcattt atggaggctg     1320
cagttttgtg cgcagcagaa gttggtggtt ttgtgtttg tgttttgcct atttggcat      1380 tgtactttgg tccatttggg actgtttct  tctcttaatt taatgatgtg cagctctcct     1440
gcgcgtttaa gaaaaaaaaa agttggctgt tttgtatttc ttgtgatcac ccatgcttgt     1500
tgtggtcaga ttaaactctc acgtttaatg ctacagaagc atccatgaga caatgaaaca     1560
ccgctcaaaa gccacgtagt agcatacct  gacttatgaa taaagcaact cgatctgatt     1620
tatttgagaa aacaggaaac tgacaagtta ttttaacac  aaaatttcat taaaaacgaa     1680
tggtagacaa ttaccaatct gtaggtccct ggcttgcaag tcctcccaat gtctaagaaa     1740
tcaaatagga actgcaggca agccagcaag aaagtattaa tcactggata taaaatataa     1800
agaaaaaaga aggaaagacg gctactcggc tagcatatgt ttttgttagg ggtgaaaatg     1860
gatacttatt cagaaatcat tttgatctt  ttttcttaa ttaggaataa ataggatata     1920
gaatatgcta agcaaattca tattcttgtt cttagcattg ggcttgtaaa gattcataaa     1980
aggtaaatct cgaatttatc atatatctta aatggtagat ataaaattca gatacaaata     2040
tttttcaact tttttgttgt agggaacaaa ttatattaaa aaaaattatg cacaattcta     2100
ttcttatttg taataatgtg cttgataaca taataaaaga ttaccatcaa atttcacaca     2160
cacccaccca cccacccacc cctgcacgca cgcgcgcgca cacacactat atgtgtgttc     2220
aaacactgat agtttaaact gaaggcggga acgacaaacc tgatcatgag cggagaatta     2280
agggagtcac gttatgaccc ccgccgatga cgcgggacaa gccgttttac gtttgg        2336
```

<210> SEQ ID NO 31
<211> LENGTH: 2127
<212> TYPE: DNA
<213> ORGANISM: Artificial Sequence
<220> FEATURE:
<223> OTHER INFORMATION: Synthetic construct, OB-4451

<400> SEQUENCE: 31

```
gggcccggta gttctacttc tgttcatgtt tgtgttagat ccgtgtttgt gttagatccg       60
tgctgctagc gttcgtacac ggatgcgacc tgtacgtcag acacgttctg attgctaact      120
tgccagtgtt tctctttggg gaatcctggg atggctctag ccgttccgca gacgggatcg      180
atttcatgat tttttttgtt tcgttgcata gggtttggtt tgcccttttc ctttatttca      240
```

```
atatatgccg tgcacttgtt tgtcgggtca tcttttcatg cttttttttg tcttggttgt     300
gatgatgtgg tctggttggg cggtcgttct agatcggagt agaattctgt tacccacttt     360
catccctagt ttttgttctg gattcaagca tctcaaaatt gtttacctga agtttatcag     420
ttttgagaaa gcggcgcccc tgtcgactac catcaggcat tcggactaca actgtcacag     480
caccctctgc gtctggagac ggttccggtg gtaatgatgc ttgcttcgaa gtgagactgg     540
actctagctc ctatttaatc aaaacatcag ggacaacatg acaaatagta gtcaaatatc     600
caggcaagaa aaaaaaacca taaacaatga aaatactgat caaaagtcct gtttggatct     660
cctaagaaaa atgagaatga gatccaaaca attggattct agaatccagc tatctatccc     720
aaacccatta tttggcgaga ttttcactat gcagaggcaa tgatcactat aagaataaga     780
ttcaaacacc cacttattat tttttttaatc cagaaaccag attctacatt cactatagaa     840
tccagaactt caatatggga atgagatcca aatagaccct aagccaaaat gaaattggtg     900
agatgaagtg gctagttgtc ataacctcct gtaaagaaga cagcggttta cagtcccaac     960
acccaaataa acatgacatt aatataatga ctacaactca caacctaaac ctaaaccaat    1020
atacatccaa acataagaca aaaggagaac tgagttttat atgatcacac tgatgaactg    1080
atgctgtagt ctagcattca agtgtttaag atagttgact ataaacccctt caccttgcag    1140 attacatgtg acagaaagat acctcttcct caagttgttt tttacgcctt tcctcctcct    1200
cttgcttctg tttctcaaga acagcttctc tcgcagctgt ttcttcaagg cgacggagct    1260
cagcctcctg tagggccttt aactccttt cttgatcagc ttgtagcgat gcaaggtact    1320
catcgtccta caaatttaaa atttataaaa gtgctcaccc atagtggcaa ttatgaacaa    1380
tggataaatc ttagacctca aacctgctgc tctcgtaata accgctgttc agttaatgct    1440
ggtgatggag aatgagatat tgggggataa taagtagagg ttctgtgaga aggcatagag    1500
aaaggatatg ttggtccacc aaacattgca gcctcaagca taacagcttc atcatgttcc    1560
tcagaagaaa tgccaccca ctttattgta aaaaagacg tcagaaatta aacaaatcca    1620
tctaatgtct tagcgcacat tggaaccaca gattataata cctcagatgg gaaatcatct    1680
ccattatact ggtgattgtt cagaacaggg ctagcacctg ggtgcactat ttttggtaat    1740
tcattgtcct cagaaggggc acgccgagaa cgacgcctaa ctaacggctg ttcttctaca    1800
tcttcagcct cctcctggaa gctctcgtca tctattggtt gcctagatgt tccagccttt    1860
cctgaagcta gtccttgcct ccaaaaggaa attgcatgta taaggaatca aatgatactg    1920
tagtagggta gcctgagtga agaggtgggt agtaaagtta acattcacct ctcaactatt    1980
ccatttgcgg tttccatgcc tgctttatca gaagaatggt ccctcaaatt cacttcctct    2040
tgatgctggc ctccttgctc gactatctga tgattattga aaaattagag atgacatcaa    2100
gataggttca agtaagcatg ttgggga                                        2127
```

<210> SEQ ID NO 32
<211> LENGTH: 4044
<212> TYPE: DNA
<213> ORGANISM: Artificial Sequence
<220> FEATURE:
<223> OTHER INFORMATION: Synthetic construct, WT_BxA (OB-4541)

<400> SEQUENCE: 32

```
caccctcgct gttggtaaac gtgcgccttg ggtatgtcct cacctgcatg atacgacatg      60
ttgaaaaagg tacaaggctg ggcggattta aacagtagaa tgaaaggtg ccacaagaaa     120
```

```
actcgtcaaa gaattgacta cgcgtcaatg ttccatagtt aaaaagactt gaactctgga      180
tcagggactt tcaaacaagg atagctgcct ggtcaccagt cattaactgt aatgtaatgg      240
ccatagatga tgcatgagta caataataaa aaaacaccat ccagccaaat atatactccc      300
tgtcacaaat gaaaattcgt tttagataat tagtggattc atacaatatt tgttgtatgt      360
gttttatgtg tctagattca tcatcctcta tttgaatata gacagaaaaa tcataactaa      420
aacgaatact atttgggaac ggagggagta ctactttggc agaatgcccc caggaaagta      480
ccagtttcag gggtagtttg aaggctaaa cctagggagg aaaaccccc cacatgtaac       540 taaatatctt attcaaatgt taccctagg gattactcac cctgggaaat gagaagggtc       600
ccaaggggat ttcggtttct attatttttt ctgcaaacca tttcagagca atgatatgaa      660
accaagctaa ctacttataa catttcttaa gaatatcaga cataggaaag tgatggcctg      720
gaaccaaagt aagactggta gataaataga tcactagaat aaaccctgac agttcatagc      780
cttcatagaa gcaaaaggaa acactacggg agcaattggt tgcttgcact agcaattcac      840
tgcattgggt ctaatgcagg atagactaag ccagcataag tgtgcgcaat gtgtttgtgt      900
ttggttgcca tgttataagt aagttgcatt tgctaatatc tttctcctga ctctaatgag      960 tccactttg ctgactggtg ggcgaaagta agtaagcaag tgcacaaatc caaagaaga      1020 ggctttaaca gtatcatcat cttgggggct tggtgtttat ggcttcatcg taataaggtg     1080
gttttgatgg tgtcagtcct tcaattattg gcataaaggc aattttttg gatgaagttg      1140 aattctggag gcttgccggt gctaggcatc ttgaggcttt ggttcctggt gctggaattt     1200
ttaggtcaag ggttctttg ggtgattagt gaagagcagg tgtgtgtggt ctgctcgcac      1260
tttttgttgt tcgttctcct attgcgtgct gttgtttcca ggcgcattta tggaggctgc     1320
agttttgtgc gcagcagaag ttggtggttt tgtgttttgt gttttgccta ttttggcatt    1380
gtactttggt ccatttggga ctgttttctt ctcttaattt aatgatgtgc agctctcctg     1440
cgcgtttaag aaaaaaaaaa gttggctgtt ttgtatttct tgtgatcacc catgcttgtt    1500
gtggtcagat taaactctca cgtttaatgc tacagaagca tccatgagac aatgaaacac    1560
cgctcaaaag ccacgtagta gcatacoctg acttatgaat aaagcaactc gatctgattt     1620
atttgagaaa acaggaaact gacaagttat ttttaacaca aaatttcatt aaaaacgaat     1680
ggtagacaat taccaatctg taggtccctg gcttgcaagt cctcccaatg tctaagaaat    1740
caaataggaa ctgcaggcaa gccagcaaga aagtattaat cactggatat aaaatataaa    1800
gaaaaaagaa ggaaagacgg ctactcggct agcatatgtt tttgttaggg gtgaaaatgg    1860
atacttattc agaaatcatt tttgatcttt tttctttaat taggaataaa taggatatag    1920
aatatgctaa gcaaattcat attcttgttc ttagcattgg gcttgtaaag attcataaaa    1980
ggtaaatctc aaatttatca tatatcttaa atggtagata taaaattcag atacaaatat    2040
ttttcaactt ttttgttgta gggaacaaat tatattaaaa aaaattatgc acaattctat    2100
tcttatttgt aataatgtgc ttgataacat aataaaagat taccatcaaa tttcacacac    2160
acccacccac ccacccaccc ctgcacgcac gcgcgcgcac acacactata tgtgtgtata    2220
tatattaaat attgaattta tcctaacaat ttggatacccc actttcatcc ctagttttg    2280 ttctggattc aagcatctca aaattgttta cctgaagttt atcagttttg agaaagcggc    2340 gccctgtcg actaccatca ggcattcgga ctacaactgt cacagcaccc tctgcgtctg    2400
gagacggttc cggtggtaat gatgcttgct tcgaagtgag actggactct agctcctatt    2460
taatcaaaac atcagggaca acatgacaaa tagtagtcaa atatccaggc aagaaaaaaa    2520
```

```
aaccataaac aatgaaaata ctgatcaaaa gtcctgtttg gatctcctaa gaaaaatgag    2580
aatgagatcc aaacaattgg attctagaat ccagctatct atcccaaacc cattatttgg    2640
cgagattttc actatgcaga ggcaatgatc actataagaa taagattcaa acacccactt    2700 attattttt taatccagaa accagattct acattcacta tagaatccag aacttcaata    2760
tgggaatgag atccaaatag accctaagcc aaaatgaaat tggtgagatg aagtggctag    2820
ttgtcataac ctcctgtaaa gaagacagcg gtttacagtc ccaacaccca aataaacatg    2880
acattaatat aatgactaca actcacaacc taaacctaaa ccaatataca tccaaacata    2940
agacaaaagg agaactgagt tttatatgat cacactgatg aactgatgct gtagtctagc    3000
attcaagtgt ttaagatagt tgactataaa cccttcacct tgcagattac atgtgacaga    3060 aagataccte ttcctcaagt tgttttttac gcctttcctc ctcctcttgc ttctgtttct    3120
caagaacagc ttctctcgca gctgtttctt caaggcgacg gagctcagcc tcctgtaggg    3180
cctttaactc cttttcttga tcagcttgta gcgatgcaag gtactcatcg tcctacaaat    3240
ttaaaattta taaaagtgct cacccatagt ggcaattatg aacaatggat aaatcttaga    3300
cctcaaacct gctgctctcg taataaccgc tgttcagtta atgctggtga tggagaatga    3360
gatattgggg gataataagt agaggttctg tgagaaggca tagagaaagg atatgttggt    3420
ccttcaggaa ctccaccaaa cattgcagcc tcaagcataa cagcttcatc atgttcctca    3480
gaagaaatgc caccccactt tattgtaaaa aaagacgtca gaaattaaac aaatccatct    3540
aatgtcttag cgcacattgg aaccacagat tataatacct cagatgggaa atcatctcca    3600
ttatactggt gattgttcag aacagggcta gcacctgggt gcactatttt tggtaattca    3660
ttgtcctcag aagggggcacg ccgagaacga cgcctaacta acggctgttc ttctacatct    3720
tcagcctcct cctggaagct ctcgtcatct attggttgcc tagatgttcc agccttttcct    3780 gaagctagtc cttgcctcca aaaggaaatt gcatgtataa ggaatcaaat gatactgtag    3840
tagggtagcc tgagtgaaga ggtgggtagt aaagttaaca ttcacctctc aactattcca    3900
tttgcggttt ccatgcctgc tttatcagaa gaatggtccc tcaaattcac ttcctcttga    3960
tgctggcctc cttgctcgac tatctgatga ttattgaaaa attagagatg acatcaagat    4020
aggttcaagt aagcatgttg ggga                                            4044
```

<210> SEQ ID NO 33
<211> LENGTH: 3539
<212> TYPE: DNA
<213> ORGANISM: Artificial Sequence
<220> FEATURE:
<223> OTHER INFORMATION: Synthetic construct, WT_E (OB-4545, OB-4546)

<400> SEQUENCE: 33

```
caccctcgct gttggtaaac gtgcgccttg ggtatgtcct cacctgcatg atacgaaatg      60
ttgaaaaagg tacaaggctg gcggattta aacagtagaa tgaaaggtg ccacaagaaa      120 actcgtcaaa gaattgacta cgcgtcaatg ttccatagtt aaaaagactt gaactctgga     180
tcagggactt tcaaacaagg atagctgcct ggtcaccagt cattaactgt aatgtaatgg     240
ccatagatga tgcatgagta caataataaa aaaacaccat ccagccaaat atatactccc     300
tgtcacaaat gaaaattcgt tttagataat tagtggattc atacaatatt tgttttatgg    360
gtgtctagat tcatcatcct ccatttgaat atagaaagaa aaatcataac taaaacgaat     420
actatttggg aacggaggga gttactattt tgcccgaatg ctcccaggaa agcacgagtt     480
```

```
tcagggctag tttggaaggc taaacctagg gagggaaaac cccccacatg taactaaata    540
tcttattcaa atgttacccc tagggattac tcaccctggg aaatgagaag ggtcccaagg    600
ggatttcggt ttctattatt ttttctgcaa accatttcag agcaatgata tgaaaccaac    660
ctaactactt ataacatttc ttaagaatat cagacatagg aaagtgatgg cctggaagca    720
aagtaagact gatagataaa tagatcacta gaataaaccc tgacagttca tagccttcat    780
agaagcaaaa ggaaacacta cgggagcaat tggttgcttg cactagcaat tcactgcatt    840
gggtctaatg caggatagac taagccagca taagtgtgca caatgtgttt gtgtttggtt    900
gccatgttat aagtaagttg catttgctaa tataatgttt ggttagttgg ctgttttgta    960
tttcttgtga tcacccatgc ttgttgtggt gagattaaac tctcacgttt aatgctacag   1020
aagcatccat gagacaatga aacatcgctc aaaagccacg tagtagcata ccctgactta   1080
tgaataaagc aactcgatct gatttatttg agaaaacagg aaactgacaa gttatttta    1140 acacaaaatt tcattaaaaa cgaatggtag acaattacca atctgtaggt ccctggcttg   1200
caagtcctcc caatgtctaa gaaatcaaat aggaactgca ggcaagccag caagaaagta   1260
ttaatcactg gatataaaat ataagaaaaa aagaaggaaa gacggctact cggctagcat   1320 atgttttgt taggggtgaa aatggatact tattcagaaa tcattttttg atcttttttc    1380
tttaattagg aataaatagg atatagaata tgctaagcaa attcatattc ttgttcttag   1440
cattgggctt gtaaagattc ataaaaggta aatctcaaat ttatcatata tcttaaatgg   1500
tagatataaa attcagatac aaatattttt caactttttt gctgtaggga acaaataata   1560 taaaaaatt tatgcacaat tctattctta tttgtaataa tgtgcttgat aacataataa    1620
aagattacca tcaaatttca cacacacaca cacacacacc cacccccccc acaccccac    1680 gcacgagcgc acacacacac tatatgtgtg tatatatatt aaatattgaa tttatcctaa   1740
caatttggat acccactttc atccctagtt tttgttctgg attcaagcat ctcaaaattg   1800
tttacctgaa gtttatcagt tttgagaaag cggcgcccct gtcgactacc atcaggcatt   1860
cggactacaa ctgtcacagc accctctgcg tctggagacg gttccggtgg taatgatgct   1920
tgcttcgaag tgagactgga ctctagttcc tatttaatca aaacatcagg acaacatga    1980 caaatagtag tcaaatatcc aggcaagaaa aaaaaccata aacaatgaaa atactgatca   2040
aaagtcctgt ttggatctcc taagaaaaat gagaatgaga tccaaacaat tggattctag   2100
aatccagcta tctatcccaa acccattatt tggcgagatt ttcactatgc agaggcaatg   2160
atcactataa gaataagatt caaacaccca cttattattt ttttaatcca gaaaccagat   2220
tctacattca ctatagaatc cagaacttca atatgggaat gagatccaaa tagaccctaa   2280
gccaaaatga aattggtgag atgaagtggc tagttgtcat aacctcctgt aaagaagaca   2340
gcggtttaca gtcccaactc ccaaataaac atatgacatt aatataatga ctacaactca   2400
caacctaaac ctaaaccaat atacatccaa acataagaca aaaggagaac tgagttttat   2460
atgatcacac tgatgaactg atgctgtagt ctagcattcc agtgtttaag atagttgact   2520 ataaacccttt caccttgcag attacatgtg acagaaagat acctcttcct caagttgttt   2580
tttacgcctt tcctcctcct cttgcttctg tttctcaaga acagcttctc tcgcagctgt   2640
ttcttcaagg cgacggagct cagcctcctg tagggccttt aactccttt cttgatcagc    2700 ttgtagcgat gcaaggtact catcgtccta caaatttaaa atttataaaa gtgctcaccc   2760
atagtggcaa ttatgagcaa tggataaatc ttagacctca aacctgctgc tctcgtaata   2820
accgctgttc agttaatgct ggtgatggag aatgagatat tgggggataa taagtagagg   2880
```

```
ttctgtgaga aggcatagag aaaggatatg ttggtccttc aggaactcca ccaaacattg    2940
cagcctcaag cataacagct tcatcatgtt cctcagaaga aatgccaccc cactttattg    3000
taaaaagacg tcagaaatta aacaaatcca tctaatgtct tagcgcacat tggaaccaca    3060
gattatataa tacctcagat gggaaatcat ctccattata ctggtgattg ttcagaacag    3120
ggctagcacc tgggtgcact attttggta attcattgtc ctcagaaggg gcacgccgag     3180
aacgacgcct aactaacggc tgttcttcta catcttcagc ctcctcctgg aagctctcgt    3240
catctattgg ttgcctagat gttccagcct tttctgaagc tagtccttgc ctccaaaagg    3300
aaattgcatg tataaggaat caaatgatac tgtagtaggg tagcctgagt gaagaggtgg    3360
gtagtaaagt taacattcac ctctcaacta ttccatttgc ggtttccatg cctgctttat    3420
cagaagaatg gtccctcaaa ttcacttcct cttgatgctg gcctccttgc tcgactatct    3480
gatgattatt gaaaaattag agatgacatc aagataggtt caagtaagca tgttgggga    3539
```

<210> SEQ ID NO 34
<211> LENGTH: 3540
<212> TYPE: DNA
<213> ORGANISM: Artificial Sequence
<220> FEATURE:
<223> OTHER INFORMATION: Synthetic construct, WT_G (OB-4547, OB-4548)

<400> SEQUENCE: 34

```
caccctcgct gttggtaaac gtgcgccttg ggtatgtcct cacctgcatg atacgaaatg     60
ttgaaaaagg tacaaggctg ggcggattta acagtagaa tgaaaaggtg ccacaagaaa     120
actcgtcaaa gaattgacta cgcgtcaatg ttccatagtt aaaaagactt gaactctgga    180
tcagggactt tcaaacaagg atagctgcct ggtcaccagt cattaactgt aatgtaatgg    240
ccatagatga tgcatgagta caataataaa aaaacaccat ccagccaaat atatactccc    300
tgtcacaaat gaaaattcgt tttagataat tagtggattc atacaatatt tgttttatgg    360
gtgtctagat tcatcatcct ccatttgaat atagaaagaa aaatcataac taaaacgaat    420
actatttggg aacggaggga gttactattt tgcccgaatg ctcccaggaa agcacgagtt    480
tcagggctag tttggaaggc taaacctagg gagggaaaac ccccacatg taactaaata     540 tcttattcaa atgttacccc tagggattac tcaccctggg aaatgagaag ggtcccaagg    600
ggatttcggt ttctattatt ttttctgcaa accatttcag agcaatgata tgaaaccaac    660
ctaactactt ataacatttc ttaagaatat cagacatagg aaagtgatgg cctggaagca    720
aagtaagact gatagataaa tagatcacta gaataaaccc tgacagttca tagccttcat    780
agaagcaaaa ggaaacacta cgggagcaat tggttgcttg cactagcaat tcactgcatt    840
gggtctaatg caggatagac taagccagca taagtgtgca caatgtgttt tgtgtttggtt   900 gccatgttat aagtaagttg catttgctaa tataatgttt ggttagttgg ctgttttgta    960
tttcttgtga tcacccatgc ttgttgtggt gagattaaac tctcacgttt aatgctacag    1020
aagcatccat gagacaatga acatcgctc aaaagccacg tagtagcata ccctgactta     1080
tgaataaagc aactcgatct gatttatttg agaaaacagg aaactgacaa gttattttta    1140
acacaaaatt tcattaaaaa cgaatggtag acaattacca atctgtaggt ccctggcttg    1200
caagtcctcc caatgtctaa gaaatcaaat aggaactgca ggcaagccag caagaaagta    1260
ttaatcactg gatataaaat ataagaaaaa aagaaggaaa gacggctact cggctagcat    1320
atgtttttgt taggggtgaa aatggatact tattcagaaa tcattttttg atctttttc     1380
```

```
tttaattagg aataaatagg atatagaata tgctaagcaa attcatattc ttgttcttag    1440
cattgggctt gtaaagattc ataaaaggta aatctcaaat ttatcatata tcttaaatgg    1500
tagatataaa attcagatac aaatatttttt caactttttt gctgtaggga acaaataata    1560
taaaaaaatt tatgcacaat tctattctta tttgtaataa tgtgcttgat aacataataa    1620
aagattacca tcaaatttca cacacacaca cacacacacc cacccccccc cacaccccca    1680
cgcacgagcg cacacacaca ctatatgtgt gtatatatat taaatattga atttatccta    1740
acaatttgga tacccacttt catccctagt ttttgttctg gattcaagca tctcaaaatt    1800
gtttacctga agtttatcag ttttgagaaa gcggcgcccc tgtcgactac catcaggcat    1860
tcggactaca actgtcacag caccctctgc gtctggagac ggttccggtg gtaatgatgc    1920
ttgcttcgaa gtgagactgg actctagttc ctatttaatc aaaacatcag gacaacatg     1980 acaaatagta gtcaaatatc caggcaagaa aaaaaaccat aaacaatgaa atactgatc     2040 aaaagtcctg tttggatctc ctaagaaaaa tgaatgag atccaaacaa ttggattcta      2100
gaatccagct atctatccca aacccattat ttggcgagat tttcactatg cagaggcaat    2160
gatcactata agaataagat tcaaacaccc acttattatt tttttaatcc agaaaccaga    2220
ttctacattc actatagaat ccagaacttc aatatgggaa tgagatccaa atagacccta    2280
agccaaaatg aaattggtga gatgaagtgg ctagttgtca taacctcctg taaagaagac    2340
agcggtttac agtcccaact cccaaataaa catatgacat aatataatg actacaactc     2400 acaacctaaa cctaaaccaa tatacatcca aacataagac aaaaggagaa ctgagtttta    2460
tatgatcaca ctgatgaact gatgctgtag tctagcattc cagtgtttaa gatagttgac    2520
tataaaccct tcaccttgca gattacatgt gacagaaaga tacctcttcc tcaagttgtt    2580
ttttacgcct ttcctcctcc tcttgcttct gtttctcaag aacagcttct ctcgcagctg    2640
tttcttcaag gcgacggagc tcagcctcct gtagggcctt taactccttt tcttgatcag    2700
cttgtagcga tgcaaggtac tcatcgtcct acaaatttaa aatttataaa agtgctcacc    2760
catagtggca attatgagca atggataaat cttagacctc aaacctgctg ctctcgtaat    2820
aaccgctgtt cagttaatgc tggtgatgga gaatgagata ttgggggata ataagtagag    2880
gttctgtgag aaggcataga gaaaggatat gttggtcctt caggaactcc accaaacatt    2940
gcagcctcaa gcataacagc ttcatcatgt tcctcagaag aaatgccacc ccactttatt    3000 gtaaaagac gtcagaaatt aaacaaatcc atctaatgtc ttagcgcaca ttggaaccac     3060
agattatata atacctcaga tgggaaatca tctccattat actggtgatt gttcagaaca    3120
gggctagcac ctgggtgcac tatttttggt aattcattgt cctcagaagg ggcacgccga    3180
gaacgacgcc taactaacgg ctgttcttct acatcttcag cctcctcctg gaagctctcg    3240
tcatctattg gttgcctaga tgctccagcc ttttctgaag ctagtccttg cctccaaaag    3300
gaaattgcat gtataaggaa tcaaatgata ctgtagtagg gtagcctgag tgaagaggtg    3360
ggtagtaaag ttaacattca cctctcaact attccatttg cggtttccat gcctgcttta    3420
tcagaagaat ggtccctcaa attcacttcc tcttgatgct ggcctccttg ctcgactatc    3480
tgatgattat tgaaaaatta gagatgacat caagataggt tcaagtaagc atgttgggga    3540
```

<210> SEQ ID NO 35
<211> LENGTH: 3540
<212> TYPE: DNA
<213> ORGANISM: Artificial Sequence
<220> FEATURE:
<223> OTHER INFORMATION: Synthetic construct, Null_ BC2ES2_512x (OB-4578 to OB-4580)

<400> SEQUENCE: 35

| | | | | | |
|---|---|---|---|---|---|
| caccctcgct | gttggtaaac | gtgcgccttg | ggtatgtcct | cacctgcatg | atacgaaatg | 60
| ttgaaaaagg | tacaagggct | gggcggattt | aaacagtaga | atgaaaaggt | gccacaagaa | 120
| aactcgtcaa | agaattgact | acgcgtcaat | gttccatagt | taaaaagact | tgaactctgg | 180
| atcagggact | ttcaaacaag | gatagctgcc | tggtcaccag | tcattaactg | taatgtaatg | 240
| gccatagatg | atgcatgagt | acaataataa | aaaaacacca | tccagccaaa | tatatactcc | 300
| ctgtcacaaa | tgaaaattcg | ttttagataa | ttagtggatt | catacaatat | ttgttttatg | 360
| ggtgtctaga | ttcatcatcc | tccatttgaa | tatagaaaga | aaaatcataa | ctaaaacgaa | 420
| tactatttgg | gaacggaggg | agttactatt | ttgcccgaat | gctcccagga | aagcacgagt | 480
| ttcagggcta | gtttggaagg | ctaaacctag | ggagggaaaa | cccccacat | gtaactaaat | 540
| atcttattca | aatgttaccc | ctagggatta | ctcaccctgg | gaaatgagaa | gggtcccaag | 600
| gggatttcgg | tttctattat | tttttctgca | aaccatttca | gagcaatgat | atgaaaccaa | 660
| cctaactact | tataacattt | cttaagaata | tcagacatag | gaaagtgatg | gcctggaagc | 720
| aaagtaagac | tgatagataa | atagatcact | agaataaacc | ctgacagttc | atagccttca | 780
| tagaagcaaa | aggaaacact | acgggagcaa | ttggttgctt | gcactagcaa | ttcactgcat | 840
| tgggtctaat | gcaggataga | ctaagccagc | ataagtgtgc | acaatgtgtt | tgtgtttggt | 900
| tgccatgtta | taagtaagtt | gcatttgcta | ataatgtt | tggttagttg | gctgttttgt | 960
| atttcttgtg | atcacccatg | cttgttgtgg | tgagattaaa | ctctcacgtt | taatgctaca | 1020
| gaagcatcca | tgagacaatg | aaacatcgct | caaaagccac | gtagtagcat | accctgactt | 1080
| atgaataaag | caactcgatc | tgatttattt | gagaaaacag | gaaactgaca | agttattttt | 1140
| aacacaaaat | ttcattaaaa | acgaatggta | gacaattacc | aatctgtagg | tccctggctt | 1200
| gcaagtcctc | ccaatgtcta | agaaatcaaa | taggaactgc | aggcaagcca | gcaagaaagt | 1260
| attaatcact | ggatataaaa | tataaagaaa | aaagaaggaa | agacggctac | tcggctagca | 1320
| tatgttttg | ttaggggtga | aaatggatac | ttattcagaa | atcattttt | gatctttttt | 1380
| ctttaattag | gaataaatag | gatatagaat | atgctaagca | aattcatatt | cttgttctta | 1440
| gcattgggct | tgtaaagatt | cataaaaggt | aaatctcaaa | tttatcatat | atcttaaatg | 1500
| gtagatataa | aattcagata | caaatatttt | tcaacttttt | tgctgtaggg | aacaaataat | 1560
| ataaaaaaat | ttatgcacaa | ttctattctt | atttgtaata | atgtgcttga | taacataata | 1620
| aaagattacc | atcaaatttc | acacacacac | acacacacac | ccaccccccc | cacaccccca | 1680
| cgcacgagcg | cacacacaca | ctatatgtgt | gtatatatat | taaatattga | atttatccta | 1740
| acaatttgga | tacccacttt | catccctagt | ttttgttctg | gattcaagca | tctcaaaatt | 1800
| gtttacctga | agtttatcag | ttttgagaaa | gcggcgcccc | tgtcgactac | catcaggcat | 1860
| tcggactaca | actgtcacag | caccctctgc | gtctggagac | ggttccggtg | gtaatgatgc | 1920
| ttgcttcgaa | gtgagactgg | actctagttc | ctatttaatc | aaaacatcag | ggacaacatg | 1980
| acaaatagta | gtcaaatatc | caggcaagaa | aaaaaaccat | aaacaatgaa | atactgatc | 2040
| aaaagtcctg | tttggatctc | ctaagaaaaa | tgagaatgag | atccaaacaa | ttggattcta | 2100
| gaatccagct | atctatccca | aacccattat | ttggcgagat | tttcactatg | cagaggcaat | 2160
| gatcactata | agaataagat | tcaaacaccc | acttattatt | tttttaatcc | agaaaccaga | 2220
| ttctacattc | actatagaat | ccagaacttc | aatatgggaa | tgagatccaa | atagacccta | 2280

-continued

```
agccaaaatg aaattggtga gatgaagtgg ctagttgtca taacctcctg taaagaagac    2340
agcggtttac agtcccaact cccaaataaa catatgacat taatataatg actacaactc    2400
acaacctaaa cctaaaccaa tatacatcca aacataagac aaaaggagaa ctgagtttta    2460
tatgatcaca ctgatgaact gatgctgtag tctagcattc cagtgtttaa gatagttgac    2520
tataaaccct tcaccttgca gattacatgt gacagaaaga tacctcttcc tcaagttgtt    2580
ttttacgcct ttcctcctcc tcttgcttct gtttctcaag aacagcttct ctcgcagctg    2640
tttcttcaag gcgacggagc tcagcctcct gtagggcctt taactccttt tcttgatcag    2700
cttgtagcga tgcaaggtac tcatcgtcct acaaatttaa aatttataaa agtgctcacc    2760
catagtggca attatgagca atggataaat cttagacctc aaacctgctg ctctcgtaat    2820
aaccgctgtt cagttaatgc tggtgatgga gaatgagata ttgggggata taagtagag     2880 gttctgtgag aaggcataga gaaaggatat gttggtcctt caggaactcc accaaacatt    2940
gcagcctcaa gcataacagc ttcatcatgt tcctcagaag aaatgccacc ccactttatt    3000
gtaaaaagac gtcagaaatt aaacaaatcc atctaatgtc ttagcgcaca ttggaaccac    3060
agattatata atacctcaga tgggaaatca tctccattat actggtgatt gttcagaaca    3120
gggctagcac ctgggtgcac tattttggt aattcattgt cctcagaagg ggcacgccga     3180
gaacgacgcc taactaacgg ctgttcttct acatcttcag cctcctcctg gaagctctcg    3240
tcatctattg gttgcctaga tgttccagcc ttttctgaag ctagtccttg cctccaaaag    3300
gaaattgcat gtataaggaa tcaaatgata ctgtagtagg gtagcctgag tgaagaggtg    3360
ggtagtaaag ttaacattca cctctcaact attccatttg cggtttccat gcctgcttta    3420
tcagaagaat ggtccctcaa attcacttcc tcttgatgct ggcctccttg ctcgactatc    3480
tgatgattat tgaaaaatta gagatgacat caagataggt tcaagtaagc atgttgggga    3540
```

<210> SEQ ID NO 36
<211> LENGTH: 3542
<212> TYPE: DNA
<213> ORGANISM: Artificial Sequence
<220> FEATURE:
<223> OTHER INFORMATION: Synthetic construct, Null_BC1GS2_518x (OB-4582 to OB-4584)

<400> SEQUENCE: 36

```
caccctcgct gttggtaaac gtgcgccttg ggtatgtcct cacctgcatg atacgaaatg     60
ttgaaaaagg tacaaggctg ggcggattta aacagtagaa tgaaaaggtg ccacaagaaa    120
actcgtcaaa gaattgacta cgcgtcaatg ttccatagtt aaaaagactt gaactctgga    180
tcagggactt tcaaacaagg atagctgcct ggtcaccagt cattaactgt aatgtaatgg    240
ccatagatga tgcatgagta caataataaa aaaacaccat ccagccaaat atatactccc    300
tgtcacaaat gaaaattcgt tttagataat tagtggattc atacaatatt tgttttatgg    360
gtgtctagat tcatcatcct ccatttgaat atagaaagaa aaatcataac taaaacgaat    420
actatttggg aacggaggga gttactattt tgcccgaatg ctcccaggaa agcacgagtt    480
tcagggctag tttggaaggc taaacctagg gagggaaaac cccccacatg taactaaata    540
tcttattcaa atgttacccc tagggattac tcaccctggg aaatgagaag gtcccaagg     600 ggatttcggt ttctattatt tttctgcaa accatttcag agcaatgata tgaaaccaac     660
ctaactactt ataacatttc ttaagaatat cagacatagg aaagtgatgg cctgaagca     720 aagtaagact gatagataaa tagatcacta gaataaaccc tgacagttca tagccttcat    780
```

```
agaagcaaaa ggaaacacta cgggagcaat tggttgcttg cactagcaat tcactgcatt      840
gggtctaatg caggatagac taagccagca taagtgtgca caatgtgttt gtgtttggtt      900
gccatgttat aagtaagttg catttgctaa tataatgttt ggttagttgg ctgttttgta      960
tttcttgtga tcacccatgc ttgttgtggt gagattaaac tctcacgttt aatgctacag     1020
aagcatccat gagacaatga aacatcgctc aaaagccacg tagtagcata ccctgactta     1080
tgaataaagc aactcgatct gatttatttg agaaaacagg aaactgacaa gttattttta     1140
acacaaaatt tcattaaaaa cgaatggtag acaattacca atctgtaggt ccctggcttg     1200
caagtcctcc caatgtctaa gaaatcaaat aggaactgca ggcaagccag caagaaagta     1260
ttaatcactg gatataaaat ataagaaaaa agaaggaaa gacggctact cggctagcat      1320 atgttttgt taggggtgaa aatggatact tattcagaaa tcattttttg atcttttttc      1380
tttaattagg aataaatagg atatagaata tgctaagcaa attcatattc ttgttcttag     1440
cattgggctt gtaaagattc ataaaaggta aatctcaaat ttatcatata tcttaaatgg     1500
tagatataaa attcagatac aaatattttt caactttttt gctgtaggga acaaataata     1560
taaaaaaatt tatgcacaat tctattctta tttgtaataa tgtgcttgat aacataataa     1620
aagattacca tcaaatttca cacacacaca cacacacaca cccacccccc cccacccccc     1680
cacgcacgag cgcacacaca cactatatgt gtgtatatat attaaatatt gaatttatcc     1740
taacaatttg gatacccact ttcatcccta gttttgttc tggattcaag catctcaaaa      1800
ttgtttacct gaagtttatc agttttgaga aagcggcgcc cctgtcgact accatcaggc     1860
attcggacta caactgtcac agcaccctct gcgtctggag acggttccgg tggtaatgat     1920
gcttgcttcg aagtgagact ggactctagt tcctatttaa tcaaaacatc agggacaaca     1980
tgacaaatag tagtcaaata tccaggcaag aaaaaaaacc ataaacaatg aaaatactga     2040
tcaaaagtcc tgtttggatc tcctaagaaa aatgagaatg agatccaaac aattggattc     2100
tagaatccag ctatctatcc caaacccatt atttggcgag attttcacta tgcagaggca     2160
atgatcacta taagaataag attcaaacac ccacttatta tttttttaat ccagaaacca     2220
gattctacat tcactataga atccagaact tcaatatggg aatgagatcc aaatagaccc     2280
taagccaaaa tgaaattggt gagatgaagt ggctagttgt cataacctcc tgtaaagaag     2340
acagcggttt acagtcccaa ctcccaaata aacatatgac attaatataa tgactacaac     2400
tcacaaccta aacctaaacc aatatacatc caaacataag acaaaggag aactgagttt      2460 tatatgatca cactgatgaa ctgatgctgt agtctagcat tccagtgttt aagatagttg     2520
actataaacc cttcaccttg cagattacat gtgacagaaa gatacctctt cctcaagttg     2580
ttttttacgc ctttcctcct cctcttgctt ctgtttctca agaacagctt ctctcgcagc     2640
tgtttcttca aggcgacgga gctcagcctc ctgtagggcc tttaactcct tttcttgatc     2700
agcttgtagc gatgcaaggt actcatcgtc ctacaaattt aaaatttata aaagtgctca     2760
cccatagtgg caattatgag caatggataa atcttagacc tcaaacctgc tgctctcgta     2820
ataaccgctg ttcagttaat gctggtgatg gagaatgaga tattgggga taataagtag      2880 aggttctgtg agaaggcata gagaaaggat atgttggtcc ttcaggaact ccaccaaaca     2940
ttgcagcctc aagcataaca gcttcatcat gttcctcaga gaaatgcca ccccactttta     3000 ttgtaaaaag acgtcagaaa ttaaacaaat ccatctaatg tcttagcgca cattggaacc     3060
acagattata taatacctca gatgggaaat catctccatt atactggtga ttgttcagaa     3120
```

| | |
|---|---:|
| cagggctagc acctgggtgc actattttg gtaattcatt gtcctcagaa ggggcacgcc | 3180 |
| gagaacgacg cctaactaac ggctgttctt ctacatcttc agcctcctcc tggaagctct | 3240 |
| cgtcatctat tggttgccta gatgttccag ccttttctga agctagtcct tgcctccaaa | 3300 |
| aggaaattgc atgtataagg aatcaaatga tactgtagta gggtagcctg agtgaagagg | 3360 |
| tgggtagtaa agttaacatt cacctctcaa ctattccatt tgcggtttcc atgcctgctt | 3420 |
| tatcagaaga atggtccctc aaattcactt cctcttgatg ctggcctcct tgctcgacta | 3480 |
| tctgatgatt attgaaaaat tagagatgac atcaagatag gttcaagtaa gcatgttggg | 3540 |
| ga | 3542 |

<210> SEQ ID NO 37
<211> LENGTH: 3542
<212> TYPE: DNA
<213> ORGANISM: Artificial Sequence
<220> FEATURE:
<223> OTHER INFORMATION: Synthetic construct, WT_B73Chr7_141681606-
      141685147

<400> SEQUENCE: 37

| | |
|---|---:|
| caccctcgct gttggtaaac gtgcgccttg ggtatgtcct cacctgcatg atacgaaatg | 60 |
| ttgaaaaagg tacaaggctg ggcggattta acagtagaa tgaaaaggtg ccacaagaaa | 120 |
| actcgtcaaa gaattgacta cgcgtcaatg ttccatagtt aaaaagactt gaactctgga | 180 |
| tcagggactt tcaaacaagg atagctgcct ggtcaccagt cattaactgt aatgtaatgg | 240 |
| ccatagatga tgcatgagta caataataaa aaaacaccat ccagccaaat atatactccc | 300 |
| tgtcacaaat gaaaattcgt tttagataat tagtggattc atacaatatt tgttttatgg | 360 |
| gtgtctagat tcatcatcct ccatttgaat atagaaagaa aaatcataac taaaacgaat | 420 |
| actatttggg aacggaggga gttactattt tgcccgaatg ctcccaggaa agcacgagtt | 480 |
| tcagggctag tttggaaggc taaacctagg gagggaaaac cccccacatg taactaaata | 540 |
| tcttattcaa atgttacccc tagggattac tcaccctggg aaatgagaag ggtcccaagg | 600 |
| ggatttcggt ttctattatt ttttctgcaa accatttcag agcaatgata tgaaaccaac | 660 |
| ctaactactt ataacatttc ttaagaatat cagacatagg aaagtgatgg cctggaagca | 720 |
| aagtaagact gatagataaa tagatcacta gaataaaccc tgacagttca tagccttcat | 780 |
| agaagcaaaa ggaaacacta cgggagcaat tggttgcttg cactagcaat tcactgcatt | 840 |
| gggtctaatg caggatagac taagccagca taagtgtgca caatgtgttt gtgtttggtt | 900 |
| gccatgttat aagtaagttg catttgctaa tataatgttt ggttagttgg ctgttttgta | 960 |
| tttcttgtga tcacccatgc ttgttgtggt gagattaaac tctcacgttt aatgctacag | 1020 |
| aagcatccat gagacaatga acatcgctc aaaagccacg tagtagcata ccctgactta | 1080 |
| tgaataaagc aactcgatct gatttatttg agaaacagg aaactgacaa gttatttta | 1140 |
| acacaaaatt tcattaaaaa cgaatggtag acaattacca atctgtaggt ccctggcttg | 1200 |
| caagtcctcc caatgtctaa gaaatcaaat aggaactgca ggcaagccag caagaaagta | 1260 |
| ttaatcactg gatataaaat ataagaaaaa aagaaggaaa gacggctact cggctagcat | 1320 |
| atgttttgt taggggtgaa aatggatact tattcagaaa tcattttttg atctttttc | 1380 |
| tttaattagg aataaatagg atatagaata tgctaagcaa attcatattc ttgttcttag | 1440 |
| cattgggctt gtaaagattc ataaaaggta aatctcaaat ttatcatata tcttaaatgg | 1500 |
| tagatataaa attcagatac aaatatttt caacttttt gctgtaggga acaaataata | 1560 |

```
taaaaaaatt tatgcacaat tctattctta tttgtaataa tgtgcttgat aacataataa    1620
aagattacca tcaaatttca cacacacaca cacacacaca cccacccccc cccacccccc    1680
cacgcacgag cgcacacaca cactatatgt gtgtatatat attaaatatt gaatttatcc    1740
taacaatttg gataccccact ttcatcccta gtttttgttc tggattcaag catctcaaaa    1800
ttgtttacct gaagtttatc agttttgaga aagcggcgcc cctgtcgact accatcaggc    1860
attcggacta caactgtcac agcaccctct gcgtctggag acggttccgg tggtaatgat    1920
gcttgcttcg aagtgagact ggactctagt tcctatttaa tcaaacatc agggacaaca    1980
tgacaaatag tagtcaaata tccaggcaag aaaaaaaacc ataaacaatg aaaatactga    2040
tcaaaagtcc tgtttggatc tcctaagaaa aatgagaatg agatccaaac aattggattc    2100
tagaatccag ctatctatcc caaacccatt atttggcgag attttcacta tgcagaggca    2160
atgatcacta aagaataag attcaaacac ccacttatta ttttttttaat ccagaaacca    2220
gattctacat tcactataga atccagaact tcaatatggg aatgagatcc aaatagaccc    2280
taagccaaaa tgaaattggt gagatgaagt ggctagttgt cataacctcc tgtaaagaag    2340
acagcggttt acagtcccaa ctcccaaata aacatatgac attaatataa tgactacaac    2400
tcacaaccta aacctaaacc aatatacatc caaacataag acaaaaggag aactgagttt    2460
tatatgatca cactgatgaa ctgatgctgt agtctagcat tccagtgttt aagatagttg    2520
actataaacc cttcacccttg cagattacat gtgacagaaa gatacctctt cctcaagttg    2580
ttttttacgc ctttcctcct cctcttgctt ctgtttctca agaacagctt ctctcgcagc    2640
tgtttcttca aggcgacgga gctcagcctc ctgtagggcc tttaactcct tttcttgatc    2700
agcttgtagc gatgcaaggt actcatcgtc ctacaaattt aaaatttata aaagtgctca    2760
cccatagtgg caattatgag caatggataa atcttagacc tcaaacctgc tgctctcgta    2820
ataccgctg ttcagttaat gctggtgatg gagaatgaga tattgggga taataagtag    2880
aggttctgtg agaaggcata gagaaaggat atgttggtcc ttcaggaact ccaccaaaca    2940
ttgcagcctc aagcataaca gcttcatcat gttcctcaga gaaatgcca ccccacttta    3000
ttgtaaaaag acgtcagaaa ttaaacaaat ccatctaatg tcttagcgca cattggaacc    3060
acagattata taatacctca gatgggaaat catctccatt atactggtga ttgttcagaa    3120
cagggctagc acctgggtgc actattttg gtaattcatt gtcctcagaa ggggcacgcc    3180
gagaacgacg cctaactaac ggctgttctt ctacatcttc agcctcctcc tggaagctct    3240
cgtcatctat tggttgccta gatgttccag cttttctga agctagtcct tgcctccaaa    3300
aggaaattgc atgtataagg aatcaaatga tactgtagta gggtagcctg agtgaagagg    3360
tgggtagtaa agttaacatt cacctctcaa ctattccatt tgcggtttcc atgcctgctt    3420
tatcagaaga atggtccctc aaattcactt cctcttgatg ctggcctcct tgctcgacta    3480
tctgatgatt attgaaaaat tagagatgac atcaagatag gttcaagtaa gcatgttggg    3540
ga                                                                    3542
```

<210> SEQ ID NO 38
<211> LENGTH: 23
<212> TYPE: DNA
<213> ORGANISM: Artificial Sequence
<220> FEATURE:
<223> OTHER INFORMATION: Synthetic construct, primer 509 (A)

<400> SEQUENCE: 38

```
gaattgttca tcataaggcg tga                                              23
```

```
<210> SEQ ID NO 39
<211> LENGTH: 22
<212> TYPE: DNA
<213> ORGANISM: Artificial Sequence
<220> FEATURE:
<223> OTHER INFORMATION: Synthetic construct, primer 516 (B)

<400> SEQUENCE: 39
aacgtgactc ccttaattct cc                                          22

<210> SEQ ID NO 40
<211> LENGTH: 24
<212> TYPE: DNA
<213> ORGANISM: Artificial Sequence
<220> FEATURE:
<223> OTHER INFORMATION: Synthetic construct, probe PB5

<400> SEQUENCE: 40
aaactgaagg cgggaaacga caac                                        24

<210> SEQ ID NO 41
<211> LENGTH: 23
<212> TYPE: DNA
<213> ORGANISM: Artificial Sequence
<220> FEATURE:
<223> OTHER INFORMATION: Synthetic construct, primer 750 (A)

<400> SEQUENCE: 41
gagatgcttg aatccagaac aaa                                         23

<210> SEQ ID NO 42
<211> LENGTH: 22
<212> TYPE: DNA
<213> ORGANISM: Artificial Sequence
<220> FEATURE:
<223> OTHER INFORMATION: Synthetic construct, primer 751 (B)

<400> SEQUENCE: 42
ttgtcttggt tgtgatgatg tg                                          22

<210> SEQ ID NO 43
<211> LENGTH: 25
<212> TYPE: DNA
<213> ORGANISM: Artificial Sequence
<220> FEATURE:
<223> OTHER INFORMATION: Synthetic construct, primer 749 (C)

<400> SEQUENCE: 43
gattaccatc aaatttcaca cacac                                       25

<210> SEQ ID NO 44
<211> LENGTH: 22
<212> TYPE: DNA
<213> ORGANISM: Artificial Sequence
<220> FEATURE:
<223> OTHER INFORMATION: Synthetic construct, probe PB17

<400> SEQUENCE: 44
tagaacgacc gcccaaccag ac                                          22

<210> SEQ ID NO 45
<211> LENGTH: 21
<212> TYPE: DNA
<213> ORGANISM: Artificial Sequence
<220> FEATURE:
<223> OTHER INFORMATION: Synthetic construct, primer 513 (B)
```

```
<400> SEQUENCE: 45
aaacgtccgc aatgtgttat t                                              21

<210> SEQ ID NO 46
<211> LENGTH: 19
<212> TYPE: DNA
<213> ORGANISM: Artificial Sequence
<220> FEATURE:
<223> OTHER INFORMATION: Synthetic construct, primer 608 (C)

<400> SEQUENCE: 46
tcatgcaatt gtgccaacc                                                 19

<210> SEQ ID NO 47
<211> LENGTH: 23
<212> TYPE: DNA
<213> ORGANISM: Artificial Sequence
<220> FEATURE:
<223> OTHER INFORMATION: Synthetic construct, primer 609 (A)

<400> SEQUENCE: 47
acatagtcaa cctaacggct tat                                            23

<210> SEQ ID NO 48
<211> LENGTH: 22
<212> TYPE: DNA
<213> ORGANISM: Artificial Sequence
<220> FEATURE:
<223> OTHER INFORMATION: Synthetic construct, primer 371 (X)

<400> SEQUENCE: 48
ggttataagc ccggttgaag ta                                             22

<210> SEQ ID NO 49
<211> LENGTH: 21
<212> TYPE: DNA
<213> ORGANISM: Artificial Sequence
<220> FEATURE:
<223> OTHER INFORMATION: Synthetic construct, primer 525 (Y)

<400> SEQUENCE: 49
ctattccttg ctcggactga c                                              21

<210> SEQ ID NO 50
<211> LENGTH: 28
<212> TYPE: DNA
<213> ORGANISM: Artificial Sequence
<220> FEATURE:
<223> OTHER INFORMATION: Synthetic construct, probe PB2

<400> SEQUENCE: 50
cacctgatat gccagatgtt ctgtctca                                       28

<210> SEQ ID NO 51
<211> LENGTH: 137
<212> TYPE: DNA
<213> ORGANISM: Artificial Sequence
<220> FEATURE:
<223> OTHER INFORMATION: Synthetic construct, OB-2880_4588.259_locus_PCR

<400> SEQUENCE: 51
gaattgttca tcataaggcg tgatgaattc atagcgtcat ggaatattat gaaatcacat    60
gctcaaacac tgatagttta aactgaaggc gggaaacgac aacctgatca tgagcggaga   120
attaagggag tcacgtt                                                  137
```

<210> SEQ ID NO 52
<211> LENGTH: 107
<212> TYPE: DNA
<213> ORGANISM: Artificial Sequence
<220> FEATURE:
<223> OTHER INFORMATION: Synthetic construct, OB-4451_4588.652_locus_PCR

<400> SEQUENCE: 52
ttgtcttggt tgtgatgatg tggtctggtt gggcggtcgt tctagatcgg agtagaattc     60
tgttacccac tttcatccct agttttgtt ctggattcaa gcatctc                    107

<210> SEQ ID NO 53
<211> LENGTH: 174
<212> TYPE: DNA
<213> ORGANISM: Artificial Sequence
<220> FEATURE:
<223> OTHER INFORMATION: Synthetic construct, 4588.652_wt_zygosity_PCR

<400> SEQUENCE: 53
gattaccatc aaatttcaca cacacacaca cacacacacc caccccccc cacacccca      60 cgcacgagcg cacacacaca ctatatgtgt gtatatatat taaatattga atttatccta   120
acaatttgga tacccacttt catccctagt ttttgttctg gattcaagca tctc           174

<210> SEQ ID NO 54
<211> LENGTH: 100
<212> TYPE: DNA
<213> ORGANISM: Artificial Sequence
<220> FEATURE:
<223> OTHER INFORMATION: Synthetic construct, OB-3237_4588.757_locus_PCR

<400> SEQUENCE: 54
aaacgtccgc aatgtgttat taagttgtct aagcgtcaat tgtttacac cacaatataa     60 aatctacctg ttcgctgata agccgttagg ttgactatgt                           100

<210> SEQ ID NO 55
<211> LENGTH: 218
<212> TYPE: DNA
<213> ORGANISM: Artificial Sequence
<220> FEATURE:
<223> OTHER INFORMATION: Synthetic construct,
     _B73ref_4588.757_wt_zygosity_PCR

<400> SEQUENCE: 55
tcatgcaatt gtgccaacca aaatatctaa atgagatatt caagactcaa cagaattaaa     60
gtatggaata gggtgtatat acactcaacc attattaaat ggtataatca tctatctata   120
tcactataaa atctaccagt ttaaacttca caaaactcat ctagctaatg gagtagaggt   180
agcatggcct agctgataag ccgttaggtt gactatgt                             218

<210> SEQ ID NO 56
<211> LENGTH: 208
<212> TYPE: DNA
<213> ORGANISM: Artificial Sequence
<220> FEATURE:
<223> OTHER INFORMATION: Synthetic construct, ZmGWDref

<400> SEQUENCE: 56
ggttataagc ccggttgaag tatcaggtta tgtggttgtg gttgatgagt tacttgctgt     60
ccagaacaaa tcttatgata aaccaaccat ccttgtggca aagagtgtca agggagagga   120

```
agaaatacca gatggagtag ttggtgtaat tacacctgat atgccagatg ttctgtctca      180
tgtgtcagtc cgagcaagga atagcaag                                        208
```

TRANSGENIC PLANTS PRODUCING GLUCANASE

CROSS REFERENCE TO RELATED APPLICATIONS

This application is a 35 U.S.C. § 371 national phase application of PCT/US2016/032418, which was filed May 13, 2016, and claims the benefit of U.S. Provisional Application No. 62/161,482, which was filed May 14, 2015, both of which are incorporated herein by reference as if fully set forth.

The sequence listing electronically filed with this application titled "Sequence Listing," which was created on May 14, 2016 and has a size of 145,921 bytes, is incorporated by reference herein as if fully set forth.

FIELD

This disclosure relates to transgenic plants expressing glucanases with improved thermal stability, nucleic acids encoding the same, as well as methods of processing transgenic plants and tissues, and producing and utilizing animal feed. This disclosure also relates to feed additives and grain and fiber processing additives that include glucanases.

BACKGROUND

The abundance of non-starch polysaccharides (NSPs) in the diets of monogastric and ruminant animals can adversely affect the nutritional value of feed, and also present an opportunity to improve nutritional content if they can be degraded in the diet or converted into beneficial nutritional components. NSPs are among the primary structural components of plant cell wall (cellulose, hemicellulose, xyloglucans, arabionxylans, galactans, arabinogalactans, etc.) and can also serve as carbohydrate storage reserves in some plants. Additionally, pectins and gums are considered non-cell wall NSP. Because of their various structural and biological roles, NSPs often bind or encase the starch, proteins, fats and other nutrients that are present in plant-based feed ingredients (such as cereals, legumes, silage etc.) and other ingredients, inhibiting the animal's ability to digest nutrients efficiently. Increased levels of NSPs in the diet may increase viscosity of intestinal contents, which can interfere with digestive enzymes and reduce the digestibility of nutrients, thereby increasing feed conversion (mass of feed divided by the mass of meat produced) and reducing body weight gain (Iji, P. A. 1999. The impacts of cereal non-starch polysaccharides on intestinal development and function in the broiler chickens. Worlds Poult. Sci. J. 55:375-387, which is incorporated herein by reference as if fully set forth). For example, feeding increasing levels of guar meal germ (0, 5, or 7.5%) or guar meal hulls (0, 2.5, or 5%) to broilers resulted in increasing digesta viscosity (Lee, J. T., C. A. Bailey, and A. L. Cartwright. 2003. β-Mannanase ameliorates viscosity-associated depression of growth in broiler chickens fed guar germ and hull fractions. Poult. Sci. 82:1925-1931, which is incorporated herein by reference as if fully set forth). In addition to increasing the viscosity, body weight gain and feed conversion was also worse with increasing guar meal hull, demonstrating the negative effects of high viscosity on animal performance.

NSPs have also been known to inadvertently trigger immune responses in the gut, which may further detract from efficiency of feed utilization and have implications for animal health.

In addition to the cereal components, diets now also routinely contain DDGS (dried distillers grains and solubles) that is also not easily digested. Multiple studies have shown that enzyme supplementation can increase diet metabolizable energy (ME), and, or, decrease the viscosity of diets containing high levels of wheat, barley, DDGSs, or other fibrous components. The addition of carbohydrases to corn-soybean meal-based broiler diets, when formulated to have a 3% reduction in dietary ME, has been accomplished without compromising the feed conversions of broilers reared under either hot or cool seasons. It has been determined that the hydrolyzed β-d-glucan is responsible for improved growth.

SUMMARY

In an aspect, the invention relates to a method of identifying maize event 4588.259, 4588.757 or 4588.652 in a sample. The method comprises contacting a sample with a first primer and a second primer. The method comprises amplifying a nucleic acid in the sample to obtain an amplified product. The method also comprises detecting the amplified product specific to a target sequence in maize event 4588.259, 4588.757 or 4588.652.

In an aspect, the invention relates to an animal feedstock comprising a transgenic plant or part thereof. The transgenic plant or part thereof comprises a synthetic nucleic acid encoding a glucanase. The glucanase includes an amino acid sequence with at least 70% identity to a reference sequence selected from the group consisting of: SEQ ID NOS: 4-6, and is capable of degrading one or more polysaccharides.

In an aspect, the invention relates to a method of producing an animal feedstock. The method includes mixing a transgenic plant or part thereof with plant material to form a mixture. The transgenic plant or part thereof comprises a synthetic nucleic acid encoding a glucanase. The glucanase includes an amino acid sequence with at least 70% identity to a reference sequence selected from the group consisting of: SEQ ID NOS: 4-6, and is capable of degrading one or more polysaccharides.

In an aspect, the invention relates to a method of increasing metabolizable energy of a diet. The method includes mixing a transgenic plant or part thereof with a feed ingredient. The transgenic plant or part thereof comprises a synthetic nucleic acid encoding a glucanase comprising an amino acid sequence with at least 70% identity to a reference sequence selected from the group consisting of: SEQ ID NOS: 4-6, and is capable of degrading one or more polysaccharides.

In an aspect, the invention relates to a method of enhancing production of fermentable sugars from grains. The method includes mixing grains derived from any one of the transgenic plants described herein with grains derived from a different plant to form mixed grains. The method also includes processing mixed grains into fermentable sugars. The fermentable sugars are subsequently converted into ethanol or a similar fermentation product, which may include butanol, lactic acid, citric acid, acetic acid, or other fuels or chemicals.

In an aspect, the invention relates to a transgenic plant, transgenic grain, or transgenic biomass comprising a synthetic nucleic acid encoding a glucanase. The glucanase includes an amino acid sequence with at least 70% identity to a reference sequence selected from the group consisting of: SEQ ID NOS: 4-6. The glucanase is capable of degrading one or more polysaccharides.

In an aspect the invention relates to a synthetic polypeptide or a fragment thereof. The synthetic polypeptide or a fragment thereof comprises an amino acid sequence with at least 70% identity to a reference sequence selected from the group consisting of: SEQ ID NOS: 4-6. The glucanase is capable of degrading one or more polysaccharides.

BRIEF DESCRIPTION OF THE DRAWINGS

The following detailed description of preferred embodiments of the present invention will be better understood when read in conjunction with the appended drawings. For the purpose of illustrating the invention, there are shown in the drawings particular embodiments. It is understood, however, that the invention is not limited to the precise arrangements and instrumentalities shown. In the drawings:

(FIG. 19A) and 94° C. (FIG. 19B).

(FIG. 20) and 80° C. (FIG. 21).

(FIG. 23A) and 80° C. (FIG. 23B).

FIG. 24A shows glucose yield and FIG. 24B shows xylose yield.

FIG. 25A shows glucose yield and FIG. 25B shows xylose yield.

DETAILED DESCRIPTION OF EMBODIMENTS

Figure 1:
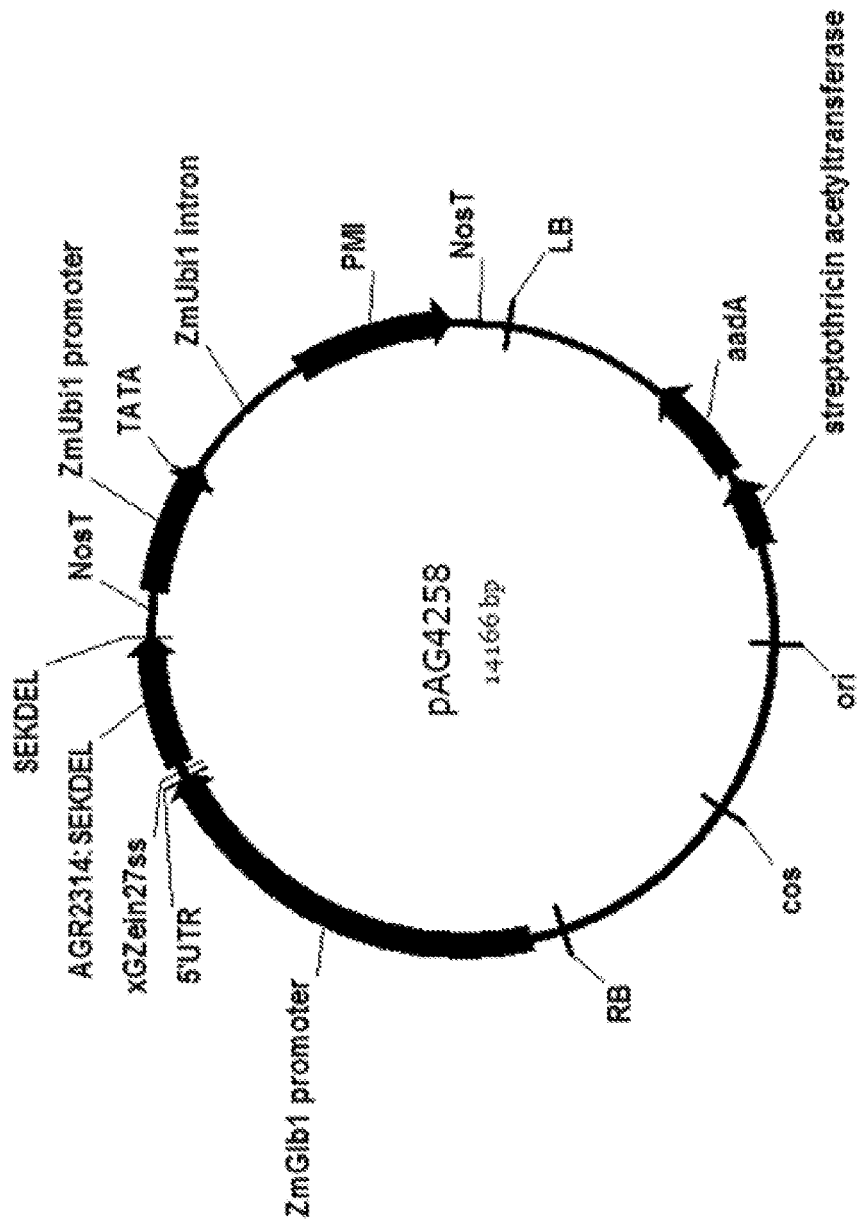
FIG. 1 illustrates the expression vector pAG4258 carrying a single feed glucanase expression unit.
Figure 2:
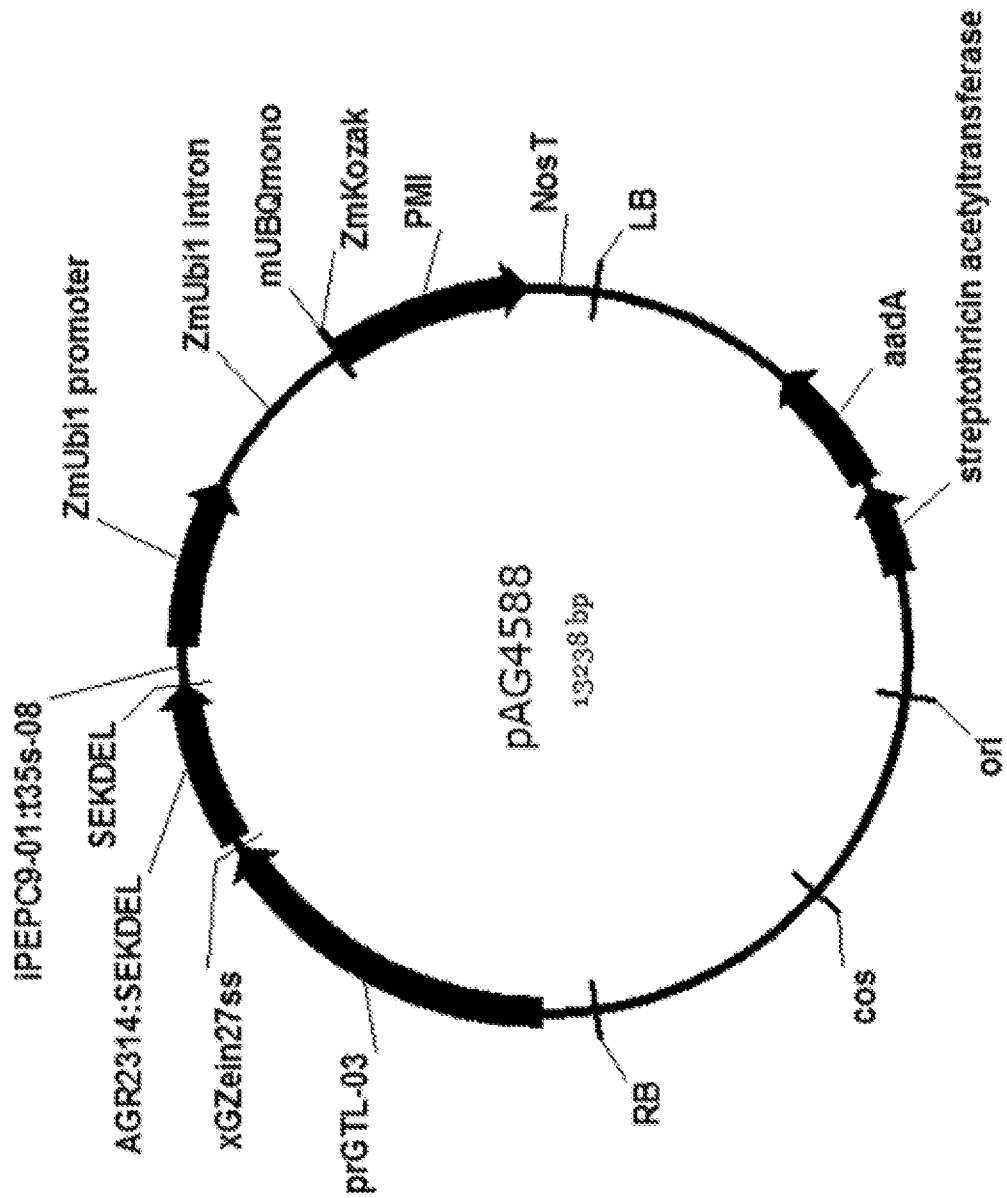
FIG. 2 illustrates the expression vector pAG4588 carrying a single feed glucanase expression unit.
Figure 3:
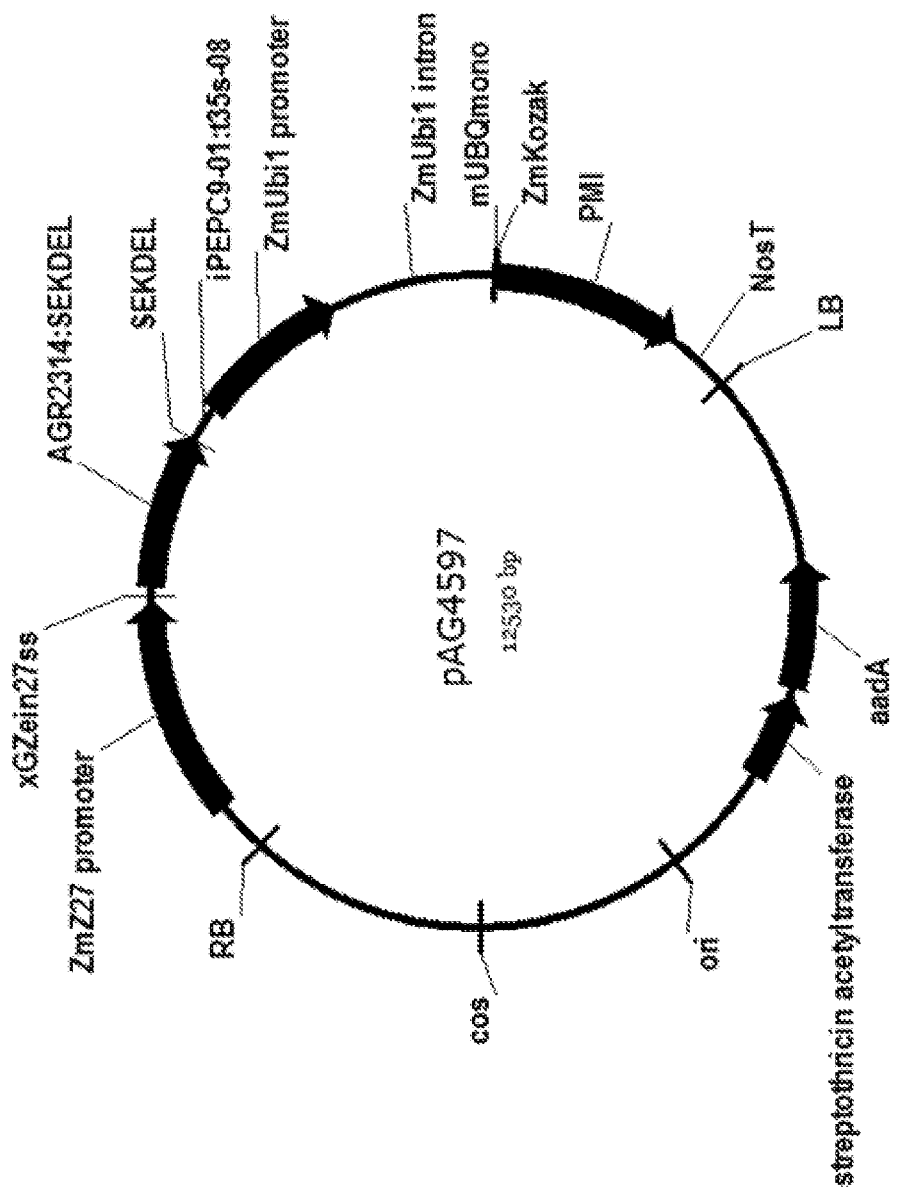
FIG. 3 illustrates the expression vector pAG4597 carrying a single feed glucanase expression unit.
Figure 4:
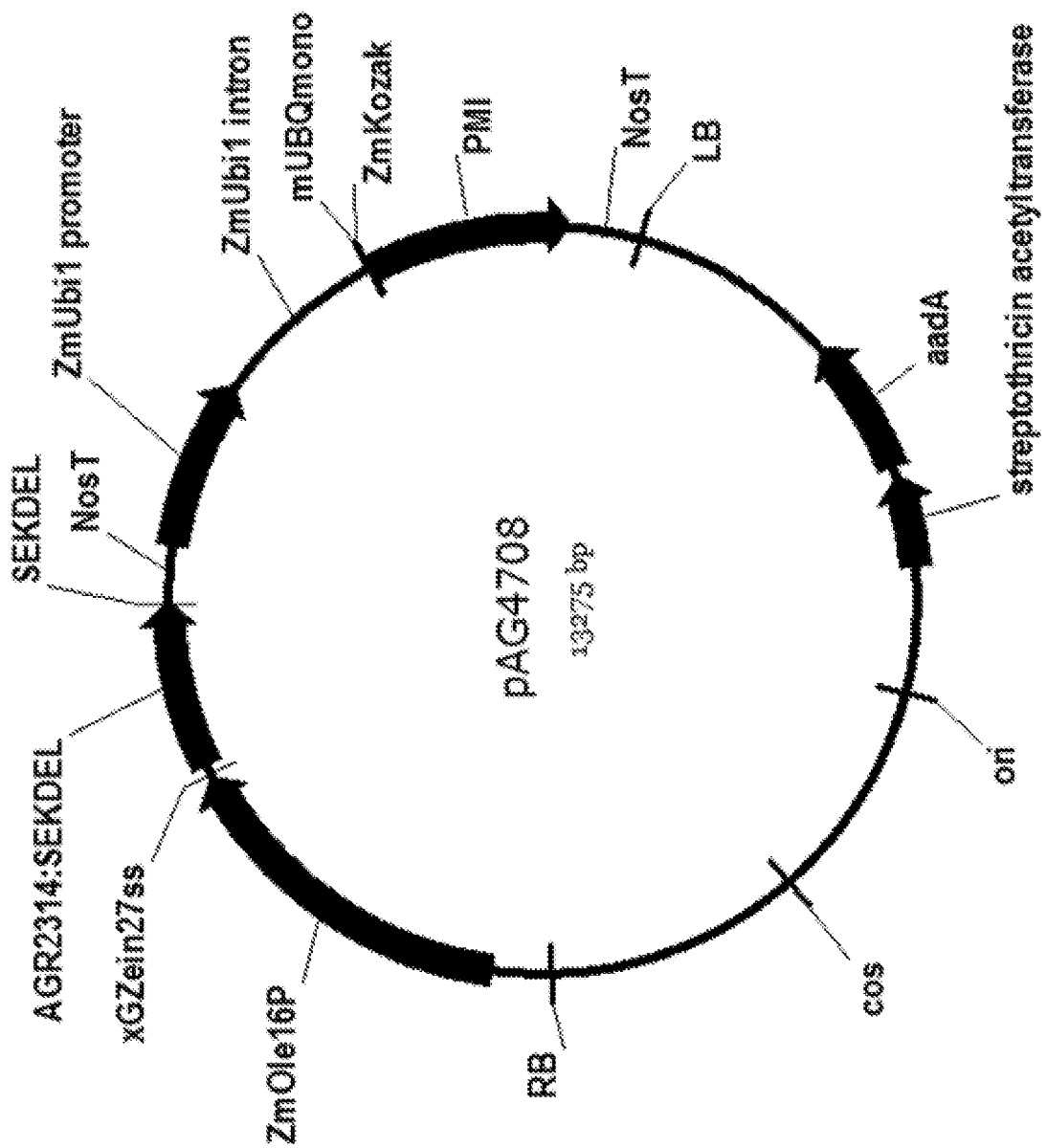
FIG. 4 illustrates the expression vector pAG4708 carrying a single feed glucanase expression unit.

Certain terminology is used in the following description for convenience only and is not limiting.

"Synthetic nucleic acid sequence," "synthetic polynucleotide," "synthetic oligonucleotide," "synthetic DNA," or "synthetic RNA" as used herein refers to a nucleic acid sequence, a polynucleotide, an oligonucleotide, DNA, or RNA that differs from one found in nature by having a different sequence than one found in nature or a chemical modification not found in nature. This can include, but is not limited to, a DNA sequence created using biotechnology tools. Such tools include but are not limited to recombinant DNA technology, polymerase chain reaction (PCR), biotechnology mutagenesis techniques using PCR or recombination techniques including digestion and ligation of DNA, chemical mutagenesis techniques, chemical synthesis, or directed use of nucleases (so called "genome editing" or "gene optimizing" technologies).

"Synthetic protein," "synthetic polypeptide," "synthetic oligopeptide," or "synthetic peptide" as used herein refers to a protein, polypeptide, oligopeptide or peptide that was made through a synthetic process. The synthetic process can include, but is not limited, to chemical synthesis or recombinant technology. The synthetic process may include production of a protein, polypeptide, oligopeptide or peptide by expression of a synthetic nucleic acid sequence in a living cell or by in vitro expression using a cell-free extract.

As used herein, "variant" refers to a molecule that retains a biological activity that is the same or substantially similar to that of the original sequence. The variant may be from the same or different species or be a synthetic sequence based on a natural or prior molecule.

As used herein, "alignment" refers to a plurality of nucleic acid or amino acid sequences aligned lengthwise for visual identification of commonly shared nucleotides or amino acids. The percentage of commonly shared nucleotides or amino acid is related to homology or identity between sequences. An alignment may be determined by or used to identify conserved domains and relatedness between the sequences. An alignment may be determined by computer programs such as CLUSTAL O (1.2.1) (Sievers et al. (2011) Molecular Systems Biology 7: 539 doi: 10. 1038/msb. 2011.75).

The words "a" and "one," as used in the claims and in the corresponding portions of the specification, are defined as including one or more of the referenced item unless specifically stated otherwise.

In an embodiment, a synthetic nucleic acid encoding a glucanase is provided. The synthetic nucleic acid may include a sequence with at least 70, 72, 75, 80, 85, 90, 91, 92, 93, 94, 95, 96, 97, 98, 99 or 100% identity to a reference sequence selected from the group consisting of: SEQ ID NO: 1 [AGR2314], SEQ ID NO: 2 [AGR2414], and SEQ ID NO: 3 [AGR2514]. The encoded glucanase may be capable of degrading one or more polysaccharides.

An embodiment includes a glucanase that includes a synthetic polypeptide having a sequence with at least 70, 72, 75, 80, 85, 90, 91, 92, 93, 94, 95, 96, 97, 98, 99 or 100% identity to a reference sequence selected from the group consisting of: SEQ ID NO: 4 [AGR2314], SEQ ID NO: 5 [AGR2414], and SEQ ID NO: 6 [AGR2514]. The glucanase may be capable of degrading one or more polysaccharides. The glucanase may be modified for improved thermal stability.

A glucanase modified for thermal stability can be produced by standard molecular biological techniques and then screened. The glucanase can be subjected to mutation and then screened for thermal stability. Screening systems that can be utilized include lambda phage, yeast, or other expression systems that allow production of the protein and/or testing of its physical and/or functional characteristics. From a population of modified proteins, candidates can be isolated and analyzed further. Further analysis may include DNA sequencing, functional assays, structural assays, enzyme activity assays, and monitoring changes in thermal stability, or structure in response to elevated temperature conditions.

In an embodiment, a glucanase may be produced in a plant or plant tissue. The glucanase may be isolated from the plant or plant tissue.

An embodiment includes a composition comprising, consisting essentially of, or consisting of one or more glucanases. The composition may be, but is not limited, to a transgenic plant including the one or more glucanases, an animal feedstock or animal feed additive including the one or more glucanases or an enzyme mixture including the one or more glucanases. A glucanase in the composition may be encoded by any one of the synthetic nucleic acids described herein. As used herein, the term "glucanase" refers to an enzyme capable of catalyzing the degradation or depolymerization of complex carbohydrates.

A glucanase in the composition may be capable of degrading one or more of disaccharides, trisaccharides, and oligosaccharides into lower molecular weight saccharides. A glucanase in the composition may be capable of degrading one or more of cellooligosaccharide, lignocellulose, cellulose, hemicellulose, and pectin. A glucanase of the composition may act upon cellulose or mixed linkage beta glucans. Some glucanases may have broader substrate specificities and may act on a wide range of carbohydrate polymers. A glucanase of the composition may have enzymatic activity on a range of carbohydrate polymers. Such enzymatic activity may be, but is not limited to, endoglucanase, exoglucanase, β-glucosidase, cellobiohydrolase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, or pectate lyase activities. The glucanase of the composition may be capable of degrading one or more of beta-glucan, cellulose, cellobiose, pNP-D-glucopyranoside and xylan. Assays for determining activity of a glucanase for degrading various substrates are known in the art. The beta-glucosidase assay, endocellulase assay, exocellulase (cellobiohydrolase) assay, amylase assay, endoxylanase assay, pectinase assay, 1,3-beta-glucosidase assay, 1,4-beta-glucosidase assay are described herein in Example 13.

A glucanase of the composition may comprise, consist essentially of, or consist of an amino acid sequence with at least 70, 72, 75, 80, 85, 90, 91, 92, 93, 94, 95, 96, 97, 98, 99, or 100% identity to a reference sequence selected from the group consisting of: SEQ ID NO: 4 [AGR2314], SEQ ID NO: 5 [AGR2414] and SEQ ID NO: 6 [AGR2514].

An embodiment includes a composition comprising, consisting essentially of, or consisting of an individual glucanase or a combination of two or more glucanases herein.

In an embodiment, a glucanase of the composition may be a variant. Variants may include conservative amino acid substitutions; i.e., substitutions with amino acids having similar properties. Conservative substitutions may be a polar for polar amino acid (Glycine (G, Gly), Serine (S, Ser), Threonine (T, Thr), Tyrosine (Y, Tyr), Cysteine (C, Cys), Asparagine (N, Asn) and Glutamine (Q, Gln)); a non-polar for non-polar amino acid (Alanine (A, Ala), Valine (V, Val), Thyptophan (W, Trp), Leucine (L, Leu), Proline (P, Pro), Methionine (M, Met), Phenilalanine (F, Phe)); acidic for acidic amino acid (Aspartic acid (D, Asp), Glutamic acid (E, Glu)); basic for basic amino acid (Arginine (R, Arg), Histidine (H, His), Lysine (K, Lys)); charged for charged amino acids (Aspartic acid (D, Asp), Glutamic acid (E, Glu), Histidine (H, His), Lysine (K, Lys) and Arginine (R, Arg)); and a hydrophobic for hydrophobic amino acid (Alanine (A, Ala), Leucine (L, Leu), Isoleucine (I, Ile), Valine (V, Val), Proline (P, Pro), Phenylalanine (F, Phe), Tryptophan (W, Trp) and Methionine (M, Met)). Conservative nucleotide substitutions may be made in a nucleic acid sequence by substituting a codon for an amino acid with a different codon for the same amino acid. Variants may include non-conservative substitutions. A variant may have 40% glucanase activity in comparison to the unchanged glucanase. A variant may have at least 40%, 45%, 50%, 55%, 60%, 65%, 70%, 75%, 80%, 85%, 90%, 91%, 92%, 93%, 94%, 95%, 96%, 97%, 98%, 99%, or 100% activity, or an integer between any of the two values herein, in comparison to the unchanged glucanase.

In an embodiment, the one or more proteins having less than 100% identity to its corresponding amino acid sequence of SEQ ID NOS: 4-6 is a variant of the referenced protein or amino acid. In an embodiment, an isolated protein, polypeptide, oligopeptide, or peptide having a sequence with at least 70, 75, 80, 85, 90, 91, 92, 93, 94, 95, 96, 97, 98, 99, or 100% identity to a protein having the sequence of any one of SEQ ID NOS: 4-6 may be a less than full length protein having the sequence with at least 70, 75, 80, 85, 90, 91, 92, 93, 94, 95, 96, 97, 98, 99, or 100% identity any one of SEQ ID NO: 4-6 along 6, 10 to 50, 10 to 100, 10 to 150, 10 to 300, 10 to 400, 10 to 500, 10 to 600, 10 to 700, 10 to 800, 10 to 900, or 10 to all amino acids of a protein. This list of sequence lengths encompasses every full length protein in SEQ ID NOS: 4-6 and every smaller length within the list, even for proteins that do not include over 400 amino acids. For example, the lengths of 6, 10 to 50, 10 to 100, 10 to 150, 10 to 300, 10 to 400, and 10 to all amino acids would apply to a sequence with 322 amino acids. A range of amino acid sequence lengths recited herein includes every length of amino acid sequence within the range, endpoints inclusive. The recited length of amino acids may start at any single position within a reference sequence where enough amino acids follow the single position to accommodate the recited length. The range of sequence lengths can be extended by increments of 10 to 100N amino acids, where N=an integer of ten or greater, for sequences of 1000 amino acids or larger. The fragment of the glucanase may be a subsequence of the polypeptides herein that retain at least 40% activity of the glucanase. The fragment may have 316, 317, or 322 amino acids. The fragments may include 20, 30, 40, 50, 100, 150, 200, or 300 contiguous amino acids. Embodiments also include nucleic acids encoding said amino acid sequences, and antibodies recognizing epitopes on said amino acid sequences.

A less than full length amino acid sequence may be selected from any portion of one of the sequences of SEQ ID NOS: 4-6 corresponding to the recited length of amino acids. A less than full length amino acid sequence may be selected from a portion of any one of SEQ ID NOS: 4-6 having a catalytic domain. The fragment may include a catalytic domain of a glucanase. For example, the catalytic domain of the glucanase of SEQ ID NO: 4 [AGR2314]includes the following sequence:

A less than full length amino acid sequence may be selected from a portion of any one of SEQ ID NO: 21 may include amino acids 136-253. A less than full length amino acid sequence may possess the glucanase activity. A less than full length amino acid sequence may be capable of degrading polysaccharides. A less than full length amino acid sequence may contain those amino acids would contain the active site residues.

A catalytic domain may be a conserved domain. A "conserved domain" herein refers to a region in a heterologous polynucleotide or polypeptide sequences where there is a relatively high degree of sequence identity between the distinct sequences. With respect to polynucleotides encoding a conserved domain is preferably at least 10 base pairs (bp) in length.

A conserved domain of any one of polypeptides described herein refers to a domain within a glucanase that exhibits a higher degree of sequence identity High degree of sequence identity may be at least 50% identity, at least 55% identity, at least 60% identity, at least 65%, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity or at least 100% identity to consecutive amino acid residues of a polypeptide described herein. Conserved domains may be identified as domains of identity to a specific consensus sequence. Conserved domains may be identified by using alignment methods. Conserved domain may be identified with multiple sequence alignments of related proteins. These alignments reveal sequence regions containing the same, or

```
                                                              (SEQ ID NO: 21)
         10        20        30        40        50        60
--GVDPFERNKILGRGINICNALEAPNEGDWGVVIKDEFFDIIKEAGFSHVRIPIRWSTHA 70        80        90       100       110       120
AFPPPYKIEPSFFKRVDEVINGALKRGLAVVINIHHYEELMNDPEEHKERFLALWKQIAD 130       140       150       160       170       180
RYKDYPETLFFEILNEPHGNLTPEKTWNELLEEALKVIRSIDKKHTVIIGTAEWGGISALE 190       200       210       220       230       240
KLRVPKWEKNAIVTIHYYNPFEFTHQGAEWVPGSEKWLGRKWGSPDDQKHLIEEFNFIEE 250       260       270       280       290       300
WSKKNKRPIYIGEFGAYRKADLESRIKWTSFVVREAEKRGWSWAWEFCSGFGVYDPLRK

310
QWNKDLLEALIGGDSIE
```

In the sequence of SEQ ID NO: 21, catalytic residues in active site are shown by enlarged characters in bold. Other active site residues that interact with the substrate are italicized, bold and underlined.

For example, positions 136 and 253 in SEQ ID NO: 21 are catalytic residues in the active site, and a less than full length amino acid sequence selected from SEQ ID NO: 21 may include residues 134 and 135 at any two respective, consecutive positions within the recited length. A less than full length amino acid sequence may be selected from a portion of any one of SEQ ID NO: 21 may have other active site residues that interact with the substrate. For example, positions 20, 35, 36, 135, 198, 205, 210 and 286 of SEQ ID NO: 21 are the active site residues that interact with the substrate, and a less than full length amino acid sequence selected from SEQ ID NO: 21 may include residues 20, 35, 36, 135, 198, 205, 210 and 286 at any respective, consecutive positions within the recited length.

similar, patterns of amino acids. Multiple sequence alignments, three-dimensional structure and three-dimensional structure superposition of conserved domains can be used to infer sequence, structure, and functional relationships. Since the presence of a particular conserved domain within a polypeptide is highly correlated with an evolutionarily conserved function, a conserved domain database may be used to identify the amino acids in a protein sequence that are putatively involved in functions such as degrading polysaccharides, as mapped from conserved domain annotations to the query sequence. For example, the presence in a protein of a sequence of SEQ ID NO: 21 that is structurally and phylogenetically similar to one or more domains in the polypeptides of the accompanying Sequence Listing is a strong indicator of a related function in plants. Sequences herein referred to as functionally-related and/or closely-related to the sequences or domains of polypeptides having sequences of SEQ ID NOS: 4-6 may have conserved domains that share at least at least ten amino acids in length and at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% or 96%, 97%, 98%, or at least 99%, or about 100% amino acid identity to the sequences of AGR2314, AGR2414 and AGR2514, and have similar functions that the polypeptides of the instant description.

In an example, sequences of AGR2314, AGR2414, and AGR2514 may be aligned as shown below.

AGR2414 sequence is a sequence of *Thermotoga maritima* Cel5A (3AMC in Protein Data Bank and in PubMed protein sequence database). Residues that interact with the substrate are underlined and are shown in enlarged bold characters: N20, H95, H96, N135, E136 (catalytic residue), Y198, 11205, W210, E253 (catalytic residue), W286. (T. Wu et al. (2011), Biochim. Biophys. Acta 1814, 1832-1840, which is incorporated herein by reference as if fully set forth). The numbering of these residues in AGR2514 is one higher because of the presence of one additional residue at the N-terminus in this sequence.

In an example, the sequences of AGR2314 and AGR2414 have 305 residues conserved out of 317 residues and have 96% identity.

```
                CLUSTAL O(1.2.1) multiple sequence alignment

AGR2414   MGVDPFERNKILGRGINIGNALEAPNEGDWGVVIKDEFFDIIKEAGFSHVRIPIRWSTHA
AGR2314   MGVDPFERNKILGRGINIGNALEAPNEGDWGVVIKDEFFDIIKEAGFSHVRIPIRWSTHA
          ************************************************************

AGR2414   YAFPPPYKIMDRFFKRVDEVINGALKRGLAVVINIHHYEELMNDPEEHKERFLALWKQIAD
AGR2314   QAFPPPYKIEPSFFKRVDEVINGALKRGLAVVINIHHYEELMNDPEEHKERFLALWKQIAD
           *******  ***************************************************

AGR2414   RYKDYPETLFFEILNEPHGNLTPEKWNELLEEALKVIRSIDKKHTIIIGTAEWGGISALE
AGR2314   RYKDYPETLFFEILNEPHGNLTPEKWNELLEEALKVIRSIDKKHTVIIGTAEWGGISALE
          ********************************************* :************

AGR2414   KLSVPKWEKNSIVTIHYYNPFEFTHQGAEWVEGSEKWLGRKWGSPDDQKHLIEEFNFIEE
AGR2314   KLRVPKWEKNAIVTIHYYNPFEFTHQGAEWVPGSEKWLGRKWGSPDDQKHLIEEFNFIEE
          ** *******:*******************.*****************************

AGR2414   WSKKNKRPIYIGEFGAYRKADLESRIKWTSFVVREMEKRRWSWAYWEFCSGFGVYDTLRK
AGR2314   WSKKNKRPIYIGEFGAYRKADLESRIKWTSFVVREAEKRGWSWAYWEFCSGFGVYDPLRK
          ***********************************  ***  **************  ***

AGR2414   TWNKDLLEALIGGDSIE (SEQ ID NO: 5)
AGR2314   QWNKDLLEALIGGDSIE (SEQ ID NO: 4)
           ****************
```

In an example, the sequences of AGR2414 and AGR2514 below have 310 residues conserved out of 318 residues and have 97% identity.

```
                CLUSTAL O(1.2.1) multiple sequence alignment

AGR2414   -MGVDPFERNKILGRGINIGNALEAPNEGDWGVVIKDEFFDIIKEAGFSHVRIPIRWSTH
AGR2514   MSGVDPFERNKILGRGINIGNALEAPNEGDWGVVIKDEYFDIIKEAGFSHVRIPIRWSTH
           ***************************************.*******************

AGR2414   AYAFPPPYKIMDRFFKRVDEVINGALKRGLAVVINIHHYEELMNDPEEHKERFLALWKQIA
AGR2514   AQAFPPPYKIEDRFFKRVDEVINGALKRGLAVVINQHHYEELMNDPEEHKERFLALWKQIA
          * ******  ****************************  ************************

AGR2414   DRYKDYPETLFFEILNEPHGNLTPEKWNELLEEALKVIRSIDKKHTIIIGTAEWGGISAL
AGR2514   DRYKDYPETLFFEILNEPHGNLTPEKWNELLEEALKVIRSIDKKHTIIIGTAEWGGISAL
          ************************************************************

AGR2414   EKLSVPKWEKNSIVTIHYYNPFEFTHQGAEWVEGSEKWLGRKWGSPDDQKHLIEEFNFIE
AGR2514   EKLRVPKWEKNAIVTIHYYNPFEFTHQGAEWVEGSEKWLGRKWGSPDDQKHLIEEFNFIE
          *** *******:************************************************

AGR2414   EWSKKNKRPIYIGEFGAYRKADLESRIKWTSFVVREMEKRRWSWAYWEFCSGFGVYDTLR
AGR2514   EWSKKNKRPIYIGEFGAYRKADLESRIKWTSFVVREAEKRRWSWAYWEFCSGFGVYDTLR
          ************************************ ***********************

AGR2414   KTWNKDLLEALIGGDSIE (SEQ ID NO: 5)
AGR2514   KTWNKDLLEALIGGDSIE (SEQ ID NO: 6)
           *****************
```

In an example, the sequences of AGR2314 and AGR2514 have 308 residues conserved out of 318 residues and have 97% identity.

```
        CLUSTAL O(1.2.1) multiple sequence alignment

AGR2314  -MGVDPFERNKILGRGINIGNALEAPNEGDWGVVIKDEFFDIIKEAGFSHVRIPIRWSTH
AGR2514  MSGVDPFERNKILGRGINIGNALEAPNEGDWGVVIKDEYFDIIKEAGFSHVRIPIRWSTH
          *******************:********************

AGR2314  AQAFPPYKIEPSFFKRVDEVINGALKRGLAVVINIHHYEELMNDPEEHKERFLALWKQIA
AGR2514  AQAFPPYKIEDRFFKRVDEVINGALKRGLAVVINQHHYEELMNDPEEHKERFLALWKQIA
         ********** ********************** **************************

AGR2314  DRYKDYPETLFFEILNEPHGNLTPEKWNELLEEALKVIRSIDKKHTVIIGTAEWGGISAL
AGR2514  DRYKDYPETLFFEILNEPHGNLTPEKWNELLEEALKVIRSIDKKHTIIIGTAEWGGISAL
         ***************************************************:************

AGR2314  EKLRVPKWEKNAIVTIHYYNPFEFTHQGAEWVPGSEKWLGRKWGSPDDQKHLIEEFNFIE
AGR2514  EKLRVPKWEKNAIVTIHYYNPFEFTHQGAEWVEGSEKWLGRKWGSPDDQKHLIEEFNFIE
         ******************************* ****************************

AGR2314  EWSKKNKRPIYIGEFGAYRKADLESRIKWTSFVVREAEKRGWSWAYWEFCSGFGVYDPLR
AGR2514  EWSKKNKRPIYIGEFGAYRKADLESRIKWTSFVVREAEKRRWSWAYWEFCSGFGVYDTLR
         ****************************************  *************** **

AGR2314  KQWNKDLLEALIGGDSIE (SEQ ID NO: 4)
AGR2514  KTWNKDLLEALIGGDSIE (SEQ ID NO: 6)
         * ****************
```

Sequences that possess or encode for conserved domains that meet these criteria of percentage identity, and that have comparable biological and regulatory activity to the present polypeptide sequences, thus being glucanases, described herein. Sequences having lesser degrees of identity, but comparable biological activity, are considered to be equivalents.

The functionality of a glucanase, variants, or fragments thereof, may be determined using any methods. The functionality of a glucanase may be measured by any one of the assays described in Example 3.

Any one or more glucanases herein may be expressed in a plant upon introduction into the plant genome of any one or more of synthetic nucleic acids described herein. The methods of introduction of synthetic nucleic acids into the plants are known in the art. The method may be transformation of the plant with a vector that includes synthetic nucleic acids.

In an embodiment, a synthetic polynucleotide having a sequence with at least 70, 72, 75, 80, 85, 90, 91, 92, 93, 94, 95, 96, 97, 98, 99, or 100% identity to a reference sequence selected from the group consisting of SEQ ID NO: 7 [pAG4258], SEQ ID NO: 8 [pAG4588], SEQ ID NO: 9 [pAG4597], SEQ ID NO: 10 [pAG4708], SEQ ID NO: 11 [pAG4766], SEQ ID NO: 12 [pAG4767], SEQ ID NO: 13 [pAG4770], SEQ ID NO: 14 [pAG4771], SEQ ID NO: 15 [pAG4257], SEQ ID NO: 16 [pAG4692], SEQ ID NO: 17 [pAG4693], SEQ ID NO: 18 [pAG4705] and SEQ ID NO: 19 [pAG4706] is provided. The synthetic polynucleotide may include any one of the synthetic nucleic acids described herein that encode glucanase and that are capable of degrading a polysaccharide.

In an embodiment, a vector is provided. The vector may include any one of the synthetic polynucleotides or nucleic acids described herein.

In an embodiment, synthetic nucleic acids are provided having a sequence as set forth in any one of the nucleic acids listed herein or the complement thereof. In an embodiment, isolated nucleic acids having a sequence that hybridizes to a nucleic acid having the sequence of any nucleic acid listed herein or the complement thereof are provided. In an embodiment, the hybridization conditions are low stringency conditions. In an embodiment, the hybridization conditions are moderate stringency conditions. In an embodiment, the hybridization conditions are high stringency conditions. The hybridization may be along the length of the synthetic nucleic acid. Examples of hybridization protocols and methods for optimization of hybridization protocols are described in the following publications: Molecular Cloning, T. Maniatis, E. F. Fritsch, and J. Sambrook, Cold Spring Harbor Laboratory, 1982; and, Current Protocols in Molecular Biology, F. M. Ausubel, R. Brent, R. E. Kingston, D. D. Moore, J. G. Seidman, J. A. Smith, K. Struhl, Volume 1, John Wiley & Sons, 2000 (standard protocol) and Amersham Gene Images AlkPhos Direct Labeling and Detection System (GE Healthcare UK, Ltd), which are incorporated by reference in their entirety as if fully set forth.

In an AlkPhos Direct Labeling and Detection System, moderate conditions may be as follows: membranes loaded with DNA samples are prehybridized for at least 15 minutes at 55° C. in the hybridization buffer (12% (w/v) urea, 0.5M NaCl, 4% (w/v) blocking reagent). The labeled probe is added to the same solution and hybridization is carried overnight at 55° C. The membranes are washed for 10 minutes at 55° C. in the primary wash solution (2M urea, 0.1% (W/v) SDS, 50 mM of 0.5M Na phosphate pH 7.0, 150 mM NaCl, 1 mM of 1.0M Mg $Cl_2$ and 0.2% (w/v) of blocking reagent). The washing procedure is repeated. The membranes are placed in a clean container and washed for 5 minutes in a secondary buffer (1M Tris base, and 2M NaCl). The washing in the secondary solution is performed two more time. Chemoluminescence was detected using CDP-STAR® substrate for alkaline phosphatase. Low stringency refers to hybridization conditions at low temperatures, for example, between 37° C. and 60° C. High stringency refers to hybridization conditions at high temperatures, for example, over 68° C.

In the standard protocol, moderate conditions may be as follows: filters loaded with DNA samples are pretreated for 2-4 hours at 68° C. in a solution containing 6× citrate buffered saline (SSC; Amresco, Inc., Solon, Ohio), 0.5% sodium dodecyl sulfate (SDS; Amresco, Inc., Solon, Ohio), 5×Denhardt's solution (Amresco, Inc., Solon, Ohio), and denatured salmon sperm (Invitrogen Life Technologies, Inc.

Carlsbad, Calif.). Hybridization is carried in the same solution with the following modifications: 0.01M EDTA (Amresco, Inc., Solon, Ohio), 100 µg/ml salmon sperm DNA, and 5-20×10⁶ cpm ³²P-labeled or fluorescently labeled probes. Filters are incubated in hybridization mixture for 16-20 hours and then washed for 15 minutes in a solution containing 2×SSC and 0.1% SDS. The wash solution is replaced for a second wash with a solution containing 0.1×SSC and 0.5% SDS and incubated an additional 2 hours at 20° C. to 29° C. below Tm (melting temperature in ° C.). Tm=81.5+16.61 Log$_{10}$([Na⁺]/(1.0+0.7[Na⁺]))+0.41(%[G+C])−(500/n)−P−F. [Na+]=Molar concentration of sodium ions. %[G+C]=percent of G+C bases in DNA sequence. N=length of DNA sequence in bases. P=a temperature correction for % mismatched base pairs (~1° C. per 1% mismatch). F=correction for formamide concentration (=0.63° C. per 1% formamide). Filters are exposed for development in an imager or by autoradiography. Low stringency conditions refers to hybridization conditions at low temperatures, for example, between 37° C. and 60° C., and the second wash with higher [Na+] (up to 0.825M) and at a temperature 40° C. to 48° C. below Tm. High stringency refers to hybridization conditions at high temperatures, for example, over 68° C., and the second wash with [Na+]= 0.0165 to 0.0330M at a temperature 5° C. to 10° C. below Tm. In an embodiment, synthetic nucleic acids having a sequence that has at least 75, 80, 85, 90, 91, 92, 93, 94, 95, 96, 97, 98, 99 or 100% identity along its length to a contiguous portion of a nucleic acid having any one of the sequences set forth herein or the complements thereof are provided. The contiguous portion may be the entire length of a sequence set forth herein or the complement thereof.

In an embodiment a synthetic nucleic acid may encode the fragment of a glucanase that have 316, 317, or 322 amino acids. The synthetic nucleic acids may encode the fragments that include 20, 30, 40, 50, 100, 150, 200, or 300 contiguous amino acids and retain at least 40% activity of the glucanase. The functionality of a glucanase, variants, or fragments thereof, may be determined using any methods. The functionality of a glucanase may be measured by any one of the assays described in Example 3.

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity can be measured by the Smith Waterman algorithm (Smith T F, Waterman M S 1981 "Identification of Common Molecular Subsequences," *Journal of Molecular Biology* 147: 195-197, which is incorporated by reference in its entirety as if fully set forth).

In an embodiment, synthetic nucleic acids, polynucleotides, or oligonucleotides are provided having a portion of the sequence as set forth in any one of the nucleic acids listed herein or the complement thereof. These isolated nucleic acids, polynucleotides, or oligonucleotides are not limited to but may have a length in the range from 10 to full length, 10 to 800, 10 to 10 to 600, 10 to 500, 10 to 400, 10 to 300, 10 to 200, 10 to 100, 10 to 90, 10 to 80, 10 to 70, 10 to 60, 10 to 50, 10 to 40, 10 to 35, 10 to 30, 10 to 25, 10 to 20, 10 to 15, or 20 to 30 nucleotides or 10, 15, 20 or 25 nucleotides. A synthetic nucleic acid, polynucleotide, or oligonucleotide having a length within one of the above ranges may have any specific length within the range recited, endpoints inclusive. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a portion of a sequence as set forth in any one of the nucleic acids listed herein. In an embodiment, a hybridization probe or primer hybridizes along its length to a corresponding length of a nucleic acid having the sequence as set forth in any one of the nucleic acids listed herein. In an embodiment, the hybridization conditions are low stringency. In an embodiment, the hybridization conditions are moderate stringency. In an embodiment, the hybridization conditions are high stringency.

In an embodiment, a transgenic plant comprising a synthetic nucleic acid encoding any one or more of the glucanases described herein is provided. The one or more glucanases expressed in the transgenic plant herein may have activity at a pH ranging from 2.0 to 10.00. The pH may be 2.0, 3.0, 4.0, 5.0, 5.5, 6.0, 7.0, 7.5, 8.0, 9.0, 9.5, or 10, or a pH within a range between any two of the foregoing pH values (endpoints inclusive). The one or more glucanases expressed in a transgenic plant herein may have activity when exposed to a temperature in the range of 25° C. to 130° C., endpoints inclusive. The temperature may be 25° C., 30° C., 35° C., 40° C., 45° C., 50° C., 55° C., 65° C., 70° C., 75° C., 80° C., 85° C., 90° C., 95° C., 100° C., 105° C., 110° C., 115° C., 120° C., 125° C., 130° C., 25° C., to 30° C., 25° C. to 35° C., 25° C. to 40° C., 25° C. to 45° C., 25° C. to 50° C., 25° C. to 55° C., 25° C. to 60° C., 25° C. to 65° C., 25° C. to 70° C., 25° C. to 75° C., 25° C. to 80° C., 25° C. to 85° C., 25° C. to 90° C., 25° C. to 95° C., 25° C. to 100° C., 25° C. to 105° C., 25° C. to 110° C., 25° C. to 115° C., 25° C. to 120° C., 25° C. to 125° C., or less than 130° C. The glucanase expressed in the transgenic plant may have the improved activity compared to the glucanase having an identical amino acid sequence but expressed in a bacterial cell. The glucanase may have improved thermal stability compared to the activity of the glucanase expressed in the bacterial cell.

The one or more glucanase may be produced in any transgenic plant. The transgenic plant may be but is not limited to wheat, maize, soybean, barley, and sorghum.

In an embodiment, a method of making a transgenic plant that includes a glucanase is provided. The method may include contacting a plant cell with any one of the synthetic nucleic acids herein. The synthetic nucleic acids may be part of any one of the vectors described herein. The vector may include a synthetic nucleic acid encoding a glucanase. The glucanase may comprise, consist essentially of, or consist of an amino acid sequence with at least 70, 72, 75, 80, 85, 90, 91, 92, 93, 94, 95, 96, 97, 98, 99, or 100% identity to a reference sequence selected from the group consisting of: SEQ ID NO: 4 [AGR2314], SEQ ID NO: 5 [AGR2414] and SEQ ID NO: 6 [AGR2514]. The method may also include regenerating a transgenic plant from the transgenic plant cell. The method may include selecting the transgenic plant expressing a glucanase.

The transgenic plant herein is also referred to as an "event." An event is characterized by presence of the transgene comprising a synthetic nucleic acid encoding a glucanase. The term "event" also refers to the genomic region of the transformed parent comprising the inserted synthetic nucleic acid sequence and the parent genomic sequences flanking the insertion. The term "event" also refers to progeny produced by crossing of the transgenic plant and a non-transgenic plant of the same genetic background. The term "line" also refers to progeny produced by crossing of the transgenic plant and a non-transgenic plant with any genetic background. After repeated crosses, the transgene and the flanking sequences of the originally transformed parent may be present in a progeny plant in the same location in the genome or on the same chromosome as in the transformed parent.

Applicant made a deposit of at least 2500 seeds of maize event 4588.259(FG 259) with the ATCC, Manassas, Va. 20110-2209 U.S.A., on May 10, 2019, and the deposits were assigned ATCC Deposit No. PTA-125919. These deposits will be maintained under the terms of the Budapest Treaty on the International Recognition of the Deposit of Microorganisms for the Purposes of Patent Procedure.

The transgenic plant may be homozygous for the transgene comprising a synthetic nucleic acid encoding a glucanase.

The transgenic plant may be hemizygous for the transgene comprising a synthetic nucleic acid encoding a glucanase. To produce homozygous plants expressing a glucanase, a hemizygous transgenic plant may be self-crossed. Progeny may be obtained from such crosses. The progeny may include homozygous, hemizygous and wild type plants. A hemizygous plant may be phenotypically indistinguishable from the wild type plants. The method may include analyzing the progeny for the presence of the transgene and selecting a progeny plant that includes the transgene. A method of identifying the homozygous event by PCR is described herein in Example 8.

In an embodiment, the method may further include crossing a hemizygous transgenic plant to another transgenic plant hemizygous for the same transgene. The method may include selecting a first progeny plant that is homozygous for the transgene. The method may further include crossing the transgenic plant to a wild type plant of the same, or different, genetic background. Progeny may be obtained from such crosses. The progeny may include hemizygous and wild type plants. The method may include selecting a first progeny plant that is hemizygous for the transgene. The method may further include selfing the first hemizygous progeny plant and selecting a second progeny plant that is homozygous for the transgene comprising a synthetic nucleic acid sequence encoding a glucanase.

The glucanase may have activity and improved thermal stability when exposed to high temperatures as here described.

It has been unexpectedly discovered that expression and accumulation of an enzyme in a plant provides the enzyme with additional thermal stability relative to the same enzyme that is produced microbially.

In an embodiment, the method of making a transgenic plant includes transformation. For transformation, the nucleic acid may be introduced into a vector. Suitable vectors may be cloning vectors, transformation vectors, expression vectors, or virus-based vectors. The expression cassette portion of a vector may further include a regulatory element operably linked to a nucleic acid encoding a glucanase. In this context, operably linked means that the regulatory element imparts its function on the nucleic acid. For example, a regulatory element may be a promoter, and the operably linked promoter would control expression of the nucleic acid.

The expression of a nucleic acid encoding a glucanase from the expression cassette may be under the control of a promoter which provides for transcription of the nucleic acid in a plant. The promoter may be a constitutive promoter or, tissue specific, or an inducible promoter. A constitutive promoter may provide transcription of the nucleic acid throughout most cells and tissues of the plant and during many stages of development but not necessarily all stages. An inducible promoter may initiate transcription of the nucleic acid sequence only when exposed to a particular chemical or environmental stimulus. A tissue specific promoter may be capable of initiating transcription in a particular plant tissue. Plant tissue may be, but is not limited to, a stem, leaves, trichomes, anthers, cob, seed, endosperm, or embryo. The constitutive promoter may be, but is not limited to the maize ubiquitin promoter (ZmUbi1), Cauliflower Mosaic Virus (CAMV) 35S promoter, the Cestrum Yellow Leaf Curling Virus promoter (CMP), the actin promoter, or the Rubisco small subunit promoter. The tissue specific promoter may be the maize globulin promoter (ZmGlb1), the rice glutelin promoter (prGTL), the maize zein promoter (ZmZ27), or the maize oleosin promoter (ZmOle). The promoter may provide transcription of a synthetic polynucleotide having a sequence with at least 70, 72, 75, 80, 85, 90, 91, 92, 93, 94, 95, 96, 97, 98, 99, or 100% identity to a reference sequence selected from the group consisting of SEQ ID NO: 7 [pAG4258], SEQ ID NO: 8 [pAG4588], SEQ ID NO: 9 [pAG4597], SEQ ID NO: 10 [pAG4708], SEQ ID NO: 11 [pAG4766], SEQ ID NO: 12 [pAG4767], SEQ ID NO: 13 [pAG4770], SEQ ID NO: 14 [pAG4771], SEQ ID NO: 15 [pAG4257], SEQ ID NO: 16 [pAG4692], SEQ ID NO: 17 [pAG4693], SEQ ID NO: 18 [pAG4705] and SEQ ID NO: 19 [pAG4706] and expression of glucanase that is capable of degrading a polysaccharide.

In an embodiment, the transformation in the method of making a transgenic plant may be stable transformation, wherein the nucleic acid encoding the glucanase integrates into the genome of the transformed plant. The transformation may be *Agrobacterium*-mediated transformation using a vector suitable for stable transformation described herein. The method of making a transgenic plant may include any other methods for transforming plants, for example, particle bombardment, or protoplast transformation via direct DNA uptake. The transgenic plant may include any synthetic nucleic acid, amino acid sequence, or vector herein.

In an embodiment, the method of making a transgenic plant may include transient transformation to transiently express the recombinant protein. The term "transient expression" refers to the expression of an exogenous nucleic acid molecule delivered into a cell: e.g., a plant cell, and not integrated in the plant's cell chromosome. Expression from extra-chromosomal exogenous nucleic acid molecules can be detected after a period of time following a DNA-delivery. Virus-based vectors may be used to carry and express exogenous nucleic acid molecules. Virus-based vectors may replicate and spread systemically within the plant. Use of virus based vectors may lead to very high levels of glucanase accumulation in transgenic plants.

Methods of making a transgenic plant, methods of increasing utilization of non-starch polysaccharides in an animal, methods for enhancing production of fermentable sugars from grains, methods for increasing metabolizable energy of a diet, methods preparing and animal feedstock and methods for producing genetically engineered plants homozygous for a synthetic nucleic acid that encodes a glucanase may comprise a method of detection herein as part of making transgenic plants and/or identifying plants, plant biomass or animal feed that comprise a synthetic nucleic acid herein.

An embodiment comprises a kit for identifying maize event 4588.259, 4588.757 or 4588.652 in a sample. The kit may comprise a first primer and a second primer.

The first primer and the second primer may be capable of amplifying a target sequence specific to an event. The target sequence may include a nucleic acid with at least 70, 72, 75, 80, 85, 90, 91, 92, 93, 94, 95, 96, 97, 98, 99, or 100% identity to a reference sequence selected from SEQ ID NOS: 51-55. The target sequence may be a sequence included in a junction between a genomic sequence of a transformed plant and a sequence of the T-DNA insertion. The target sequence may be included in a sequence with at least 70, 72, 75, 80, 85, 90, 91, 92, 93, 94, 95, 96, 97, 98, 99, or 100% identity to a reference sequence selected from SEQ ID NOS: 22-31.

The kit may comprise the first primer comprising a nucleic acid sequence selected from SEQ ID NOS: a nucleic acid sequence selected from SEQ ID NOS: 38, 41, and 47. The kit may comprise the second primer comprising a nucleic acid sequence selected from SEQ ID NOS: 39, 42, 43, 45, and 46. The kit may comprise the first primer comprising the nucleic acid sequence of SEQ ID NO: 38 and the second primer comprising the nucleic sequence of SEQ ID NO: 39. The kit may comprise the first primer comprising the nucleic acid sequence of SEQ ID NO: 41 and the second primer comprising the nucleic acid sequence of SEQ ID NO: 42. The kit may comprise the first primer comprising the nucleic acid sequence of SEQ ID NO: 41 and the second primer comprising the nucleic acid sequence of SEQ ID NO: 43. The kit may comprise the first primer comprising the nucleic acid sequence of SEQ ID NO: 47 and the second primer comprising the nucleic acid sequence of SEQ ID NO: 45. The kit may comprise the first primer comprising the nucleic acid sequence of SEQ ID NO: 47 and the second primer comprising the nucleic acid sequence of SEQ ID NO: 46. The first primer and the second primer may be capable of amplifying the target sequence to produce an amplified product. The amplified product or the target sequence may be capable of hybridizing to the sequence of the nucleic acid comprising a sequence of SEQ ID NO: 40, or SEQ ID NO: 44 under conditions of high stringency. The target sequence may be used as a probe for diagnosing any one of the events described herein.

A sample may include any sample in which nucleic acids from plant matter are present. A sample may be a protein sample. A protein sample may include any sample in which proteins from plant matter are present. The sample or protein sample may include any plant matter. The plant matter may derive from a plant or part thereof. The plant material may derive from an animal feed or food.

In an embodiment, a method of identifying maize event 4588.259, 4588.757 or 4588.652 in a sample is provided. The method may include contacting a sample with a first primer and a second primer. The method may include amplifying a synthetic polynucleotide comprising a target sequence specific to the maize event. The target sequence may be any target sequence described herein. The first primer and the second primer may be capable of amplifying the target sequence to produce an amplified product. The amplified product may be used to determine whether a plant resulted from a sexual crossing or selfing contains one or more of the target sequences and diagnose specific events. The length of the amplified product from the sample of the maize event may differ from the length of the amplified product from the sample of wild type plant of the same genetic background. The amplified product from the event sample may be further used as probe that hybridizes to a synthetic polynucleotide comprising a specific region encoding a glucanase under conditions of high stringency. The method may include further detecting hybridization of the at least one probe to the specific region of the target sequence.

In an embodiment, an animal feedstock comprising any one or more of the transgenic plants described herein or parts of the transgenic plants is provided. The term "animal feedstock" refers to any food, feed, feed composition, diet, preparation, additive, supplement, or mixture suitable and intended for intake by animals for their nourishment, maintenance, or growth. The glucanases included in the transgenic plants and in the animal feedstock may be active in the gastrointestinal or rumen environment of animals. The animal may be a monogastric animal. The animal may be a ruminant animal. The monogastric animal may be but is not limited to a chicken, a turkey, a duck, a swine, a fish, a cat, or a dog. The ruminant animal may be but is not limited to cattle, a cow, a steer, a sheep, or a goat. The glucanases may be active after preparation of the animal feed. The temperatures which feeds are exposed to during ensiling may be within range of 20° C. to 70° C. The temperatures which feeds are exposed to during pelleting may be within range of 70° C. to 130° C. The glucanases may have improved thermal stability and may retain activity after being exposed to high temperatures during feed pelleting. The glucanase with improved thermal stability may comprise, consist essentially of, or consist of an amino acid sequence with at least 70, 72, 75, 80, 85, 90, 91, 92, 93, 94, 95, 96, 97, 98, 99, or 100% identity to a reference sequence selected from the group consisting of: SEQ ID NO: 4 [AGR2314], SEQ ID NO: 5 [AGR2414] and SEQ ID NO: 6 [AGR2514].

In an embodiment, a glucanase may be isolated from the transgenic plant prior to being included into the animal feedstock. The glucanase may be any one of the glucanases described herein.

In an embodiment, the animal feedstock may further include a feed supplement. The feed supplement may be any plant material. The plant material may be a non-transgenic plant or a part thereof. The plant material may include an engineered plant or a mutant plant. The feed supplement may be a mineral. The mineral may be a trace mineral. The mineral may be a macro mineral. The feed supplement may be at least one vitamin. The at least one vitamin may be a fat-soluble vitamin. The feed supplement may include one or more exogenous enzymes. The one or more exogenous enzymes may include a hydrolytic enzyme. The hydrolytic enzyme. The hydrolytic enzyme may be an enzyme classified under EC3.4 as hydrolase. The hydrolytic enzymes may be but are not limited to xylanases, mannanases, carbohydrases, proteases, peptidases, phytases, cellulases, lipases, phospholipases, pectinases, galactosidases, laccases, amylases, hemicellulases, or cellobiohydrolases. The hydrolytic enzymes may be expressed in the engineered plants or parts thereof included in the feed supplement. The feed supplement may include purified hydrolytic enzymes. The feed supplements may be but are not limited to growth improving additives, coloring agents, flavorings, stabilizers, limestone, stearine, starch, saccharides, fatty acids, or a gum. The coloring agents may be carotenoids. The carotenoids may be but are not limited to cantaxanthin, beta-carotene, astaxanthin, or lutein. The fatty acids may be polyunsaturated fatty acids. The polyunsaturated fatty acids may include but are not limited to arachidonic acid, docosohexaenoic acid (DHA), eicosapentaenoic acid (EPA) or gamma-linoleic acid. The feed supplement may be a non-transgenic plant or a part thereof. The non-transgenic plant or part thereof may include at least one component selected from the group consisting of: barley, wheat, rye, oat, corn, rice, triticale beet, sugar beet, spinach, cabbage, quinoa, corn meal, corn pellets, corn oil, distillers grains, forage, wheat meal, wheat pellets, wheat grain, barley grain, barley pellets, soybean meal, soybean oilcake, lupin meal, rapeseed meal, sorghum grain, sorghum pellets, rapeseed, sunflower seed, and cotton seed.

The feed supplement may include at least one component selected from the group consisting of: soluble solids, fat, vermiculite, limestone, plain salt, DL-methionine, L-lysine, L-threonine, monensin sodium COBAN® PREMIX, vitamin premix, inorganic feed phosphates, monocalcium phosphate, dicalcium phosphate, tricalcium phosphate, monodicalcium phosphate, rock phosphate, selenium premix, choline chloride, sodium chloride, and mineral premix.

The feed supplement may include fish meal, fish oil, bone meal, feather meal and animal fat. The feed supplement may include yeast or yeast extract.

In an embodiment, a method of producing an animal feedstock is provided. The method may comprise including a transgenic plant that includes any one or more glucanase described herein in the animal feedstock. The animal feedstock may comprise, consist essentially of or consist of the transgenic plant. The method may further include combining the transgenic plant with a feed supplement. The feed supplement may be a non-transgenic plant or a part thereof. The transgenic plant may be produced by any one of the methods described herein. The feed supplement may be a mineral. The supplement may include one or more exogenous enzymes. The exogenous enzymes may be but are not limited to xylanases, mannanases, carbohydrases, proteases, peptidases, phytases, cellulases, lipases, phospholipases, pectinases, galactosidases, laccases, amylases, hemicellulases, or cellobiohydrolases.

In an embodiment, a method of meat production is provided. The method may include feeding an animal feedstock or one produced by any of the methods described herein to the animal. The method may include preparing an animal feedstock that includes a transgenic plant expressing a glucanase.

In an embodiment, a method of feeding an animal is provided. The method may include feeding an animal feedstock or one produced by any of the methods described herein to the animal. The method may include preparing an animal feedstock that includes a transgenic plant expressing a glucanase.

In an embodiment, a method of increasing utilization of non-starch polysaccharides in an animal is provided. The method may include feeding an animal with an animal feedstock that includes any one or more of the transgenic plants described herein. The method may include preparing the animal feedstock.

In an embodiment, a method of decreasing gastrointestinal viscosity in an animal is provided. The method may include feeding an animal with an animal feedstock that includes any one or more of the transgenic plants described herein. The method may include preparing the animal feedstock.

Addition of exogenous enzymes collectively known as carbohydrases may ameliorate the effects of non-starch polysaccharides (NSPs) in the diet of an animal. An animal feedstock that includes any one or more of glucanases described herein may increase utilization of NSPs by the animal that ingested the feedstock, or may decrease the anti-nutritional effects of the NSP on the animal that ingested the feedstock, and improve growth of the animal. Preparing the animal feedstock may include combining one or more transgenic plant herein with any other feed supplement. The glucanase may be isolated, purified and added to the animal feedstock as a pure glucanase. The glucanase may be added to the animal feedstock in admixture with other feed supplements. The transgenic plant including the glucanase or the purified glucanase may be combined with other feed supplements to form premixes.

An animal feedstock may be produced as mash feed. The animal feedstock may be produced as pellets. The milled feed stuffs may be mixed with the premix that includes any one of the transgenic plants that include a glucanase. The milled feed stuffs may include the plant material and the feed supplements described herein. The feed supplements may include one or more exogenous enzymes described herein. Enzymes may be added as liquid or solid formulations. For mash feed, a solid or liquid enzyme formulation may be added before or during the mixing step. For pelleted feed, the enzyme preparation may be added before or after the pelleting step. The glucanase may be included in a premix. The premix may also include vitamins and trace minerals. Macro minerals may be added separately to animal feedstock.

In an embodiment, a method of increasing metabolizable energy of a diet is provided. Metabolizable energy (ME) refers to the net energy of a diet or feed that is available to an animal after the utilization of some energy in the processes of digestion and absorption and the loss of some of the material as being undigested or indigestible. Metabolizable energy may be apparent metabolizable energy (AME) measured as the difference between the calories of the feed consumed by an animal and excrements collected after feed consumption. Metabolizable energy may be true metabolizable energy (TME), which is similar to AME except that it also takes into account endogenous energy. Energy contents in a diet or feed ingredients may be determined using one of several methodologies (NRC. 1994. Nutrient Requirements of Poultry. 9th rev. ed. Natl. Acad. Press, Washington, D.C., which is incorporated herein by reference as if fully set forth). Gross energy (GE) is direct measurement using an adiabatic bomb calorimeter, which measures the heat of combustion of a sample within a high oxygen atmosphere. Apparent digestible energy (DE) is GE of a feed or feedstuff minus GE of feces only. Apparent metabolizable energy (AME) is GE of a feed or feedstuff minus GE of feces, urine, and gaseous products from digestion. For poultry, the gaseous release is very low, and typically neglected due to its very small value, and the urine and feces are excreted together and are not collected separately in most cases. True metabolizable energy (TME) accounts for only the GE from excreta that is from the feed or feedstuff origin, by subtracting the endogenous energy loss from non-feed origin (i.e. sloughing of intestinal tract cells). Another energy measurement used for feedstuffs in animals is net energy (NE) which adjusts for heat increment. Since heat increment is dependent on level of productivity, which fluctuates in poultry because of short lifespan, this variable is not frequently used in poultry.

The TME rooster assay may be used to account for endogenous (non-feed) losses of GE by including a fasted rooster and collecting excreta to correct the GE from the fed (feed/feedstuff) rooster. See Sibbald, 1976, Poultry Science 55: 303-308, which is incorporated herein by reference as if fully set forth. This assay has commonly been used for determining TME of individual feedstuffs rather than complete feed, and requires cecetomized roosters (ceca surgically removed) to always be on hand. The assay involves force-feeding (into the crop) a known quantity of an ingredient (in birds that were previously fasted 24-48 hr) and then collect feces for a 24-48 hour period. The equation used to calculate TME is given as TME={(GE$_f$×FI)−[(GE$_e$×EO)$^+$−(GE$_e$×EO)$^-$]}/FI, where Gross Energy (GE) is determined by bomb calorimetry in kcal/kg; FI is feed intake (kg); EO is excreta output fed birds (kg); GE$_e$ is the Gross Energy of the excreta content; GE$_f$ is the Gross Energy of the feed; "+" signifies the quantity is from the fed birds energy output; and "−" signifies that the quantity is from the fasted birds energy output. The roosters (or turkeys) used in TME assays are adult birds with a fully developed digestive tract. Research has shown that there are differences in ME determinations using roosters (layer breeds), turkeys and broilers when analyzing same feed ingredients (Cozannet et al, 2010 J. Anim, Sci., 88(7):2382-2392, which is incorporated herein by reference as if fully set forth). So determining TME or AME using rooster model may not be equivalent to what is observed in a young broiler, but is a commonly used proxy in research and industry.

For broilers, the AME assay may be used for determining complete feed and some energy supplying feedstuffs, as well as the effect from adding feed ingredients that aid in digestion. There are two common methods for determining ME: 1) doing a total excreta collection and weighing and record feed consumption during the time period (Equation 1 below) or 2) using an indigestible marker in feed (chromic oxide, titanium oxide or acid insoluble ash) and taking a subsample of feces with no weighing required (Equation 2 below). The marker method of AME determination may be used, in which no weighing of feed consumption or total fecal collection and no need to separate feed spilled from feces pan are required. With the marker method, birds are fed the marker for at least two days (but preferably five or more days). Feces are collected over several days (e.g., three days) with daily collection composited into one sample.

AME using the total collection method (Equation 1) is calculated as follows:

$$AME=[(GE_f \times FI)-(GE_e \times EO)]/FI,$$

where Gross Energy (GE) is measured in bomb calorimetry (kcal/kg); FI is feed intake (kg); EO is excreta output (kg); $_e$ refers to excreta content; and $_f$ refers to the feed content. AME using the marker method is calculated as AME=[(GE$_e$/M$_e$)−(GE$_f$/M$_f$)]/(GE$_e$/M$_e$), where Gross Energy is GE (kcal/kg); M is the marker (ppm or %); "$_e$"=excreta content; "$_f$"=feed content.

Another method that may be used to determine AME of feed when investigating feed additives that aid in digestion is Ileal digestible energy (IDE). This method uses the AME marker method (described above), but the birds are euthanized and a section of ileum excised and contents removed, dried and analyzed for GE and the marker. The IDE method may be used effectively for testing and comparing feed additives used to improve digestion/absorption of feed energy. The benefit of IDE, is no cages with collection pans are required and can collect during a floor-pen study. With the marker method, birds are fed the marker for at least two days (and preferably five or more days).

AME using the IDE marker method (Equation 2) is calculated as follows:

$$AME=GE_f \times (GE_d \times M_f/M_d),$$

where GE (kcal/kg); M represents the marker; "$_d$" represents the digesta content; and "$_f$" signifies the feed content.

AME and TME may be corrected for nitrogen retention (AMEn and TMEn). To adjust, the grams of N are multiplied by 8.22 kcal/g (GE of uric acid; primary excretory product of protein tissue oxidized for energy), which also is sub- tracted off of the GE consumed. See Hill, F. W., and D. L. Anderson, 1958, "Comparison of metabolizable energy and productive energy determinations with growing chicks." J. Nutr. 64:587-603, which is incorporated herein by reference as if fully set forth. Calculations for total collection of marker method for AMEn are shown in Equation 3 and Equation 4 below, respectively.

$$AMEn=\{(GE_f \times FI)-(GE_e \times EO)-[8.22\times(N_f-N_e)]\}/FI, \quad \text{Equation 3: AMEn, total collection:}$$

where GE=kcal/kg; FI=feed intake (kg); EO=excreta output (kg); N=nitrogen (g); $_e$=excreta content; $_f$=feed content.

$$AMEn=GE_f-(GE_d \times M_f/M_d)-\{8.22\times[N_f-(N_d \times M_f/M_d)]\}, \quad \text{Equation 4: IDEn, marker method:}$$

where GE=kcal/kg; M=marker; N=nitrogen (g/kg) "$_d$"=digesta content; "$_f$"=feed content.

While the TME method may be used for determining ME of individual ingredients, the AME (IDE) method may be used with broilers to measure ME in individual ingredients or total diet and testing effects improving ME by use of enzymes or other feed additives.

A diet or feed may include any feed ingredient or mixture of ingredients including water. The diet may be any food, feed, feed composition, diet, preparation, additive, supplement, or mixture included in an animal feedstock described herein. The diets are known in the art and described at least in the following publications: Nutrient Requirements of Poultry, 1994, National Research Council, National Academy Press, Washington, D.C.; Broiler Performance and Nutrition Supplement, Cobb-500™, L-2114-07EN, July, 2015; Broiler Performance and Nutrition Supplement, Cobb-700™, L-21124-13EN, Dec. 21, 2012; Broiler Performance and Nutrition Supplement, CobbAvian™, L-2144-04EN, April, 2012; Broiler Performance and Nutrition Supplement, CobbSasso™, L-2154-01, May 7, 2008; Ross 308 Broiler: Nutrition Specifications, 2014 Aviagen, 0814-AVNR-035; Ross Nutrition Supplement 2009, Aviagen; Ross 708 Broiler: Nutrition Specification, 2014 Aviagen, 0814-AVNR-036; Ross PM3 Brioler Nutrition Specification, 2014 Aviagen, 0814-AVNR-037; Arbor Acres Plus Broiler Nutrition Specifications, 2014 Aviagen, 1014-AVNAA-043; Arbor Acres Broiler Nutrition Supplement, 2009 Aviagen; and Association of American Feed Control Officials (AAFCO) 2015 Official Publication, Nutrient Requirements for Poultry, all of which are incorporated herein by reference as if fully set forth.

In an embodiment, the diet may be a diet for broilers. The diet for broilers may be composed of one or more of the following ingredients: 51.49% (w/w)-61.86% (w/w) corn, 25.45% (w/w)-35.03% (w/w) soybean meal, 5.00% (w/w) corn distillers dry grains plus soluble solids, 2.00% (w/w) vermiculite, 0.30% (w/w)-1.99% (w/w) dicalcium phosphate, 1.00% (w/w) poultry fat, 0.81% (w/w)-4.01% (w/w) limestone, 0.24% (w/w)-0.50% (w/w) salt (NaCl), 0.13% (w/w)-0.45% (w/w) DL-methionine, 0.20% (w/w) choline chloride 60, 0.20% (w/w) mineral premix, 0.05% (w/w) vitamin premix, 0.13% (w/w)-0.23% (w/w) L-lysine, 0.08% (w/w)-0.14% (w/w) L-threonine, 0.05% (w/w) coban, 0.05% (w/w) selenium premix, 0.15% (w/w) sodium bicarbonate and 0.10% (w/w) sand. Digestible lysine in the diet may be 1.00% (w/w) to 1.20% (w/w). Digestible methionine in the diet may be 0.47% (w/w) to 0.54% (w/w). Digestible methionine and cysteine in the diet may be 0.98% (w/w) to 1.10% (w/w). Digestible threonine in the diet may be 0.68% (w/w) to 0.84% (w/w). Digestible tryptophan in the diet may be 0.17% (w/w) to 0.22% (w/w). Calcium in the diet may be 0.71% (w/w) to 0.96% (w/w). Available phosphorus in the diet may be 0.17% (w/w) to 0.46% (w/w). Sodium in the diet may be 0.17% (w/w) to 0.19% (w/w). The concentration of each ingredient within any one of the ranges herein may be any value between any two of the concentration points included in the range. In an embodiment, the diet may be the diet for broilers composed of one or more of the following ingredients: 30.00% (w/w)-75.00% (w/w) corn, 5.00% (w/w)-75.00% (w/w) wheat; 5.00% (w/w)-65.00% (w/w) barley; 5.00% (w/w)-30.00% (w/w) sorghum, 5.00% (w/w)-50.00% (w/w) millet, 10.00% (w/w)-45.00% (w/w) soybean meal, 5.00% (w/w)-20.00% (w/w) Canola (Rapeseed) meal, 2.00% (w/w)-15.00% (w/w) corn gluten meal, 5.00% (w/w)-15.00% (w/w) sunflower meal, 5.00% (w/w)-30.00% (w/w) corn distillers dry grains plus soluble solids, 1.00% (w/w)-8.00% (w/w) poultry/porcine/bovine meat and bone meal, 1.00% (w/w)-8.00% (w/w) fish meal, 0.10% (w/w)-2.1% (w/w) dicalcium or monocalcium or defluorinated phosphate, 0.50% (w/w)-6.00% (w/w) soy oil or vegetable oil or animal fat or grease or combination, 0.81% (w/w)-2.00% (w/w) limestone, 0.50% (w/w)-7.00% soy hulls, 0.24% (w/w)-0.50% (w/w) salt (NaCl), 0.13% (w/w)-0.50% (w/w) DL-methionine, 0.01% (w/w)-0.20% (w/w) choline chloride 60, 0.10% (w/w)-0.20% (w/w) mineral premix, 0.05% (w/w)-0.25% (w/w) vitamin premix, 0.05% (w/w)-0.30% (w/w) L-lysine, 0.10% (w/w)-0.30% (w/w) DL-Methionine or methionine analog (MHA), 0.05% (w/w)-0.20% (w/w) L-threonine, 0.05% (w/w) coban, 0.05% (w/w) selenium premix, 0.05% (w/w)-0.15% (w/w) sodium bicarbonate and 250 FTU/kg-2000 FTU/kg Phytase. Metabolizable energy of the diet may be 1225 (kcal/lb)-1491 (kcal/lb). Crude protein (CP) in the diet may be 15% (w/w) to 25% (w/w). Digestible lysine in the diet may be 0.85% (w/w) to 1.30% (w/w). Digestible methionine in the diet may be 0.45% (w/w) to 0.70% (w/w). Digestible methionine and cystine in the diet may be 0.65% (w/w) to 1.10% (w/w). Digestible threonine in the diet may be 0.60% (w/w) to 0.84% (w/w). Digestible tryptophan in the diet may be 0.10% (w/w) to 0.25% (w/w). Calcium in the diet may be 0.68% (w/w) to 1.10% (w/w). Available phosphorus in the diet may be 0.17% (w/w) to 0.50% (w/w). Sodium in the diet may be 0.17% (w/w) to 0.19% (w/w). Phytase in the diet may be 500 FTU/kg (w/w) to 8,000 FTU/kg (w/w). The concentration of each ingredient within any one of the ranges herein may be any value between any two of the concentration points included in the range. Variations in the concentrations of these ingredients may also be used in a diet.

The method may include mixing a transgenic plant or part thereof with a feed ingredient to obtain a mixture. The feed ingredient may be one or more ingredients included in the diet described herein. The transgenic plant or part thereof may be any transgenic plant or part thereof described herein. The method may include feeding an animal with the mixture. The body weight gain (BWG) in an animal fed with the mixture comprising a glucanase may be higher than the BWG in a control animal fed with identical feed ingredients not mixed with a transgenic plant including a glucanase. In an embodiment, the BWG in an animal fed with the mixture comprising a glucanase may be similar to the BWG in a control animal fed with a high energy diet or a diet that includes more or higher concentrations of the ingredients compared to the mixture including a glucanase. In an embodiment, the feed conversion ratio (FCR) in an animal fed with the mixture comprising a glucanase may be lower than the FCR in a control animal fed with identical feed ingredients not mixed with a transgenic plant including a glucanase. The FCR is defined as the mass of the feed eaten by the animal divided by the animal's mass. In an embodiment, the FCR in an animal fed with the mixture comprising a glucanase may be similar to the FCR in a control animal fed with a high energy diet or a diet that includes more or higher concentrations of the ingredients compared to the mixture including a glucanase.

In an embodiment, a method of enhancing thermal stability of a glucanase is provided. The method may include producing a transgenic plant that includes a synthetic nucleic acid encoding the glucanase. The synthetic nucleic acid may include any one the sequences described herein. The glucanase may be thermally stable upon exposure to temperatures in the range of 70° C. to 130° C., endpoints inclusive.

The glucanase may be thermally stable upon exposure to temperatures in the range of 25° C. to 130° C., endpoints inclusive. The glucanase may be thermally stable upon exposure to temperatures in the range from 25° C., 30° C., 35° C., 40° C., 45° C., 50° C., 55° C., 65° C., 70° C., 75° C., 80° C., 85° C., 90° C., 95° C., 100° C., 105° C., 110° C., 115° C., 120° C., 125° C., 130° C., 25° C., to 30° C., 25° C. to 35° C., 25° C. to 40° C., 25° C. to 45° C., 25° C. to 50° C., 25° C. to 55° C., 25° C. to 60° C., 25° C. to 65° C., 25° C. to 70° C., 25° C. to 75° C., 25° C. to 80° C., 25° C. to 85° C., 25° C. to 90° C., 25° C. to 95° C., 25° C. to 100° C., 25° C. to 105° C., 25° C. to 110° C., 25° C. to 115° C., 25° C. to 120° C., 25° C. to 125° C., or less than 130° C. The glucanase may be thermally stable upon exposure to temperatures in the range of 70° C. to 130° C., endpoints inclusive. The glucanase may be thermally stable upon exposure to temperatures in the range from 7° C. to 75° C., 70° C. to 80° C., 70° C. to 85° C., 70° C. to 90° C., 70° C. to 95° C., 70° C. to 100° C., 70° C. to 105° C., 70° C. to 110° C., 70° C. to 115° C., 70° C. to 120° C., or 70° C. to 130° C., endpoints inclusive.

The above mentioned synthetic nucleic acids may be provided in embodiments herein alone, as part of another nucleic acid, as part of a vector or as stated above as part of a transgenic plant.

In an embodiment, the transgenic plant may be derived from one of corn, rye, switchgrass, miscanthus, sugarcane or sorghum. The transgenic plant may be made by *Agrobacterium* mediated transformation using a vector having a nucleic sequence as set forth above.

In an embodiment, a method for enhancing production of fermentable sugars from grains is provided. The method may include mixing grains derived from any one of the transgenic plants described herein with grains from a different plant to form mixed grains. The different plant may be a non-transgenic plant. The different plant may be an engineered plant that includes a synthetic nucleic acid encoding at least one hydrolytic enzyme. The hydrolytic enzyme may be but is not limited to xylanase, an amylase, an endoglucanase, an exoglucanase, a feruloyl esterase, a glucoamylase, an intein-modified amylase, an intein-modified xylanase, an intein-modified endoglucanase, an intein-modified exoglucanase, an intein-modified feruloyl esterase, a protease, an intein-modified protease, a phytase, or an intein-modified phytase. The method may include processing the mixed grains. The processing may include one or more operations selected from the group consisting of harvesting, baling, grinding, milling, chopping, size reduction, crushing, pellitizing, extracting a component from the mixed grains, purifying a component or portion of the mixed grains, extracting or purifying starch, hydrolyzing polysaccharides into oligosaccharides or monosaccharides, ensiling, mixing with silage or other biomass and ensiling, fermentation, chemical conversion, and chemical catalysis. The biomass may be but is not limited to hay, straw, stover, silage, compressed and pelleted feeds, soybeans, sprouted grains, legumes, feed grains, maize, rice, barley or wheat grains. The biomass may be any biomass derived from agricultural waste. The method may include converting fermentable sugars into a biochemical product. The biochemical product may be but is not limited to ethanol, butanol, lactic acid, citric acid, and acetic acid.

In an embodiment, a method for reducing the viscosity of a grain mixture is provided. The method may include mixing grains derived from any one of the transgenic plants described herein with grains from a different plant to form mixed grains. Water may be added to the mixed grains to form the grain mixture. The viscosity of the grain mixture may be lower when it includes any one of the glucanases described herein. The viscosity may be intestinal viscosity, which is typically measured from an intestinal sample removed from a bird or pig after euthanization. In this method, the digesta sample is centrifuged and the viscosity of supernatant is analyzed using a viscometer. For example, as describe by Lee et al., ileal digesta was centrifuged for 10 min at 3,500× gravity and 0.5 ml of supernatant was put in a Brookfield Cone and Plate Viscometer[1] with a CPE-40 spindle. See Lee, J. T., C. A. Bailey, and A. L. Cartwright. 2003. β-Mannanase ameliorates viscosity-associated depression of growth in broiler chickens fed guar germ and hull fractions. Poult. Sci. 82:1925-1931, which is incorporated herein by reference as if fully set forth. Samples are analyzed for 30 sec at 40° C. and 5 rpm, to determine centipoise (cP units) readings. The higher the cP, the higher the viscosity of the sample.

The different plant may be a non-transgenic plant. The different plant may be an engineered plant that includes a synthetic nucleic acid encoding at least one hydrolytic enzyme. The hydrolytic enzyme may be but is not limited to xylanase, an amylase, an endoglucanase, an exoglucanase, a feruloyl esterase, a glucoamylase, an intein-modified amylase, an intein-modified xylanase, an intein-modified endoglucanase, an intein-modified exoglucanase, an intein-modified feruloyl esterase, a protease, an intein-modified protease, a phytase, or an intein-modified phytase. The method may include processing the grain mixture. The processing may include one or more operations selected from the group consisting of harvesting, grinding, milling, size reduction, crushing, heating, gelotinzing, liquefaction, extracting a component from the mixed grains, purifying a component or portion of the mixed grains, extracting or purifying starch, hydrolyzing polysaccharides into oligosaccharides or monosaccharides, saccharifying, fermentation, chemical conversion, and chemical catalysis.

In an embodiment, a method for enhancing ethanol production from grains is provided. The method includes performing any one of the methods for enhancing production of fermentable sugars described herein.

The following list includes particular embodiments of the present invention. But the list is not limiting and does not exclude alternate embodiments, as would be appreciated by one of ordinary skill in the art.

Embodiments

1. A transgenic plant comprising a synthetic nucleic acid encoding a glucanase, wherein the glucanase includes an amino acid sequence with at least 70% identity to a reference sequence selected from the group consisting of: SEQ ID NOS: 4-6, and is capable of degrading one or more polysaccharides.

2. The transgenic plant of embodiment 1, wherein the one or more polysaccharides is selected from the group consisting of beta-glucan, cellulose, cellobiose, pNP-D-glucopyranoside and xylan.

3. The transgenic plant of any one or both of the preceding embodiments, wherein the glucanase is active upon expression in the plant and exposure to a pH in the range from 4.0 to 10.0.

4. The transgenic plant of any one or more of the preceding embodiments, wherein the glucanase is active upon expression in the plant and exposure to a temperature in the range from 25° C. to 130° C.

5. The transgenic plant of any one or more of the preceding embodiments, wherein the glucanase activity has improved stability upon expression in the plant compared to the activity of a glucanase having an identical amino acid sequence and expressed in a bacterial cell.

6. The transgenic plant of any one or more of the preceding embodiments, wherein a plant is selected from the group consisting of: wheat, maize, barley, rice, and sorghum.

7. A transgenic plant comprising a synthetic nucleic acid including a sequence with at least 70% identity to a reference sequence selected from the group consisting of: SEQ ID NOS: 1-3, wherein the glucanase is capable of degrading one or more polysaccharides.

8. The transgenic plant of embodiment 7, wherein the one or more polysaccharides is selected from the group consisting of beta-glucan, cellulose, cellobiose, pNP-D-glucopyranoside and xylan.

9. The transgenic plant of any one or more of embodiments 7-8, wherein the glucanase is active upon expression in the plant and exposure to a pH in the range from 4.0 to 10.0.

10. The transgenic plant of any one or more of embodiments 7-9, wherein the glucanase is active upon expression in the plant and exposure to a temperature in the range from 25° C. to 130° C.

11. The transgenic plant of any one or more of embodiments 7-10, wherein the glucanase activity has improved stability upon expression in the plant compared to the activity of a glucanase having an identical amino acid sequence and expressed in a bacterial cell.

12. The transgenic plant of any one or more of embodiments 7-11, wherein the transgenic plant is a plant is selected from the group consisting of: wheat, maize, barley, rice, and sorghum.

13. The transgenic plant of any one or more of embodiments 7-12, which comprises the nucleic acid sequence of SEQ ID NO: 1 and produces an amplicon for diagnosing event 4588.259, 4588.757, or 4588.652.

14. A synthetic nucleic acid comprising a sequence with at least 70% identity to a reference sequence selected from the group consisting of: SEQ ID NOS: 1-3, wherein the glucanase is capable of degrading one or more polysaccharides.

15. The synthetic nucleic acid of embodiment 14, wherein the one or more polysaccharides is selected from the group consisting of beta-glucan, cellulose, cellobiose, pNP-D-glucopyranoside and xylan.

16. A synthetic polynucleotide comprising a sequence with at least 70% identity to a reference sequence selected from the group consisting of SEQ ID NO: 7-19, wherein the synthetic polynucleotide comprises a synthetic nucleic acid encoding a glucanase that is capable of degrading one or more polysaccharides.

17. The synthetic polynucleotide of embodiment 16, wherein the one or more polysaccharides is selected from the group consisting of beta-glucan, cellulose, cellobiose, pNP-D-glucopyranoside and xylan.

18. A vector comprising a synthetic polynucleotide, or a fragment of a synthetic polynucleotide, of embodiment 17.

19. A method of making a transgenic plant that includes a glucanase comprising:
contacting a plant cell with a synthetic nucleic acid encoding an amino acid sequence with at least 70% identity to a reference sequence selected from the group consisting of: SEQ ID NOS: 1-3, wherein the glucanase is capable of degrading one or more polysaccharides;
regenerating a transgenic plant from the transgenic plant cell; and
selecting the transgenic plant expressing a glucanase, wherein the glucanase is active and thermally stable upon exposure to a temperature in the range from 25° C. to 130° C.

20. The method of embodiment 19, wherein the one or more polysaccharide is selected from the group consisting of beta-glucan, cellulose, cellobiose, pNP-D-glucopyranoside and xylan.

21. The method of any one or both of embodiments 19-20, wherein the synthetic nucleic acid is part of a vector of embodiment 13.

22. An animal feedstock comprising a transgenic plant or part thereof of any one or more of embodiments 1-13, the product of any one or more of embodiments, 19-21, or a synthetic polypeptide of any one or more of embodiments 51-54.

23. The animal feedstock of embodiment 22 further comprising a feed supplement or feed additive.

24. The animal feedstock of any one or both of embodiments 22-23, wherein the feed supplement is plant material.

25. The animal feedstock of any one or more of embodiments 22-24, wherein the plant material is a non-transgenic plant.

26. The animal feedstock of any one or more of embodiments 22-24 wherein the plant material is an engineered plant.

27. The animal feedstock of any one or more of embodiments 22-26, wherein the feed supplement includes one or more exogenous enzymes.

28. The animal feedstock of embodiment 27, wherein the one or more exogenous enzyme includes a hydrolytic enzyme selected from the group consisting of: xylanase, endoglucanase, cellulase, exoglucanase, feruloyl esterase, an intein-modified xylanase, an intein-modified endoglucanase, an intein-modified cellulase, an intein-modified exoglucanase, an intein-modified feruloyl esterase, mannanase, amylase, an intein-modified amylase, phytase, an intein-modified phytase, protease, and an intein-modified protease.

29. The animal feedstock of any one or more embodiments 22-28, wherein the plant material includes at least one component selected from the group consisting of: forage, biomass, corn meal, corn pellets, wheat meal, wheat pellets, wheat grain, barley grain, barley pellets, soybean meal, soybean oilcake, silage, sorghum grain and sorghum pellets.

30. The animal feedstock of any one or more of embodiments 23-29, wherein the feed supplement includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix.

31. A method of producing an animal feedstock comprising mixing 1) a transgenic plant or part thereof of any one or more of embodiments 1-13, 2) the product of any one or more of embodiments 19-41, or 3) a synthetic polypeptide of any one or more of embodiments 51-54 with plant material.

32. The method of embodiment 31 further comprising pelletizing the mixture.

33. The method of embodiment 32 further comprising adding a feed supplement to the mixture.

34. The method of embodiment 33, wherein the feed supplement includes at least one exogenous enzyme.

35. The method of embodiment 34, wherein the at least one exogenous enzyme includes a hydrolytic enzyme selected from the group consisting of: xylanase, endoglucanase, cellulase, exoglucanase, feruloyl esterase, an intein-modified xylanase, an intein-modified endoglucanase, an intein-modified exoglucanase, an intein-modified cellulase, an intein-modified feruloyl esterase, amylase, an intein-modified amylase, mannanase, phytase, and protease.

36. A method of increasing utilization of non-starch polysaccharides in an animal comprising feeding an animal with an animal feedstock 1) including a transgenic plant of any one or more of embodiments 1-13, 2) of any or more of embodiments 22-30, 3) produced by the method of any one or more of embodiments 31-35, or 4) including a synthetic polypeptide of any one or more of embodiments 51-54.

37. The method of embodiment 36 further comprising preparing the animal feedstock.

38. The method of any or both of embodiments 36-37, wherein the animal is a monogastric animal or a ruminant animal.

39. A method of enhancing thermal stability of a glucanase comprising producing a transgenic plant that includes a synthetic nucleic acid comprising, consisting essentially of, or consisting of an amino acid a sequence having 70% identity to a reference sequence of selected from the group consisting of: SEQ ID NOS: 4-6, wherein the sequence encodes a glucanase capable of degrading one or more polysaccharides.

40. The method of embodiment 39, wherein the one or more polysaccharides is selected from the group consisting of beta-glucan, cellulose, cellobiose, pNP-D-glucopyranoside and xylan.

41. The method of any or both of embodiments 39-40, wherein expression of the nucleic acid produces the glucanase and the glucanse is thermally stable upon exposure to a temperature in the range of 25° C. to 130° C.

42. A method for enhancing production of fermentable sugars from grains comprising: mixing grains derived from a transgenic plant of any one of any one or more of embodiments 1-13 with grains derived from a different plant to form mixed grains; and processing the mixed grains.

43. The method of embodiment 42, wherein the different plant is an engineered plant that includes a synthetic nucleic acid encoding at least one hydrolytic enzyme.

44. The method of any or both of embodiments 42-43, wherein the at least one hydrolytic enzyme is selected from the group consisting of: xylanase, an endoglucanase, an exoglucanase, cellulase, a feruloyl esterase, an intein-modified xylanase, an intein-modified endoglucanase, an intein-modified exoglucanase, an intein-modified cellulase, an intein-modified feruloyl esterase, amylase, phytase and protease.

45. The method of any one or more of embodiments 42-43, wherein the processing includes at least one operations selected from the group consisting of harvesting, baling, grinding, milling, chopping, size reduction, crushing, pellitizing, extracting a component from the mixed grains, purifying a component or portion of the mixed grains, extracting or purifying starch, hydrolyzing polysaccharides into oligosaccharides or monosaccharides, ensiling, fermentation, chemical conversion, and chemical catalysis.

46. The method of embodiment 45 further comprising producing a biochemical product.

47. The method of embodiment 46, wherein the biochemical product is selected from the group consisting of ethanol, butanol, lactic acid, citric acid, and acetic acid.

48. A method for enhancing ethanol production from grains comprising performing a method of any one or more of embodiments 42-47.

49. A method for enhancing ethanol production from a transgenic plant comprising:
   mixing a transgenic plant or part thereof of any one or more of embodiments 1-13 with a different plant or part thereof to form mixed plant material;
   converting the mixed plant material into fermentable sugars; and
   processing the fermentable sugars into ethanol.

50. The method of embodiment 49, wherein the plant material includes fiber, grain, or a combination thereof.

51. A synthetic polypeptide that includes an amino acid sequence with at least 70% identity to a reference sequence selected from the group consisting of: SEQ ID NOS: 4-6, and capable of degrading one or more polysaccharides.

52. The synthetic polypeptide of embodiment 51, wherein the one or more polysaccharides is selected from the group consisting of beta-glucan, cellulose, cellobiose, pNP-D-glucopyranoside and xylan.

53. A synthetic polypeptide that includes an amino acid sequence comprising a contiguous amino acid sequence having at least 90% identity to 50 to 100, 50 to 150, 50 to 200, 50 to 250, 50 to 300, 50 to 322, or 50 to all contiguous amino acid residues of a glucanase having the sequence of any of SEQ ID NOS: 4-6, wherein the glucanase is capable of degrading one or more polysaccharides.

54. The synthetic polypeptide of embodiment 51, wherein the one or more polysaccharides is selected from the group consisting of beta-glucan, cellulose, cellobiose, pNP-D-glucopyranoside and xylan.

55. A method of increasing metabolizable energy of a diet comprising mixing a transgenic plant or part thereof with a feed ingredient, wherein the transgenic plant or part thereof comprises a synthetic nucleic acid encoding a glucanase comprising an amino acid sequence with at least 70% identity to a reference sequence selected from the group consisting of SEQ ID NOS: 4-6, and and capable of degrading one or more polysaccharides.

56. The synthetic polypeptide of embodiment 55, wherein the one or more polysaccharides is selected from the group consisting of beta-glucan, cellulose, cellobiose, pNP-D-glucopyranoside and xylan.

57. The method of any one or both of embodiments 55-56, wherein the synthetic nucleic acid comprises a sequence with at least 70% identity to a reference sequence selected from the group consisting of: SEQ ID NOS: 1-3.

58. The method of any one or more of embodiments 55-57, wherein the glucanase is active upon expression in the plant and exposure to a pH in the range from 5.0 to 10.0.

59. The method of any one or more of embodiments 55-58, wherein the glucanase is active upon expression in the plant and exposure to a temperature in the range from 25° C. to 130° C.

60. The method of any one or more of embodiments 55-59, wherein the feed ingredient includes at least one component selected from the group consisting of: corn meal, corn pellets, wheat meal, wheat pellets, wheat grain, wheat middlings, barley grain, barley pellets, soybean meal, soy hulls, dried distillers grain, soybean oilcake, sorghum grain and sorghum pellets.

61. The method of any one or more of embodiments 55-60, wherein the feed ingredient includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, mineral premix, and one or more exogenous enzymes.

62. A method for producing an animal feedstock comprising mixing a transgenic plant or part thereof of any one or more of embodiments 1-13 with plant material. The method may also comprise the method for producing a plant that includes a glucanase of any one or more of embodiments 63-68.

63. A method for producing a plant that includes a glucanase comprising crossing a plant with a transgenic plant comprising event 4588.259, 4588.757 or 4588.652, and selecting a first progeny plant comprising event 4588.259, 4588.757 or 4588.652 and capable of degrading one or more polysaccharides.

64. The method of embodiment 63, wherein the one or more polysaccharides is selected from the group consisting of beta-glucan, cellulose, cellobiose, pNP-D-glucopyranoside and xylan.

65. The method of any one or more of embodiments 63-64 further comprising selfing the first progeny plant and selecting a second progeny plant comprising event 4588.259, 4588.757 or 4588.652 and capable of degrading one or more polysaccharides.

66. The method of embodiment 65, wherein the second progeny plant is homozygous for event 4588.259, 4588.757 or 4588.652.

67. The method of embodiment 65, wherein the second progeny plant is heterozygous for event 4588.259, 4588.757 or 4588.652.

68. The method of embodiment 67 further comprising selfing the second progeny plant and selecting a third progeny plant homozygous event 4588.259, 4588.757 or 4588.652 and capable of degrading one or more polysaccharides.

69. A kit for identifying maize event 4588.259, 4588.757 or 4588.652 in a sample comprising a first primer and a second primer, wherein the first primer and the second primer are capable of amplifying a target sequence specific to maize event 4588.259, 4588.757 or 4588.652.

70. The kit of any one or more of embodiment 69 wherein, the first primer comprises a nucleic acid sequence selected from SEQ ID NOS: 38, 41, and 47.

71. The kit of any one or more of embodiments 69-70, wherein the second primer comprises a nucleic acid sequence selected from SEQ ID NOS: 39, 42, 43, 45, and 46.

72. The kit of any one or more of embodiments 69-71, wherein the target sequence comprises a sequence selected from the group consisting of SEQ ID NOS: 51-55.

73. The kit of any one or more of embodiments 69-72, wherein the target sequence is capable of hybridizing to the sequence of the nucleic acid comprising a sequence of SEQ ID NOS: 40 or 44 under conditions of high stringency.

74. The kit of any one or more of embodiments 69-73, wherein the sample comprises plant matter derived from a transgenic plant of any one or more of embodiments 1-13.

75. A method of identifying maize event 4588.259, 4588.757 or 4588.652 in a sample comprising:
   contacting a sample with a first primer and a second primer of the kit of any one or more of embodiments 69-74;
   amplifying a nucleic acid in the sample to obtain an amplified product; and
   detecting an amplified product specific to a target sequence in maize event 4588.259, 4588.757 or 4588.65.

76. The method of embodiment 75, wherein the target sequence comprises a sequence selected from SEQ ID NOS: 51-55. The method of identifying may be added to any one or more of embodiments 63-68.

77. The method of embodiment 75, wherein the target sequence is at least one sequence selected from the group consisting of SEQ ID NOS: 22-31.

78. The method of embodiment 75, wherein the step of detecting comprises hybridizing the amplified product to the nucleic acid comprising a sequence of SEQ ID NOS: 40 under conditions of high stringency, and selecting the amplified product specific to maize event 4588.259.

79. The method of embodiment 75, wherein the step of detecting comprises hybridizing the amplified product to the nucleic acid comprising a sequence of SEQ ID NOS: 44 under conditions of high stringency, and selecting the amplified product specific to maize event 4588.652.

80. A method for reducing the viscosity of a grain mixture comprising combining grains from a transgenic plant of any one or more of embodiments 1-13, a different plant, and liquid to form a grain mixture.

81. The method of embodiment 80, wherein the different plant is a non-transgenic plant.

82. The method of embodiment 80, wherein the different plant is a genetically engineered plant.

83. The method of embodiment 80 and 82, wherein the genetically engineered plant comprises a synthetic nucleic acid encoding at least one hydrolytic enzyme.

84. The method of embodiment 83, wherein the at least one hydrolytic enzyme is selected from the group consisting of: xylanase, an amylase, an endoglucanase, an exoglucanase, a feruloyl esterase, a glucoamylase, an intein-modified amylase, an intein-modified xylanase, an intein-modified endoglucanase, an intein-modified exoglucanase, an intein-modified feruloyl esterase, a protease, an intein-modified protease, a phytase, or an intein-modified phytase.

85. The method of any one or more of embodiments 80-84 further comprising processing the grain mixture.

86. The method of embodiment 85, wherein the step of processing includes one or more operations selected from the group consisting of harvesting, grinding, milling, size reduction, crushing, heating, gelatinizing, liquefaction, extracting a component from the mixed grains, purifying a component or portion of the mixed grains, extracting or purifying starch, hydrolyzing polysaccharides into oligosaccharides or monosaccharides, saccharifying, fermentation, chemical conversion, and chemical catalysis.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1. Feed Glucanase Expression Vectors

A codon optimized nucleotide sequence for expression of the AGR2314 feed glucanase in maize was synthesized. For generating initial plant transformation constructs, single AGR2314 expression cassettes were assembled in vectors pAG4000 (pAG4258) or pAG4500 (pAG4588, pAG4597, and pAG4708). The vector pAG4000 has been created by replacing the rice ubiquitin 3 promoter with the first intron by the maize ubiquitin 1 promoter containing its own first intron for driving expression of the selectable marker gene encoding E. coli phosphomannose isomerase (PMI). The vector pAG4500 represents further improvement of pAG4000 and contains three modifications such as 1) insertion after the first maize ubiquitin intron of a 9 bp sequence (ATCCAGATC) representing the first three codons of the ubiquitin monomer with ATG converted into ATC; 2) insertion of the maize Kozak element (TAAACC) after the 9 bp sequence ubiquitin monomer; 3) replacement of the old multiple cloning site (MCS) by a new MCS that was synthesized by PCR and that was designed to contain multiple sites for several rare cutting enzymes (NotI, PacI, FseI, SwaI, AscI, AsiSI) to facilitate cloning of up to 4-5 expression cassettes on one T-DNA.

Sequence of the New MCS in pAG4500 (PmeI-KpnI Fragment):

```
                                    (SEQ ID NO: 20)
GTTTAAACTGAAGGCGGGAAACGACAACCTGATCATGAGCGGAGAATTAA

GGGAGTCACGTTATGACCCCCGCCGATGACGCGGGACAAGCCGTTTTACG

TTTGGAACTGACAGAACCGCAACGTTGAAGGAGCCACTCAGCCTAAGCGG

CCGCATTGGACTTAATTAAGTGAGGCCGGCCAAGCGTCGATTTAAATGTA

CCACATGGCGCGCCAACTATCATGCGATCGCTTCATGTCTAACTCGAGTT

ACTGGTACGTACCAAATCCATGGAATCAAGGTACC.
```

Figure 5:
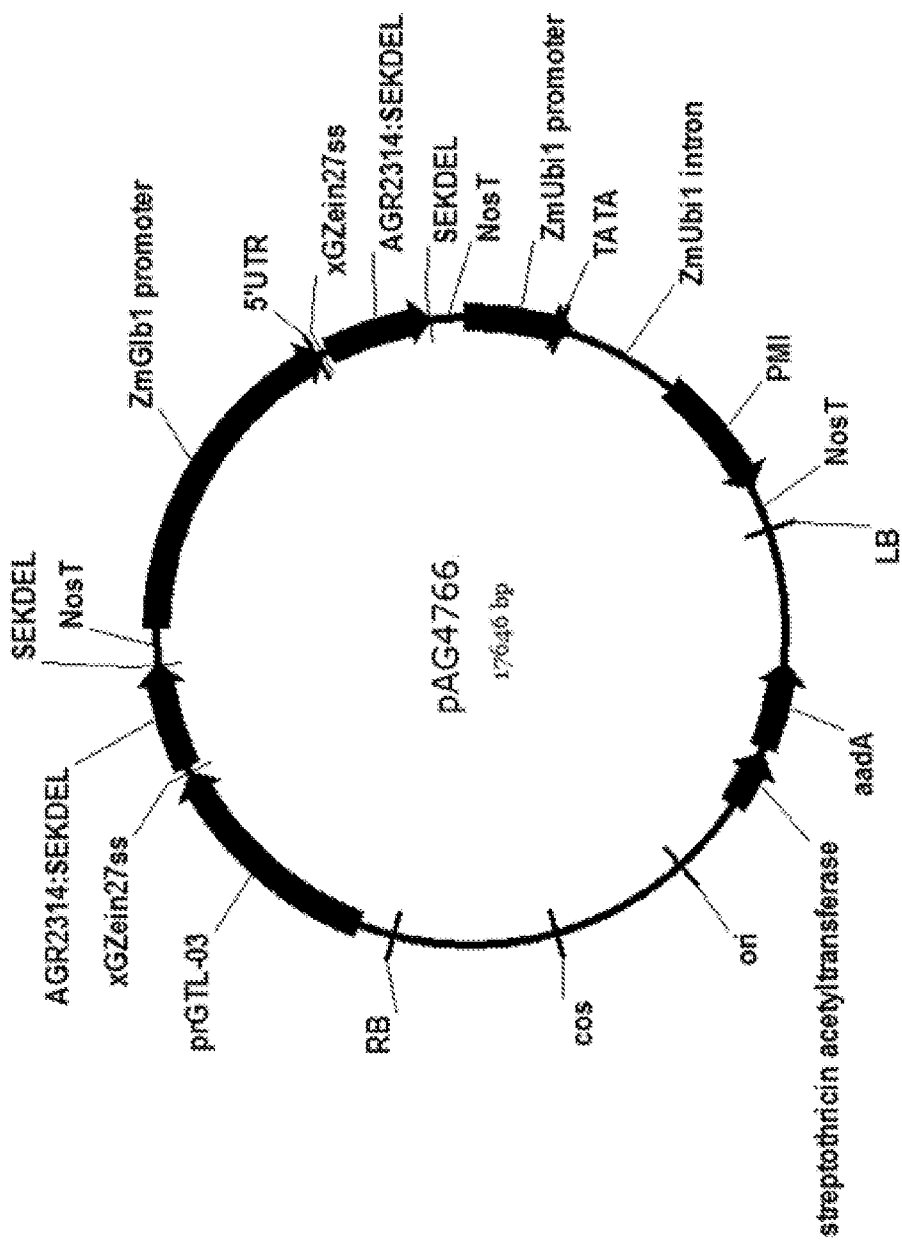
FIG. 5 illustrates the expression vector pAG4766 carrying two feed glucanase expression units.
Figure 6:
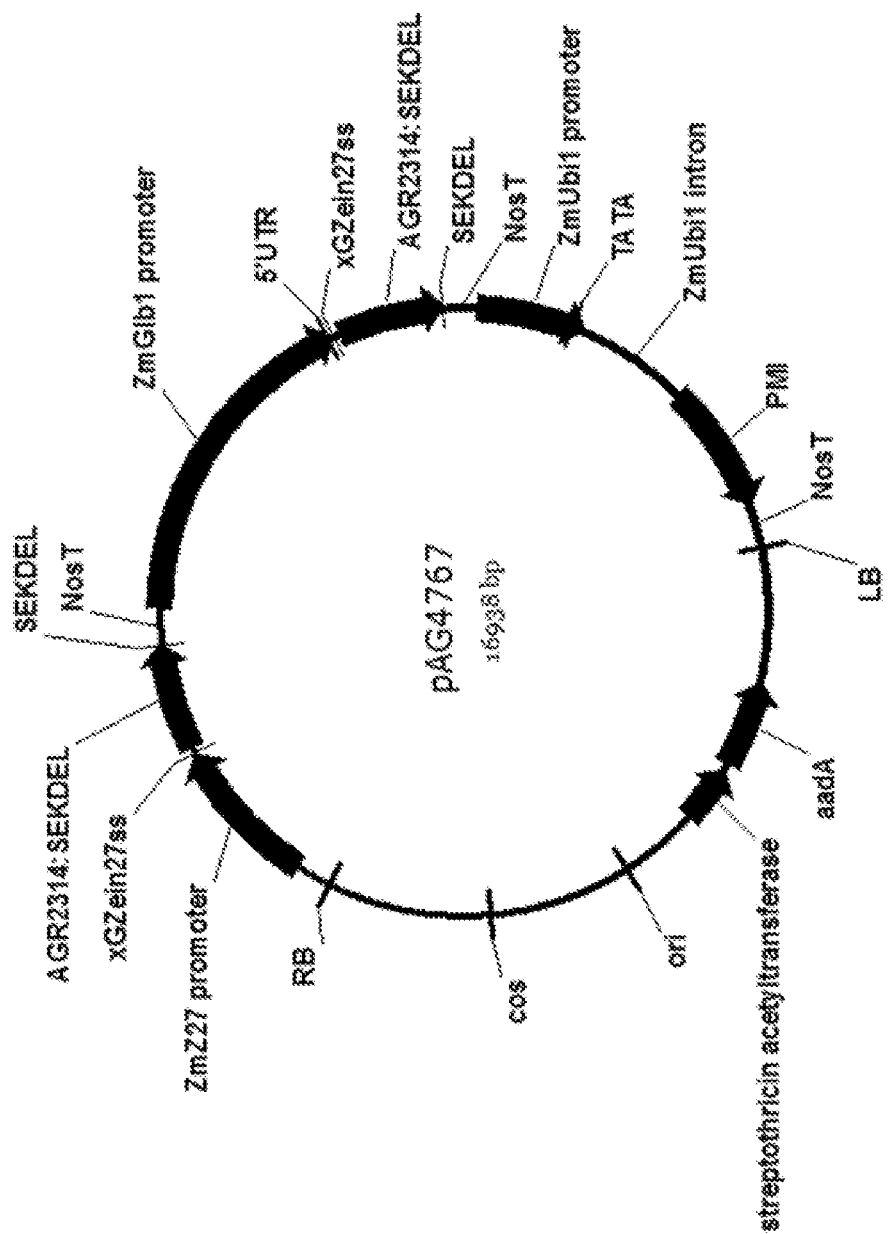
FIG. 6 illustrated the expression vector pAG4767 carrying two feed glucanase expression units.
Figure 7:
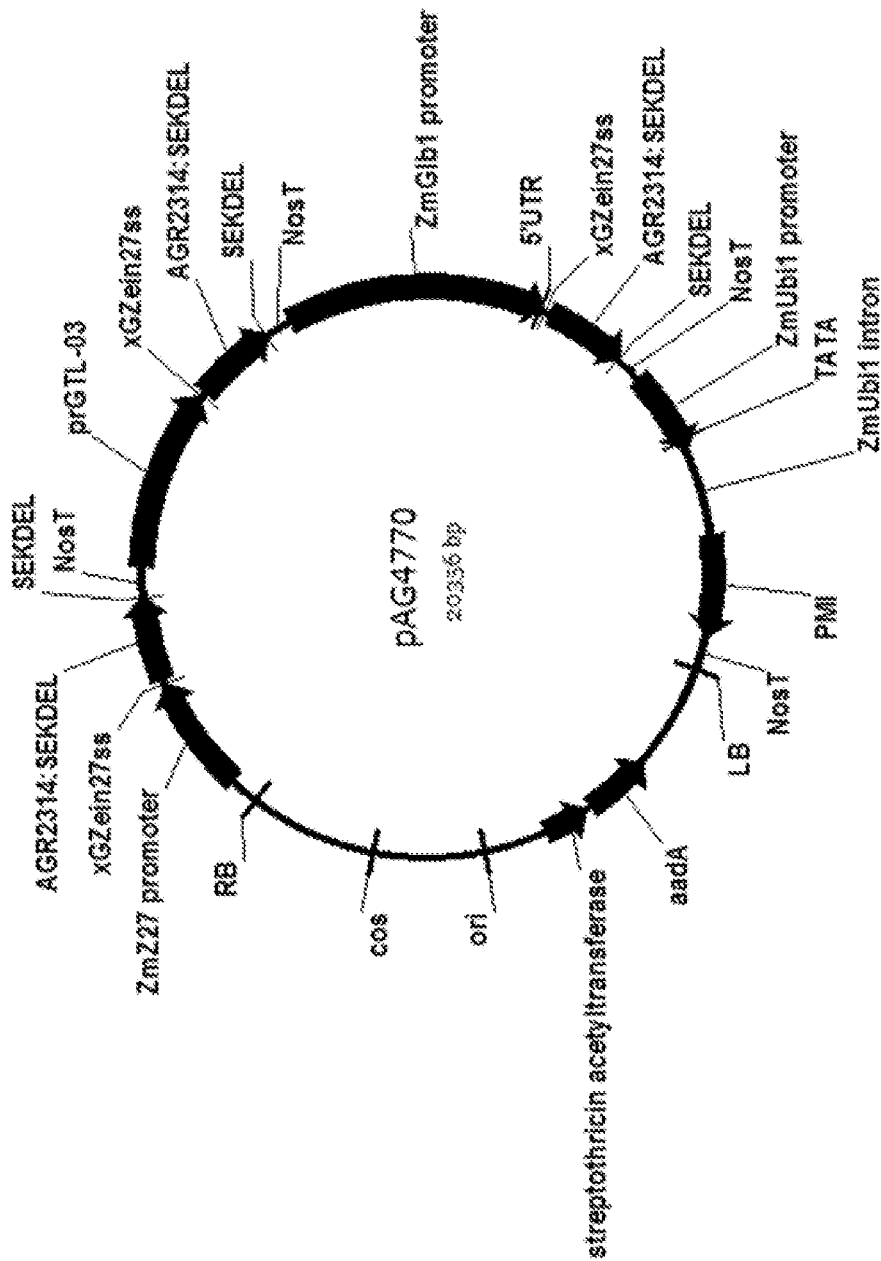
FIG. 7 illustrates the expression vector pAG4770 carrying three feed glucanase expression units.
Figure 8:
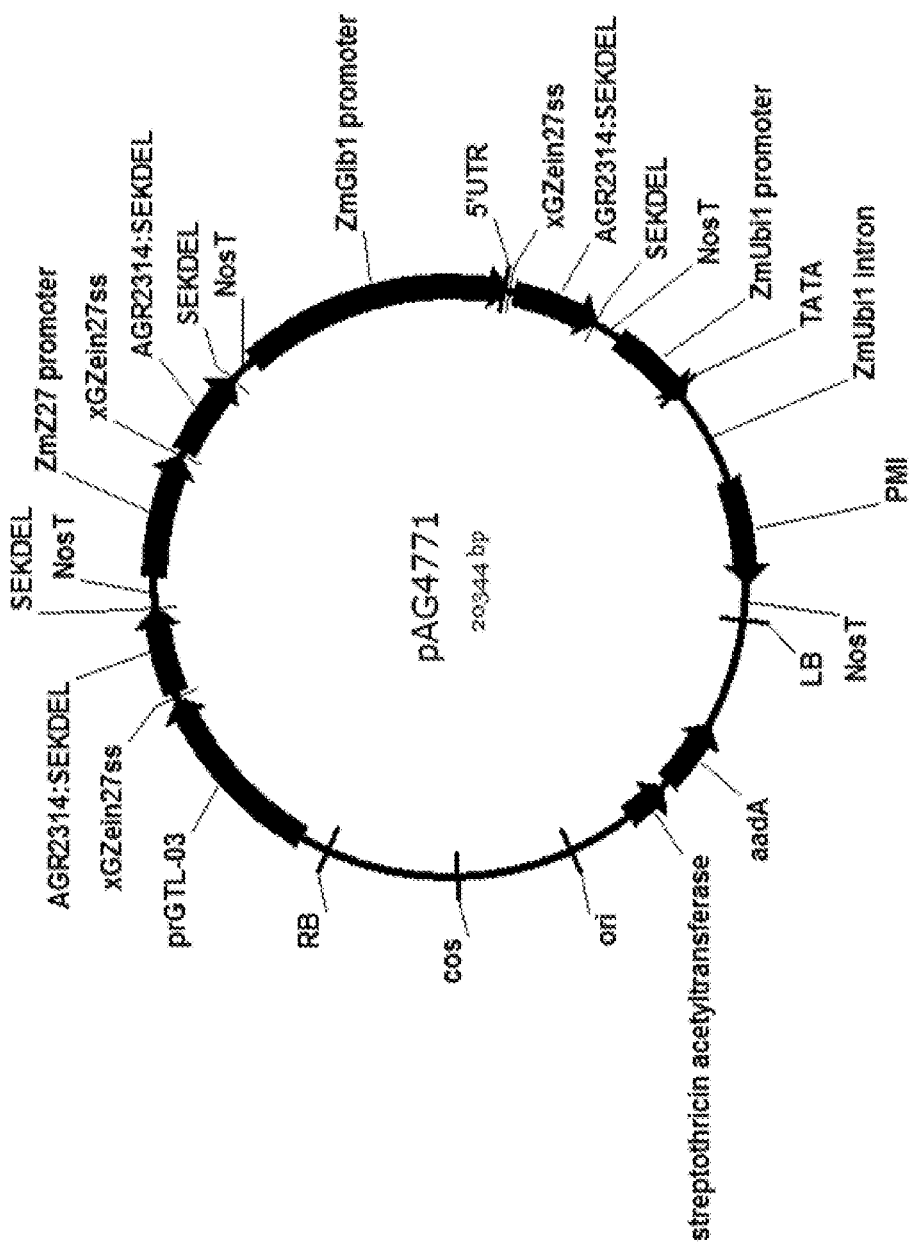
FIG. 8 illustrates the expression vector pAG4771 carrying three feed glucanase expression units.

FIGS. 1-4 illustrate the expression vectors pAG4258, pAG4588, pAG4597, and pAG4708, respectively, carrying a single feed glucanase expression unit. The vector pAG4258 (FIG. 1; SEQ ID NO 7) has been cloned by assembling an expression cassette that was composed of the maize Glb1 promoter fused to the maize codon optimized AGR2314 sequence in KpnI-AvrII sites of pAG4000. The vectors pAG4588 (FIG. 2; SEQ ID NO 8) and pAG4597 (FIG. 3; SEQ ID NO 9) were developed by assembling their corresponding AGR2314 expression cassettes in KpnI-EcoRI sites of pAG4500, while the vector pAG4708 (FIG. 4; SEQ ID NO 10) was produced by cloning AGR2314 expression cassette into XmaI-AvrII sites of pAG4500. FIGS. 5-6 illustrate the expression vectors pAG4766 and pAG4767, respectively, carrying two feed glucanase expression units. FIGS. 7-8 illustrate the expression vectors pAG4770 and pAG4771, respectively, carrying three feed glucanase expression units. The unique rare cutting restriction sites that are available within the MCS of the pAG4500 were subsequently used in order to develop additional expression constructs containing either double AGR2314 expression units, such as pAG4766 (FIG. 5; SEQ ID NO 11) and pAG4767 (FIG. 6; SEQ ID NO 12), or triple AGR2314 expression units, such as pAG4770 (FIG. 7; SEQ ID NO 13) and pAG4771 (FIG. 8; SEQ ID NO 14), on the same T-DNA. The constructed vectors for expression of AGR2314 glucanase in plants are listed in Table 1. E. coli strains carrying the expression vectors were used for conjugation with Agrobacterium and subsequent transformation of maize.

TABLE 1

Description of Sequences

| SEQ ID NO | Construct | Description | Sequence Type |
|---|---|---|---|
| 1 | | AGR2314 maize-optimized protein coding sequence (including C-terminal ER-retention signal "SEKDEL" | DNA |
| 2 | | AGR2414 coding sequence | DNA |
| 3 | | AGR2514 coding sequence | DNA |
| 4 | | AGR2314 Mature protein sequence (including C-terminal ER-retention signal "SEKDEL") | Amino acid |
| 5 | | AGR2414 protein | Amino acid |
| 6 | | AGR2514 protein | Amino acid |
| 7 | pAG4258 | Glb1:mZ27:AGR2314:SEKDEL:NOS | DNA |
| 8 | pAG4588 | Glu1:mZ27:AGR2314:SEKDEL:T35S | DNA |
| 9 | pAG4597 | mZein:mZ27:AGR2314:SEKDEL:T35S | DNA |
| 10 | pAG4708 | Ole:mZ27:AGR2314:SEKDEL:NOS | DNA |
| 11 | pAG4766 | Glu1:mZ27:AGR2314:SEKDEL:NOS, Glb1:mZ27:AGR2314:SEKDEL:NOS | DNA |
| 12 | pAG4767 | mZein:mZ27:AGR2314:SEKDEL, Glb1:mZ27:AGR2314:SEKDEL:NOS | DNA |
| 13 | pAG4770 | mZein:mZ27:AGR2314:SEKDEL:NOS, Glu1:mZ27:AGR2314:SEKDEL:NOS, Glb1:mZ27:AGR2314:SEKDEL:NOS | DNA |
| 14 | pAG4771 | Glu1:mZ27:AGR2314:SEKDEL:NOS, mZein:mZ27:AGR2314:SEKDEL:NOS, Glb1:mZ27:AGR2314:SEKDEL:NOS | DNA |
| 15 | pAG4257 | mZein:mZ27:AGR2514:SEKDEL:NOS | DNA |
| 16 | pAG4692 | Glu1:mZ27:AGR2414:SEKDEL:T35S | DNA |
| 17 | pAG4693 | mZein:mZ27:AGR2414:SEKDEL:T35S | DNA |
| 18 | pAG4705 | Glu1:mZ27:AGR2514:SEKDEL:T35S | DNA |
| 19 | pAG4706 | Ole:mZ27:AGR2514:SEKDEL:NOS | DNA |

Expression cassettes for related beta glucanases, AGR2414 and AGR2514, were prepared using similar strategies, and sequences are provided for these expression cassettes as they are found in the expression vectors pAG4257 pAG4692, pAG4693, pAG4705, pAG4706, pAG4766, pAG4257, pAG4692, pAG4693, pAG4705, and pAG4706.

Example 2. Feed Glucanase Protein Extraction Procedure

Flour was prepared from about 20 transgenic seeds by milling in an Udy cyclone mill or knife mill with 0.5 mm or 1 mm screen. About 0.5 ml of protein extraction buffer (100 mM sodium phosphate, pH 6.5, 0.01% Tween 20) was added to 20 mg flour in a 2 ml tube. In some cases, 2 g, 10 g, or 20 g ground samples was mixed with 10 ml, 50 ml or 100 ml of the extraction buffer in 15 ml tubes or 250 ml bottles. Larger masses and volumes can be used by scaling these amounts appropriately. After vortexing, the tubes were placed on a rotating platform in a 60° C. incubator and rotated for 1 hour for protein extraction. After centrifugation at 16,000×g for 10 min in a tabletop centrifuge, the supernatant was diluted 20-fold for enzyme assay by adding 20 µl supernatant to 380 µl protein extraction buffer. In some cases, other dilution factors were used, as necessary.

Example 3. Feed Glucanase Activity Measurement

Colorimetric Assay. Fifty microliters of the diluted (20-fold to 360-fold) protein extract was mixed with 450 µl of 100 mM sodium phosphate buffer, pH 6.5, 0.01% Tween 20 and 1 tablet of β-glucazyme from Megazyme (Wicklow Ireland), and then incubated at 80° C. for 1 hour before adding 1 ml of 2% Tris base. After centrifugation at 3000×g for 10 min, 100 µl of supernatant was transferred to a microplate for absorbance measurement at 590 nm (A590). The activity was recorded as A590/mg flour after multiplying the dilution factors: A590×A×(500/50)/20 mg, where A is protein extraction dilution factor; 500 is the volume (ml) of buffer used for protein extraction; 50 is the volume of protein extraction (ml) used in the activity test.

Unit Activity Measurement. The assay involves the quantitation of reducing sugars that are released during a time course digestion of a model substrate (barley-β-glucan) obtained from Megazyme (Wicklow, Ireland).

Hydrolysis of Model Substrate. Test 2 ml tubes were labeled with "+" sign, and 5 mg barley-β-glucan substrate (reaction) was added to each test tube; no substrate was added to control tubes (control). Four hundred fifty microliters of 100 mM sodium phosphate buffer, pH 6.5, was added to each tube (reactions and controls), and tubes were placed into a Thermo-shaker with temperature set at 80° C. and shaking speed set at 1000 rpm. Tubes were shaken at 1000 rpm at 80° C. for 20 min until the substrate was completed dissolved. A tube with 2 ml of diluted grain protein extract, extracted as described above was placed in the Thermo-shaker to be pre-warmed.

Fifty microliters of the pre-warmed sample were added to the control and reaction tubes. Shaking was resumed and a timer was started. After 15 minute of shaking at 80° C., 50 µl of each of the reaction and control samples were removed and mixed with 10 µl of 0.5N HCl in separate microplates. Shaking of the samples was resumed until all samples were removed and mixed with acid.

BCA Quantification of Glucose Reducing Equivalents. Glucose standards were prepared in protein extraction buffer at the following concentrations: 0.05 mM, 0.1 mM, 0.2 mM, 0.4 mM, 0.6 mM, and 0.8 mM. BCA reagent (from Thermo Scientific) was prepared by mixing reagent A with reagent B in a ratio of 50:1. To make a glucose standard curve, 75 µl of buffer were dispensed into the first well of row A (A1) in a microplate and 75 µl of each glucose standard were dispensed into wells A2 through A7. To detect the reducing sugars from the feed glucanase reaction and control samples, 25 µl from each reaction were dispensed into rows of the microplate in the order of their incubation time with barley-β-glucan (e.g., row B1-B2: 15 min-30 min), then added 25 µl of corresponding control to another row of the microplate (e.g., row C1-C2: 15 min-30 min). Subsequently, 50 µl of sodium phosphate buffer were dispensed in each well in these two rows (reaction and control), and 175 µl BCA reagent were added to each well using a multichannel pipette. Mixing was achieved by pipetting up and down. The microplate was sealed and incubated at 80° C. in a heat block. After 10 min incubation, the microplate was chilled on ice for 10 minutes and centrifuged to bring down condensate. Subsequently, the absorbance at 560 nm of each well was measured on a microplate reader.

Calculating Units of Feed Glucanase Activity from A560. The absorbance from the reagent blank was subtracted from the absorbance values for each of the glucose standards, and the resulting values were plotted according to their glucose concentrations. Linear regression was then used to calculate the "best fit" line through the data set. To determine glucose reducing equivalents in glucanase/barley-β-glucan reactions, for each time point, the absorbance value from the control sample was subtracted from the reaction sample, and the resulting value was used to calculate the concentration of reducing sugars by comparison to the glucose standard curve. One unit (U) of glucanase activity is the amount of enzyme required to release 1 µmol glucose reducing equivalents from 1% Barley-β-glucan per minute at 80° C., pH 5.3, using the BCA method of quantitation.

Unit Activity Measurement (Semi-High Throughput Method). As described herein, the method detects the reducing sugars such as glucose released from the model substrate (barley-3-glucan) by glucanase treatment at 80° C. for 40 minutes or 90 minutes. When protein extract from grain or feed is appropriately diluted, the initial velocity is detected within 40 minutes (grain product) or 90 minutes (feed sample) of the reaction. The reactions were carried out in 96-well block (Costar, Cat#3960) or strip tubes (VWR, Cat#29442-610).

Substrate Preparation: Barley-β-glucan (low viscosity) was weighed based on the number of reactions, e.g., 10 samples, 4 dilutions for each sample needed a total of 40 reactions. Each reaction needed 5 mg substrate, therefore, at least 40×5=200 mg of barley-3-glucan was required. The substrate was completely dissolved with the extraction buffer at 80° C. water bath for 20 minutes, and vortexed at every 5 to 10 minutes.

The cluster tubes were used for 90 minutes endpoint activity unit assay of feed samples. Protein extract was diluted to 2-, 6-, 10- and 20-fold dilutions.

Purified protein diluted 100-fold was used as a positive control for assay validation. Purified glucanase protein (200,000 ppb) was stored in 50 mM MES, 150 mM sodium chloride, pH6.3 buffer plus 40% glycerol at −20° C. Ten microliters of protein were mixed with 990 μl of the extraction buffer, and 50 μl were used for activity assay.

Barley-β-glucan digestion by feed glucanase was carried out at a water bath set at 80° C. In the block of cluster tubes, 450 μl of the substrate were dispensed into tubes of A2 to D12 referring Table 2. These rows served as the reaction.

Four hundred fifty microliters of the extraction buffer (no substrate) were added to each control tubes from rows E2 to H12, which served as blank to correct protein content detected by BCA method for each reaction as described in Table 2 (A2 to D12).

Fifty microliters of the diluted sample extract including the negative control and positive control were added first to each blank tube, E2 to H12, and then to each reaction tube, A2 to D12, as described in Table 2.

TABLE 2

Example of enzyme hydrolysis of feed samples in cluster tubes

| | 1 | 2 | Columns 1 to 11 | 12 | |
|---|---|---|---|---|---|
| A | Neg. Ctr, 2x | Sample_X, 2x dilution | | Pos. Ctr | Reaction |
| B | Neg. Ctr, 6x | Sample_X, 6x dilution | | Pos. Ctr | |
| C | Neg. Ctr, 10x | Sample_X, 10x dilution | | Pos. Ctr | |
| D | Neg. Ctr, 20x | Sample_X, 20x dilution | | Pos. Ctr | |
| E | Neg. Ctr, 2x | Sample_X, 2x dilution | | Pos. Ctr | Blank |
| F | Neg. Ctr, 6x | Sample_X, 6x dilution | | Pos. Ctr | |
| G | Neg. Ctr, 10x | Sample_X, 10x dilution | | Pos. Ctr | |
| H | Neg. Ctr, 20x | Sample_X, 20x dilution | | Pos. Ctr | |

The tubes were covered with Corning™ Storage Mat III, the Corning Storage Mat Applicator was used to seal the tubes. The plate was shaken at a low speed. The block was placed in the water bath at 80° C. for the 90 minutes incubation period. The reaction was terminated by adding 100 μl of 0.5N HCl to each well and cooling the block on ice.

BCA Quantification of Glucose Reducing Equivalents. Glucose standards were prepared in 100 mM sodium phosphate buffer, pH6, at the following concentrations: 0.05 mM, 0.1 mM, 0.2 mM, 0.4 mM, 0.6 mM, and 0.8 mM. BCA reagent (from Thermo Scientific) was prepared by mixing reagent A with reagent B in a ratio of 50:1. To make a glucose standard curve in column 1 on a microplate, 75 μl of buffer was dispensed into the first well of row A (A1) and 75 μl of each glucose standard were dispensed into wells A2 through A7. To detect the reducing sugars from the feed glucanase reaction and control samples, 25 μl from each reaction were dispensed into rows of the microplate according to the order displayed on Table 2. Subsequently, 50 μl of the extraction buffer was dispensed in each sample well (reaction and blank) referring to Table 2 from A2 to H12 to make a total volume 75 μl. One hundred seventy five microliters of the BCA reagent were added to each well and mixed. The microplate was sealed and incubated at 80° C. on a heat block. After 10 min incubation, the microplate was chilled on ice for 10 min and centrifuged to bring down condensate. Subsequently, the absorbance at 560 nm of each well was measured on a microplate reader.

Calculating Units of Feed Glucanase Activity from A560. The absorbance value for the reagent blank was subtracted from the absorbance values for each of the glucose standards, and the resulting values were plotted according to their glucose concentrations. Linear regression was then used to calculate the "best fit" line for the data set. To determine glucose reducing equivalents in the glucanase/barley-β-glucan reactions, the absorbance value from the control sample was subtracted from absorbance value of the corresponding reaction sample, and the resulting value was used to calculate the concentration of reducing sugars by comparison to the glucose standard curve. One unit (U) of glucanase activity equals 1 μmol glucose reducing equivalents released from 1% barley-β-glucan per minute at 80° C., using the BCA method of quantitation.

Calculating units of positive controls from A560 to validate the assay. The value of absorbance for blank samples (E12, F12, G12, H12) was subtracted from the value of absorbance for each reaction sample (A12, B12, C12, D12). The regression equation for the glucose standard was used to calculate the glucose content (μmol). To determine the amount of reducing units produced per minute (A), the value for the amount of glucose (μmol) released from barley-β-glucan in the reaction was divided by the reaction time, for example 90, if the reaction time was 90 minutes. The unit value of positive controls equals the dilution×(A)/mg of protein in the assay. The dilution factor in the assay described herein equals 24. The dilution factor of 24 was determined by comparing the ratio of the total reaction volume to the portion of the reaction that was used in the BCA assay. In the assay, the total reaction volume was 600 μl including 500 μl reaction and 100 μl of HCl used to stop the reaction. The portion of the reaction that was used in the BCA assay was 25 μl. Therefore, the dilution factor of 24 was calculated by dividing 600 μl by 25 μl.

The amount of protein in the assay was calculated as follows. The concentration of the positive control was 2000 ng/ml, 50 μl was the aliquot of the positive control used in the test (or 50/1000 if calculated in mL). The amount of protein calculated in nanograms was 2000×(50/1000), or 2000×(50/1000)/1000000 if calculated in milligrams.

Example 4. Glucanase Activity in Seed from Transgenic Maize

Figure 9:
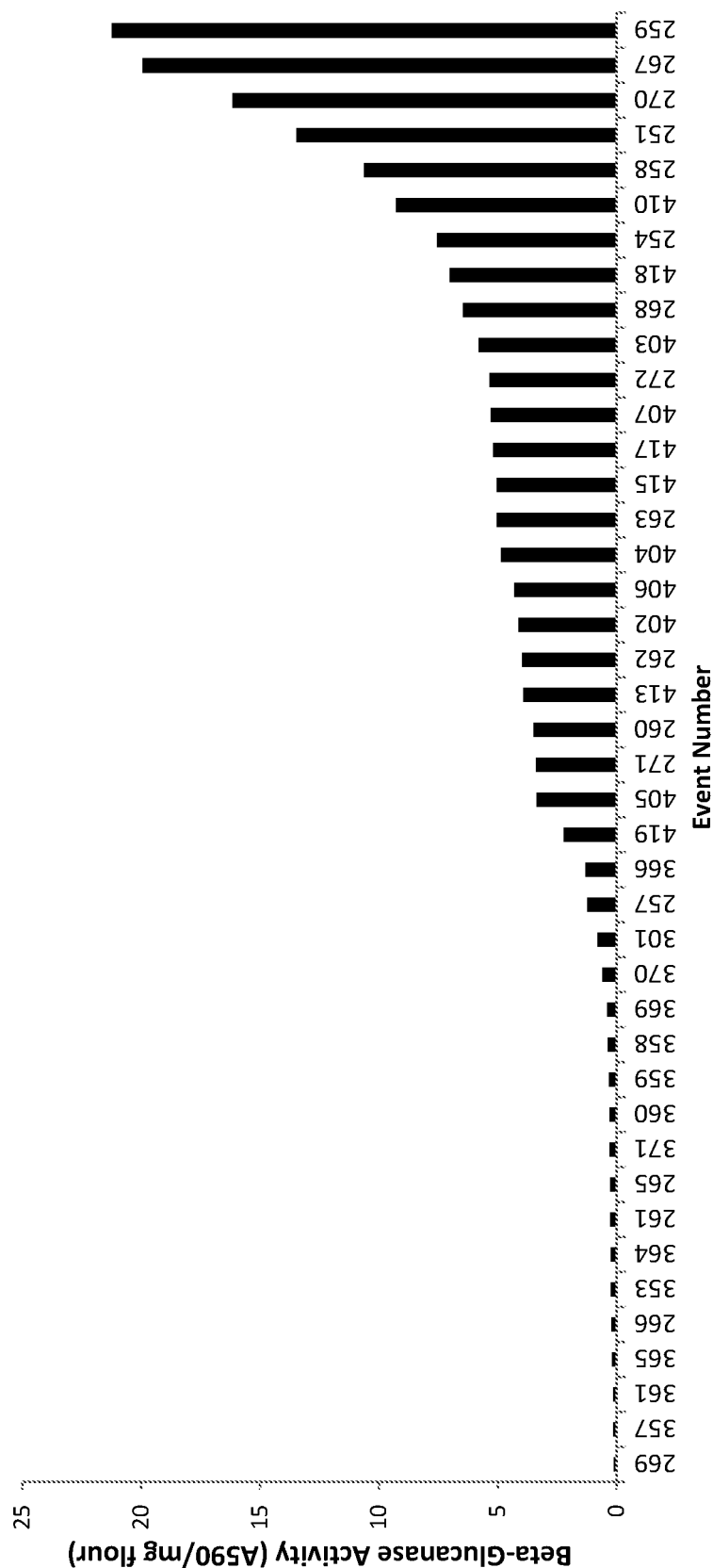
FIG. 9 is a chart illustrating the range of glucanase activity recovered from ears of the maize plants that carried pAG4588 construct.

Silks on untransformed (wild type) maize plants were pollinated with pollen from individual transgenic maize plants that carried the pAG4588 construct. Mature, dried seeds were harvested from the resulting ears and assayed for activity via the colorimetric assay. FIG. 9 illustrates the range of activities recovered from 42 independent ears. In this figure, the numbers along the abscissa correspond to individual event identifiers. The highest activity was observed in the event 259. In the T0 transgenic maize plants 757 that also carried the pAG4588 construct, the activity was about 25 A590/mg. The average activity of the homozygous seeds derived from the first generation of the selfed plants was approximately 116±15 A590/mg. The activity of heterozygous seeds from this population was about 59±18 A590/mg.

Figure 10:
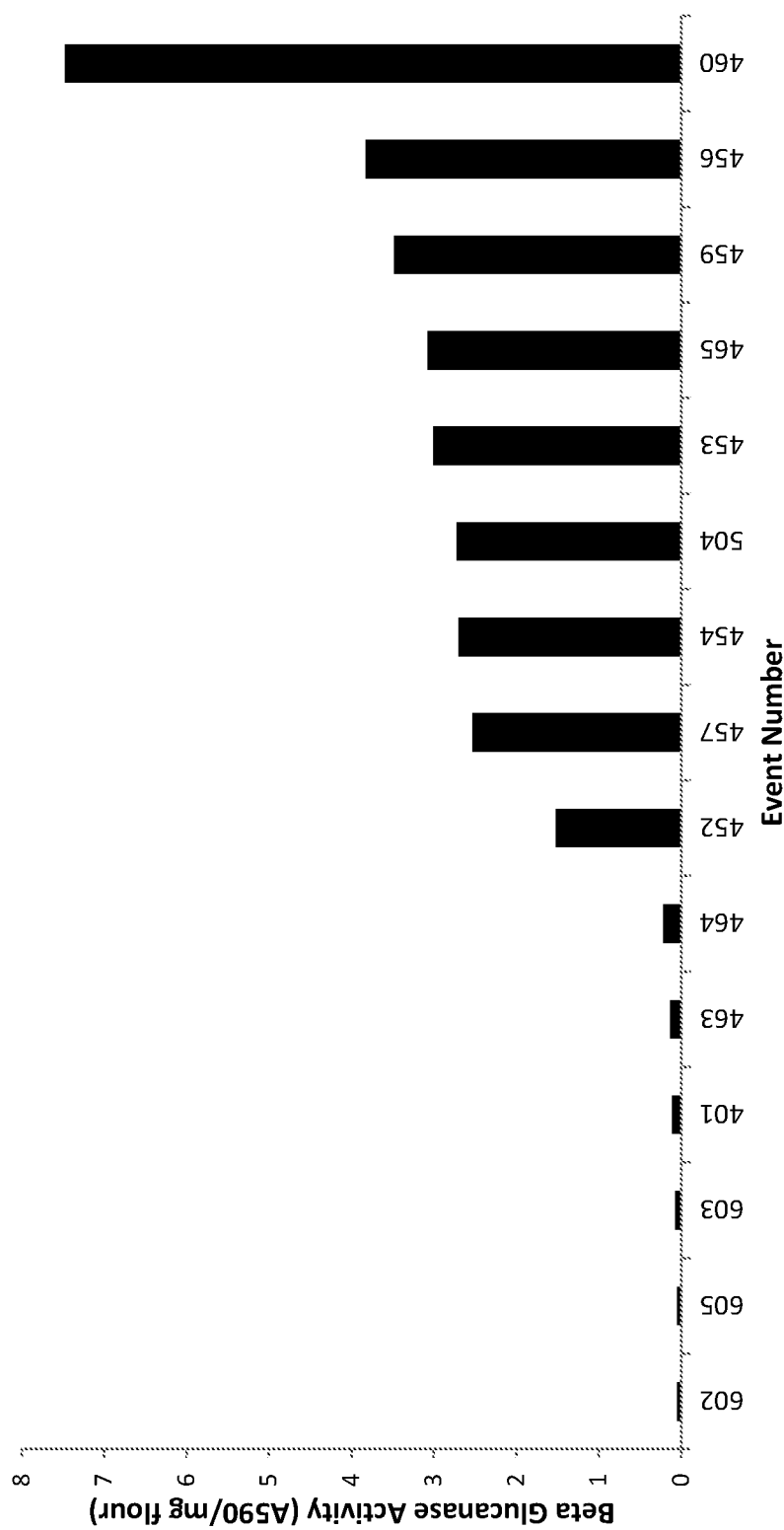
FIG. 10 is a chart illustrating the range of glucanase activity recovered from ears of the maize plants that carried pAG4597 construct.

Silks on untransformed (wild type) maize plants were pollinated with pollen from individual transgenic maize plants that carried the pAG4597 construct. Mature, dried seed were harvested from the resulting ears and assayed for activity via the colorimetric assay. FIG. 10 illustrates the range of activities recovered from 15 independent ears. In this figure, the numbers along the abscissa correspond to individual event identifiers. The highest activity was observed in the event 460.

Example 5. Maize Genomic Sequences Flanking T-DNA Integration Sites in Transgenic Events 4588.259, 4588.757 and 4588.652

Event 4588.259: The event 4588.259 carries two independent T-DNA integration sites that are located on the maize chromosomes 4 and 8. The chromosomal locations of the T-DNA integration sites were determined through BLASTN searches, in which the maize genomic DNA sequences that are contained in OB-2880, OB-2832 and OB-3252 sequences isolated from T-DNA insertion sites at the right and left T-DNA borders, were used as the queries for screening publicly available maize B73 genome sequence databases, such as the Maize Genetics and Genome Database. See also Andorf, CM, Cannon, EK, Portwood, JL, Gardiner, JM, Harper, LC, Schaeffer, ML, Braun, BL, Campbell, DA, Vinnakota, AG, Sribalusu, VV, Huerta., M, Cho, KT, Wimalanathan. K, Richter, JD, Mauch, ED, Rao, BS, Birkett, SM, Richter, JD, Sen, TZ, Lawrence, CJ. (2015) MaizeGDB 2015: New tools, data, and interface for the maize model organism database. Nucleic Acids Research doi: 10.10931/nar/ gkv1007; Lawrence, CJ, Seigfried, TE, and Brendel, V. (2005) The Maize Genetics and Genomics Database. The community resource for access to diverse maize data. *Plant Physiology* 138:55-58; Lawrence, CJ, Dong, Q, Polacco, ML, Seigfried, TE, and Brendel V. (2004) MaizeGDB, the community database for maize genetics and genomics. *Nucleic Acids Research* 32:1)393-1)397, all of which incorporated herein by reference as if fully set forth. Because both loci segregate independently, plants carrying both loci and each individual locus were evaluated.

In the flanks OB-2880, OB-2832 and OB-3252, which are provided below, the maize genomic DNA is shown in the uppercase letters, while the pAG4588 vector sequences are indicated in the lowercase letters and are underlined.

Integration Site on the Maize Chromosome 4:

The T-DNA integration site on the maize chromosome 4 is characterized by the 795 bp right T-DNA border flanking sequence OB-2880, which contains 677 bp of maize genomic. The isolated 677 bp maize genomic DNA flank has 99.3% sequence identity to the sequence derived from the antisense DNA strand of the maize chromosome 4 (nucleotide coordinates 56612593-56612026).

>OB-2880

(SEQ ID NO: 22)
CTTAGATTAGAGAATGAAAATTTGATTGCTAAGGCCCAAGATTTTGATGT

TTGCAAAGATACAATTACCGATCTTAGAGATAAGAATGATATACTTCGTG

CTAAGATTGTTGAACTTACACCACAACCTTCTATGCCTTCTGTGACATTA

ACATTACGTCACAAACAATAGTATTTTTGTCATACCTTACATGTTGGTGA

CGTGATTGTGACGAAAATCACATCGTCACAGAAGGTGCGTGTTAAATGGT

GTACTATGACGAATAACAAAAAAACGTCATAATAGTTTATGACGCAAACT

ACAAACGTCACTAATCTATGACACTCGAATTCGTCACTAATTATGTCTAA

ATACGTCACAATTCATGTAGTCGTGCCTTGCCACGTGGCTGATTACGTGG

CGAGATGACATGGCAGTTGACGTGGCAGGTGATGTGGCGAAAATGTTGTG

ACGAGTTCATTCGTCACAGATGTTATGACGTGGCATGCCACATGGCAGAT

GATGTGGCAAAATTATGTGACAAAAATATTTGTCATAAATATCAATGAGG

TGGCAATATATGTGTGACGAAATTTTTCATCACAAAGTACGATGACGTTG

CAATATATTTATGACGAATTGTTCATCATAAGGCGTGATGAATTCATAGC

GTCATGGAATATTATGAAATCACATGCtcaaacactgatagtttaaactg aaggcgggaaacgacaacctgatcatgagcggagaattaagggagtcacg ttatgaccccgccgatgacgcgggacaagccgttttacgtttgg Integration Site on the Maize Chromosome 8:

The T-DNA insertion site on the chromosome 8 is characterized by the sequences OB-2832 and OB-3252 that represent, accordingly, left and right flanks for the T-DNA integrated into this locus.

The 1211 bp OB-2832 sequence contains 864 bp of maize genomic DNA. The isolated 864 bp maize genomic DNA flank has 99.65% sequence identity to the sequence derived from the maize chromosome 8 with nucleotide coordinates 100613054-100613915.

> OB-2832

(SEQ ID NO: 23)
tcgttcaaacatttggcaataaagtttcttaagattgaatcctgttgccg gtcttgcgatgattatcatataatttctgttgaattacgttaagcatgta ataattaacatgtaatgcatgacgttatttatgagatgggtttttatgat tagagtcccgcaattatacatttaatacgcgatagaaaacaaaatatagc gcgcaaactaggataaattatcgcgcgcggtgtcatctatgttactagat cgggaattggcgagctcgaattaattcagtacattaaaaacgtccgcaat gtgttattaagttgtctaagcgtcaatttgtttacaccacaatatatACT

AAAAAAACTCAAGGATCTGTCTCCAGAAAGGCCTTGCAGGGTTTGGCCAC

GCCCACGGACATTCCATCTCAGAGCCATGATTAGAACGAAAAACACATGA

GAGCCGTCGTTGCTAGGAGTCGGTTTCATATGTTCGCTAAAACAAGAGAT

TTGTTTTTTTTCTCTCTCGTACATACACGAGTCAGCCCTTTTAATCTCAG

GTTGACGTGCAATGTCGCTCGTCTAAGCAGAACATTTTGAGAACAAATGT

-continued
GTTGTACATGAGAGTTTTGTGTACATGGTACGTACATTAAAACATCATCA

TTTATCTTAGATCTAACATCTCTACTTGCTTGTTATATATTTTTTTTGTA

AAATAACATCTTTCACCACTTTATATGGTGTTGTTTGCAAAATATACAGA

GCAATTAGAGACGTTAGATTTGAGATGGACGGTGATAATTTAATACATGC

ATAATGTACAAGAAAATCCTAACTGCACTAGATATGTTGTCAAACATTTT

ACCTTTGTTACAAAAAGAAATGAATAGATGTTGAACGGTTGTCTTTCAAG

CCTGTTCGCTGCGGCTTTAATTCACCAACTGCAATGAACAACCTGAAAGG

TGATCGTTGCCGAACACATGCTGTTTGGCAAAGCTAGTAGTACCTTTTTT

GTCTGTCACCTGGAATGATGAGAAAGGAGACAAGAGGAGAGGGCTGGCCA

TTGTTTATATATATACGTATTTCCATTGCTTTGTGGCATGCAACAGTTCA

AGGGTCCAAACTGGCAGGTTTTCAGCCCCGACAAATATAATAAAAAAACT

ACAAAAAAAAAAGGTCCGTTTACATTCCTTTTTTGACAACGCTAGTCCGT

GCGGAGCGAGC

The 696 bp OB-3252 sequence contains 95 bp of maize genomic DNA. The OB-3252 does not contain left T-DNA border sequence. The isolated 95 bp flank has 100% sequence identity to the sequence derived from the antisense DNA strand of the maize chromosome 8 with nucleotide coordinates 100613034-100612940.

>OB-3252
(SEQ ID NO: 24)
Ggtgaaacaaggtgcagaactggacttcccgattccagtggatgattttg ccttctcgctgcatgaccttagtgataaagaaaccaccattagccagcag agtgccgccatttttgttctgcgtcgaaggcgatgcaacgttgtggaaagg ttctcagcagttacagcttaaaccgggtgaatcagcgtttattgccgcca acgaatcaccggtgactgtcaaaggccacggccgtttagcgcgtgtttac aacaagctgtaagagcttactgaaaaaattaacatctcttgctaagctgg gagctctagatccccgaatttccccgatcgttcaaacatttggcaataaa gtttcttaagattgaatcctgttgccggtcttgcgatgattatcatataa tttctgttgaattacgttaagcatgtaataattaacatgtaatgcatgac gttatttatgagatgggttttttatgattagagtcccgcaattatacattt aatacgcgatagaaaacaaaatatagcgcgcaaactaggataaattatcg cgcgcggtgtcatctatgttactagatcgggaattggcgagctcgaatta aTTCAAGTGTCTTCGTACAAACTGGGGGATGGGGCAGACCGCCAGGTTCA

AACCGTTTGACTAGATGCGGCTGGCAGGCTACTTTGCAGTGCATGC

The maize genomic DNA flanks in sequences OB-2832 and OB-3252 are separated by 20 nucleotides on the maize chromosome 8, which indicates that during T-DNA integration 20 bp of the original maize genomic DNA sequence were replaced by the inserted T-DNA sequences.

There is also an OB-2861 sequence and an OB-2868 sequence within the 259 event. The 970 bp OB-2861 sequence consists of the re-arranged pAG4588 sequences including a partial 223 bp Nos terminator sequence (uppercase letters, nucleotides 3290-3512 in pAG4588); the 73 bp sequence near the left T-DNA border with the first 3 bp of the processed left T-DNA border sequence (italicized lowercase letters, nucleotides 3513-3585); the 299 bp sequence near the right T-DNA border with 5 bp of the processed right T-DNA border sequence and polylinker sequence with multiple cloning sites (lowercase letters, nucleotides 9647-9945); the 359 bp 5' sequence of the rice glutelin promoter prGTL-03 (uppercase letters, nucleotides 9946-10304). The underlined are 18 bp of a duplicated sequence that has been created during T-DNA integration process. The OB-2861 sequence is as follows:

(SEQ ID NO: 25)
GAATCCTGTTGCCGGTCTTGCGATGATTATCATATAATTTCTGTTGAATT

ACGTTAAGCATGTAATAATTAACATGTAATGCATGACGTTATTTATGAGA

TGGGTTTTTATGATTAGAGTCCCGCAATTATACATTTAATACGCGATAGA

AAACAAAATATAGCGCGCAAACTAGGATAAATTATCGCGCGCGGTGTCAT

CTATGTTACTAGATCGGGAATTG*gcgagctcgaattaattcagtacatta*

*aaaacgtccgcaatgtgttatt*<u>aagttgtctaagcgtcaa</u>*tttgttatca*

<u>agttgtctaagcgtcaaa</u>*cactgatagtttaaactgaaggcgggaaacga*

*caacctgatcatgagcggagaattaagggagtcacgttatgaccccgcc*

*gatgacgcgggacaagccgttttacgtttggaactgacagaaccgcaacg*

*ttgaaggagccactcagcctaagcggccgcattggacttaattaagtgag*

*gccggccaagcgtcgatttaaatgtaccacatggcgcgccaactatcatg*

*cgatcgcttcatgtctaactcgagttactggtacgtaccaaatccatgga*

*atcaaggtaccTCCATGCTGTCCTACTACTTGCTTCATCCCCTTCTACAT

TTTGTTCTGGTTTTTGGCCTGCATTTCGGATCATGATGTATGTGATTTCC

AATCTGCTGCAATATaAATGGAGACTCTGTGCTAACCATCAACAACATGA

AATGCTTATGAGGCCTTTGCTGAGCAGCCAATCTTGCCTGTGTTTATGTC

TTCACAGGCCGAATTCCTCTGTTTTGTTTTTCACCCTCAATATTTGGAAA

CATTTATCTAGGTTGTTTGTGTCCAGGCCTATAAATCATACATGATGTTG

TCGTATTGGATGTGAATGTGGTGGCGTGTTCAGTGCCTTGGaTTTGAGTT

TGATGAGAGTTGCTTCTGGG

The 1127 bp OB-2868 sequence consists of re-arranged pAG4588 sequences including the 595 bp 3' sequence of the PMI marker gene (uppercase letters, nucleotides 2594-3188 in pAG4588); the 48 bp sequence between PMI and Nos terminator (lowercase letters, nucleotides 3189-3236); the 276 bp Nos terminator sequence (uppercase letters, nucleotides 3237-3512); the 73 bp sequence near the left T-DNA border with the first 3 bp of the processed left T-DNA border sequence (italicized lowercase letters, nucleotides 3513-3585); the 119 bp sequence near the right T-DNA border with 5 bp of the processed right T-DNA border and a partial polylinker sequence (lowercase letters, nucleotides 9647-9765). The underlined are 18 bp of a duplicated sequence that has been created during T-DNA integration process. The OB-2868 sequence is as follows:

(SEQ ID NO: 26)
AAAATCCCGCGCGCTGGCGATTTTAAAATCGGCCCTCGATAGCCAGCAGG

GTGAACCGTGGCAAACGATTCGTTTAATTTCTGAATTTTACCCGGAAGAC

AGCGGTCTGTTCTCCCCGCTATTGCTGAATGTGGTGAAATTGAACCCTGG

CGAAGCGATGTTCCTGTTCGCTGAAACACCGCACGCTTACCTGCAAGGCG

```
TGGCGCTGGAAGTGATGGCAAACTCCGATAACGTGCTGCGTGCGGGTCTG

ACGCCTAAATACATTGATATTCCGGAACTGGTTGCCAATGTGAAATTCGA

AGCCAAACCGGCTAACCAGTTGTTGACCCAGCCGGTGAAACAAGGTGCAG

AACTGGACTTCCCGATTCCAGTGGATGATTTTGCCTTCTCGCTGCATGAC

CTTAGTGATAAAGAAACCACCATTAGCCAGCAGAGTGCCGCCATTTTGTT

CTGCGTCGAAGGCGATGCAACGTTGTGGAAAGGTTCTCAGCAGTTACAGC

TCAAACCGGGTGAATCAGCGTTTATTGCCGCCAACGAATCACCGGTGACT

GTCAAAGGCCACGGCCGTTTAGCGCGTGTTTACAACAAGCTGTAAgagct tactgaaaaaattaacatctcttgctaagctgggagctctagaTCCCCGA

ATTTCCCCGATCGTTCAAACATTTGGCAATAAAGTTTCTTAAGATTGAAT

CCTGTTGCCGGTCTTGCGATGATTATCATATAATTTCTGTTGAATTACGT

TAAGCATGTAATAATTAACATGTAATGCATGACGTTATTTATGAGATGGG

TTTTTATGATTAGAGTCCCGCAATTATACATTTAATACGCGATAGAAAAC

AAAATATAGCGCGCAAACTAGGATAAATTATCGCGCGCGGTGTCATCTAT

GTTACTAGATCGGGAATTGgcgagctcgaattaattcagtacattaaaaa cgtccgcaatgtgttattaagttgtctaagcgtcaatttgttatcaagtt gtctaagcgtcaaacactgatagtttaaactgaaggcgggaaacgacaac ctgatcatgagcggagaattaagggagtcacgttatgaccccgccgatg acgcgggacaagccgttttacgtttgg
```

Event 4588.757: The event 4588.757 carries one T-DNA integration site that is located on the maize chromosome 8.

The chromosomal location of the T-DNA integration site was determined through BLASTN searches, in which the maize genomic DNA sequences that are contained in OB-3170 and OB-3237 sequences isolated accordingly from T-DNA insertion sites at the right or left T-DNA borders, were used as the queries for screening publicly available maize B73 genome sequence databases. See also Andorf, CM et al.(2015) Nucleic Acids Research doi: 10.1.093/nar/gkv1007; Lawrence, GT et al, (2005) *Plant Physiology* 1.38:55-58; Lawrence, tie et al., (2004) *Nucleic Acids Research* 32:D393-D397, all of which incorporated herein by reference as if fully set forth.

In the flanks OB-3170 and OB-3237, which are provided below, the maize genomic DNA is shown in the uppercase letters, while the pAG4588 vector is indicated in the lowercase underlined letters.

The 1303 bp OB-3170 right T-DNA border flanking sequence consists of the 975 bp maize genomic DNA attached to the 328 bp of the pAG4588 vector borderless sequence proximal to the right T-DNA border site. The isolated 975 bp maize genomic DNA flank has 99.38% sequence identity to the sequence derived from the maize chromosome 8 with nucleotide coordinates 62661042-62662016.

The OB-3170 sequence is as follows:

```
                                             (SEQ ID NO: 27)
TTGGGGTTCCTTATCCTGTTGTCGGAGTTGTGCCATTATCCTTTCCATGG

TTGACCTGAGCTTTAGCCTGTACACTGTAGACTCTACTAGAGGTTTACCT

GAGGCTGAATTCCCGCTGCTAAGATGTGATGTTCCCGGCCATAAGCAAAG

ATGCAGGTTGTCTTTGCTTTGTAAAGATGAAGGTTGTCTTTGTTTTGTAA

TCGAAAAAAAAACCCTCCGACTTCGATAGCAATCCATTTCTTGAAACGAT

ATAGCTATAAGCTGCAGCCACACCTTGCGTTGATGATGCCAAAGCTTTCT

TTCGAGTGCGATGCATGCACTGGCCTGTTGAGATCTTATCAATATGGCAA

ACAGTAACCTAACGTATATGACTACATGGTCTTCATGCTTTTGAGAGGTG

CCTCATAGGAAACAGTCAGGCCAATGATTTTAGGGAATACAATATATTTT

TGCTGTTTTTTTTTGCAAATTGTCCATATTATTACAAAAAAAACTAAAC

ATGCCCAAAGGCAATAGCTTTCTAAATAAAAATGAATAACGGTCCACTTA

TATATGTTGGCCAGTAATCAATTCTGAGGCCTGACAAACCATGCATATAT

TAACAGTAGGTTAATGGCCGTGCGTGAAAAAATTTCAATACAACAAGAGA

TTGAAAAAAAAGAGTGTCTTACCAATATGTTATTTTATAAGTACCAAATG

TGTAGGAAACTTGCATTCATTTTTTCCCTGAGAATGGAAAAAAACAAGAC

ATACTCATTTTCAAGTTGAATTGTCATAGCAACACACATGTTGTATCTGC

CGGTTCATGCAATTGTGCCAACCAAAATATCTAAATGAGATATTCAAGAC

TCAACAGAATTAAAGTATGGAATAGGGTGTATATACACTCAACCATTATT

AAATGGTATAATCATCTATCTATATCACTATAAAATCTACCAGTTTAAAC

TTCACAAAACTCATCTAGCTAATGGaggcgggaaacgacaacctgatcat gagcggagaattaagggagtcacgttatgaccccgccgatgacgcggga caagccgttttacgtttggaactgacagaaccgcaacgttgaaggagcca ctcagcctaagcggccgcattggacttaattaagtgaggccggccaagcg tcgatttaaatgtaccacatggcgcgccaactatcatgcgatcgcttcat gtctaactcgagttactggtacgtaccaaatccatggaatcaaggtacct ccatgctgtcctactacttgcttcatccccttctacattttgttctggtt ttg
```

The 960 bp OB-3237 left T-DNA border flanking sequence consists of the 620 bp of the maize genomic DNA attached to the 340 bp pAG4588 vector sequence (nucleotides 3260-3599 in pAG4588), which includes 253 bp Nos terminator sequence and 70 bp sequence upstream of the 17 bp processed left T-DNA border sequence. The isolated 620 bp maize genomic DNA flank has 100% sequence identity to the sequence derived from the maize chromosome 8 with nucleotide coordinates 62662037-62662642.

The OB-3237 sequence is as follows:

```
                                             (SEQ ID NO: 28)
Aaacatttggcaataaagtttcttaagattgaatcctgttgccggtcttg cgatgattatcatataatttctgttgaattacgttaagcatgtaataatt aacatgtaatgcatgacgttatttatgagatgggttttttatgattagagt cccgcaattatacatttaatacgcgatagaaaacaaaatatagcgcgcaa actaggataaattatcgcgcgcggtgtcatctatgttactagatcgggaa ttggcgagctcgaattaattcagtacattaaaaacgtccgcaatgtgtta ttaagttgtctaagcgtcaatttgtttacaccacaatataAAATCTACCT

GTTCGCTGATAAGCCGTTAGGTTGACTATGTGACTGTTGGGCGGCAAAAT

GACCACGCGGACGGTCTAGCCCCAAAGCCGGACGGTCCGCGGTCCAGACA
```

```
-continued
GTCTGCACTGGTGGTGTCGGCGTTTCGACCCCGGGGGGTCCCTGGACCGA

CGAGTAAATTGTCGCTGCGTGTCCCAGCCCAGATGGGTCCGCGCGAGACG

GAACGCGAAGATGGGAAAACAGCAAAGGGGAACCCGCGGCCTTCGTGTTG

TCCTGCGCCCAGGTCGGGTGCGCTTGCAGTAGGGGGTTACAACCGTTCGC

GTGGGAGAGACAGAGAGAGAGCGAGAGCCTTATGCGTCGGCCCGTTCTCC

CGCGCGGCCAACCCTCTCGTACGAGAGCCCTGGACCTTCCTTTTATAGAC

GTAAGGAGAGGGCCCAGGTGTACAATGGGGGGTGTAGCAGAGTGCTAACG

TGTCTAGCAGAGAGGAGCCGGAGCCCTAAGTACATGTCGTCGTGGCTGTC

GGAGAGGTTTTGGCGCCCTGTTCATGTGATGTCGTGGCCGTCGGAGGAGC

GCTTGAGCCCCGTGGAAGTACAGCTGTCGGGGCTGTCGGATCCTTGCTGA

CGTCTCCTTG
```

The maize genomic DNA flanks in sequences OB-3170 and OB-3237 are separated by 21 nucleotides on the maize chromosome 8, which indicates that during T-DNA integration 21 bp of the original maize genomic DNA sequence were replaced by the inserted T-DNA sequences.

Figure 11:
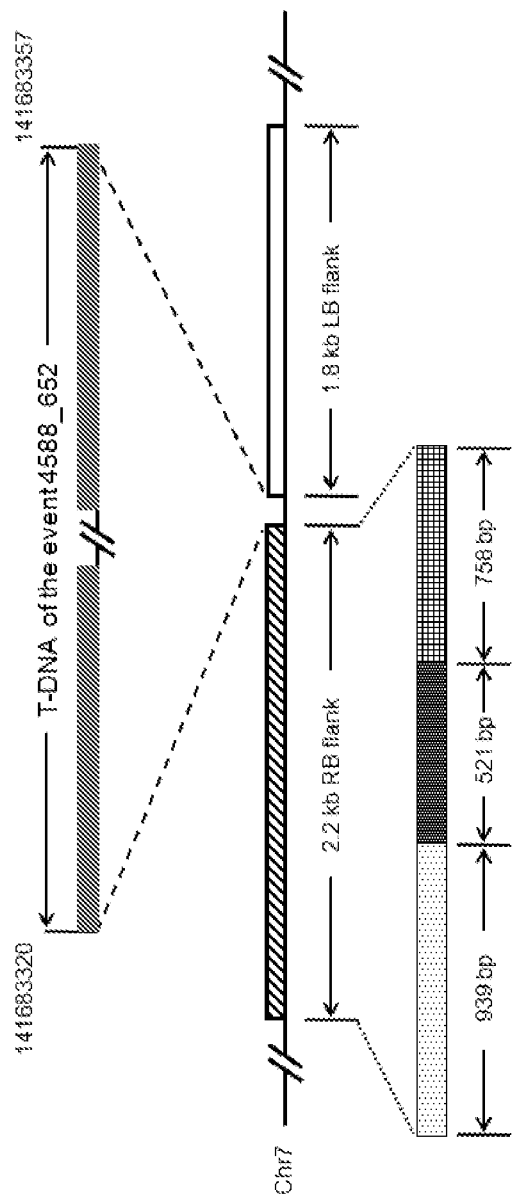
FIG. 11 is a diagram showing the T-DNA integration site in chromosome 7 of maize event 4588.652.

Event 4588.652: FIG. 11 illustrates a diagram showing positions of the characterized flanking sequences in 4588.652.

Sequences Isolated at the T-DNA Insertion Site in 4588.652. T-DNA in the event 4588.652 has integrated into chromosome 7 of the maize genome in B×A genotype, which was used for maize transformation with the pAG4588 construct. The T-DNA insertion occurred between nucleotides 141683320-141683357 of the publicly available reference B73 maize genome. The T-DNA integration displaced 38 bp of the native maize genomic sequence at this site. This 38 bp DNA is underlined and the sequences of pAG4588 are underlined and shown in bold characters in the sequences of the T-DNA insertions shown below. The diagram illustrated in FIG. 11 depicts locations of the sequences in the locus in 4588.652. The right and the left border T-DNA flanking sequences, OB-4448 and OB-4451 respectively, were isolated from multiple 4588.652 progeny using a PCR-based genome walking approach. The entire genomic regions between the right and the left border flanks were isolated and sequence characterized from WT genotypes B×A, 19545 (E), 15009 (G) as well as the nulls BC2ES2_512x and BC1GS2_518x. The following wild type maize genomic DNA sequences were used for reference: the WT_B×A (OB-4541; SEQ ID NO: 32), the WT_E sequence (OB-4545, OB-4546; SEQ ID NO: 33), the WT_G sequence (OB-4547, OB-4548; SEQ ID NO: 34), the Null_BC2ES2_512x sequence (OB-4578 to OB-4580; SEQ ID NO: 35), the Null_BC1GS2_518x sequence (OB-4582 to OB-4584; SEQ ID NO: 36), and the WT_B73Chr7_141681606-141685147 reference sequence (SEQ ID NO: 37). Furthermore, the right and the left border flanks were additionally isolated and entirely sequenced from the more advanced 4588_652 transgenic progeny BC2ES2_472x. The entire 4044 bp B×A genomic sequence containing the right and the left border flanking sequences have high BLASTN identity hits to two nucleotide positions 141681606-141682538 and 141682550-141685147 on the chromosome 7 in the maize B73 genome.

Analysis of Nucleotide Sequences in the Left T-DNA Border Flank

The left T-DNA border flank OB-4451 has 98.66% BLASTN sequence identity to nucleotides 141683358-141685147 on the maize chromosome 7 in B73 genome. Multiple sequence alignment of the left border specific sequences from the wild type genotypes B73, B×A, 19545 (E), 15009 (G), nulls BC2ES2_512x and BC1GS2_518x as well as 4588_652 transgenic progenies 116_F1G and BC2ES2_472x and the reference public sequence of B73 genome revealed that these 1.8 kb sequences are nearly 100% identical between all genotypes.

Analysis of Nucleotide Sequences in the Right T-DNA Border Flank

The 2218 bp right border flank OB-4448 has high BLASTN sequence identity to two nucleotide positions 141681606-141682538 and 141682550-141683319 on the maize chromosome 7 in B73 genome. Multiple sequence alignment of the right border specific sequences from 4588_652 transgenic progenies 116_F1G and BC2ES2_472x with the WT sequence of B×A revealed that these three 2.2 kb sequences are nearly 100% identical.

A 521 bp "unique" sequence that is specific to the right T-DNA border flank has originated from genotype B×A, which was used for transformation with the pAG4588 construct. No BLASTN sequence identity hits to this sequence were identified at the T-DNA integration site within the reference B73 genome. On the other hand, the 521 bp sequence has multiple BLASTN identity hits on different chromosomes in maize B73 genome indicating that this sequence is highly repetitive. The 521 bp sequence is shown in italicized lowercase letters.

Sequences characterized at 4588_652 T-DNA integration site. The OB-4448 sequence (extended right border flank in 4588_652 isolated from F1G of 4588_652) is as follows:

```
                                            (SEQ ID NO: 29)
CACCCTCGCTGTTGGTAAACGTGCGCCTTGGGTATGTCCTCACCTGCATG

ATACGACATGTTGAAAAAGGTACATGGCTGGGCGGATTTAAACAGTAGAA

TGAAAAGGTGCCACAAGAAAACTCGTCAAAGAATTGACTACGCGTCAATG

TTCCATAGTTAAAAAGACTTGAACTCTGGATCAGGGACTTTCAAACAAGG

ATAGCTGCCTGGTCACCAGTCATTAACTGTAATGTAATGGCCATAGATGA

TGCATGAGTACAATAATAAAAAAACACCATCCAGCCAAATATATACTCCC

TGTCACAAATGAAAATTCGTTTTAGATAATTAGTGGATTCATACAATATT

TGTTGTATGTGTTTTATGTGTCTAGATTCATCATCCTCTATTTGAATATA

GACAGAAAAATCATAACTAAAACGAATACTATTTGGGAACGGAGGGAGTA

CTACTTTGGCAGAATGCCCCCAGGAAAGTACCAGTTTCAGGGGTAGTTTG

GAAGGCTAAACCTAGGGAGGGAAAACCCCCCACATGTAACTAAATATCTT

ATTCAAATGTTACCCCTAGGGATTACTCACCCTGGGAAATGAGAAGGGTC

CCAAGGGGATTTCGGTTTCTATTATTTTTTCTGCAAACCATTTCAGAGCA

ATGATATGAAACCAAGCTAACTACTTATAACATTTCTTAAGAATATCAGA

CATAGGAAAGTGATGGCCTGGAACCAAAGTAAGACTGGTAGATAAATAGA

TCACTAGAATAAACCCTGACAGTTCATAGCCTTCATAGAAGCAAAAGGAA

ACACTACGGGAGCAATTGGTTGCTTGCACTAGCAATTCACTGCATTGGGT

CTAATGCAGGATAGACTAAGCCAGCATAAGTGTGCGCAATGTGTTTGTGT

TTGGTTGCCATGTTATAAGTAAGTTGCATTTGCTAATAT*ctttctcctga*

*ctctaatgagtccacttttgctgactggtgggcgaaagtaagtaagcaag*
```

-continued

```
tgcacaaatccaaaagaagaggctttaacagtatcatcatcttgggggct
tggtgtttatggcttcatcgtaataaggtggtttttgatggtgtcagtcc
ttcaattattggcataaaggcaattttttttggatgaagttgaattctgga
ggcttgccggtgctaggcatcttgaggctttggttcctggtgctggaatt
tttaggtcaagggttcttttgggtgattagtgaagagcaggtgtgtgtgg
tctgctcgcacttttgttgttcgttctcctattgcgtgctgttgtttcc
aggcgcatttatggaggctgcagttttgtgcgcagcagaagttggtggtt
ttgtgttttgtgttttgcctattttggcattgtactttggtccattttgg
actgttttcttctcttaatttaatgatgtgcagctctcctgcgcgtttaa
gaaaaaaaaaAGTTGGCTGTTTTGTATTTCTTGTGATCACCCATGCTTGT
TGTGGTCAGATTAAACTCTCACGTTTAATGCTACAGAAGCATCCATGAGA
CAATGAAACACCGCTCAAAAGCCACGTAGTAGCATACCCTGACTTATGAA
TAAAGCAACTCGATCTGATTTATTTGAGAAAACAGGAAACTGACAAGTTA
TTTTTAACACAAAATTTCATTAAAAACGAATGGTAGACAATTACCAATCT
GTAGGTCCCTGGCTTGCAAGTCCTCCCAATGTCTAAGAAATCAAATAGGA
ACTGCAGGCAAGCCAGCAAGAAAGTATTAATCACTGGATATAAAATATAA
AGAAAAAAGAAGGAAAGACGGCTACTCGGCTAGCATATGTTTTTGTTAGG
GGTGAAAATGGATACTTATTCAGAAATCATTTTTGATCTTTTTTCTTTAA
TTAGGAATAAATAGGATATAGAATATGCTAAGCAAATTCATATTCTTGTT
CTTAGCATTGGGCTTGTAAAGATTCATAAAAGGTAAATCTCAAATTTATC
ATATATCTTAAATGGTAGATATAAAATTCAGATACAAATATTTTTCAACT
TTTTTGTTGTAGGGAACAAATTATATTAAAAAAAATTATGCACAATTCTA
TTCTTATTTGTAATAATGTGCTTGATAACATAATAAAAGATTACCATCAA
ATTTCACACACACCCACCCACCCACCCCTGCACGCACGCGCGCGCA
CACACACTATATGTGTGTtcaaacactgatagtttaaactgaaggcggga
aacgacaacctgatcatgagcggagaattaagggagtcacgttatgaccc
ccgccgatgacgcgggacaagccgttttacgtttggaactgacagaaccg
caacgttgaaggagccactcagcctaagcggccgcattggacttaattaa
gtgaggccggccaagcgtcgatttaaatgtaccacatggcgcgccaacta
tcatgcgatcgcttcatgtctaactcgagttactggtacgtaccaaatcc
atggaatcaaggtacctccatgctgtcctactacttgcttcatcccttc
tacattttgttctggttttggcctgcatttcggatcatgatgtatgtga
tttccaatctgctgcaatatgaatggagactctgtgctaaccatcaacaa
catgaaatgcttatgaggcctttgctgagcagccaatcttgcctgtgttt
atgtcttcacaggccgaattcctctgttttgtttttcaccctcaatattt
ggaaacatttatctaggttgttttgtgtccaggcctataaatcataaatg
atgttgtcgtattggatgtgaatgtggtggcgtgttcagtgccttggatt
tgagt
```

The RB_BC2ES2_472x sequence (extended RB flank isolated from the advanced progeny of 4588_652) is as follows:

(SEQ ID NO: 30)
```
CACCCTCGCTGTTGGTAAACGTGCGCCTTGGGTATGTCCTCACCTGCATG
ATACGACATGTTGAAAAAGGTACAAGGCTGGGCGGATTTAAACAGTAGAA
TGAAAAGGTGCCACAAGAAAACTCGTCAAAGAATTGACTACGCGTCAATG
TTCCATAGTTAAAAAGACTTGAACTCTGGATCAGGGACTTTCAAACAAGG
ATAGCTGCCTGGTCACCAGTCATTAACTGTAATGTAATGGCCATAGATGA
TGCATGAGTACAATAATAAAAAAACACCATCCAGCCAAATATATACTCCC
TGTCACAAATGAAAATTCGTTTTAGATAATTAGTGGATTCATACAATATT
TGTTGTATGTGTTTTATGTGTCTAGATTCATCATCCTCTATTTGAATATA
GACAGAAAATCATAACTAAAACGAATACTATTTGGGAACGGAGGGAGTA
CTACTTTGGCAGAATGCCCCCAGGAAAGTACCAGTTTCAGGGGTAGTTTG
GAAGGCTAAACCTAGGGAGGGAAAACCCCCCACATGTAACTAAATATCTT
ATTCAAATGTTACCCCTAGGGATTACTCACCCTGGGAAATGAGAAGGGTC
CCAAGGGGATTTCGGTTTCTATTATTTTTTCTGCAAACCATTTCAGAGCA
ATGATATGAAACCAAGCTAACTACTTATAACATTTCTTAAGAATATCAGA
CATAGGAAGTGATGGCCTGGAACCAAAGTAAGACTGGTAGATAAATAGA
TCACTAGAATAAACCCTGACAGTTCATAGCCTTCATAGAAGCAAAAGGAA
ACACTACGGGAGCAATTGGTTGCTTGCACTAGCAATTCACTGCATTGGGT
CTAATGCAGGATAGACTAAGCCAGCATAAGTGTGCGCAATGTGTTTGTGT
TTGGTTGCCATGTTATAAGTAAGTTGCATTTGCTAATATctttctcctga
ctctaatgagtccacttttgctgactggtgggcgaaagtaagtaagcaag
tgcacaaatccaaaagaagaggctttaacagtatcatcatcttgggggct
tggtgtttatggcttcatcgtaataaggtggtttttgatggtgtcagtcc
ttcaattattggcataaaggcaattttttttggatgaagttgaattctgga
ggcttgccggtgctaggcatcttgaggctttggttcctggtgctggaatt
tttaggtcaagggttcttttgggtgattagtgaagagcaggtgtgtgtgg
tctgctcgcacttttgttgttcgttctcctattgcgtgctgttgtttcc
aggcgcatttatggaggctgcagttttgtgcgcagcagaagttggtggtt
ttgtgttttgtgttttgcctattttggcattgtactttggtccattttgg
actgttttcttctcttaatttaatgatgtgcagctctcctgcgcgtttaa
gaaaaaaaaaAGTTGGCTGTTTTGTATTTCTTGTGATCACCCATGCTTGT
TGTGGTCAGATTAAACTCTCACGTTTAATGCTACAGAAGCATCCATGAGA
CAATGAAACACCGCTCAAAAGCCACGTAGTAGCATACCCTGACTTATGAA
TAAAGCAACTCGATCTGATTTATTTGAGAAAACAGGAAACTGACAAGTTA
TTTTTAACACAAAATTTCATTAAAAACGAATGGTAGACAATTACCAATCT
GTAGGTCCCTGGCTTGCAAGTCCTCCCAATGTCTAAGAAATCAAATAGGA
ACTGCAGGCAAGCCAGCAAGAAAGTATTAATCACTGGATATAAAATATAA
AGAAAAAAGAAGGAAAGACGGCTACTCGGCTAGCATATGTTTTTGTTAGG
GGTGAAAATGGATACTTATTCAGAAATCATTTTTGATCTTTTTTCTTTAA
```

-continued
TTAGGAATAAATAGGATATAGAATATGCTAAGCAAATTCATATTCTTGTT

CTTAGCATTGGGCTTGTAAAGATTCATAAAAGGTAAATCTCGAATTTATC

ATATATCTTAAATGGTAGATATAAAATTCAGATACAAATATTTTTCAACT

TTTTTGTTGTAGGGAACAAATTATATTAAAAAAAATTATGCACAATTCTA

TTCTTATTTGTAATAATGTGCTTGATAACATAATAAAAGATTACCATCAA

ATTTCACACACACCCACCCACCCACCCACCCCTGCACGCACGCGCGCGCA

CACACACTATATGTGTGTtcaaacactgatagtttaaactgaaggcggga aacgacaacctgatcatgagcggagaattaagggagtcacgttatgaccc ccgccgatgacgcgggacaagccgttttacgtttgg The OB-4451 sequence (extended left border flank in 4588_652 is as follows:

(SEQ ID NO: 31)
gggcccggtagttctacttctgttcatgtttgtgttagatccgtgtttgt gttagatccgtgctgctagcgttcgtacacggatgcgacctgtacgtcag acacgttctgattgctaacttgccagtgtttctctttggggaatcctggg atggctctagccgttccgcagacgggatcgatttcatgattttttttgtt tcgttgcatagggtttggtttgccctttcctttatttcaatatatgccg tgcacttgtttgtcgggtcatcttttcatgctttttttgtcttggttgt gatgatgtggtctggttgggcggtcgttctagatcggagtagaattctgt

TACCCACTTTCATCCCTAGTTTTTGTTCTGGATTCAAGCATCTCAAAATT

GTTTACCTGAAGTTTATCAGTTTTGAGAAAGCGGCGCCCCTGTCGACTAC

CATCAGGCATTCGGACTACAACTGTCACAGCACCCTCTGCGTCTGGAGAC

GGTTCCGGTGGTAATGATGCTTGCTTCGAAGTGAGACTGGACTCTAGCTC

CTATTTAATCAAAACATCAGGGACAACATGACAAATAGTAGTCAAATATC

CAGGCAAGAAAAAAAACCATAAACAATGAAAATACTGATCAAAAGTCCT

GTTTGGATCTCCTAAGAAAAATGAGAATGAGATCCAAACAATTGGATTCT

AGAATCCAGCTATCTATCCCAAACCCATTATTTGGCGAGATTTTCACTAT

GCAGAGGCAATGATCACTATAAGAATAAGATTCAAACACCCACTTATTAT

TTTTTTAATCCAGAAACCAGATTCTACATTCACTATAGAATCCAGAACTT

CAATATGGGAATGAGATCCAAATAGACCCTAAGCAAAATGAAATTGGTG

AGATGAAGTGGCTAGTTGTCATAACCTCCTGTAAAGAAGACAGCGGTTTA

CAGTCCCAACACCCAAATAAACATGACATTAATATAATGACTACAACTCA

CAACCTAAACCTAAACCAATATACATCCAAACATAAGACAAAAGGAGAAC

TGAGTTTTATATGATCACACTGATGAACTGATGCTGTAGTCTAGCATTCA

AGTGTTTAAGATAGTTGACTATAAACCCTTCACCTTGCAGATTACATGTG

ACAGAAAGATACCTCTTCCTCAAGTTGTTTTTTACGCCTTTCCTCCTCCT

CTTGCTTCTGTTTCTCAAGAACAGCTTCTCTCGCAGCTGTTTCTTCAAGG

CGACGGAGCTCAGCCTCCTGTAGGGCCTTTAACTCCTTTTCTTGATCAGC

TTGTAGCGATGCAAGGTACTCATCGTCCTACAAATTTAAAATTTATAAAA

GTGCTCACCCATAGTGGCAATTATGAACAATGGATAAATCTTAGACCTCA

AACCTGCTGCTCTCGTAATAACCGCTGTTCAGTTAATGCTGGTGATGGAG

-continued
AATGAGATATTGGGGGATAATAAGTAGAGGTTCTGTGAGAAGGCATAGAG

AAAGGATATGTTGGTCCACCAAACATTGCAGCCTCAAGCATAACAGCTTC

ATCATGTTCCTCAGAAGAAATGCCACCCCACTTTATTGTAAAAAAAGACG

TCAGAAATTAAACAAATCCATCTAATGTCTTAGCGCACATTGGAACCACA

GATTATAATACCTCAGATGGGAAATCATCTCCATTATACTGGTGATTGTT

CAGAACAGGGCTAGCACCTGGGTGCACTATTTTTGGTAATTCATTGTCCT

CAGAAGGGGCACGCCGAGAACGACGCCTAACTAACGGCTGTTCTTCTACA

TCTTCAGCCTCCTCCTGGAAGCTCTCGTCATCTATTGGTTGCCTAGATGT

TCCAGCCTTTCCTGAAGCTAGTCCTTGCCTCCAAAAGGAAATTGCATGTA

TAAGGAATCAAATGATACTGTAGTAGGGTAGCCTGAGTGAAGAGGTGGGT

AGTAAAGTTAACATTCACCTCTCAACTATTCCATTTGCGGTTTCCATGCC

TGCTTTATCAGAAGAATGGTCCCTCAAATTCACTTCCTCTTGATGCTGGC

CTCCTTGCTCGACTATCTGATGATTATTGAAAAATTAGAGATGACATCAA

GATAGGTTCAAGTAAGCATGTTGGGGA

Example 6. Feed Glucanase Expression in Subsequent Generations

Figure 12:
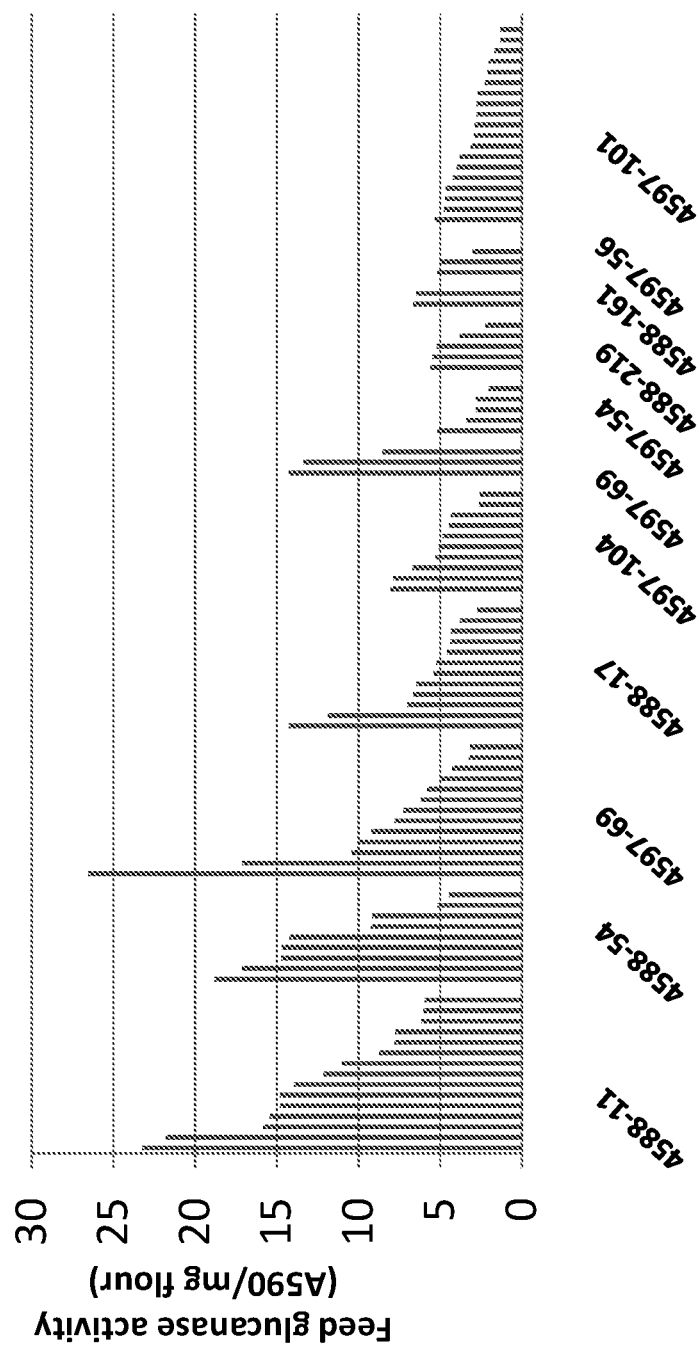
FIG. 12 is a chart illustrating glucanase activity observed in T1 plants.

Several "T1" progeny from original "T0" transgenic maize plants were grown, and individual ears were either self-pollinated or pollinated with pollen from wild-type maize plants. Mature seed from the resulting ears was then assayed for feed glucanase activity via the colorimetric assay. FIG. 12 illustrates that glucanase activity was observed in T1 events. In this figure, the numbers along the abscissa correspond to the event identifiers of the original T0 plants from which the progeny were derived. The highest activity was observed for seeds of T1 plant derived from the 4597_69 event.

Example 7. Feed Glucanase Expression in Multi-generations of Hemizygous, Homozygous and Hybrid Seeds Progeny from original "T0" transgenic maize plants were grown and backcrossed (pollinated with pollen from the wild type maize parents or pollinated onto the wild type parents) for 4 generations (in maize inbred line E (BC4E), or in maize inbred line G (BC4G)). At each generation, some individual ears were self-pollinated. PCR method was applied to select homozygous plants as described in Example 8. Hybrid ears were made by cross-pollinating transgenic line G plants with transgenic line E plants, or vice versa.

Figure 13:
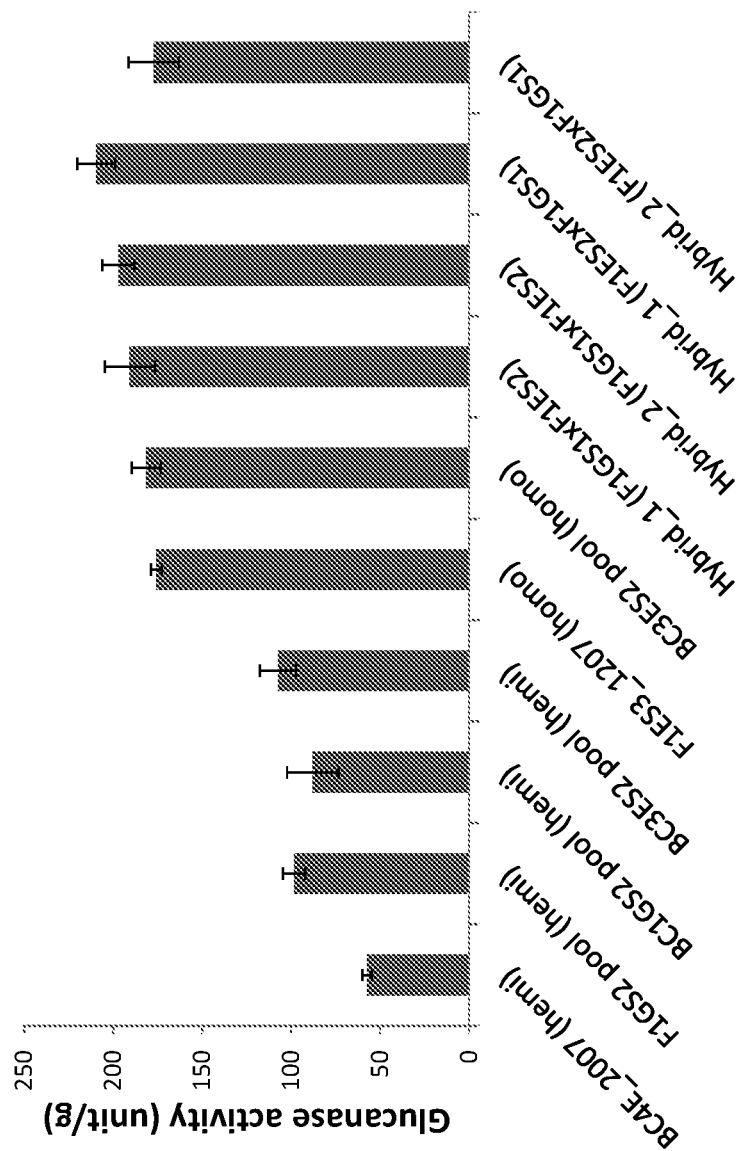
FIG. 13 is a chart illustrating the glucanase activity in the seeds of hemizygous, homozygous, and hybrid plants.

FIG. 13 illustrates that glucanase activity in the hemizygous, homozygous and hybrid ears of event 4588.259. The homozygous and hybrid ears contained average activity of 190 units/g, which was approximately double of ears from hemizygous plants.

Example 8. PCR Assays for Identifying and Determining Zygosity of the Glucanase Events 4588.259, 4588.652, and 4588.757

Maize glucanase events 4588.259, 4588.652, and 4588.757 carry transgenes that result in seed-specific expression of glucanase enzyme. Event 4588.259 originally carried two T-DNA insertions at independently segregating loci, but subsequently a single genetic locus was selected for propagation and development. Events 4588.652 and 4588.757 carry two or more T-DNAs at a single genetic locus. Molecular identification and tracking of these transgenes can be done using standard PCR analysis (visually scoring an endpoint in a gel-based electrophoresis and staining of the PCR products) or real-time PCR. In addition to determining whether a plant is carrying a transgene, some of these PCR assays can also determine whether a plant is hemizygous (carrying one copy of the insertion) or homozygous (carrying two copies of the insertion).

FIG. 24 illustrates general real-time PCR assay design used to determine T-DNA locus presence (standard and real-time PCR) and zygosity (real-time PCR only).

Figure 14:
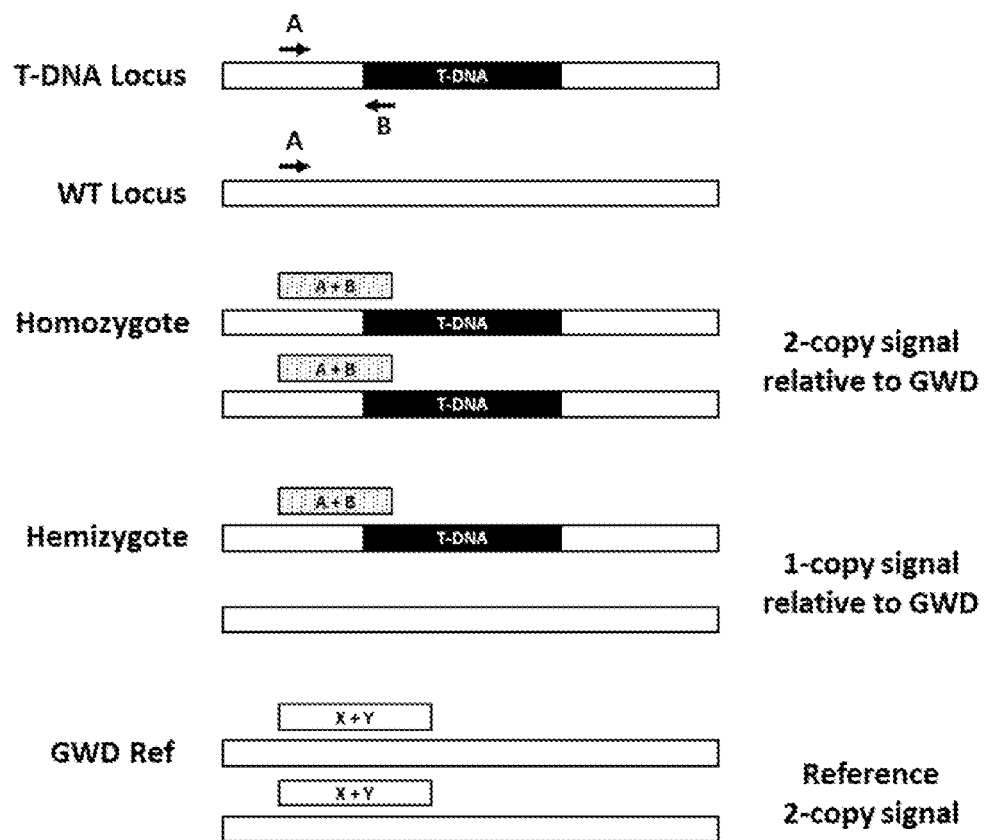
FIG. 14 illustrates general design of the real-time PCR assay used to determine presence of the T-DNA locus (standard and real-time PCR) and zygosity (real-time PCR only) in transgenic events. Letters A, B, X and Y with arrows indicate primer binding sites. Rectangular boxes A+B and X+Y represent PCR products amplified from respective primer pairs.

In FIG. 14, the standard and real-time PCR assays include, for each T-DNA locus, one primer (Primer A) that binds to a maize genomic region that is adjacent to where the T-DNA insert is located and one primer (Primer B) that binds to a region in the T-DNA that is close to Primer A. To determine zygosity in the real-time PCR assay, a second reference gene (GWD, glucan water dikinase) is amplified (X and Y primers) along with the locus primers. Real-time PCR amplification of product from Primers A+B would indicate that the T-DNA locus is present and its fluorescence relative to the GWD reference (ref) fluorescence from amplification of product from Primers X+Y would determine whether it is hemizygous (one-copy) or homozygous (two-copy).

Figure 15:
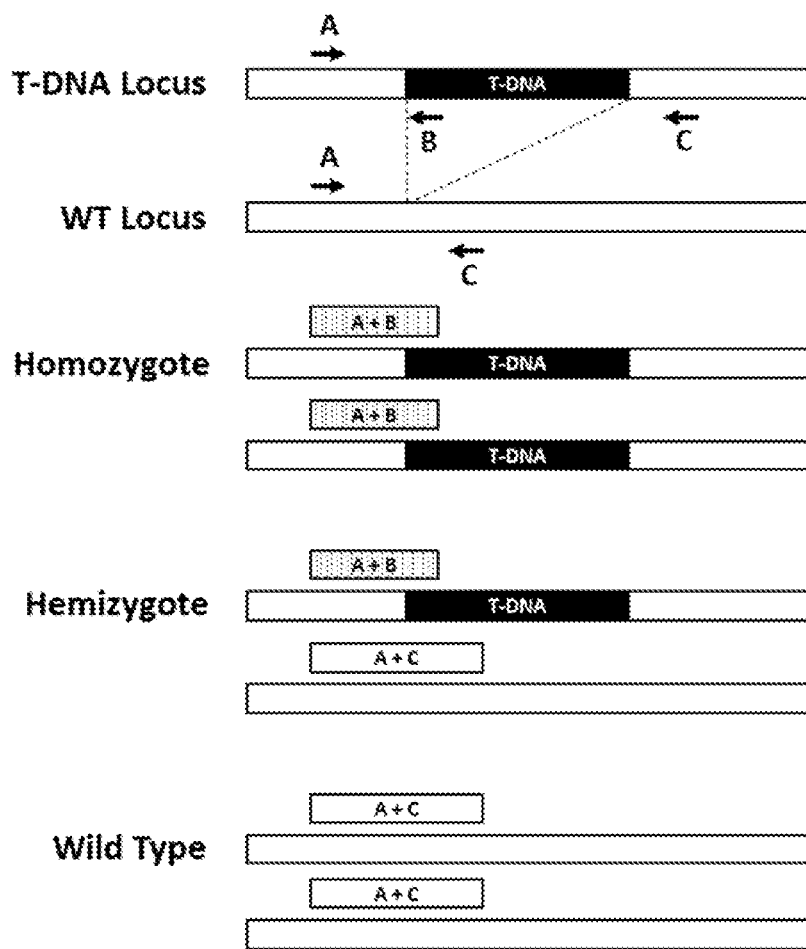
FIG. 15 illustrates general design of the standard PCR assay used to determine presence of the T-DNA locus and zygosity in transgenic events. Letters A, B, and C with arrows indicate primer binding sites. Rectangular boxes A+B and A+C represent PCR products amplified from respective primer pairs.

The standard multiplex PCR assay includes Primer A and B, as described above, but also another primer (Primer C) that binds to a maize genomic region on the other side of the T-DNA, opposite Primer A, and would be close to Primer A if the T-DNA insertion was not present, as in a wild type (WT) locus. FIG. 15 illustrates general standard PCR assay design used to determine T-DNA locus presence and zygosity. When the T-DNA insertion is present, the distance between Primer A and Primer C would be too large to amplify a product under our PCR amplification conditions and therefore absence of this amplification product is used to determine zygosity. PCR amplification of products from Primer A+B and Primer A+C indicates that the T-DNA locus is present and is hemizygous (one-copy). PCR amplification of product from Primer A+B, but not Primer A+C, indicates that the T-DNA locus is present and is homozygous (two-copy). PCR amplification of product from Primer A+C only, indicates that no T-DNA is present and the plant is WT at this locus. Primers and probes for all of these assays are listed in Tables 3 and 4.

TABLE 3

Standard and real-time (RT) PCR primers and probes used to determine T-DNA locus presence and zygosity of 4588.259, 4588.652, and 4588.757 events

| PCR Assay | Event | Primer or Probe | Primer/ Probe ID (type) | Primer Sequence | Fluor* | Quencher |
|---|---|---|---|---|---|---|
| Standard/ RT | 4588.259 | Primer | 509 (A) | GAATTGTTCATCATAAG GCGTGA (SEQ ID NO: 38) | | |
| Standard/ RT | 4588.259 | Primer | 516 (B) | AACGTGACTCCCTTAAT TCTCC (SEQ ID NO: 39) | | |
| RT | 4588.259 | Probe | PB5 | AAACTGAAGGCGGGAA ACGACAAC (SEQ ID NO: 40) | HEX | BHQ1 |
| Standard/ RT | 4588.652 | Primer | 750 (A) | GAGATGCTTGAATCCA GAACAAA (SEQ ID NO: 41) | | |
| Standard/ RT | 4588.652 | Primer | 751 (B) | TTGTCTTGGTTGTGATG ATGTG (SEQ ID NO: 42) | | |
| Standard | 4588.652 | Primer | 749 (C) | GATTACCATCAAATTTC ACACACAC (SEQ ID NO: 43) | | |
| RT | 4588.652 | Probe | PB17 | TAGAACGACCGCCCAA CCAGAC (SEQ ID NO: 44) | HEX | BHQ1 |
| Standard | 4588.757 | Primer | 513 (B) | AAACGTCCGCAATGTG TTATT (SEQ ID NO: 45) | | |
| Standard | 4588.757 | Primer | 608 (C) | TCATGCAATTGTGCCAA CC (SEQ ID NO: 46) | | |
| Standard | 4588.757 | Primer | 609 (A) | ACATAGTCAACCTAACG GCTTAT (SEQ ID NO: 47) | | |

TABLE 3-continued

Standard and real-time (RT) PCR primers and probes used to determine T-DNA locus presence and zygosity of 4588.259, 4588.652, and 4588.757 events

| PCR Assay | Event | Primer or Probe | Primer/ Probe ID (type) | Primer Sequence | Fluor* | Quencher |
|---|---|---|---|---|---|---|
| RT | GWDref | Primer | 371 (X) | GGTTATAAGCCCGGTT GAAGTA (SEQ ID NO: 48) | | |
| RT | GWDref | Primer | 525 (Y) | CTATTCCTTGCTCGGAC TGAC (SEQ ID NO: 49) | | |
| RT | GWDref | Probe | PB2 | CACCTGATATGCCAGAT GTTCTGTCTCA (SEQ ID NO: 50) | FAM | BHQ1 |

*Fluor = fluorophore.

TABLE 4

4588.259, 4588.652, and 4588.757 event-specific PCR primer combinations and PCR product sizes

| Event | Primer A | Primer B | Primer C | PCR Product (bp) | Assay Identifies |
|---|---|---|---|---|---|
| 4588.259 | 509 | 516 | | 137 | T-DNA locus: OB-2880 (SEQ ID NO: 51) |
| 4588.652 | 750 | 751 | | 107 | T-DNA locus: OB-4451 (SEQ ID NO: 52) |
| 4588.652 | 750 | | 749 | 174 | WT locus (SEQ ID NO: 53) |
| 4588.757 | 609 | 513 | | 100 | T-DNA locus: OB-3237 (SEQ ID NO: 54) |
| 4588.757 | 609 | | 608 | 218 | WT locus: B73ref (SEQ ID NO: 55) |

PCR assay using primers X (371) and Y(525) identifies the ZmGWDref locus (SEQ ID NO: 56).

DNA Extraction

These PCR assays will work with any DNA extraction method that yields DNA that can be amplified with PCR. A standard DNA extraction method (10×TE+Sarkosyl) that was used in this example is as follows: leaf tissue (standard 1 cm hole punch) is sampled into a 96 deep-well block, metal beads are added, and the block is frozen at −80° C. for at least 30 min. The block is then ground for 45 sec in a Kleco Pulverizer, centrifuged at 4,000 RPM for 3 min, the lid is removed, 300 µl of 10×TE+Sarkosyl is added, the block is resealed, and the block is mixed at room temperature for 10-20 min. After incubation, the block is centrifuged at 4,000 RPM for 5 min, 165 µl of upper aqueous phase is removed and added to a 96-well PCR block, the PCR block is sealed, and the block is incubated at 90° C. for 30 min. After incubation, 20 µl of extract is added to 180 µl of sterile water in a 96-well plate (1:10 dilution) to create the final DNA sample for PCR.

PCR

Events 4588.259, 4588.652, and 4588.757 standard and real-time PCR primers are listed in Table 3 and standard PCR primer combinations with expected PCR product sizes are listed in Table 4.

Standard PCR is performed with 2 µl of DNA extract and GoTaq (Promega) or Kapa 3G (Kapa Biosystems) PCR Mix in 30 µl reaction volumes with the following components and conditions for each event:

Event 4588.259 Standard PCR:

Components (final concentration) were as follows: PCR Mix with buffer, MgCl$_2$, nucleotides, and enzyme (1×); primer 509 (400 nM) and primer 516 (400 nM). Conditions were as follows: 95° C., 3 min; 33 cycles (95° C., 30 sec; 55° C., 30 sec; 72° C., 30 sec); 72° C., 8 min.

Event 4588.652 Standard PCR:

Components (final concentration) were as follows: PCR Mix with buffer, MgCl$_2$, nucleotides, and enzyme (1×), primer 749 (400 nM), primer 750 (400 nM), and primer 751 (400 nM). Conditions were as follows: 95° C., 3 min; 33 cycles (95° C., 30 sec; 55° C., 30 sec; 72° C., 30 sec); 72° C., 8 min.

Figure 16:
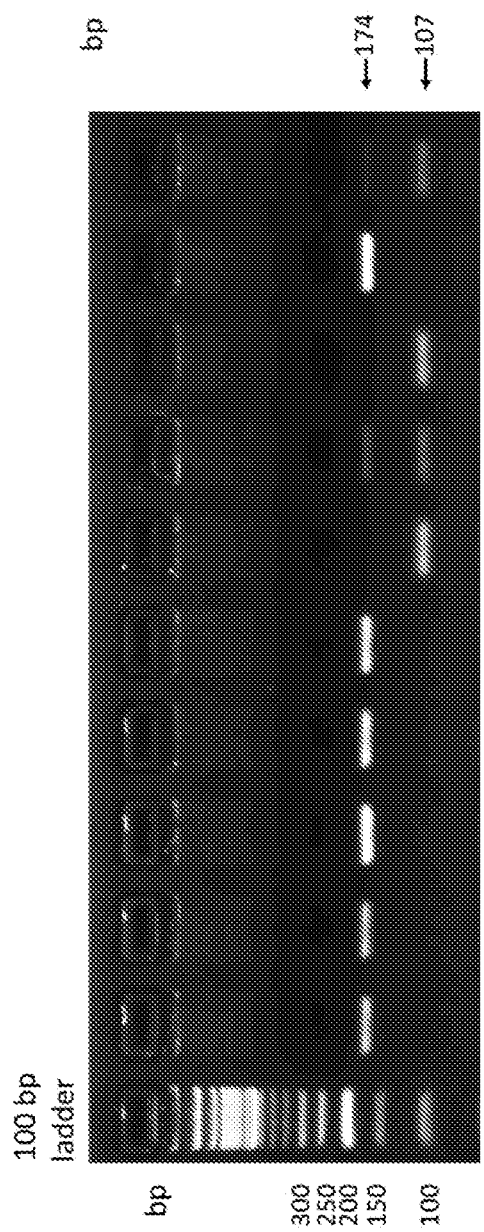
FIG. 16 illustrates the standard multiplex PCR analysis of the selfed segregating 4588.652 plants.

Event 4588.757 Standard PCR:

Components (final concentration) were as follows: PCR Mix with buffer, MgCl$_2$, nucleotides, and enzyme (1×), primer 513 (400 nM), primer 608 (400 nM), and primer 609 (400 nM). Conditions were as follows: 95° C., 3 min; 33 cycles (95° C., 30 sec; 55° C., 30 sec; 72° C., 30 sec); 72° C., 8 min Standard PCR was analyzed by running approximately 15 µl of PCR product on a 3% agarose gel at 95V for 30 min. An example of results from a standard PCR analysis of the 4588.652 selfed segregating plants is shown in FIG. 16. Referring to this figure, ten PCR reactions from 10 independent plants were separated on a 3% agarose gel stained with ethidium bromide. Expected locus and zygosity band sizes are indicated on the right side of the image.

Locus presence and zygosity is scored by visualizing specific bands in each lane.

Real-Time PCR was performed with 2 µl of DNA extract in 20 µl reaction volumes with the following components and conditions for each event:

Event 4588.259 Real-Time PCR:

Components (final concentration) were as follow: PCR Mix with buffer, MgCl$_2$, nucleotides, and enzyme (1×), primer 509 (400 nM, primer 516 (400 nM), primer 371 (400 nM), primer 525 (400 nM), probe PB5 (200 nM) and probe PB2 (200 nM). Conditions were as follows: 95° C., 4 min; 40 cycles (95° C., 5 sec; 60° C., 45 sec)

Event 4588. 652 Real-Time PCR:

Components (final concentration) were as follows: PCR Mix with buffer, MgCl$_2$, nucleotides, and enzyme (1×), primer 750 (400 nM), primer 751 (400 nM), primer 371 (400 nM), primer 525 (400 nM), probe PB17 (200 nM) and probe PB2 (200 nM). Conditions were as follows: 95° C., 4 min; 40 cycles (95° C., 5 sec; 60° C., 45 sec)

Figure 17:
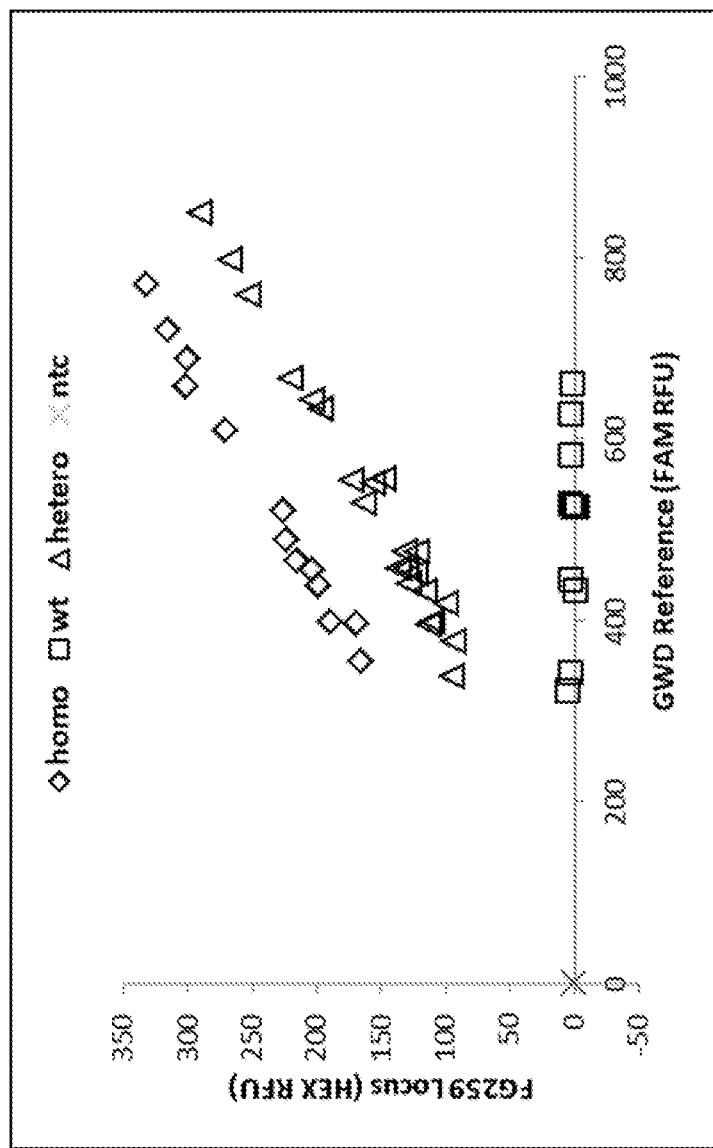
FIG. 17 is a graph illustrating real-time PCR data to determine presence of the T-DNA locus and zygosity for maize event 4588.259 (FG259).

Event 4588. 259 Real-Time PCR. Real-Time PCR can be analyzed by any real-time PCR machine and software capable of four-channel fluorescence detection. A Bio-Rad CFX96 real-time PCR machine and CFX Manager Software were used to run an example of the 4588.259 real-time PCR assay on a selfed segregating population of 4588.259 plants. FIG. 17 illustrates an example of real-time PCR data for 4588.259 to determine locus presence and zygosity. In this figure, "RFU" refers to relative fluorescence units; "ntc" refers no target control. Presence of the 4588.259 locus and zygosity was scored by the clustering of data points on the graph.

Example 9. Germination Rates Among Seed from Independent Transgenic Plants that Express Feed Glucanase Silks on wild-type plants were pollinated with pollen from individual transgenic plants (WT×Transgenic), or silks on transgenic plants were pollinated with pollen from wild-type plants (Transgenic×WT). Mature, dried seed were collected from the resulting ears and planted into soil. Following 1-2 weeks of incubation, germination rates were calculated. In some cases, this test was repeated following a second generation of growth and pollination (T2). Examples of results from such germination tests are shown in Table 5.

TABLE 5

Germination rates among seed expressing beta glucanase

| Vector | Event | WT x Transgenic | Transgenic x WT | Generation | Sow | Germination % |
|---|---|---|---|---|---|---|
| 4588 | 54  | x |   | T1 | 50 | 92  |
| 4588 | 17  | x |   | T1 | 50 | 82  |
| 4588 | 11  | x |   | T1 | 30 | 80  |
| 4588 | 161 |   | x | T1 | 15 | 67  |
| 4588 | 162 |   | x | T1 | 11 | 27  |
| 4588 | 215 | x |   | T1 | 13 | 62  |
| 4588 | 219 |   | x | T1 | 10 | 80  |
| 4597 | 18  |   | x | T1 | 30 | 37  |
| 4597 | 54  |   | x | T1 | 10 | 100 |
| 4597 | 56  |   | x | T1 | 10 | 100 |
| 4597 | 69  |   | x | T1 | 14 | 14  |
| 4597 | 69  | x |   | T1 | 30 | 73  |
| 4588 | 161 |   | x | T1 | 20 | 100 |
| 4597 | 101 |   | x | T1 | 33 | 90  |
| 4597 | 104 |   | x | T1 | 30 | 70  |
| 4588 | 259 | x |   | T2 | 17 | 100 |
| 4588 | 251 | x |   | T2 | 17 | 100 |
| 4588 | 54  | x |   | T2 | 17 | 47  |
| 4597 | 101 |   | x | T2 | 20 | 100 |
| 4597 | 104 |   | x | T2 | 20 | 100 |

The germination rate in T1 and/or T2 for events 4597_54, 4597_56, 4588_161, 4588_252, 4588_259, 4597_101, and/or 4597_104 was observed to be 100%.

Example 10. Survival of Feed Glucanase Activity During Preparation of Poultry Feed Pelleting Milled grain from transgenic plants expressing the feed glucanase was mixed with starter and grower corn-soy diets that were formulated for broiler chickens. The basal corn-soy diet for starter broilers was composed as follows: 54.89% corn 08-2012, 32.81% soybean oilcake, 5.00% distillers dry grains plus soluble solids, 2.00% vermiculite, 1.99% dicalcium phosphate, 1.00% poultry fat, 0.81% limestone fine, 0.50% plain salt (NaCl), 0.20% DL-methionine, 0.20% choline chloride 60, 0.20% mineral premix, 0.13% L-lysine, 0.12% L-threonine, 0.05% vitamin premix, 0.05% coban, and 0.05% selenium premix. The basal corn-soy diet for grower broilers was composed as follows: 58.53% corn, 26.63% soybean oilcake, 8.00% distillers dry grains plus soluble solids, 2.00% vermiculite, 1.69% dicalcium phosphate, 1.00% poultry fat, 0.76% limestone fine, 0.50% plain salt (NaCl), 0.20% mineral premix, 0.20% choline chloride 60, 0.13% DL-methionine, 0.13% L-lysine, 0.08% L-threonine, 0.05% vitamin premix, 0.05% coban, and 0.05% selenium premix.

Fine corn was ground using the hammermill screens: no. 4/4 for the starter diet and no. 6/6 for the grower and finisher diets. Coarse corn (5% of total corn) was ground with the roller mill with 0/100 gap openings.

Four diets were formulated for the pelleting trial as follows: Diet A was a basal diet, Diet D was the basal diet mixed with a control enzyme, Diet E was the basal diet mixed with the milled transgenic corn grain containing a high level of glucanase, and Diet F was the basal diet mixed with the milled transgenic corn grain containing a low level of glucanase.

Milled grain from transgenic plants expressing the feed glucanase was mixed with the basal diets at a ratio of approximately 1 lb transgenic grain per 2000 lbs basal diet mixture. For the low dose diet, transgenic grain was first mixed with non-transgenic grain at a weight ratio of 1:4 (1 gram of transgenic grain per 4 grams non-transgenic grain) to dilute the enzyme concentration prior to adding this ingredient to the basal diets.

All feed diets were pelleted at 175-180° F. into 4.4 mm pellets, and the starter diets were crumbled.

Figure 18A:
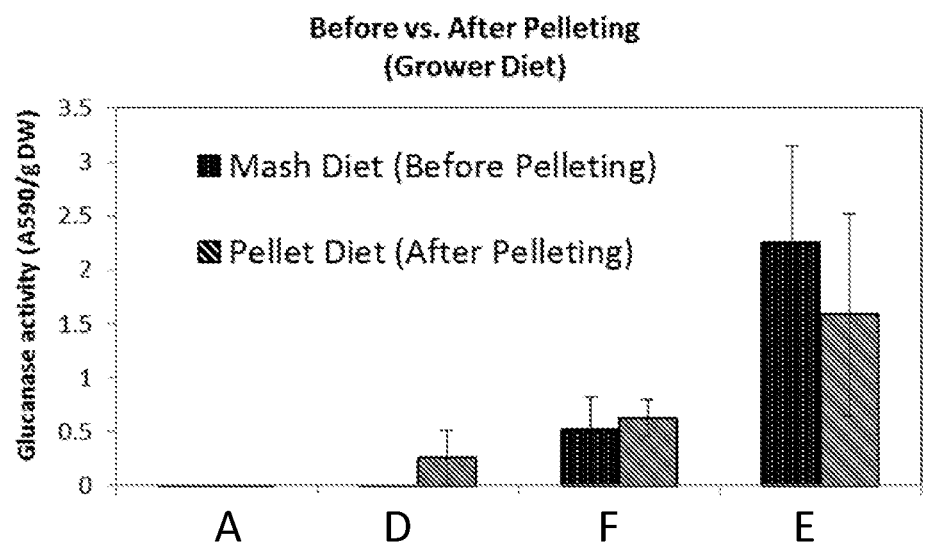
FIGS. 18A and 18B are charts illustrating glucanase activity in the Grower Diet (FIG. 18A) and the Starter Diet (FIG. 18B) before and after pelleting.
Figure 18B:
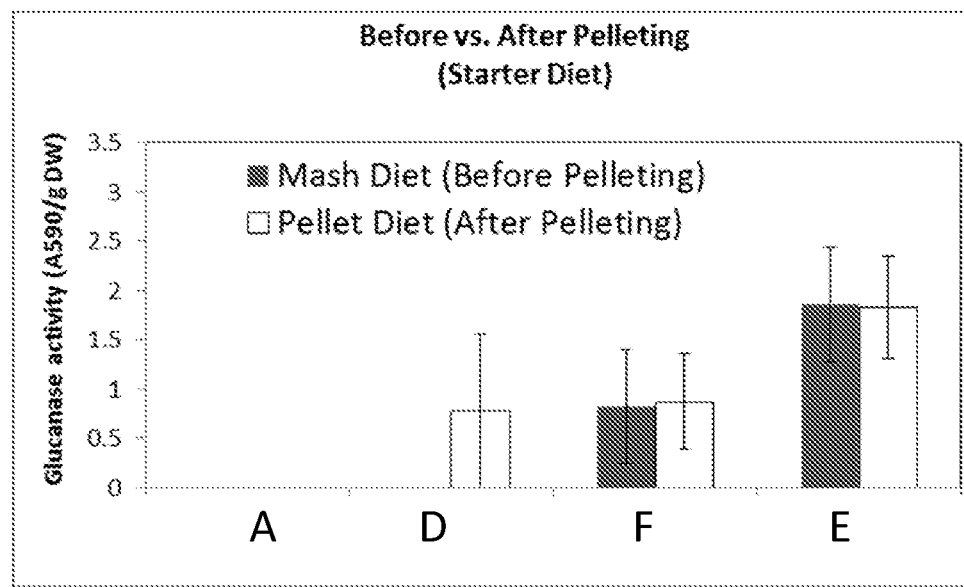

FIGS. 18A and 18B illustrate glucanase activity before and after pelleting in the Grower Diet (FIG. 18A) and the Starter Diet (FIG. 18B). Referring to these figures, samples from the resulting mixture were then removed before and after pelleting of the feed. These samples were then tested via the colorimetric glucanase assay to determine whether the enzyme survived the pelleting process. The identity of the various diets shown in FIGS. 18A and 18B were as follows: A, basal control diet (no external enzyme); D, positive control diet (commercially available enzyme added); F, low-dose diet (including milled grain from plants that express the feed glucanase); E, high-dose diet (including milled grain from plants that express the feed glucanase). It was observed that glucanase activity was high in the high-dose diet for both the Starter Diet and the Grower Diet and survived pelleting.

Example 11. Thermal Stability of Grain-expressed Feed Glucanase

Figure 19A:
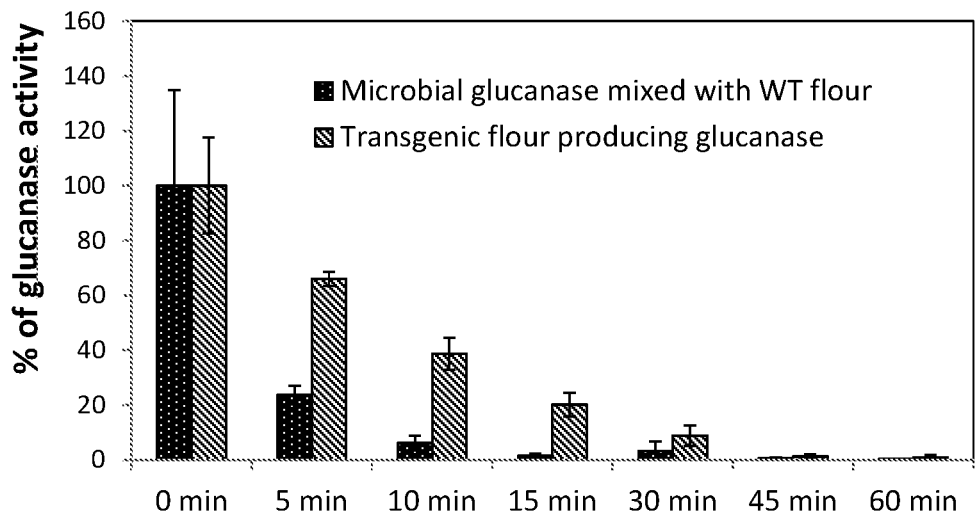
FIGS. 19A and 19B are charts illustrating glucanase activity in wild type (WT) flour mixed with microbial glucanase and transgenic flour producing glucanase after heat treatment at temperatures of 130° C.
Figure 19B:
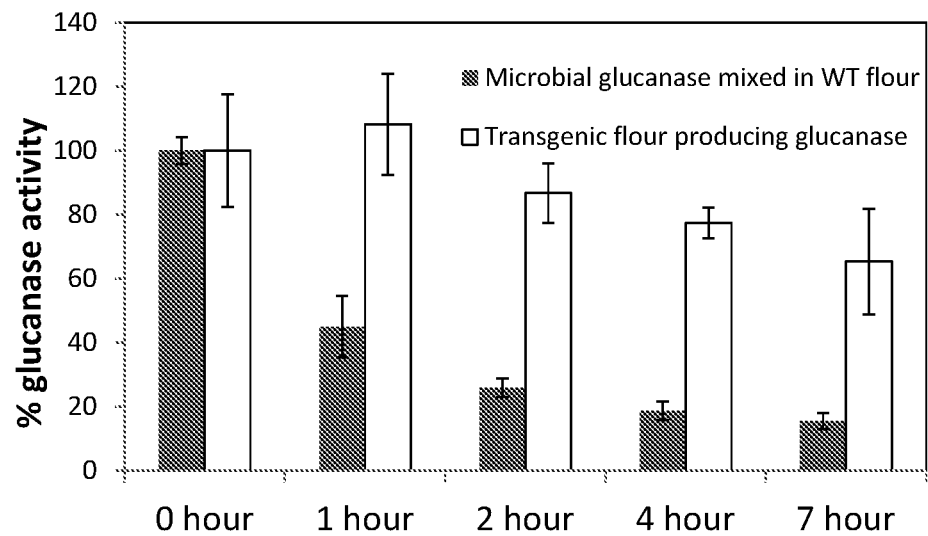

Feed glucanase was prepared via microbial expression and purification, and suspended in SEC buffer (100 mM MES, 300 mM NaCl, pH6.3). Five microliters of this preparation was mixed with 20 mg milled grain from wild-type maize. In parallel, 5 µl of SEC buffer was mixed with 20 mg milled grain from transgenic plants that express feed glucanase. Replicates from each of these two sets of samples were incubated at 94° C. or ~130° C. for various periods of time, then allowed to cool to room temperature. Subsequently, residual glucanase activity was measured via the colorimetric assay. FIGS. 19 A and 19B illustrate glucanase activity after heat treatment. FIG. 19A illustrates glucanase activity after treatment at 130° C. FIG. 19B illustrates glucanase activity after treatment at 94° C. In these experiments, more activity survived when the feed glucanase was produced in the grain itself than when it was added to the grain exogenously. This finding demonstrates that expression and accumulation of the enzyme in grain effectively provides the enzyme with additional thermal stability relative to the same enzyme that is produced microbially. In this particular instance both the grain-expressed and the microbially-expressed enzymes have the same primary amino acid sequence. Therefore, the enhanced thermal stability that was observed in the flour from transgenic grain is a function of the expression host.

Example 12. Activity of Microbially-produced AGR2314 at Various pH Values

AGR2314 activity was measured at several pH values between 3 and 8.5. Each assay (500 µL) contained Britton-Robinson polybuffer (40 mM sodium phosphate, 40 mM sodium borate, and 40 mM sodium acetate), 0.01% (v/v) Tween 20, one Beta-glucazyme substrate tablet (Megazyme, Wicklow, Ireland), and 20 nM of AGR2314 in a 2 mL Eppendorf tube. Samples were incubated for 1 hour at 37° C. or 80° C. Reactions were terminated by the addition of 1 mL of 2% (w/v) tris base. Samples were centrifuged at 15,000×g for 10 minutes, and 100 µL of each supernatant (37° C. assays) or 5 µL supernatant plus 100 µL of water (80° C. assays) was transferred to a flat-bottomed 96-well microplate. Absorbances were read at 590 nm. Assays at each pH value were performed in triplicate. Single blank assays (containing no enzyme) were performed at each pH, and these absorbance values were subtracted from the assays containing enzyme.

Figure 20:
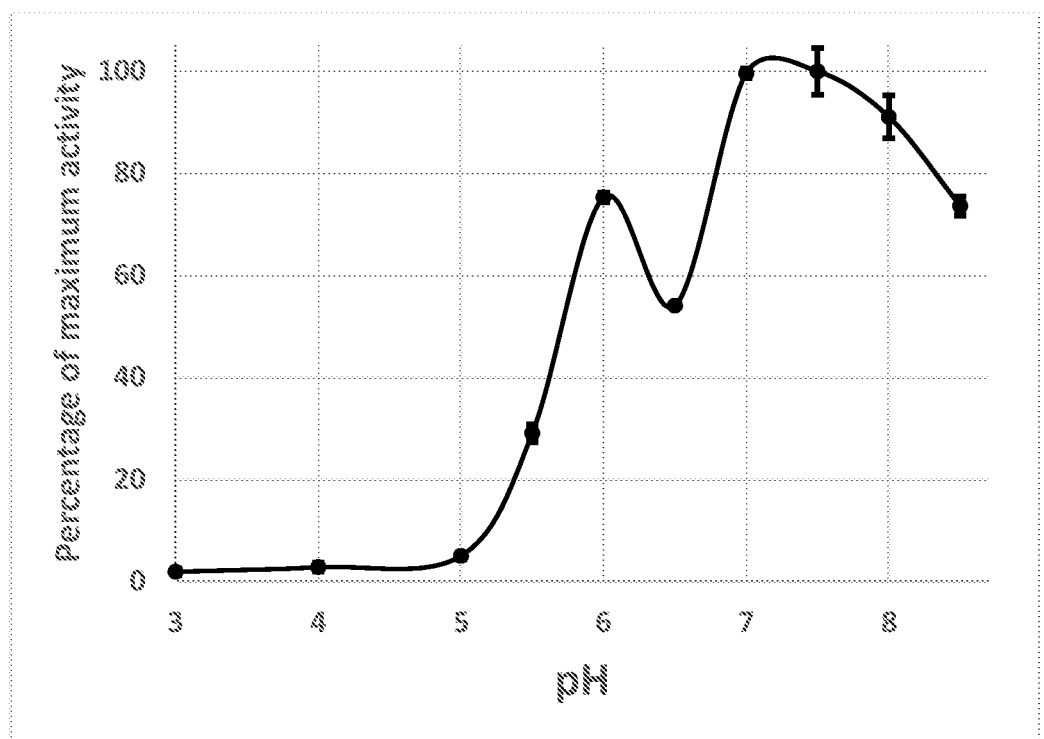
FIGS. 20 and 21 are graphs illustrating the optimum pH for measuring AGR2314 activity in an assay at 37° C.
Figure 21:
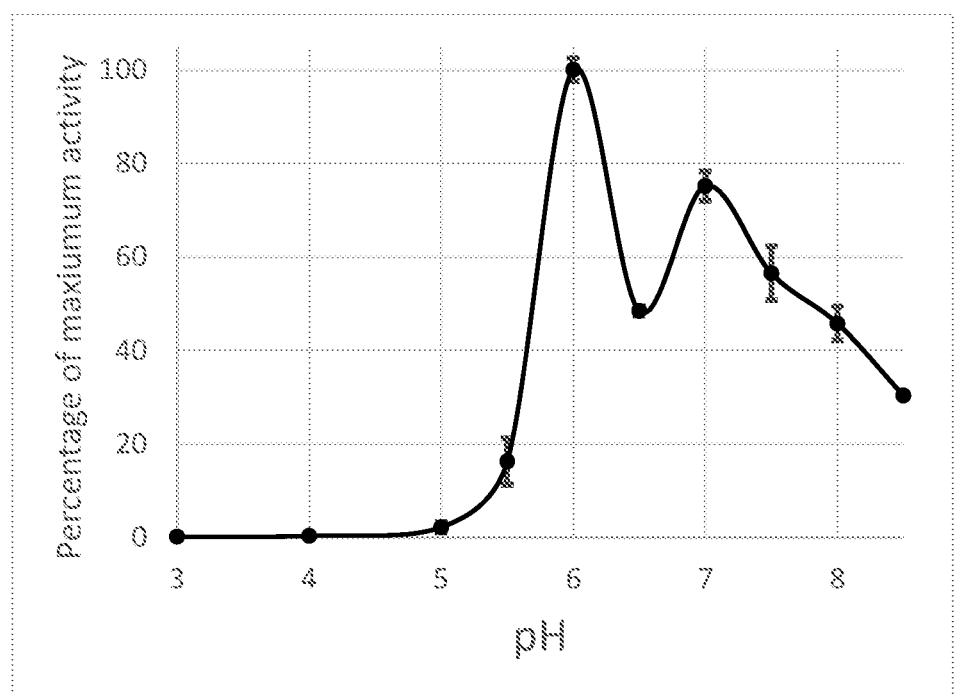

FIGS. 20 and 21 illustrate the optimum pH for measuring AGR2314 activity at 37° C. (FIG. 20) and 80° C. (FIG. 21). Referring to FIG. 20, the optimum pH was determined to be 7-7.5 at 37° C. FIG. 21 illustrates that the optimum was determined to be 6 at 80° C.

Figure 22:
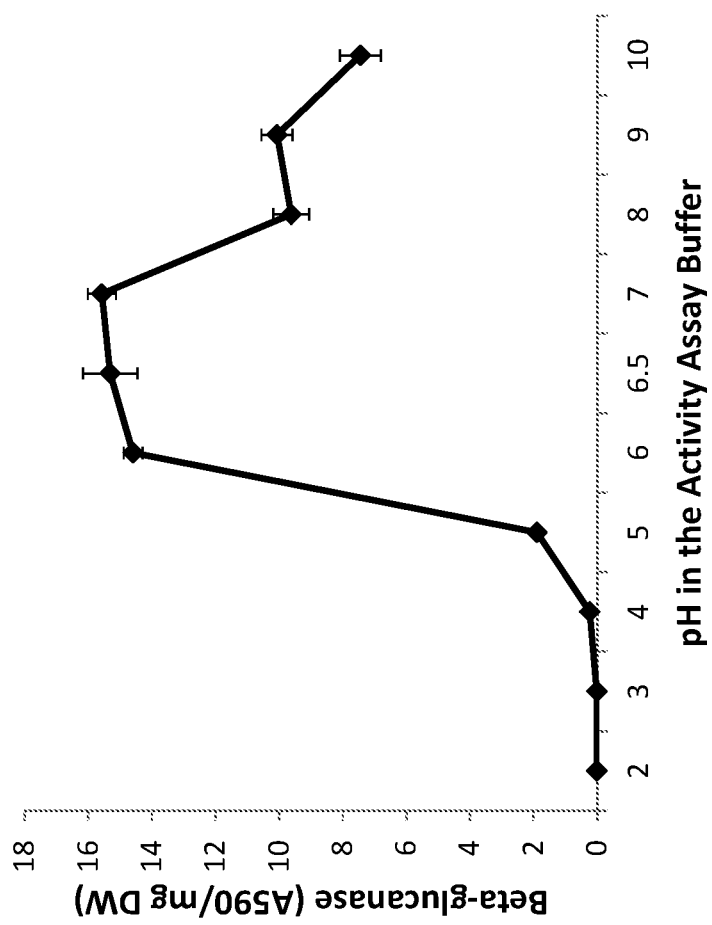
FIG. 22 is a graph illustrating an example of the optimum pH of the feed glucanase that is produced in transgenic flour.

FIG. 22 shows an example of pH optimum of the feed glucanase that is produced in transgenic flour.

To determine the relationship between the pH of the assay conditions and the activity of the enzyme that was derived from transgenic grain, 5 ml of water containing 0.2% Tween-20 was mixed with 200 mg of flour from transgenic seed on a rotating platform for 1 hour at 60° C. Following centrifugation at 1500×g for 20 minutes in a clinical centrifuge, the supernatant was transferred to a 15 mL Eppendorf tube. This sample was centrifuged at 1500×g for 10 minutes in a tabletop centrifuge. Aliquots of this protein extract were diluted 20-fold in assays to test each pH condition by mixing 50 µl of extract with 950 µl of Britton-Robinson polybuffer (40 mM sodium phosphate, 40 mM sodium borate, and 40 mM sodium acetate) that had been prepared at pH 2-10. The pH of each reaction mixture was checked using a pH strip. Five hundred microliters from each mixture was transferred to a 96 deep-well plate for the assay. One beta-glucazyme tablet was added to each well and mixed by gentle vortexing, the plate was sealed and incubated at 80° C. for 1 hour. The reactions were stopped by adding 1 mL of 2% (w/v) Tris-base to each well. The 96-well plate was centrifuged at 3000×g for 10 minutes in a clinical centrifuge, then 100 µL of the supernatant from each of the samples was transferred to wells in a flat-bottom microplate, and the absorbance at 590 nm was determined on a microplate spectrophotometer. As shown in FIG. 22, the seed-produced enzyme has a pH optimum between pH6 and pH7, but still retains a large fraction of its activity at a pH as high as 10.

Example 13. Activity of Microbially-produced AGR2314 and AGR2414 on Various Substrates All reactions used 5 nM of AGR2314, AGR2414, or 5 µL of control enzyme at the indicated concentrations, in 200 mM sodium phosphate, 0.01% (v/v) Tween 20, pH 6.5. Reactions were carried out for one hour at either 37° C. or 80° C. and terminated as described.

Beta-glucosidase Assays: the substrate was 1 mM pNP-D-glucopyranoside (Sigma Chemical Co. catalog # N7006) and the positive control enzyme was Rhizobium etli beta-glucosidase (Prozomix, catalog No. PRO-E0110; 315.9 Unit/mL). Reaction volumes were 500 µL; reactions were terminated by the addition of 500 µL of 2% (w/v) tris base. After centrifugation at 3000×g for 10 minutes, 100 µL of supernatant was transferred to a microplate and the absorbance at 405 nm was recorded.

Endocellulase Assays: each assay contained one tablet of Cellazyme C substrate (Megazyme, catalog No. T-CCZ) in 500 µL buffer. Reactions were terminated by the addition of 1 mL of 2% tris base. Samples were centrifuged for 10 minutes at 15,000×g. 100 µL, of supernatant was transferred to a microplate, and the absorbance at 590 nm was recorded.

Exocellulase (Cellobiohydrolase) Assays: the substrate was 1 mM pNP-D-cellobioside (Sigma catalog No. N5759) and the positive control enzyme was CBHI from Trichoderma longibrachiatum (Megazyme catalog No. E-CBHI; 0.5 Units/µL). Reaction conditions were as described above for the beta-glucosidase assays.

Amylase Assays: the substrate was Red Starch (Megazyme catalog No. S-RTAR; prepared as directed by the manufacturer) and the positive control enzyme was α-amylase from Bacillus licheniformis (Megazyme catalog No. E-BLAAM; 3000 Units/mL). 245 µL buffer, 5 µL of enzyme, and 125 µL of Red Starch reagent were mixed and incubated as described above. Reactions were terminated by the addition of 625 µL ethanol. After incubating at room temperature for 1.0 minutes, samples were centrifuged for 10 minutes at 3000×g, and 100 μL of supernatant was transferred to a microplate; absorbance at 51.0 nm was recorded.

Endoxylanase Assays: each assay contained one tablet of Xylazyrne AX substrate (Megazyme catalog No. No. XAX-1000) and the positive control enzyme was 100 mg/mL of *Thermomyces lanuginosis* xylanase (Sigma catalog #X2753) in assay buffer. Reactions were carried out as described above for the endocellulase assays.

Pectinase Assays: the substrate was 25 mg/mL pectin (Sigma catalog No. P7536) in assay buffer and the positive control enzyme was pectinase from *Aspergillus niger* (Sigma catalog No. 17389) at 100 mg/mL in assay buffer. Five L of enzyme was added to 35 μL of pectin solution and incubated as described above. Reactions were terminated by the addition of 60 μL of DNS stop/reagent solution (Wicher et al. [2001], *Appl. Microbiol. Biotechnol.* 55, p. 578) followed by heating at 95° C. for 15 minutes. Samples were centrifuged at 3000×g for 10 minutes, 20 μL supernatant was mixed with 100 μL water in a microplate, and the absorbance at 550 nm was recorded.

1,3-beta-glucosidase Assays: each assay contained one tablet of 1,3-beta-glucazyme HS substrate (Megazyme catalog No. ET-CUR200) and the positive control enzyme was *Trichoderma* sp. 1,3-β-D-glucanase (Megazyme catalog No. E-LAMSE; 50 Units/mL). Reactions were carried out as described above for the endocellulase assays.

1,4-beta-glucosidase Assays: each assay contained one tablet of Beta-glucazyme substrate (Megazyme catalog No. TBGZ-1000T). Reactions were carried out as described above for the endocellulase assays, except that 5 μL of supernatant was mixed with 100 μL of water in a microplate for recording of absorbance.

Figure 23A:
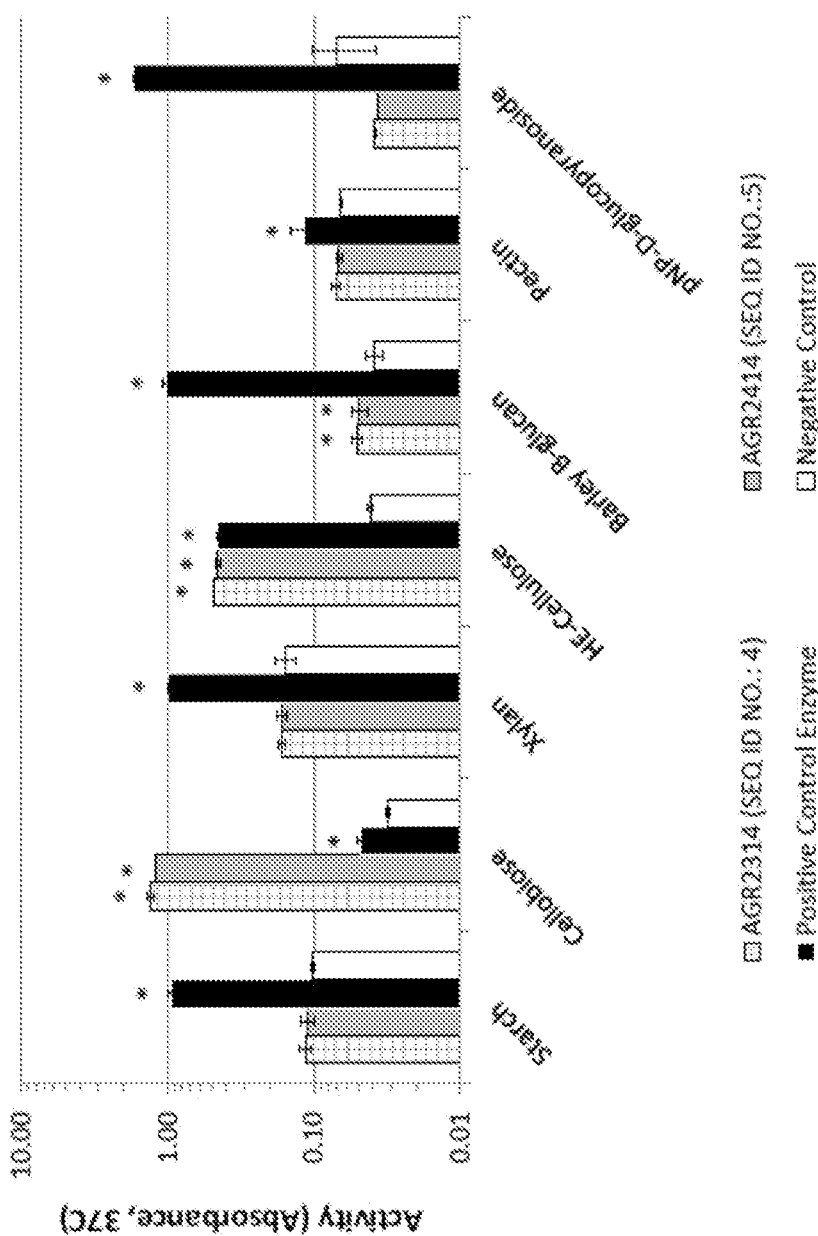
FIGS. 23A and 23B are charts illustrating glucanase activity on multiple substrates at 37° C.
Figure 23B:
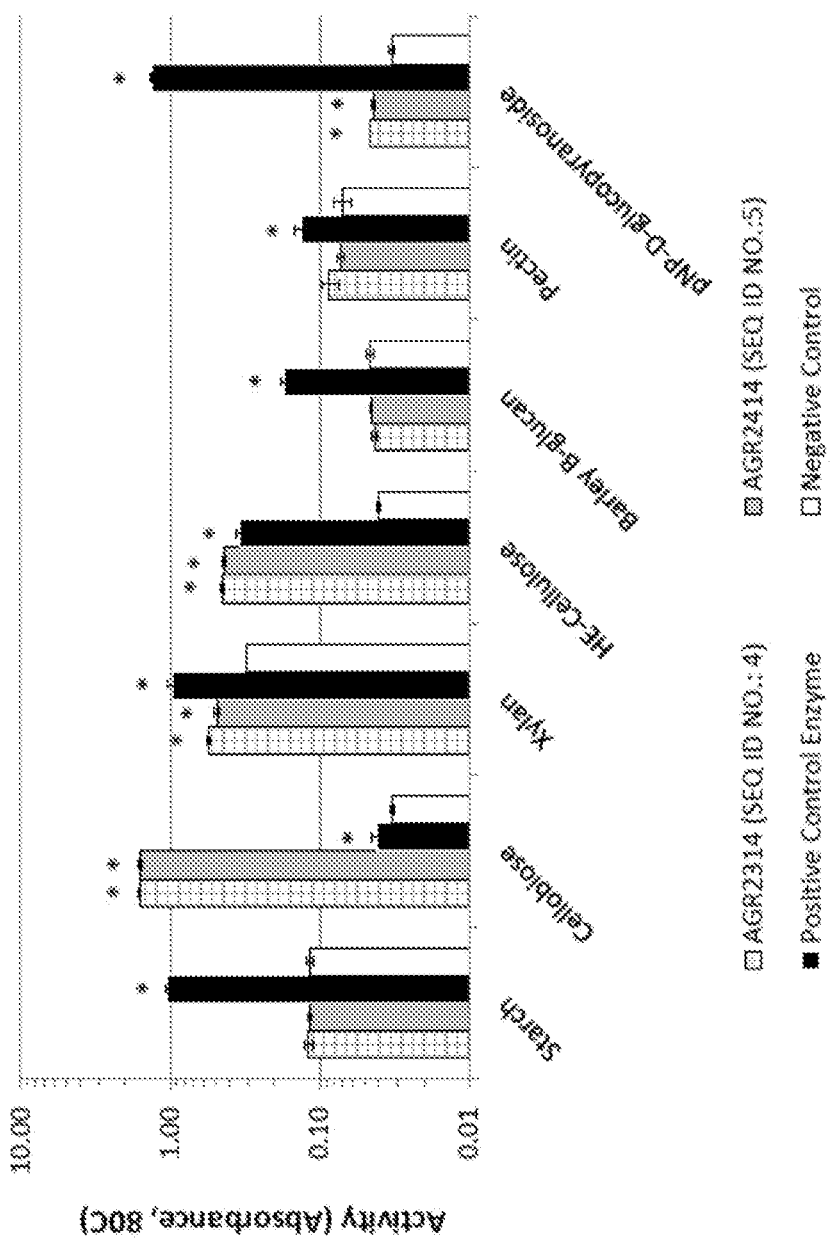

FIGS. 23A and 23B illustrate the glucanase activity for hydrolyzing starch, cellobiose (pNP-D-cellobioside), xylan (Xylazyme AX), HE-cellulose (Cellazyme C), barley-B-glucan (Beta-glucazyme), pectin and PNP-D-gluopyranoside at 37° C. (FIG. 23A) and 80° C. (FIG. 23B). Referring to these figures, it was observed that both AGR2314 and AGR2414 enzymes were highly active in hydrolyzing cellobiose and HE-cellulose at 37° C. and 80° C.

Example 14. Glucanase Activity on Seed Fiber

Figures 24A, 24B:
FIGS. 24A and 24B are charts illustrating enzymatic hydrolysis of untreated seeds fiber of transgenic maize plants expressing AGR2314.

Glucose release from untreated seed fiber 20 mg seed fiber was digested at pH 5.0 with 5 μM AGR2314 protein for 72 hours at 55 C. A commercial enzyme cocktail was used at full loading (FCT) as a positive control. After enzymatic hydrolysis, the soluble sugars in reaction supernatant were hydrolyzed into monomers via acid hydrolysis at 121° C. FIGS. 24A and 24B illustrate release of monomeric sugars after enzymatic hydrolysis of the seed fiber. FIG. 24A shows glucose yield and FIG. 24B shows xylose yield. Pre-acid hydrolysis (light gray bars) and total (dark gray bars) sugars were separated and quantified via HPLC using a Bio-Rad Aminex HPX-87-P ion-exclusion column. AGR2314 does not release monomeric glucose or xylose from untreated seed fiber. However, this enzyme was able to solubilize untreated seed fiber into oligosaccharides which account for approximately 80% of the total sugars released by a commercially-available cellulase-enzyme cocktail.

Figures 25A, 25B:
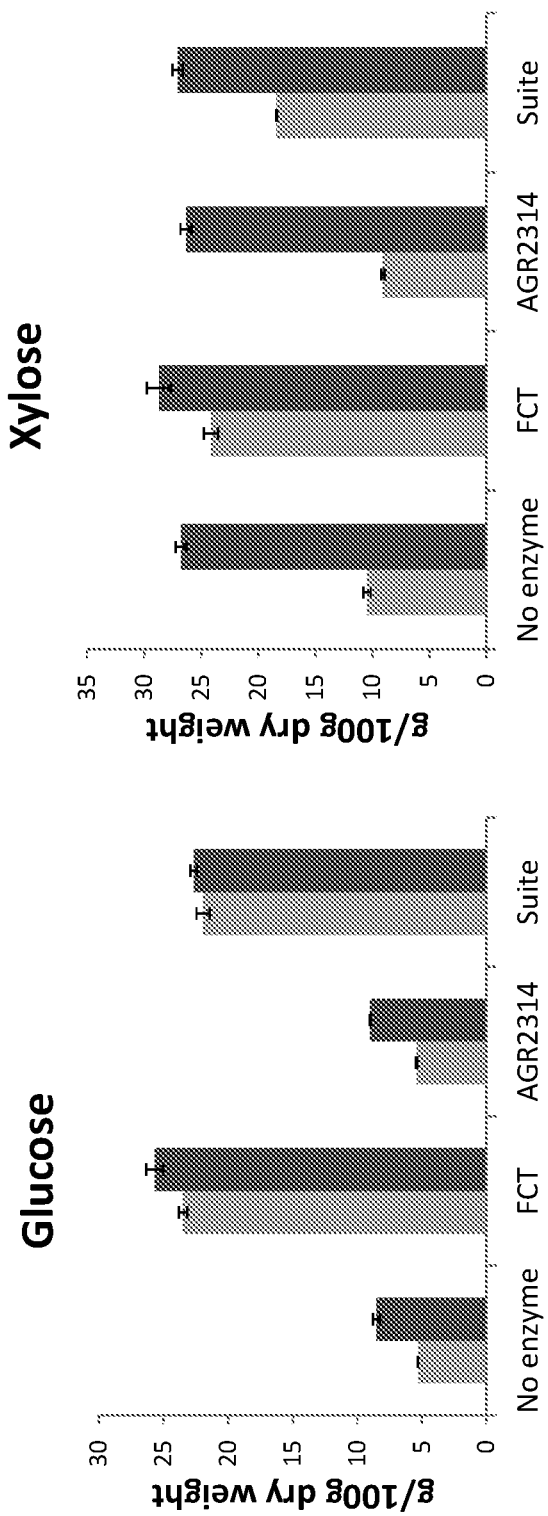
FIGS. 25A and 25B are charts illustrating enzymatic hydrolysis of seed fiber of transgenic maize plants expressing AGR2314 pretreated with the dilute acid.

Glucose Release from Dilute Acid-Pretreated Seed Fiber 20 mg seed fiber was pretreated at 80 C in 0.5% $H_2SO_4$ for 16 hours, then neutralized to pH 5.0. The pretreated seed fiber was digested at pH 5.0 with 2 μM AGR2314 and a suite of glucanase, cellobiohydrolase, endoglucanase, and beta-glucosidase (all at 2 μM loading) for 72 hours at 55° C. A commercial enzyme cocktail (Accellerase XY, Genencor) was used at full loading (FCT) as a positive control. After enzymatic hydrolysis, the soluble sugars in reaction supernatant were hydrolyzed into monomers via acid hydrolysis at 121° C. FIGS. 25A and 25B illustrate release of monomeric sugars after enzymatic hydrolysis of the seed fiber. FIG. 25A shows glucose yield and FIG. 25B shows xylose yield. Pre-acid hydrolysis (light gray bars) and total (dark gray bars) sugars were separated and quantified via HPLC using a Bio-Rad Aminex HPX-87-P ion-exclusion column.

AGR2314 did not release sugars from pretreated seed fiber at greater levels than the pretreatment itself. When combined with other cell-wall degrading enzymes, approximately 90% of total sugars were released as compared to a commercially-available cellulase-enzyme cocktail.

Example 15. The Use of Alucanase Enzymes on Broiler Live Performance

The chemical energy contained within an animal's diet, and its availability to the animal eating the diet, are critical characteristics influencing the nutritional value of any diet. Diets rich in energy, provide adequate nutrition and promote rapid growth to higher levels than diets that are deficient in energy. Therefore, determining the energy within a diet, and altering energy availability by using glucanase enzymes, provides an important set of tools to improve animal nutrition and therefore animal performance.

To demonstrate the use of glucanase enzymes in broiler production, metabolizable energy and nutrient digestibility, male broilers were fed with alternative feed ingredients (wheat, barley and low-fat DDGS) with or without supplemental glucanase. Broiler body weight gain, feed consumption, and feed conversion rate were determined and feed glucanase enzyme was evaluated.

Dietary Treatments and Procedures

Day-old male broiler were obtained from a commercial hatchery and randomly allocated to 64 battery cages in groups of 10. Experimental diets were fed from 0 to 28 d of ages. Initial group weights were obtained and equalized amongst the treatments. Feed disappearance and body weight were measured weekly (7, 14, 21, and 28 d of age) to calculate live performance parameters (feed consumption, body weight gain, and feed conversion ratio). In addition, excreta were collected twice to determine apparent metabolizable energy (AME) of the diets at 14 and 29 d of age.

Dietary treatments were fed in a 4×2 factorial design and further delineated below. Four different diets (corn/soybean meal based, corn/wheat based, corn/barley based, and corn/LF-DDGS based diets) and two levels of glucanase (with or without) were fed. Diets were formulated to be isocaloric and all nutrients, with the exception of energy, were formulated to meet or exceed the nutrient requirements. The enzyme treatments had the enzyme added on top of the diet. In addition, titanium dioxide was added to the diets as an indigestible marker to determine AME and nutrient digestibility. Table 6 describes dietary treatments.

TABLE 6

Treatment delineation

| Trt | Diet | Enzyme |
|---|---|---|
| 1 | Corn-soybean meal | − |
| 2 | Corn-soybean meal | + |
| 3 | Corn-soybean meal-wheat | − |
| 4 | Corn-soybean meal-wheat | + |
| 5 | Corn-soybean meal-LF- | − |

TABLE 6-continued

Treatment delineation

| Trt | Diet | Enzyme |
|---|---|---|
| 6 | DDGS Corn-soybean meal-LF-DDGS | + |
| 7 | Corn-soybean meal-barley | − |
| 8 | Corn-soybean meal-barley | + |
|   | Total | 640 male broilers |

Total Males needed: 8 treatments × 8 reps × 10 birds/cage = 640 male broilers + 60 for equating = 700 male broilers Temperature Battery cages: 92° F. from placement to 4 d, 90° F. from 5 to 9 d, 84° F. from 10 to 15 d, 80° F. from 16 to 24 d, 78° F. from 25 to 29 d, Room Setup Prior to bird placement, lighting and temperature in the battery cage rooms were set 48 hours in advance. Wire bottoms were added to the battery cages until day 0 to 4. Unless noted in the schedule, for collection periods, excreta pans were scrapped on a regular basis to avoid any pest and odor issues.

Lighting Program

A 23 light:1 dark with a lighting intensity of 3.0 $ft^2$ was implemented from placement until 7 d of age. A 23 light: 1 dark lighting schedule was implemented from 8-21 d with a lighting intensity of 1.0 ft candles. A 23 light: 1 dark lighting schedule was implemented from 22-28 d of age with a lighting intensity of 0.3 ft candles.

Special Instructions

Wire bottoms were placed into all battery cages prior to the start of the experiment or day-old chicks will fall through the floors. Wire bottoms were removed at d 7. In addition, cage doors were modified to accommodate smaller birds from 0 to 7 d of age.

Any mortality was not replaced.

All diets were fed in mash form. Mix sheets were forthcoming.

To avoid cross contamination of the enzyme, separate feed scoops were needed. Table 7 describes experimental timeline.

TABLE 7

Timeline of dietary treatments

| Day | Age of birds | Experimental Timeline | Lighting | Temperature |
|---|---|---|---|---|
| Tue | −2 | | 23L:1D 3.0 $ft^2$ | 92° F. |
| Thu | 0 | Place 720 male broilers in battery cages Equate weights Start experimental diets | | |
| Tue | 5 | | | 90° |
| Thu | 7 | Weigh all birds and feed Remove wire bottoms | | |
| Fri | 8 | | 23L:1D 1.0 $ft^2$ | |
| Sat | 9 | | | |
| Sun | 10 | | | 84° |
| Mon | 11 | Clean excreta pans Start 14 d collection period | | |
| Thu | 14 | Weigh all birds and feed Collect excreta for 14 d collection period | | |
| Sat | 16 | | | 80° |
| Sun | 17 | | | |

TABLE 7-continued

Timeline of dietary treatments

| Day | Age of birds | Experimental Timeline | Lighting | Temperature |
|---|---|---|---|---|
| Wed | 20 | | | 80°$B$-east |
| Thu | 21 | Weigh all birds and feed | | |
| Fri | 22 | | 23L:1D 0.3 $ft^2$ | |
| Tues | 25 | Clean excreta pans Start d 29 collection period | | 78° |
| Fri | 28 | Weigh all birds and feed Collect excreta for 29 d collection period END OF EXPERIMENT | | 75° |

Figure 26:
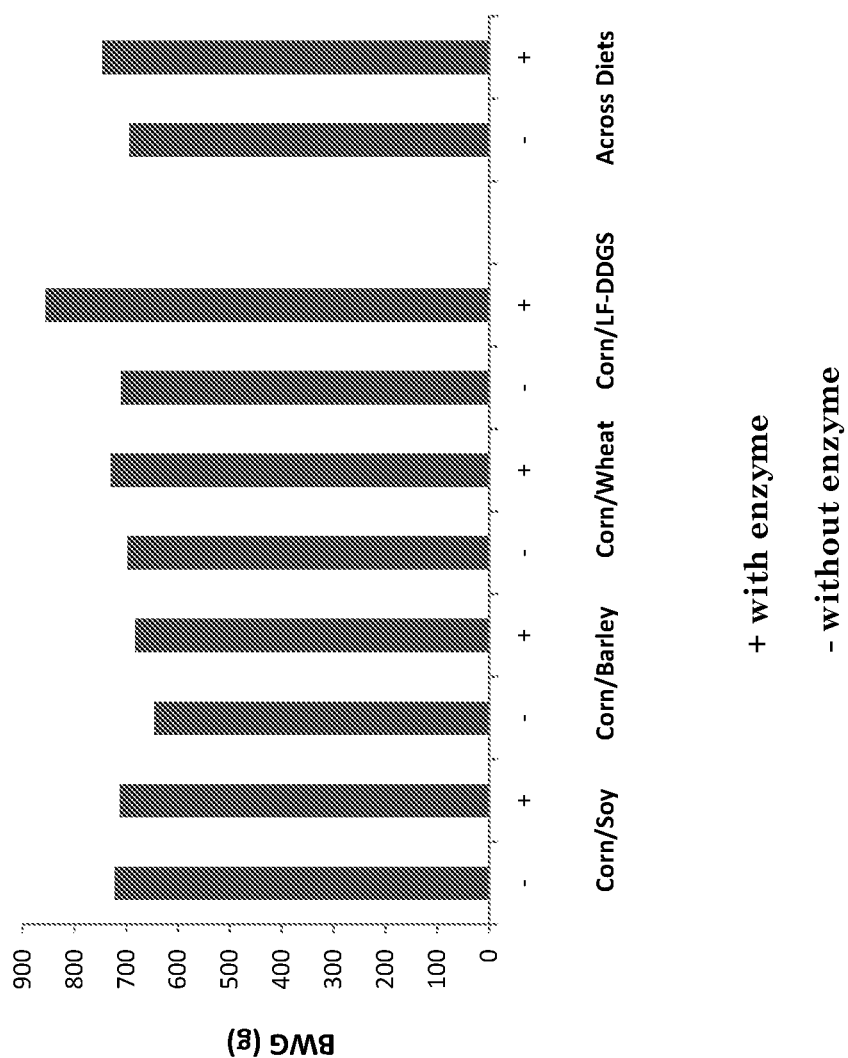
FIG. 26 is a chart illustrating the body weight gain (BWG) during the 28-day poultry feeding trial.

FIG. 26 illustrates the body weight gain (BWG) during the 28-day poultry feeding trial. Referring to FIG. 26, four different diets, corn/soybean meal based, corn/barley based, corn/wheat based, and corn/LF-DDGS based, with (+) or without (−) a glucanase were tested. Still referring to FIG. 26, average of BWG with or without glucanase across the four diets was shown. It was observed, that body wait gain was on average higher in chickens fed with the diets that included a glucanase.

Figure 27:
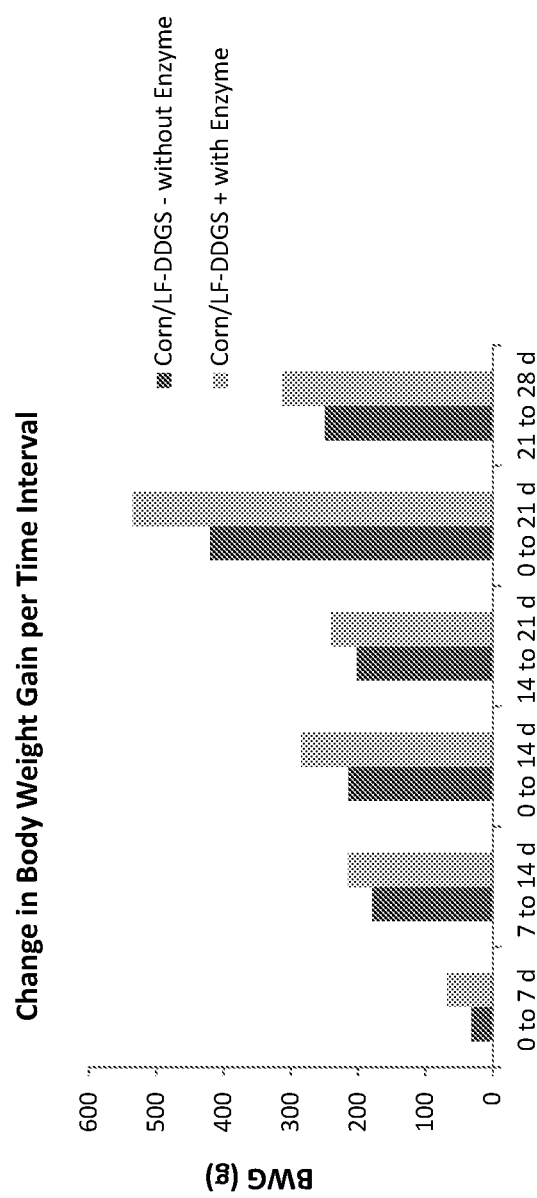
FIG. 27 is a chart illustrating the changes in poultry BWG per time interval during 28 day feeding trial.

FIG. 27 illustrates the changes in poultry BWG per time interval during 28 day feeding trial. Referring to FIG. 27, initial group weights were obtained and equalized amongst the treatments. BWG was measured weekly (7, 14, 21, and 28 d of age) for broilers feed using the corn/LF-DDGS diet with (+) or without (−) a glucanase. Still referring to FIG. 27, it was observed across all treatments that body wait gain in chickens fed with the glucanase including diets was higher than in chickens fed with diets without glucanase.

Figure 28:
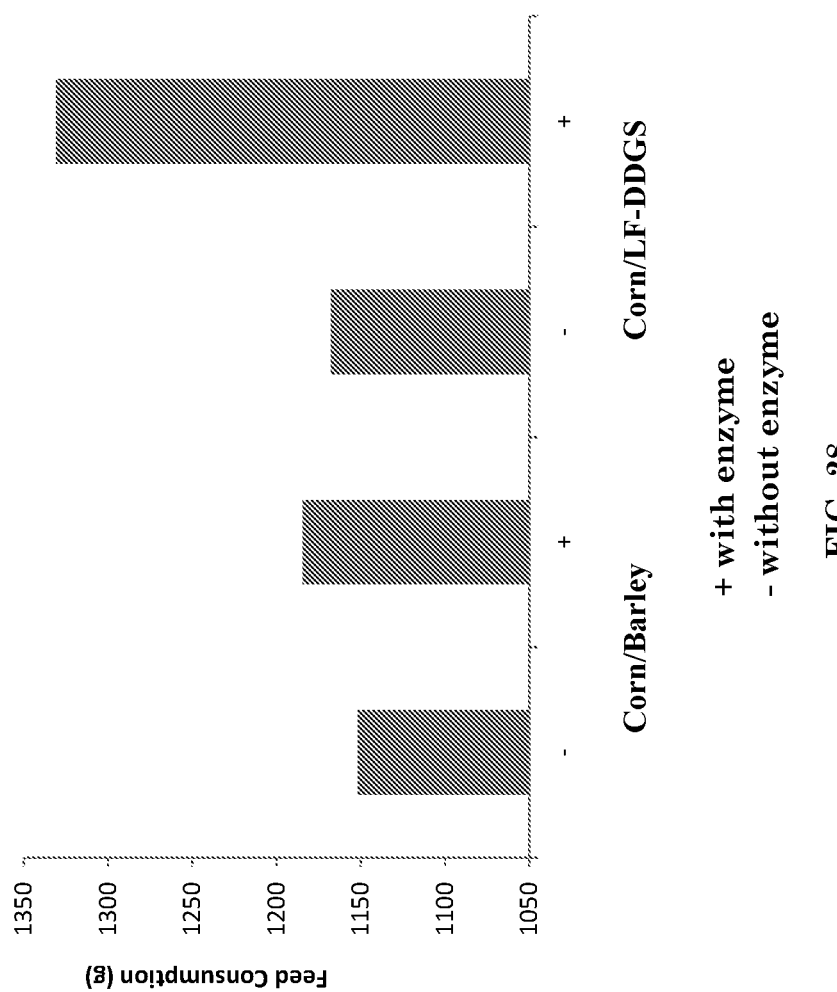
FIG. 28 is a chart illustrating feed consumption during the 28-day poultry feeding trial using two different diets (corn/barley based and corn/LF-DDGS based) with (+) or without (−) a glucanase.

FIG. 28 illustrates feed consumption during the 28-day poultry feeding trial using two different diets (corn/barley based and corn/LF-DDGS based) with (+) or without (−) a glucanase. Referring to FIG. 28, it was found that feed consumption was higher for the diets that included a glucanase.

Figure 29:
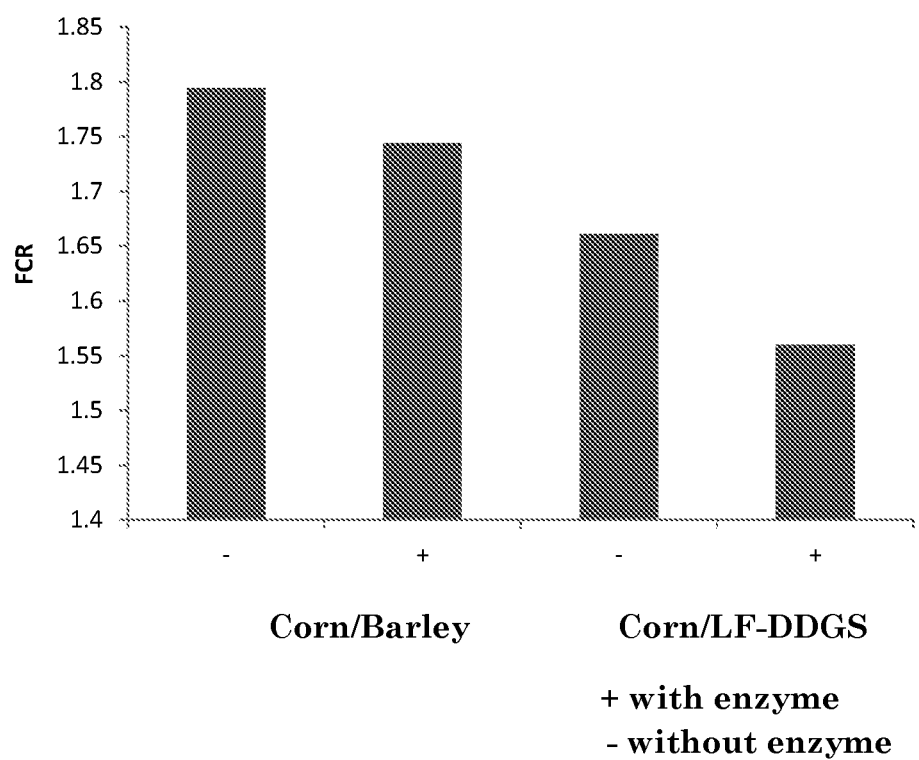
FIG. 29 is a chart illustrating feed conversion rate (FCR) during the 28-day poultry feeding trial with two different diets (corn/barley based and corn/LF-DDGS based diets) with (+) or without (−) a glucanase.

FIG. 29 illustrates the feed conversion rate (FCR) during the 28-day poultry feeding trial with two different diets (corn/barley based and corn/LF-DDGS based diets) with (+) or without (−) a glucanase. The feed conversion rate refers to the feed consumption required for gaining the body weight for a tested animal. The FCR is calculated by dividing the value of feed consumption by the value of body weight gain. Referring to FIG. 29, it was observed that the FCR was lower for the diets that included a glucanase. These data indicates that diets that included a glucanase facilitated digestion and feed consumption in the tested animals.

Example 16. The Use of Glucanase Enzymes for Broiler Live Performance

To demonstrate the effect of glucanase enzymes in broiler production, 936 male broilers were feed with varies glucanase concentrations in a 17 day battery trial. Birds were weighed at day 17. Feed composition includes corn, soybean meal and fat (soybean oil). Table 8 describes experimental details of the 17 day battery trial.

TABLE 8

Experimental Treatments: (diets were fed through day 17) - total of 9 TRTs

| Trt Code | Description | Dose |
|---|---|---|
| 1 | Positive Control (PC) | — |
| 2 | Negative Control (NC, less 50-60 kcal/lb of PC) | — |
| 3 | NC + Industry Std Enzyme_1* | 0.25 lb/ton |
| 4 | NC + Industry Std Enzyme_2** | 0.2 lb/ton |
| 5 | NC + Glucanase | 5 |
| 6 | NC + Glucanase | 50 |
| 7 | NC + Glucanase | 100 |
| 8 | NC + Glucanase | 250 |
| 9 | NC + Glucanase | 500 |

*Industry Std Enzyme_1 refers to ENSPIRA ™ (JBS United)
**Industry Std Enzyme_2 refers to HOSTAZYM X ® (Huvepharma)

| | | | |
|---|---|---|---|
| No. of treatments | 9 | Broilers per replicate | 8 |
| Replicates per treatment | 13 | Broilers per treatment | 104 |
| Total No. of replicates | 117 | Total No. of broilers | 936 |

Figure 30:
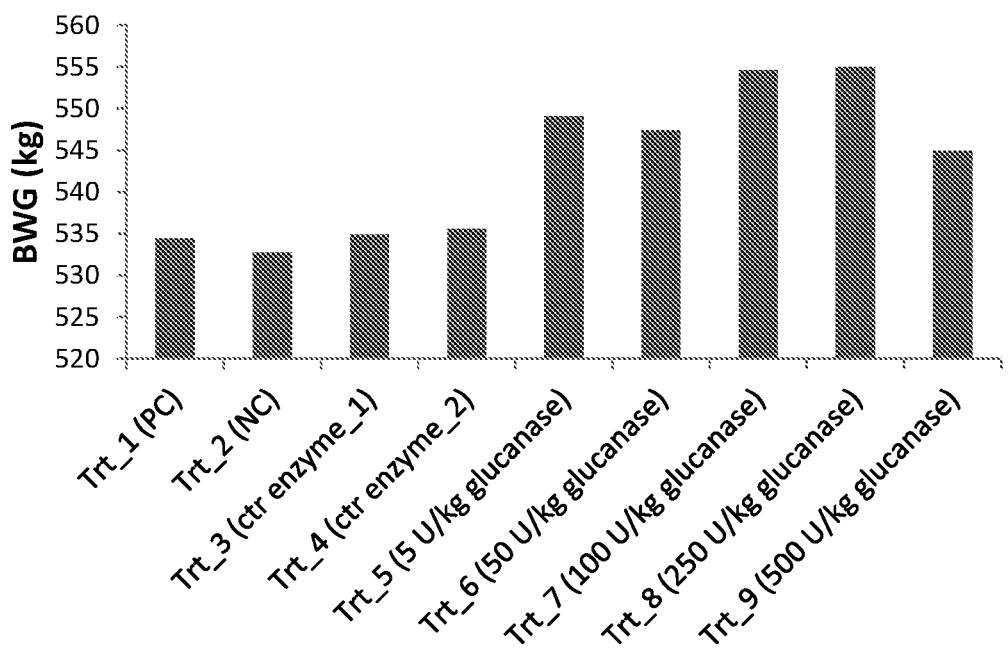
FIG. 30 is a chart illustrating the effect of glucanase on poultry BWF in experimental treatment.

Referring to FIG. 30, the inclusion of beta-glucanase in treatments 7 (Trt_7) and 8 (Trt_8) significantly (p-value<0.05) increased body weight gain compared to the positive control (PC), negative control (NC), and treatments 3 (Trt_3) and 4 (Trt_4), which contained a commercial NSPase inclusion. The glucanase inclusion in treatments 5 (Trt_5), 6 (Trt_6), and 9 (Trt_9) produced intermediate results.

REFERENCES

Leeson, S. and L. Caston. 2000. Commercial enzyme and their influence on broilers fed wheat or barley. J. Appl. Poult. Res. 9:242-251.

Yu, B. and T. K. Chung. 2004. Effects of multiple-enzyme mixtures on growth performance of broilers fed corn-soybean meal diets. J. Appl. Poult. Res. 13:178-182.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of determining the presence or absence of maize event 4588.259 (FG259) in a sample; said method comprising:
contacting the sample with a first primer and a second primer, wherein the primers are capable of amplifying a fragment of genomic DNA from an event 4588.259 (FG259) plant that comprises SEQ ID NO: 22, 23, 24, 25, or 26;
amplifying a nucleic acid in the sample to obtain an amplified product; and
detecting in the amplified product the presence or absence of SEQ ID NO: 22, 23, 24, 25, or 26.

2. The method of claim 1, wherein the nucleic acid comprises the sequence of SEQ ID NO: 51.

3. The method of claim 1, wherein the first primer comprises the nucleic acid sequence SEQ ID NO: 38.

4. The method of claim 1, wherein the second primer comprises the nucleic acid sequence of SEQ ID NO: 39.

5. The method of claim 1, wherein the step of determining further comprises hybridizing the amplified product to a nucleic acid comprising the sequence of SEQ ID NOS: 40, and detecting the amplified product specific to maize event 4588.259 (FG259).

6. A transgenic maize plant, part, or seed thereof comprising one or more of synthetic nucleic acids encoding a glucanase and at least one synthetic polynucleotide selected from the group consisting of SEQ ID NOS: 22 -26,
wherein the glucanase is capable of degrading one or more polysaccharides,
wherein the at least one synthetic polynucleotide produces a diagnostic amplicon for identifying event 4588.259 (FG259), and
wherein a representative sample of the seed comprising the event 4588.259 (FG259) has been deposited under ATCC Accession No. PTA-125919.

7. The method of claim 1, wherein the sample comprises plant matter derived from the transgenic maize plant, part or seed thereof of claim 6.

8. An animal feedstock comprising the transgenic maize plant, part, or seed thereof of claim 6.

9. The animal feedstock of claim 8 further comprising a feed supplement.

10. The animal feedstock of claim 9, wherein the feed supplement is plant material.

11. The animal feedstock of claim 10, wherein the plant material is from a non-transgenic plant, another transgenic, mutant or engineered plant.

12. The animal feedstock of claim 9, wherein the feed supplement includes one or more exogenous enzymes.

13. The animal feedstock of claim 12, wherein the one or more exogenous enzymes includes a hydrolytic enzyme selected from the group consisting of: xylanase, endoglucanase, cellulase, protease, phytase, amylase, and mannanase.

14. The animal feedstock of claim 10, wherein the plant material includes at least one component selected from the group consisting of: corn meal, corn pellets, wheat meal, wheat pellets, wheat grain, barley grain, barley pellets, soybean meal, soybean oilcake, sorghum grain, and sorghum pellets.

15. The animal feedstock of claim 9, wherein the feed supplement includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix.

16. A method of producing an animal feedstock comprising mixing the transgenic maize plant, part, or seed thereof of claim 6 with other plant material to form a mixture.

17. The method of claim 16 further comprising pelletizing the mixture.

18. The method of claim 17 further comprising adding a feed supplement to the mixture.

19. The method of claim 18, wherein the feed supplement includes at least one exogenous enzyme.

20. The method of claim 19, wherein the at least one exogenous enzyme is a hydrolase selected from the group consisting of: xylanase, mannanase, protease, phytase, and cellulase.

21. A method of increasing metabolizable energy of a diet; said method comprising mixing the transgenic maize plant, part, or seed thereof of claim 6 with a feed ingredient.

22. The method of 21 wherein the feed ingredient includes at least one component selected from the group consisting of: corn meal, corn pellets, wheat meal, wheat pellets, wheat grain, wheat middlings, barley grain, barley pellets, soybean meal, soy hulls, dried distillers grain, soybean oilcake, sorghum grain, and sorghum pellets.

23. The method of claim 21, wherein the feed ingredient includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, mineral premix, and one or more exogenous enzymes.

24. A method for enhancing production of fermentable sugars from grains; said method comprising:
mixing grains derived from the transgenic maize plant of claim 6 with grains derived from a different plant to form mixed grains; and
processing the mixed grains.

25. The method of claim 24, wherein the different plant is an engineered plant that includes a synthetic nucleic acid encoding at least one hydrolytic enzyme.

26. The method of claim 25, wherein the at least one hydrolytic enzyme is selected from the group consisting of: xylanase, an endoglucanase, an exoglucanase, a feruloyl esterase, an intein-modified xylanase, an intein-modified endoglucanase, an intein-modified exoglucanase, and an intein-modified feruloyl esterase, phytase and protease.

27. The method of claim 24, wherein the processing includes at least one operation selected from the group consisting of harvesting, baling, grinding, milling, chopping, size reduction, crushing, pellitizing, extracting a component from the mixed grains, purifying a component or portion of the mixed grains, extracting or purifying starch, hydrolyzing polysaccharides into oligosaccharides or monosaccharides, ensiling, fermentation, chemical conversion, and chemical catalysis.

28. The method of claim 27 further comprising producing a biochemical product.

29. The method of claim 28, wherein the biochemical product is selected from the group consisting of ethanol, butanol, lactic acid, citric acid, and acetic acid.

* * * * *